(12) United States Patent
Young et al.

(10) Patent No.: US 9,617,513 B2
(45) Date of Patent: *Apr. 11, 2017

(54) PLURIPOTENT EMBRYONIC-LIKE STEM CELLS, COMPOSITIONS, METHODS AND USES THEREOF

(75) Inventors: Henry E. Young, Macon, GA (US); Paul A. Lucas, Poughkeepsie, NY (US)

(73) Assignee: ABT Holding Company, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/029,763

(22) Filed: Jan. 5, 2005

(65) Prior Publication Data

US 2005/0255588 A1 Nov. 17, 2005

Related U.S. Application Data

(63) Continuation of application No. 09/820,320, filed on Mar. 28, 2001, now abandoned, which is a continuation-in-part of application No. 09/668,508, filed on Sep. 22, 2000, now abandoned, which is a continuation-in-part of application No. 09/404,895, filed on Sep. 24, 1999, now abandoned.

(51) Int. Cl.
| | | |
|---|---|---|
| *A61K 48/00* | (2006.01) | |
| *A61K 35/12* | (2015.01) | |
| *C12N 5/0775* | (2010.01) | |
| *C12N 5/074* | (2010.01) | |

(52) U.S. Cl.
CPC ......... *C12N 5/0607* (2013.01); *C12N 5/0675* (2013.01); *A61K 35/12* (2013.01); *A61K 48/00* (2013.01); *C12N 2502/03* (2013.01); *C12N 2502/21* (2013.01); *C12N 2510/00* (2013.01)

(58) Field of Classification Search
CPC  C12N 5/0607; C12N 5/0675; C12N 2502/03; C12N 2510/00; A61K 35/12; A61K 48/00
USPC .......... 435/325, 455; 514/44; 424/93.1, 93.2
See application file for complete search history.

(56) References Cited

U.S. PATENT DOCUMENTS

| | | | |
|---|---|---|---|
| 5,827,735 A | 10/1998 | Young et al. | |
| 5,903,934 A | 5/1999 | Sears, III | |
| 6,248,587 B1 * | 6/2001 | Rodgers et al. | 435/375 |

FOREIGN PATENT DOCUMENTS

| | | |
|---|---|---|
| JP | 2001-521380 A | 6/2001 |
| WO | WO 98/07841 | 2/1998 |
| WO | 98-43679 | 10/1998 |
| WO | WO 01/11011 A2 | 2/2001 |
| WO | 2007067280 A2 | 6/2007 |

OTHER PUBLICATIONS

Sylvester et al. Arch Surg., 139:93-99 (2004).*
Stojkovic et al. Reproduction, 128:259-267 (2004).*
Wobus et al. Physiol. Rev., 85: 635-678 (2005).*
Verfaillie et al. Hematology (Am Soc Hematol Educ Program) 2002;:369-91.*
Inverardi et al. Transplant Biology, 1996.*
Verma et al. [Nature, 389:239-242, 1997.*
Makrides et al. Protein Exp Pur. 1999; 17:183-202.*
Kiem et al. [Blood, 92(6):1878-1886, Sep. 15, 1998.*
Wang et al. Transplantation, 65(2):188-192, Jan. 1998.*
NIH: Stem Cells: Scientific Progress and Future Research Directions, Appendix C, Jun. 2001.*
Pera. J. of Cell Science, 113: 5-10, 2000.*
Eiges. FEBS Letters, 529: 135-141 , 2002.*
Gerecht-Nir, Developmental Dynamics, 232: 487-497 (2005).*
NIH. Stem Cells; Scientific Progress and Future Research Directions, Appendix F, p. F-10 only, Jun. 2001.*
Gang. Blood, 109(4): 1743-1751, Feb. 15, 2007.*
http://www.pathologyoutlines.com/cdmarkers.html#cd10, accessed online Jan. 9, 2008.*
Vormoor et al. Blood, 83(9): 2489-2497, 1994.*
Kogler J. of Exp. Med, 200(2): 123-135, 2004.*
Spector. Cells: A Laboratory Manual, 2.2-2.3, Cold Spring Harbor Laboratory Press, 1998.*
NIH. "The Stem Cell" from NIH Stem Cells: Scientific Progress and Future Research Directions.Department of Health and Human Services. Jun. 2001. </info/scireport/2001report>, Chapter 1.*
Young and Black, The Anatomical Record Part A 276A: 75-102, 2004.*
Bjornson et al, 1999, Science 283:534-7 (1999).
Brown, In Vitro Cell Dev Biol 28A:773-8 (1992).
Brugge et al., Science 260:918-919 (1993).
Davis et al., FASEB J. 9:A552 (1995).
Davis et al., FASEB J. 9:A590 (1995).
Evans et al., Nature 292:154-156 (1981).
Eisenberg et al., *Dev. Biol.*,191:167-81 (1997).
Grande et al., *Tiss. Eng.*, 1:345-53 (1995).
Graves et al., *Mol Reprod Dev.*, 36:424-33 (1993).
Grigoriadis et al., *J. Cell Biol.*, 106:2139-51 (1988).
Guerriero et al., *Endocrinology*, 106:1198-1202 (1980).
Hayflick, *Perspect Virol*, 3:213-37 (1963).
Hayflick, Exper Cell Res, 37:614-35 (1965).
Hauner et al., *J. Clin. Endocrin Metab.*, 64:832-5 (1987).
Iannaccone et al., *Dev. Biol.*, 163:288-292 (1994).

(Continued)

*Primary Examiner* — Thaian N Ton
(74) *Attorney, Agent, or Firm* — Tarolli, Sundheim, Covell & Tummino LLP

(57) ABSTRACT

The present invention relates to pluripotent stem cells, particularly to pluripotent embryonic-like stem cells. The invention further relates to methods of purifying pluripotent embryonic-like stem cells and to compositions, cultures and clones thereof. The present invention also relates to a method of transplanting the pluripotent stem cells of the present invention in a mammalian host, such as human, comprising introducing the stem cells, into the host. The invention further relates to methods of in vivo administration of a protein or gene of interest comprising transfecting a pluripotent stem cell with a construct comprising DNA which encodes a protein of interest and then introducing the stem cell into the host where the protein or gene of interest is expressed. The present also relates to methods of producing mesodermal, endodermal or ectodermal lineage-committed cells by culturing or transplantation of the pluripotent stem cells of the present invention.

5 Claims, 87 Drawing Sheets

(56) References Cited

OTHER PUBLICATIONS

Kadiyala et al., *Cell Transplanta*, 6:125-34 (1997).
Klausmeyer et al., *J. Cell. Biochem.*,18B:182 (1994).
Kopen et al., *PNAS USA.*, 96:10711-16 (1999).
Langer et al., *Science.*, 260:920-26 (1993).
Li et al., *Curr Biol*, 8:971-4 (1998).
Lin et al., *Eur J. Immunol*, 25:1508-16 (1995).
Lucas et al., *J. Cell Biochem* ,17E:122.
Lucas et al., *J. Cell Biochem* ,18C:276 (1994).
Lucas et al., *Wound Rep. Reg.*, 3:449-60 (1995).
Lucas et al., *J. Surg. Res.*, 62:229-32 (1996).
Martin, *PNAS, USA*, 78:7634-8 (1981).
Notarianni et al., *J. Reprod Fertil Suppl.*, 43:255-60 (1991).
Owen et al., *Ciba Foundation Symposium*, 136:42-60 (1988).
Pate et al., *Surgical Forum*, XLIV:587-9 (1993).
Petersen et al., *Science*, 284:1168-1170 (1999).
Pittenger et al., *Science*, 148:143-7 (1999).
Prockop, *Science*, 276:71-4 (1997).
Ratajczak et al., *Leukemia*, 12:942-50 (1998).
Rogers et al., *The American Surgeon*, 61:231-6 (1995).
Saito et al., *Tiss. Eng.*, 1:327-343 (1995).
Shamblott et al., *PNAS USA*, 95:13726-31 (1998).
Stocum, *Wound Repair and Regeneration*; 6:276-90 (1998).
Taylor et al., *Cell*, 17:771-9 (1979).
Taylor et al., *J. Cell. Physiology*, 111:187-94 (1982).
Thomson et al., *PNAS USA*, 92:7844-8 (1995).
Thomson et al., *Science*, 282:1145-7 (1998).
Todaro et al., *J. Cell Biol.*, 17:299-313 (1963).
Urist et al., *In Vitro*, 14:697-706 (1978).
Wakitani et al., *J. Bone Joint Surg. Am.*, 76:579-92 (1994).
Warejcka et al., *J. Surg. Res.*, 62:233-42 (1996).
Young et al., *J. Tissue Culture Methods*, 13:275-84 (1991).
Young et al., *J. Tissue Culture Methods*, 14:85-92 (1992).
Young et al., *J. Tissue Culture Methods*, 14:31-36 (1992).
Young et al., *In Vitro Cellular & Developmental Biology*, 29A:723-36 (1993).
Young et al., *Developmental*, 202:137-144 (1995).
Young et al., *J. Orthop. Res.*, 16:406-13 (1998).
Young et al., *Wound Rep Reg*, 6:65-75 (1998).
Young et al., *Wound Rep Reg*, 6:543-54 (1998).
Young et al., *Proc. Soc. Exp. Biol. Med.*, 221:63-71 (1999).
Thomson J.A., et al. Pluripotent cell lines derived from common marmoset (Cllithrix jacchus) blastocyts. Biol Reprod; (1996); vol. 55; pp. 254-259.
Kraft, H.J., et al. Oct-4 Regulates Alternative Platelet-derived Growth Factor α Receptor Gene Promoter in Human Embryonal Carcinoma Cells. J Biol Chem; 1996; vol. 271, No. 22; pp. 12873-12878.
Young, H.E., et al. "Clonogenic analysis reveals reserve stem cells in postnatal mammals. II. Pluripotent Epiblastic-Like Stem Cells". The Anatomical Record Part A (2004) 227A:178-203.
Young, H.E., et al. "Adult Reserve Stem Cells and Their Potential for Tissue Engineering". Cell Biochem. and Biophys. (2004) vol. 40; pp. 1-80.
Young, H.E., et al. "Adult-derived Stem Cells and Their Potential for Use in Tissue Repair and Molecular Medicine". J Cell. Mol. Med. (2005) vol. 9, No. 3; pp. 753-759.
Hescheler, J., et al. "Embryonic Stem Cells: A Model to Study Structural and Functional Properties in Cardiomyogenesis". Cardiovascular Res. (1997) vol. 36; pp. 149-162.

\* cited by examiner

CT3F 46, XX
(17 year-old female dermal biopsy specimen)

FIG. 42A
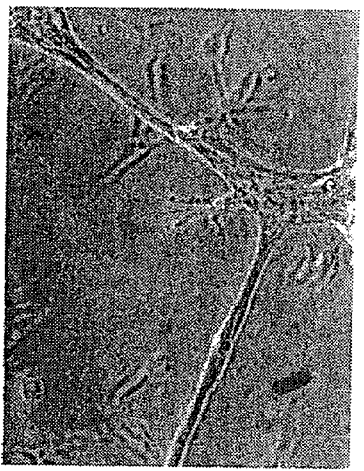
FIG. 42B
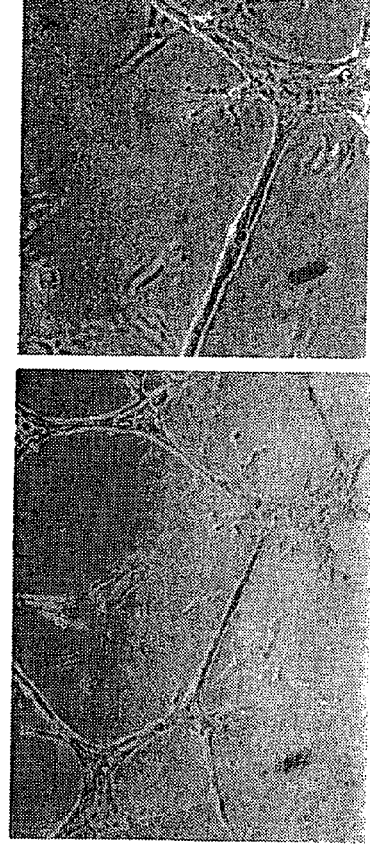
FIG. 42C
FIG. 42D
FIG. 42E
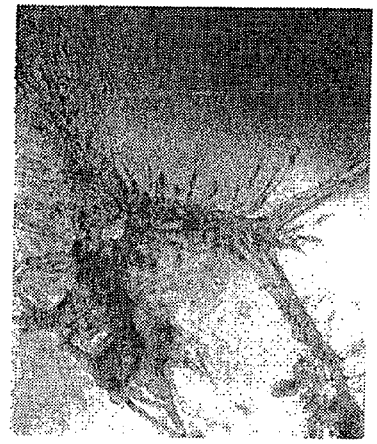

2wks

PLURIPOTENT EMBRYONIC-LIKE STEM CELLS, COMPOSITIONS, METHODS AND USES THEREOF

CROSS-REFERENCE TO RELATED APPLICATIONS

This application is a continuation of U.S. application Ser. No. 09/820,320, filed Mar. 28, 2001, which is a continuation-in-part of U.S. application Ser. No. 09/668,508, filed Sep. 22, 2000, which is aa continuation-in-part of U.S. application Ser. No. 09/404,895, filed Sep. 24, 1999.

FIELD OF THE INVENTION

This invention relates generally to pluripotent stem cells, particularly to embryonic-like pluripotent stem cells. The invention also relates to uses of the stem cells for tissue engineering in cell or tissue transplantation, in gene therapy, and in identifying, assaying or screening with respect to cell-cell interactions, lineage commitment, development genes and growth or differentiation factors.

BACKGROUND OF THE INVENTION

The formation of tissues and organs occurs naturally during prenatal development. The development of multicellular organisms follows pre-determined molecular and cellular pathways culminating in the formation of entities composed of billions of cells with defined functions. Cellular development is accomplished through cellular proliferation, lineage-commitment, and lineage-progression, resulting in the formation of differentiated cell types. This process begins with the totipotent zygote and continues throughout the life of the individual. As development proceeds from the totipotent zygote, cells proliferate and segregate by lineage-commitment into the pluripotent primary germ layers, ectoderm, mesoderm, and endoderm. Further segregation of these germ layers through progressive lineage-commitment into progenitor (multipotent, tripotent, bipotent and eventually unipotent) lineages further defines the differentiation pathways of the cells and their ultimate function.

Development proceeds from the fertilized egg, to formation of a blastula and then a gastrula. Gastrulation is the process by which the bilaminar embryonic disc is converted into a trilaminar embryonic disc. Gastrulation is the beginning of morphogenesis or development of the body form gastrulation begins with the formation of the primitive streak on the surface of the epiblast of the embryonic disk. Formation of the primitive streak, germ layers, and notochord are the important processes occurring during gastrulation. Each of the three germ layers—ectoderm, endoderm, and mesoderm—gives rise to specific tissues and organs.

The organization of the embryo into three layers roughly corresponds to the organization of the adult, with gut on the inside, epidermis on the outside, and connective tissue in between. The endoderm is the source of the epithelial linings of the respiratory passages and gastrointestinal tract and gives rise to the pharynx, esophagus, stomach, intestine and to many associated glands, including salivary glands, liver, pancreas and lungs. The mesoderm gives rise to smooth muscular coats, connective tissues, and vessels associated with the tissues and organs; mesoderm also forms most of the cardiovascular system and is the source of blood cells and bone marrow, the skeleton, striated muscles, and the reproductive and excretory organs. Ectoderm will form the epidermis (epidermal layer of the skin), the sense organs, and the entire nervous system, including brain, spinal cord, and all the outlying components of the nervous system.

While a majority of the cells progress through the sequence of development and differentiation, a few cells leave this pathway to become reserve stem cells that provide for the continual maintenance and repair of the organism. Reserve stem cells include progenitor stem cells and pluripotent stem cells. Progenitor cells (e.g., precursor stem cells, immediate stem cells, and forming or -blast cells, e.g., myoblasts, adipoblasts, chondroblasts, etc.) are lineage-committed. Unipotent stem cells will form tissues restricted to a single lineage (such as the myogenic, fibrogenic, adipogenic, chondrogenic, osteogenic lineages, etc.). Bipotent stem cells will form tissues belonging to two lineages (such as the chondro-osteogenic, adipo-fibroblastic lineages, etc.). Tripotent stem cells will form tissues belonging to three lineages (such as chondro-osteo-adipogenic lineage, etc.). Multipotent stem cells will form multiple cell types within a lineage (such as the hematopoietic lineage). Progenitor stem cells will form tissues limited to their lineage, regardless of the inductive agent that may be added to the medium. They can remain quiescent. Lineage-committed progenitor cells are capable of self-replication but have a limited life-span (approximately 50-70 cell doublings) before programmed cell senescence occurs. They can also be stimulated by various growth factors to proliferate. If activated to differentiate, these cells require progression factors (i.e., insulin, insulin-like growth factor-I, and insulin-like growth factor-II) to stimulate phenotypic expression.

In contrast, pluripotent cells are lineage-uncommitted, i.e., they are not committed to any particular tissue lineage. They can remain quiescent. They can also be stimulated by growth factors to proliferate. If activated to proliferate, pluripotent cells are capable of extended self-renewal as long as they remain lineage-uncommitted. Pluripotent cells have the ability to generate various lineage-committed progenitor cells from a single clone at any time during their life span. For example, a prenatal pluripotent mouse clone after more than 690 doublings (Young et al 1998a) and a postnatal pluripotent rat clone after more than 300 doublings (Young et al 1999) were both induced to form lineage-committed progenitor cells that after long term dexamethasone exposure, went on to differentiate into skeletal muscle, fat, cartilage, that exhibited characteristic morphological and phenotypic expression markers. This lineage-commitment process necessitates the use of either general (e.g., dexamethasone) or lineage-specific (e.g., bone morphogenetic protein-2, muscle morphogenetic protein, etc.) commitment induction agents. Once pluripotent cells are induced to commit to a particular tissue lineage, they assume the characteristics of lineage-specific progenitor cells. They can remain quiescent or they can proliferate, under the influence of specific inductive agents. Their ability to replicate is limited to approximately 50-70 cell doublings before programmed cell senescence occurs and they require the assistance of progression factors to stimulate phenotypic expression.

Embryonic stem cells are uncommitted, totipotent cells isolated from embryonic tissue. When injected into embryos, they can give rise to all somatic lineages as well as functional gametes. In the undifferentiated state these cells are alkaline phosphatase-positive, express immunological markers for embryonic stem and embryonic germ cells, are telomerase positive, and show capabilities for extended self-renewal. Upon differentiation these cells express a wide variety of cell types, derived from ectodermal, mesoderm, and endodermal embryonic germ layers. Embryonic stem (ES) cells have been isolated from the blastocyst, inner cell mass or gonadal ridges of mouse, rabbit, rat, pig, sheep, primate and human embryos (Evans and Kauffman, 1981; Iannaccone et al., 1994; Graves and Moreadith, 1993; Martin, 1981; Notarianni et al., 1991; Thomson, et al., 1995; Thomson, et al., 1998; Shamblott, et al., 1998).

ES cells are used for both in vitro and in vivo studies. ES cells retain their capacity for multilineage differentiation during genetic manipulation and clonal expansion. The uncommitted cells provide a model system from which to study cellular differentiation and development and provide a powerful tool for genome manipulation, e.g. when used as vectors to carry specific mutations into the genome (particularly the mouse genome) by homologous recombination (Brown et al., 1992). While ES cells are a potential source of cells for transplantation studies, these prospects have been frustrated by the disorganized and heterogeneous nature of development in culture, stimulating the necessary development of strategies for selection of lineage-restricted precursors from differentiating populations (Li et al., 1998). E cells implanted into animals or presented subcutaneously form teratomas-tumors containing various types of tissues containing derivatives of all three germ layers (Thomson et al., 1988).

Examples of progenitor and pluripotent stem cells from the mesodermal germ layer include the unipotent myosatellite myoblasts of muscle (Mauro, 1961; Campion, 1984; Grounds et al., 1992); the unipotent adipoblast cells of adipose tissue (Ailhaud et al., 1992); the unipotent chondrogenic cells and osteogenic cells of the perichondrium and periosteum, respectively (Cruess, 1982; Young et al., 1995); the bipotent adipofibroblasts of adipose tissue (Vierck et al., 1996); the bipotent chondrogenic/osteogenic stem cells of marrow (Owen, 1988; Beresford, 1989; Rickard et al., 1994; Caplan et al., 1997; Prockop, 1997); the tripotent chondrogenic/osteogenic/adipogenic stem cells of marrow (Pittenger et al., 1999); the multipotent hematopoietic stem cells of marrow (Palis and Segel, 1998; McGuire, 1998; Ratajczak et al., 1998); the multipotent cadiogenic/hematopoietic/endotheliogenic cells of marrow (Eisenberg and Markwald, 1997); and the pluripotent mesenchymal stem cells of the connective tissues (Young et al., 1993, 1998a; Rogers et al., 1995).

Pluripotent mesenchymal stem cells and methods of isolation and use thereof are described in U.S. Pat. No. 5,827,735, issued Oct. 27, 1998, which is hereby incorporated by reference in its entirety. Such pluripotent mesenchymal stem cells are substantially free of lineage-committed cells and are capable of differentiating into multiple tissues of mesodermal origin, including but not limited to bone, cartilage, muscle, adipose tissue, vasculature, tendons, ligaments and hematopoietic. Further compositions of such pluripotent mesenchymal stem cells and the particular use of pluripotent mesenchymal stem cells in cartilage repair are described in U.S. Pat. No. 5,906,934, issued May 25, 1999, which is hereby incorporated by reference in its entirety.

Progenitor or pluripotent stem cell populations having mesodermal lineage capability have been isolated from multiple animal species, e.g., avians (Young et al., 1992a, 1993, 1995), mice (Rogers et al., 1995; Saito et al., 1995; Young et al., 1998a), rats (Grigoriadis et al., 1988; Lucas et al., 1995, 1996; Dixon et al., 1996; Warejcka et al., 1996), rabbits (Pate et al., 1993; Wakitani et al., 1994; Grande et al., 1995; Young, R. G. et al., 1998), and humans (Caplan et al., 1993; Young, 1999a-c). Clonogenic analysis (isolation of individual clones by repeated limiting serial dilution) from populations of mesodermal stem cells isolated from prenatal chicks (Young et al., 1993) and prenatal mice (Rogers et al., 1995; Young et al., 1998a) revealed two categories of cells: lineage-committed progenitor cells and lineage-uncommitted pluripotent cells. Non-immortalized progenitor cells are capable of self-replication but have a finite life-span limited to approximately 50-70 cell doublings before programmed cell senescence occurs. They can remain quiescent or be induced to proliferate, progress down their lineage pathway, and/or differentiate. One unique characteristic of progenitor cells is that their phenotypic expression can be accelerated by treatment with progression factors such as insulin, insulin-like growth factor-I (IGF-I), or insulin-like growth factor-II (IGF-II) (Young et al., 1993, 1998a,b; Young, 1999a; Rogers et al., 1995).

Progenitor cells are lineage-committed and lineage-restricted. They can remain quiescent or be induced to proliferate, progress down their lineage pathway, and/or differentiate by treatment with appropriate bioactive factors (Young et al., 1998b). By contrast, pluripotent mesenchymal stem cells PPMSCs were found to be lineage-uncommitted and lineage-unrestricted, with respect to the mesodermal germ layer. PPMSCs from prenatal animals were capable of extended self-renewal as long as they remain uncommitted to a particular lineage. Once PPMSCs commit to a particular tissue lineage they assume the characteristics of progenitor cells for that lineage and their ability to replicate is limited to approximately 50-70 cell doublings before programmed cell senescence occurred. PPMSCs could remain quiescent, and if not, appropriate bioactive factors were necessary to induce proliferation, lineage-commitment, lineage-progression, and/or differentiation of stem cells (Young et al., 1998b).

The formation of tissues and organs occurs naturally in early normal human development, however, the ability to regenerate most human tissues damaged or lost due to trauma or disease is substantially diminished in adults. Every year millions of Americans suffer tissue loss or end-stage organ failure. The total national health care costs for these patients exceeds 400 billion dollars per year. Currently over 8 million surgical procedures are performed annually in the United States to treat these disorders and 40 to 90 million hospital days are required. Although these therapies have saved and improved countless lives, they remain imperfect solutions. Options such as tissue transplantation and surgical intervention are severely limited by a critical donor shortage and possible long term morbidity. Indeed, donor shortages worsen every year and increasing numbers of patients die while on waiting lists for needed organs (Langer and Vicanti, 1993).

Tissue engineering is an interdisciplinary field that applies the principles of engineering and the life sciences toward the development of biological substitutes that restore, maintain, or improve tissue function (Langer and Vicanti, 1993). Three general strategies have been adopted for the creation of new tissue: (1). Isolated cells or cell substitutes applied to the area of tissue deficiency or compromise. (2). Cells placed on or within matrices. In closed systems, cells are isolated from the body by a membrane allowing permeation of nutrients and wastes while excluding large entities such as antibodies or immune cells from destroying the implant. In open systems, cells attached to matrices are implanted and become incorporated into the body. (3). Tissue-inducing substances, that rely on growth factors to regulate specific cells to a committed pattern of growth resulting in tissue regeneration, and methods to deliver these substances to their targets.

Based on available evidence, a wide variety of transplants, congenital malformations, elective surgeries, diseases, and genetic disorders have the potential for treatment with pluripotent stem cells, alone or in combination with morphogenetic proteins, growth factors, genes, and/or controlled-release delivery systems. A preferred treatment is the treatment of tissue loss where the object is to increase the number of cells available for transplantation, thereby recreating the missing tissue (i.e., tissue loss, congenital malformations, breast reconstruction, blood transfusions, or muscular dystrophy) or providing sufficient numbers of cells for ex vivo gene therapy (muscular dystrophy). The expected benefit using pluripotent stem cells, is its potential for unlimited proliferation prior to (morphogenetic protein-induced) commitment to a particular tissue lineage and then once committed as a progenitor stem cell, an additional fifty to seventy doublings before programmed cell senescence. These proliferative attributes are very important when limited amounts of tissue are available for transplantation. Tissue loss may result from acute injuries as well as surgical interventions, i.e., amputation, tissue debridement, and surgical extirpations with respect to cancer, traumatic tissue injury, congenital malformations, vascular compromise, elective surgeries, etc. and account for approximately 3.5 million operations per year in the United States.

The expected benefits from the use of various pluripotent stem cells can be illustrated in considering, for example, applications of pluripotent mesenchymal stem cells. Pluripotent mesenchymal stem cells can be utilized for the replacement of potentially multiple tissues of mesodermal origin (i.e., bone, cartilage, muscle, adipose tissue, vasculature, tendons, ligaments and hematopoietic), such tissues generated, for instance, ex vivo with specific morphogenetic proteins and growth factors to recreate the lost tissues. The recreated tissues would then be transplanted to repair the site of tissue loss. An alternative strategy could be to provide pluripotent stem cells, as cellular compositions or incorporated, for instance, into matrices, transplant into the area of need, and allow endogenous morphogenetic proteins and growth factors to induce the pluripotent stem cells to recreate the missing histoarchitecture of the tissue. This approach is exemplified in U.S. Pat. No. 5,903,934 which is incorporated herein in its entirety, which describes the implanting of pluripotent mesenchymal stem cells into a polymeric carrier, to provide differentiation into cartilage and/or bone at a site for cartilage repair.

The identification of an additional tissue source for transplantation therapies, that (a) can be isolated and sorted; (b) has unlimited proliferation capabilities while retaining pluripotency; (c) can be manipulated to commit to multiple separate tissue lineages; (d) is capable of incorporating into the existing tissue; and (d) can subsequently express the respective differentiated tissue type, may prove beneficial to therapies that maintain or increase the functional capacity and/or longevity of lost, damaged, or diseased tissues.

The citation of references herein shall not be construed as an admission that such is prior art to the present invention.

SUMMARY OF THE INVENTION

In its broadest aspect, the present invention extends to an stem cell, derived from non-embryonic animal cells or tissue, capable of self regeneration and capable of differentiation to cells of endodermal, ectodermal and mesodermal lineages.

In a particular aspect, the present invention extends to an pluripotent embryonic-like stem cell, derived from postnatal animal cells or tissue, capable of self regeneration and capable of differentiation to cells of endodermal, ectodermal and mesodermal lineages.

In a further aspect, the present invention extends to an pluripotent embryonic-like stem cell, derived from adult animal cells or tissue, capable of self regeneration and capable of differentiation to cells of endodermal, ectodermal and mesodermal lineages.

The pluripotent embryonic-like stem cell of the present invention may be isolated from non-human cells or human cells.

The pluripotent embryonic-like stem cell of the present invention may be isolated from the non-embryonic tissue selected from the group of muscle, dermis, fat, tendon, ligament, perichondrium, periosteum, heart, aorta, endocardium, myocardium, epicardium, large arteries and veins, granulation tissue, peripheral nerves, peripheral ganglia, spinal cord, dura, leptomeninges, trachea, esophagus, stomach, small intestine, large intestine, liver, spleen, pancreas, parietal peritoneum, visceral peritoneum, parietal pleura, visceral pleura, urinary bladder, gall bladder, kidney, associated connective tissues or bone marrow.

This invention further relates to cells, particularly pluripotent or progenitor cells, which are derived from the pluripotent embryonic-like stem cell. The cells may be lineage-committed cells, which cells may be committed to the endodermal, ectodermal or mesodermal lineage. For instance, a lineage-committed cell of the mesodermal lineage, for instance an adipogenic, myogenic or chondrogenic progenitor cell may be derived from the pluripotent embryonic-like stem cell.

The invention also relates to pluripotent cells derived from the pluripotent embryonic-like stem cells, including pluripotent mesenchymal stem cells, pluripotent endodermal stem cells and pluripotent ectodermal stem cells. Any, such pluripotent cells are capable of self-renewal and differentiation.

In a further aspect, the present invention relates to a culture comprising:
(a) Pluripotent embryonic-like stem cells, capable of self regeneration and capable of differentiation to cells of endodermal, ectodermal and mesodermal lineages; and
(b) a medium capable of supporting the proliferation of said stem cells.

Such stem cell containing cultures may further comprise a proliferation factor or lineage commitment factor. The stem cells of such cultures may be isolated from non-human cells or human cells.

The invention further relates to methods of isolating an pluripotent embryonic-like stem cell. In particular, a method of isolating an pluripotent embryonic-like stem cell of the present invention, comprises the steps of:
(a) obtaining cells from a non-embryonic animal source;
(b) slow freezing said cells in medium containing 7.5% (v/v) dimethyl sulfoxide until a final temperature of −80° C. is reached; and
(c) culturing the cells.

The invention further relates to methods of isolating an pluripotent embryonic-like stem cell. In particular, a method of isolating an pluripotent embryonic-like stem cell of the present invention, comprises the steps of:

(a) obtaining cells from a postnatal animal source;
(b) slow freezing said cells in medium containing 7.5% (v/v) dimethyl sulfoxide until a final temperature of −80° C. is reached; and
(c) culturing the cells.

The invention further relates to methods of isolating an pluripotent embryonic-like stem cell. In particular, a method of isolating an pluripotent embryonic-like stem cell of the present invention, comprises the steps of:
(a) obtaining cells from an adult animal source;
(b) slow freezing said cells in medium containing 7.5% (v/v) dimethyl sulfoxide until a final temperature of −80° C. is reached; and
(c) culturing the cells.

The invention further relates to methods of isolating an pluripotent embryonic-like stem cell. In particular, a method of isolating an pluripotent embryonic-like stem cell of the present invention, comprises the steps of:
(a) obtaining cells from a non-embryonic animal source;
(b) filtering said cells through a 20 µm filter;
(c) slow freezing said cells in medium containing 7.5% (v/v) dimethyl sulfoxide until a final temperature of −80° C. is reached; and
(d) culturing the cells.

In a further aspect, the methods of isolating an pluripotent embryonic-like stem cell relate to methods whereby a clonal population of such stem cells is isolated, wherein a single pluripotent embryonic-like stem cell is first isolated and then further cultured and expanded to generate a clonal population. A single pluripotent embryonic-like stem cell may be isolated by means of limiting dilution or such other methods as are known to the skilled artisan.

Thus, the present invention also relates to a clonal pluripotent embryonic-like stem cell line developed by such method.

In a particular aspect, the present invention relates to pluripotent embryonic-like stem cells or populations of such cells which have been transformed or transfected and thereby contain and can express a gene or protein of interest. Thus, this invention includes pluripotent embryonic-like stem cells genetically engineered to express a gene or protein of interest. In as much as such genetically engineered stem cells can then undergo lineage-committment, the present invention further encompasses lineage-committed cells, which are derived from a genetically engineered pluripotent embryonic-like stem cell, and which express a gene or protein of interest. The lineage-committed cells may be endodermal, ectodermal or mesodermal lineage-committed cells and may be pluripotent, such as a pluripotent mesenchymal stem cell, or progenitor cells, such as an adipogenic or a myogenic cell.

The invention then relates to methods of producing a genetically engineered pluripotent embryonic-like stem cell comprising the steps of:
(a) transfecting pluripotent embryonic-like stem cells with a DNA construct comprising at least one of a marker gene or a gene of interest;
(b) selecting for expression of the marker gene or gene of interest in the pluripotent embryonic-like stem cells;
(c) culturing the stem cells selected in (b).

In a particular aspect, the present invention encompasses genetically engineered pluripotent embryonic-like stem cell(s), including human and non-human cells, produced by such method.

The present invention further relates to methods for detecting the presence or activity of an agent which is a lineage-commitment factor comprising the steps of:

A. contacting the pluripotent embryonic-like stem cells of the present invention with a sample suspected of containing an agent which is a lineage-commitment factor; and
B. determining the lineage of the so contacted cells by morphology, mRNA expression, antigen expression or other means;
wherein the lineage of the contacted cells indicates the presence or activity of a lineage-commitment factor in said sample.

The present invention also relates to methods of testing the ability of an agent, compound or factor to modulate the lineage-commitment of a lineage uncommitted cell which comprises
A. culturing the pluripotent embryonic-like stem cells of the present invention in a growth medium which maintains the stem cells as lineage uncommited cells;
B. adding the agent, compound or factor under test; and
C. determining the lineage of the so contacted cells by morphology, mRNA expression, antigen expression or other means.

The invention includes an assay system for screening of potential agents, compounds or drugs effective to modulate the proliferation or lineage-commitment of the pluripotent embryonic-like stem cells of the present invention.

In a further such aspect, the present invention relates to an assay system for screening agents, compounds or factors for the ability to modulate the lineage-commitment of a lineage uncommitted cell, comprising:
A. culturing the pluripotent embryonic-like stem cells of the present invention in a growth medium which maintains the stem cells as lineage uncommited cells;
B. adding the agent, compound or factor under test; and
C. determining the lineage of the so contacted cells by morphology, mRNA expression, antigen expression or other means.

The invention also relates to a method for detecting the presence or activity of an agent which is a proliferation factor comprising the steps of:
A. contacting the pluripotent embryonic-like stem cells of the present invention with a sample suspected of containing an agent which is a proliferation factor; and
B. determining the proliferation and lineage of the so contacted cells by morphology, mRNA expression, antigen expression or other means;
wherein the proliferation of the contacted cells without lineage commitment indicates the presence or activity of a proliferation factor in said sample.

In a further aspect, the invention includes methods of testing the ability of an agent, compound or factor to modulate the proliferation of a lineage uncommitted cell which comprises
A. culturing the pluripotent embryonic-like stem cells of the present invention in a growth medium which maintains the stem cells as lineage uncommited cells;
B. adding the agent, compound or factor under test; and
C. determining the proliferation and lineage of the so contacted cells by mRNA expression, antigen expression or other means.

The invention further relates to an assay system for screening agents, compounds or factors for the ability to modulate the proliferation of a lineage uncommitted cell, comprising:

A. culturing the pluripotent embryonic-like stem cells of the present invention in a growth medium which maintains the stem cells as lineage uncommited cells;
B. adding the agent, compound or factor under test; and
C. determining the proliferation and lineage of the so contacted cells by mRNA expression, antigen expression or other means.

The assay system could importantly be adapted to identify drugs or other entities that are capable of modulating the pluripotent embryonic-like stem cells of the present invention, either in vitro or in vivo. Such an assay would be useful in the development of agents, factors or drugs that would be specific in modulating the pluripotent embryonic-like stem cells to, for instance, proliferate or to commit to a particular lineage or cell type. For example, such drugs might be used to facilitate cellular or tissue transplantation therapy.

The assay system(s) could readily be adapted to screen, identify or characterize genes encoding proliferation or lineage-commitment factors or encoding proteins or molecules otherwise involved in cellular differentiation and development. For instance, genes encoding proteins involved in or expressed during differentiation along a particular lineage could be identified by known methods (for instance cDNA libraries, differential display, etc). Thus, the pluripotent embryonic-like stem cells of the present invention could be cultured under conditions giving rise to a particular lineage and the genes therein expressed then characterized. Factors and proteins necessary for maintaining the pluripotent embryonic-like stem cells of the present invention in a pluripotent embryonic-like state might also be similarly identified and characterized by culturing the pluripotent embryonic-like stem cells of the present invention under conditions maintaining their self-renewal capacity and characterizing the genes and proteins so expressed or which, when provided exogenously, will maintain the self-renewal capacity.

In a further embodiment, the present invention relates to certain therapeutic methods which would be based upon the activity of the pluripotent embryonic-like stem cells of the present invention, including cells or tissues derived therefrom, or upon agents or other drugs determined to act on any such cells or tissues, including proliferation factors and lineage-commitment factors. One exemplary therapeutic method is associated with the prevention or modulation of the manifestations of conditions causally related to or following from the lack or insufficiency of cells of a particular lineage, and comprises administering the pluripotent embryonic-like stem cells of the present invention, including cells or tissues derived therefrom, either individually or in mixture with proliferation factors or lineage-commitment factors in an amount effective to prevent the development or progression of those conditions in the host.

In a further and particular aspect the present invention includes therapeutic methods, including transplantation of the pluripotent embryonic-like stem cells of the present invention, including lineage-uncommitted populations of cells, lineage-committed populations of cells, tissues and organs derived therefrom, in treatment or alleviation of conditions, diseases, disorders, cellular debilitations or deficiencies which would benefit from such therapy. These methods include the replacement or replenishment of cells, tissues or organs. Such replacement or replenishment may be accomplished by transplantation of the pluripotent embryonic-like stem cells of the present invention or by transplantation of lineage-uncommitted populations of cells, lineage-committed populations of cells, tissues or organs derived therefrom.

Thus, the present invention includes a method of transplanting pluripotent embryonic-like stem cells in a host comprising the step of introducing into the host the pluripotent embryonic-like stem cells of the present invention.

In a further aspect this invention provides a method of providing a host with purified pluripotent embryonic-like stem cells comprising the step of introducing into the host the pluripotent embryonic-like stem cells of the present invention.

In a still further aspect, this invention includes a method of in vivo administration of a protein or gene of interest comprising the step of transfecting the pluripotent embryonic-like stem cells of the present invention with a vector comprising DNA or RNA which expresses a protein or gene of interest.

The present invention provides a method of tissue repair or transplantation in mammals, comprising administering to a mammal a therapeutically effective amount of pluripotent embryonic-like stem cells.

The present invention provides a method of preventing and/or treating cellular debilitations, derangements and/or dysfunctions and/or other disease states in mammals, comprising administering to a mammal a therapeutically effective amount of pluripotent embryonic-like stem cells.

In a further aspect, the present invention provides a method of preventing and/or treating cellular debilitations, derangements and/or dysfunctions and/or other disease states in mammals, comprising administering to a mammal a therapeutically effective amount of a endodermal, ectodermal or mesodermal lineage-committed cell derived from the pluripotent embryonic-like stem cells of the present invention.

The therapeutic method generally referred to herein could include the method for the treatment of various pathologies or other cellular dysfunctions and derangements by the administration of pharmaceutical compositions that may comprise proliferation factors or lineage-commitment factors, alone or in combination with the pluripotent embryonic-like stem cells of the present invention, or cells or tissues derived therefrom, or other similarly effective agents, drugs or compounds identified for instance by a drug screening assay prepared and used in accordance with a further aspect of the present invention.

It is a still further object of the present invention to provide pharmaceutical compositions for use in therapeutic methods which comprise or are based upon the pluripotent embryonic-like stem cells of the present invention, including lineage-uncommitted populations of cells, lineage-committed populations of cells, tissues and organs derived therefrom, along with a pharmaceutically acceptable carrier. Also contemplated are pharmaceutical compositions comprising proliferation factors or lineage commitment factors that act on or modulate the pluripotent embryonic-like stem cells of the present invention and/or the cells, tissues and organs derived therefrom, along with a pharmaceutically acceptable carrier. The pharmaceutical compositions of proliferation factors or lineage commitment factors may be further comprise the pluripotent embryonic-like stem cells of the present invention, or cells, tissues or organs derived therefrom. The pharmaceutical compositions may comprise the pluripotent embryonic-like stem cells of the present invention, or cells, tissues or organs derived therefrom, in a polymeric carrier or extracellular matrix.

This invention also provides pharmaceutical compositions for the treatment of cellular debilitation, derangement and/or dysfunction in mammals, comprising:

A. a therapeutically effective amount of the pluripotent embryonic-like stem cells of the present invention; and
B. a pharmaceutically acceptable medium or carrier.

Pharmaceutical compositions of the present invention also include compositions comprising endodermal, ectodermal or mesodermal lineage-committed cell(s) derived from the pluripotent embryonic-like stem cells of the present invention, and a pharmaceutically acceptable medium or carrier. Any such pharmaceutical compositions may further comprise a proliferation factor or lineage-commitment factor.

The present invention relates to pluripotent stem cells capable of differentiating into cells of the mesenchymal type (PPMSCs), wherein such cells are positive for or express the antigenic markers CD10, CD13, CD34, CD56, CD90 and MHC Class-I. The PPMSCs of the present invention are negative for the markers CD1a, CD2, CD3, CD4, CD5, CD7, CD8, CD9, CD11b, CD11c, CD14, CD15, CD16, CD18, CD19, CD20, CD22, CD23, CD24, CD25, CD31, CD33, CD36, CD38, CD41, CD42b, CD44, CD45, CD49d, CD55, CD57, CD59, CD61, CD62E, CD65, CD66e, CD68, CD69, CD71, CD79, CD83, CD95, CD105, CD117, CD123, CD166, Glycophorin-A, DRII, FLT3, FMC-7, Annexin, and LIN.

The present invention further relates to pluripotent embryonic-like stem cells which are positive for or express the antigenic markers CD10 and CD66e and are negative for or do not express the markers CD1a, CD2, CD3, CD4, CD5, CD7, CD8, CD9, CD11b, CD11c, CD13, CD14, CD15, CD16, CD18, CD19, CD20, CD22, CD23, CD24, CD25, CD31, CD33, CD34, CD36, CD38, CD41, CD42b, CD44, CD45, CD49d, CD55, CD56, CD57, CD59, CD61, CD62E, CD65, CD68, CD69, CD71, CD79, CD83. CD90, CD95, CD105, CD117, CD123, CD166, Glycophorin-A, DRII, Class-I, FLT3. FMC-7, Annexin and LIN.

The present invention further relates to pluripotent stem cells which are positive for or express the antigenic markers CD1a, CD10, CD41, CD66e and Annexin and are negative for or do not express the markers CD2, CD3, CD4, CD5, CD7, CD8, CD9, CD11b, CD11c, CD13, CD14, CD15, CD16, CD18, CD19, CD20, CD22, CD23, CD24, CD25, CD31, CD33, CD34, CD36, CD38, CD42b, CD44, CD45, CD49d, CD55, CD56, CD57, CD59, CD61, CD62E, CD65, CD68, CD69, CD71, CD79, CD83, CD90, CD95, CD105, CD117, CD123, CD166, Glycophorin-A, DRII, Class-I, FLT3, FMC-7, and LIN.

The present invention also includes pluripotent stem cells which are positive for or express the antigenic markers CD1a, CD10, CD22 and Annexin and are negative for or do not express the markers CD2, CD3, CD4, CD5, CD7, CD8, CD9, CD11b, CD11c, CD13, CD14, CD15, CD16, CD18, CD19, CD20, CD23, CD24, CD25, CD31, CD33, CD34, CD36, CD38, CD41, CD42b, CD44, CD45, CD49d, CD55, CD56, CD57, CD59, CD61, CD62E, CD65, CD66e, CD68, CD69, CD71, CD79, CD83, CD90, CD95, CD105, CD117, CD123, CD166, Glycophorin-A, DRII, Class-I, FLT3, FMC-7, Annexin, and LIN.

The present invention still further relates to pluripotent stem cells which are positive for or express the antigenic markers CD10 and CD22 and are negative for or do not express the markers CD1a, CD2, CD3, CD4, CD5, CD7, CD8, CD9, CD11b, CD11c, CD13, CD14, CD15, CD16, CD18, CD19, CD20, CD23, CD24, CD25, CD31, CD33, CD34, CD36, CD38, CD41, CD42b, CD44, CD45, CD49d, CD55, CD56, CD57, CD59, CD61, CD62E, CD65, CD66e, CD68, CD69, CD71, CD79, CD83, CD90, CD95, CD105, CD117, CD123, CD166, Glycophorin-A, DRII, Class-I, FLT3, FMC-7, Annexin, and LIN.

The present invention naturally contemplates several means or methods for preparation or isolation of the pluripotent embryonic-like stem cells of the present invention including as illustrated herein, and the invention is accordingly intended to cover such means or methods within its scope.

Other objects and advantages will become apparent to those skilled in the art from a review of the following description which proceeds with reference to the following illustrative drawings.

d Single very small cell (arrow) heavily stained with antibody to stage-specific embryonic antigen-4 (MC813-70).

e Four cells (arrows) stained with antibody to nestin (MAB353).

f Four cells stained with antibody to neurons (S-100).

g Multiple cells stained with antibody to neurofilaments (RT-97).

h Single cell with long cell processes (arrows) stained with antibody to neurofilaments (N-200).

i Single cell stained with antibody for neuroglia (CNPase).

j Two cells (arrows stained with antibody for keratinocytes (VM-1).

k Two cells (arrows) stained with antibody to myogenin (F5D).

l Two structures (arrows) containing multiple linearly arranged nuclei.

m Multiple cells containing Oil Red-O stained intracellular vesicles.

n Single cell stained with antibody to type-II collagen (CIIC1).

o Four cells (arrows) stained intracellularly with antibody to bone sialoprotein-II (WV1D1).

p Multiple cells staining with an antibody to peripheral cell adhesion molecule (PECAM, P2B1).

q Three cells (arrows) with intracellular vesicles stained for antibody to human-specific alpha-fetoprotein (HAFP).

r Single cell (arrow) heavily stained with antibody to human-specific gastrointestinal epithelial-specific antigen (HESA).

Figure 35:
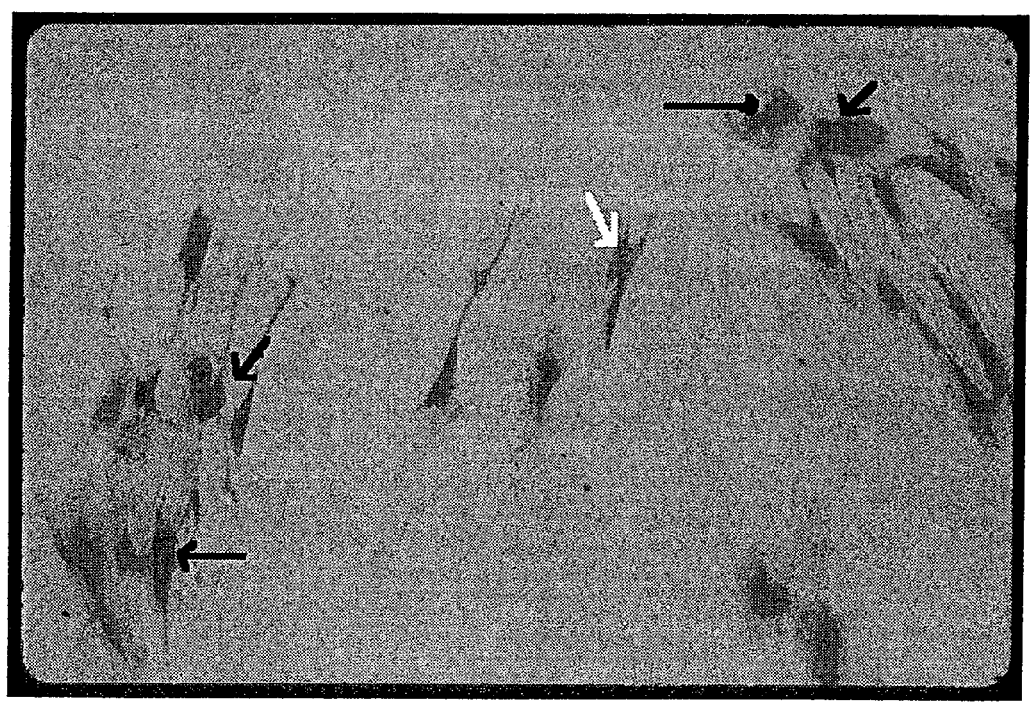

FIG. 35: Co-culture of ROSA26 PPSCs and rat astrocytes for 21 days stained with X-gal and GFAP. 100×. Cells stained with both the dark blue of the antibody color reagent and blue-green of X-gal. Black arrows point to double-stained cells and white arrows to ROSA PPSCs not stained for GFAP.

Figure 36:
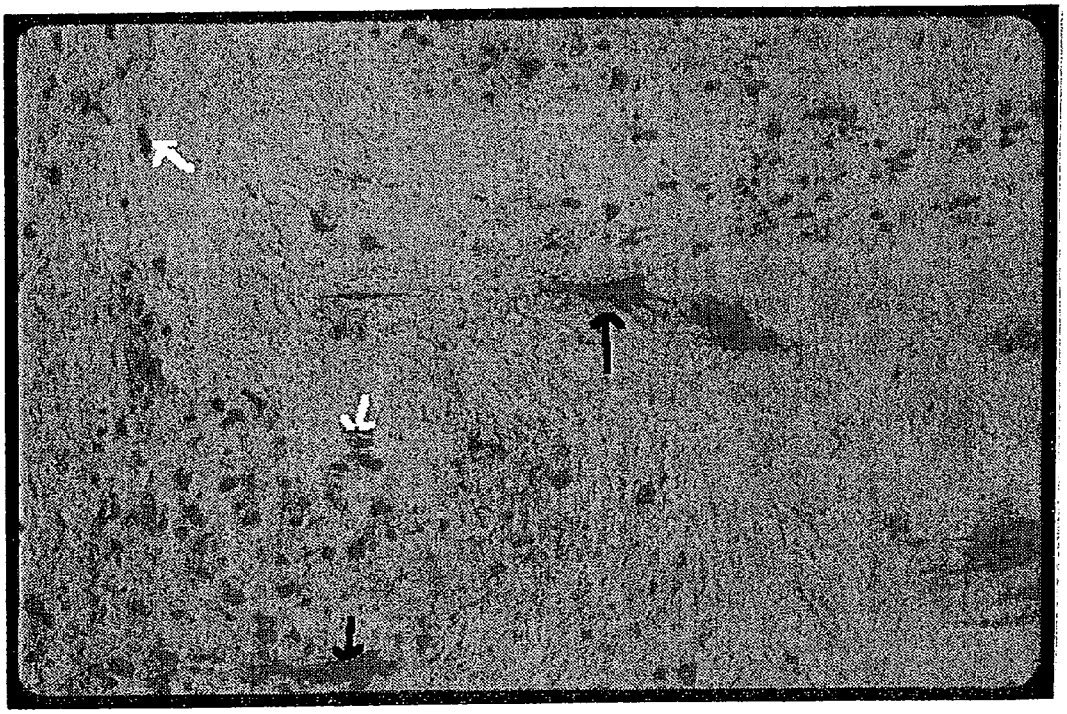

FIG. 36: Co-culture of ROSA26 PPSCs and rat astrocytes for 21 days stained with X-gal and GFAP. 40×. Can see astrocytes stained (white arrows) and then cells double-stained (black arrows).

Figure 37:

FIG. 37: Co-culture of ROSA26 PPSCs and rat astrocytes for 21 days stained with X-gal and GFAP. 40×. White arrows point to ROSA26 PPSCs single stained for X-gal (undifferentiated) while black arrows point to ROSA cells double stained for X-gal and GFAP (differentiated).

Figure 38:
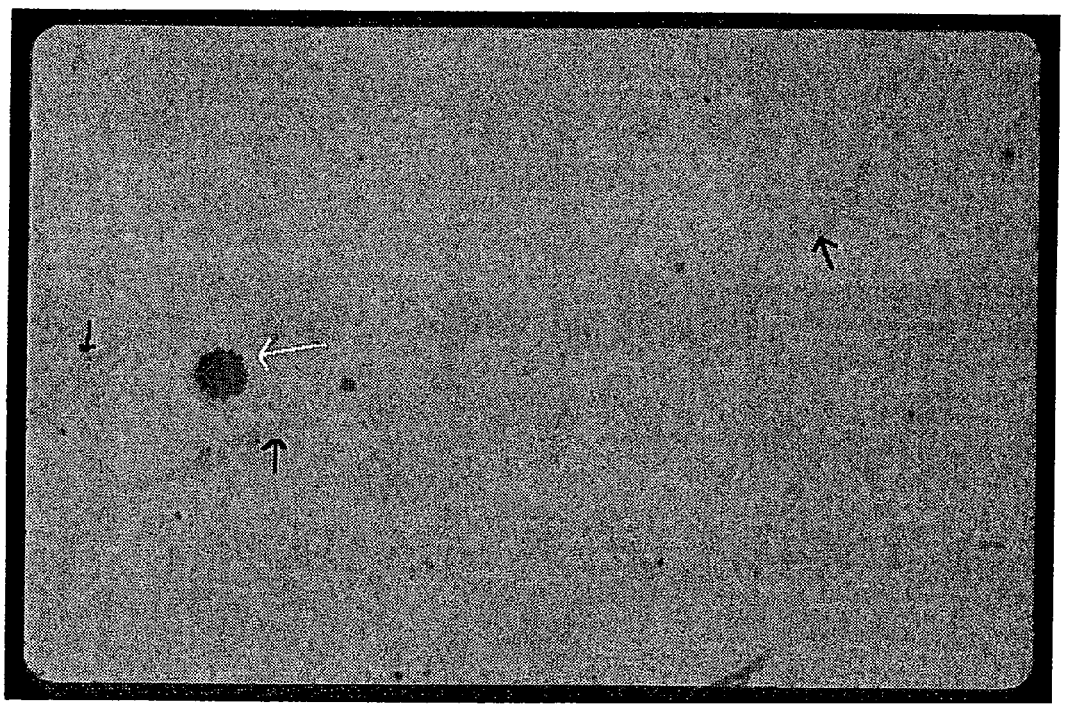

FIG. 38: PPSCs isolated from rat skeletal muscle (RmSC-1) treated with 10–7 M dexamethasone for 21 days and then stained with anti-CNPase. 100×. White arrow points to artifact. Black arrows point to cells positive for CNPase.

Figure 39:
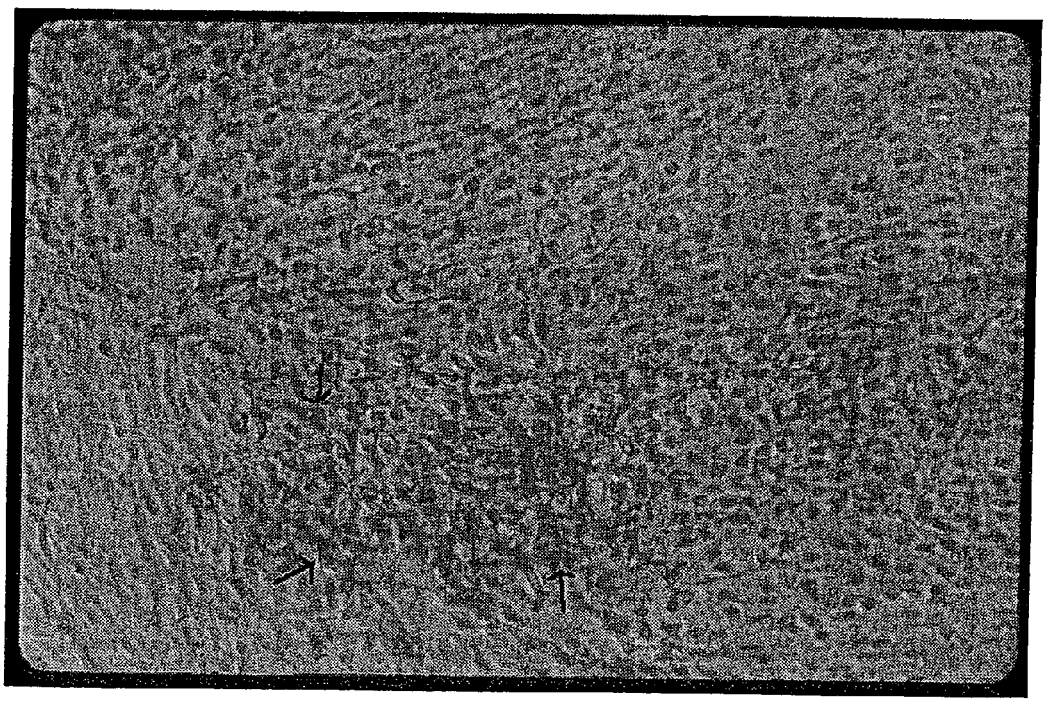

FIG. 39: PPSCs isolated from rat skeletal muscle (RmSC-1) treated with 10-7 M dexamethasone for 21 days and then stained with antibody to IA4. Phase contrast; 100×. Black arrows point to stained cells.

Figure 40:
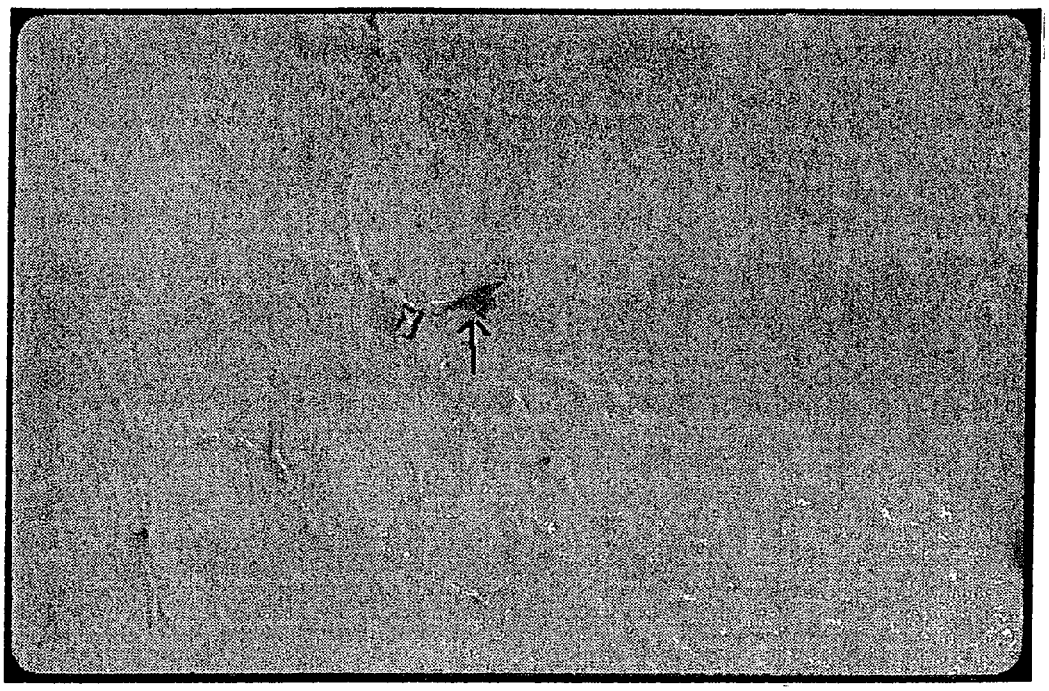

FIG. 40: PPSCs isolated from rat skeletal muscle (RmSC-1) then treated with conditioned medium from rat astrocytes for 21 days and stained with antibody RT-97. Phase contrast; 100×.

Figure 41:
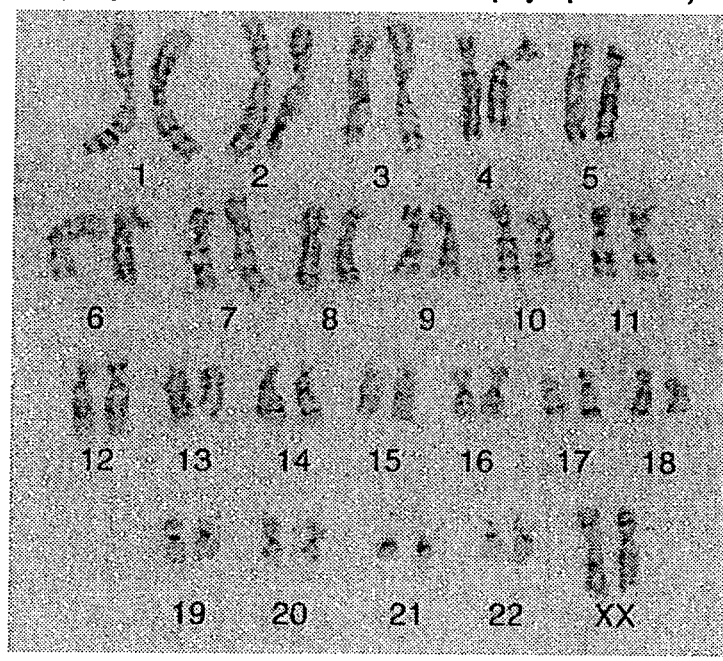
Figure 43B:
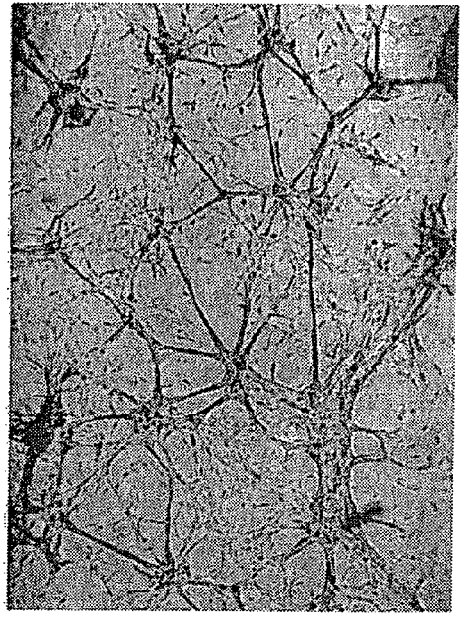
Figure 43A:
Figure 43E:
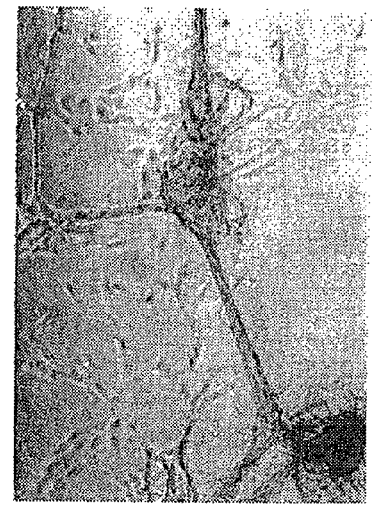
Figure 43D:
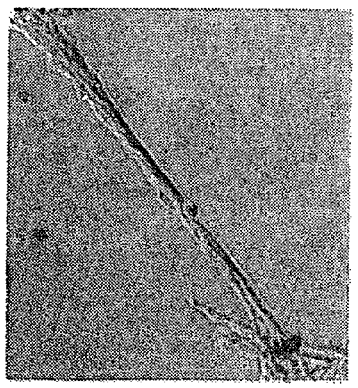
Figure 43C:
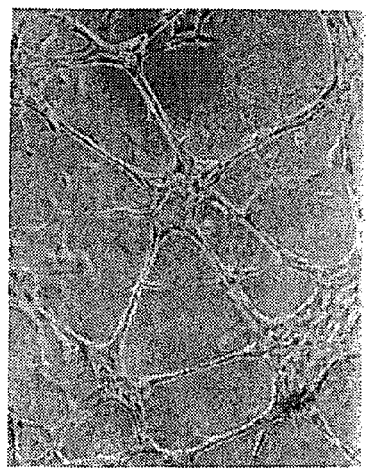

FIG. 41: Karyotype 46, XX of CT3F cells at 37 cell doublings, isolated from a 17 year old female dermal biopsy.

FIG. 42 depicts in vitro differentiation of PPSCs on Matrigel in the presence of 1% HS 10. Tube formation is evident.

FIG. 43 depicts in vitro differentiation of PPSCs on Matrigel in the presence of 1% HS 10 and VEGF. Tube formation is evident.

Figure 44:

FIG. 44 depicts PPSC localization in the bone marrow one week after IV injection into an ischemic animal.

Figure 45:
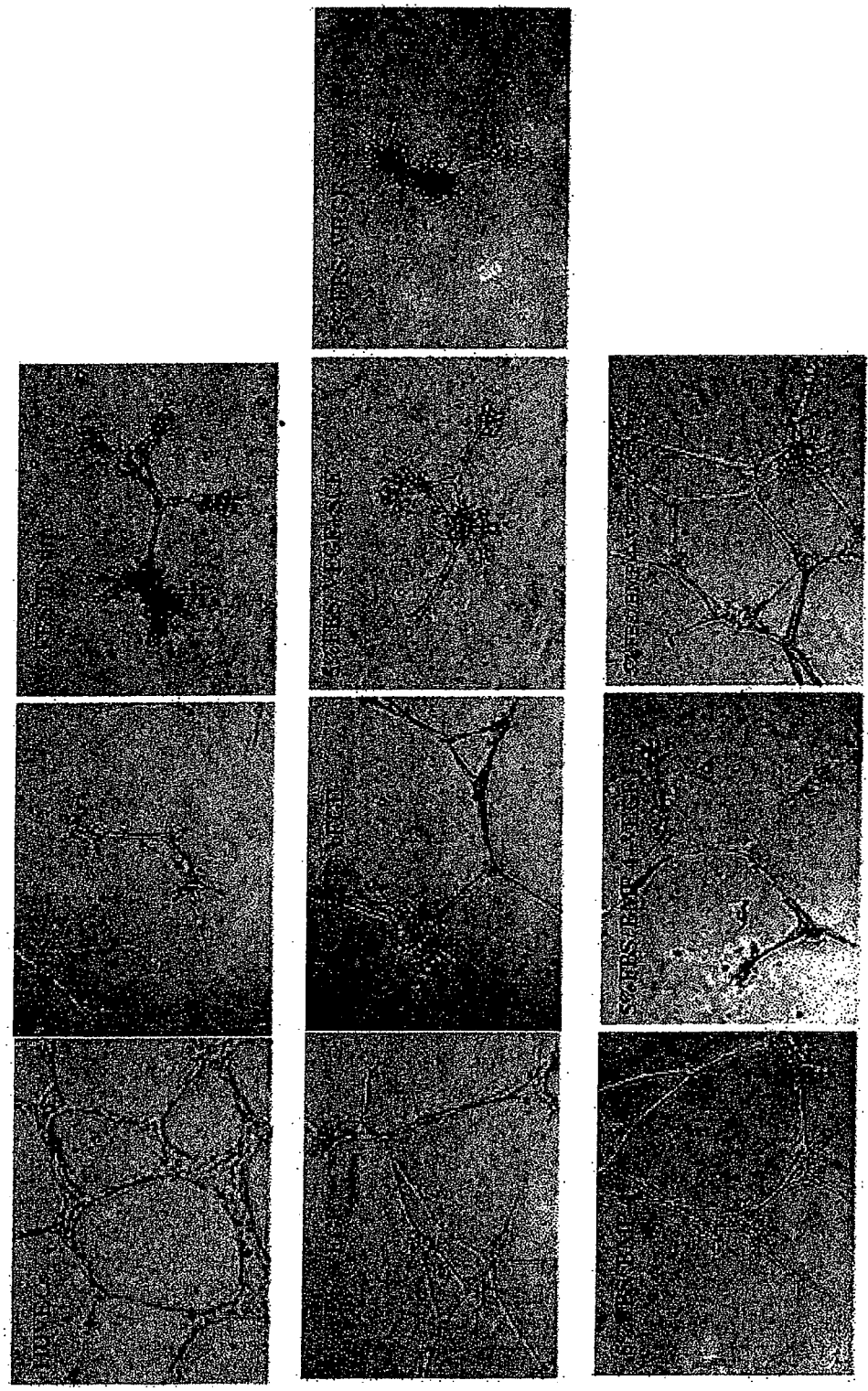

FIG. 45 depicts ELSCs grown under different conditions 12 hours after reseeding in Matrigel.

Figure 46:
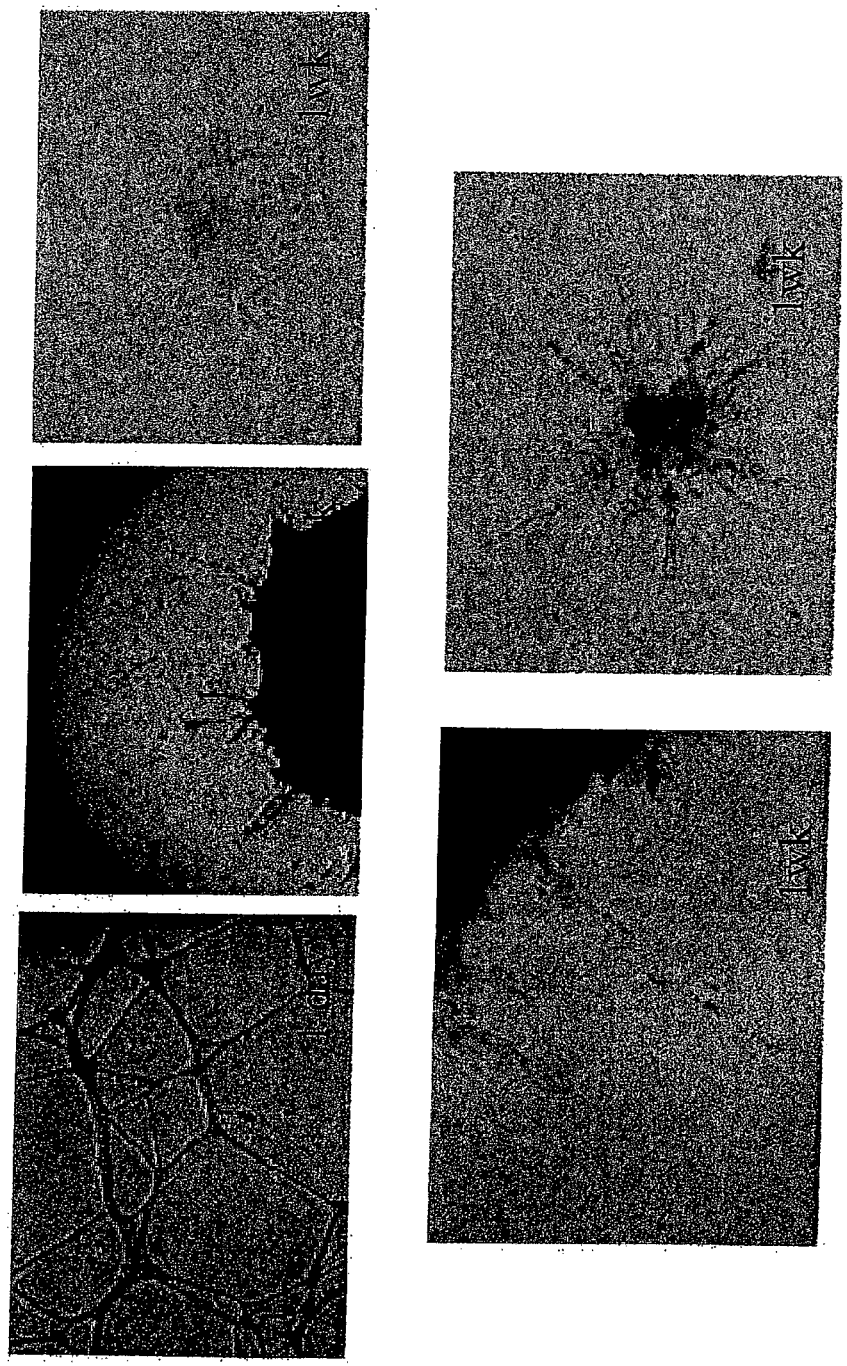

FIG. 46 depicts ELSCs grown under different conditions after reseeding in Matrigel.

Figure 47:
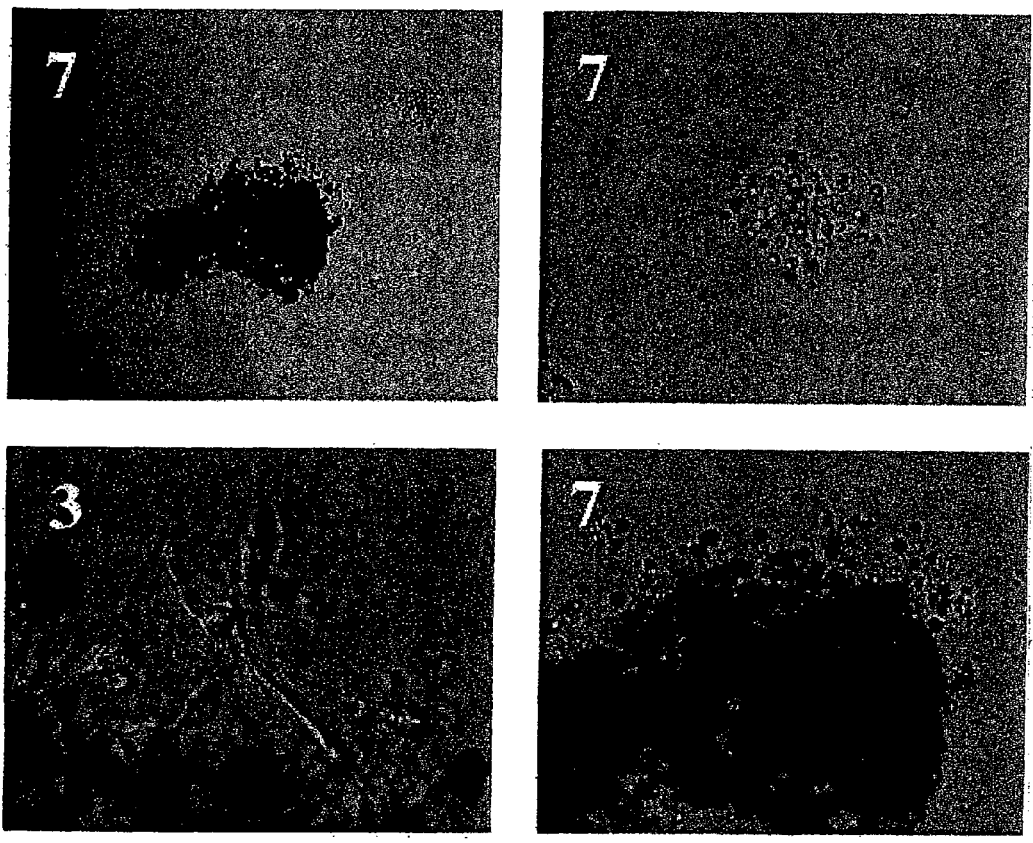

FIG. 47 depicts ELSCs grown under different conditions after reseeding in Matrigel.

Figure 48:

FIG. 48 depicts ELSC transplantation into a hindlimb ischemia model at 2 weeks post cell transplantation.

Figure 49:
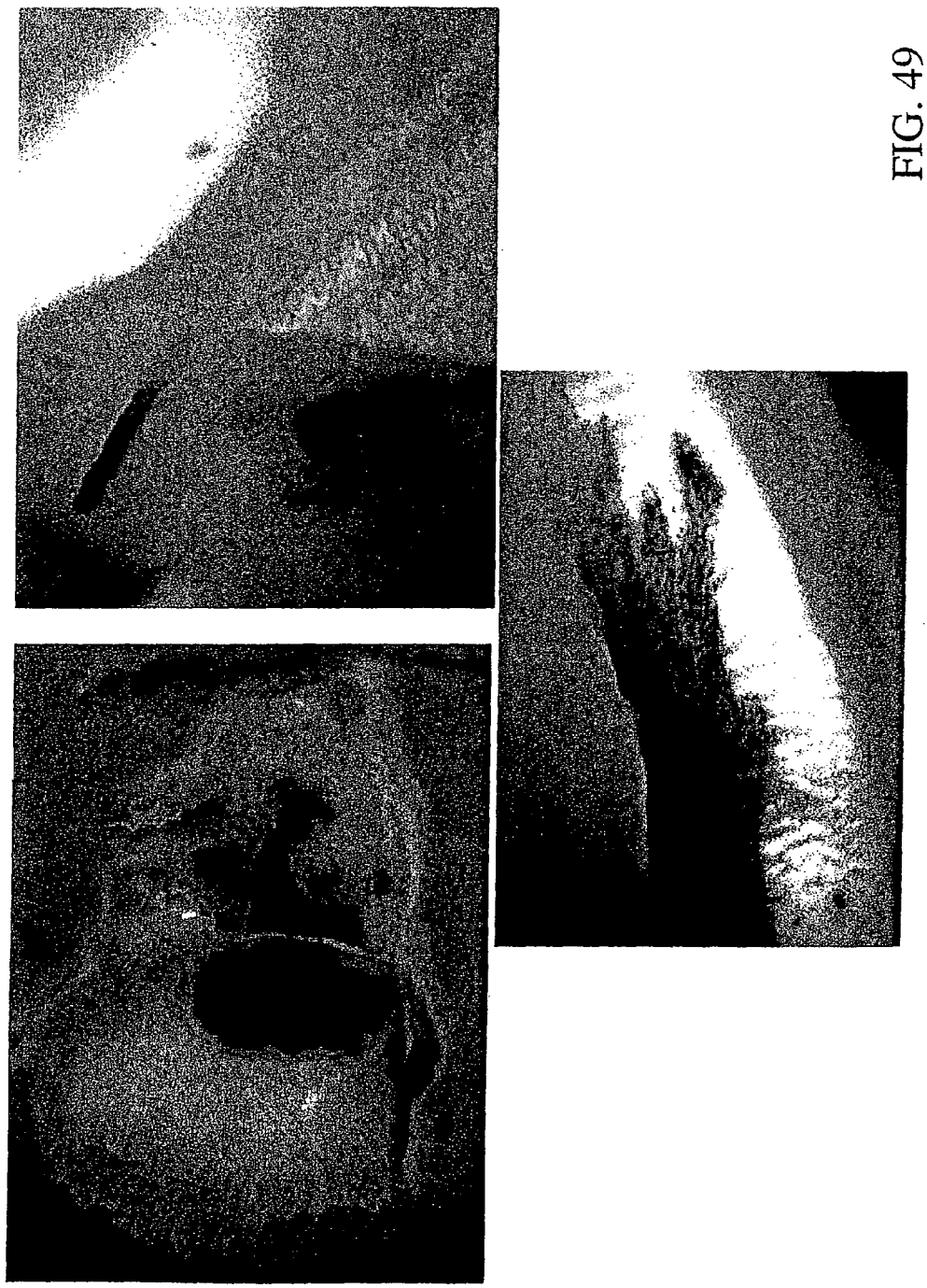

FIG. 49 depicts ELSC transplantation into a hindlimb ischemia model at 2 weeks post cell transplantation.

Figure 50:
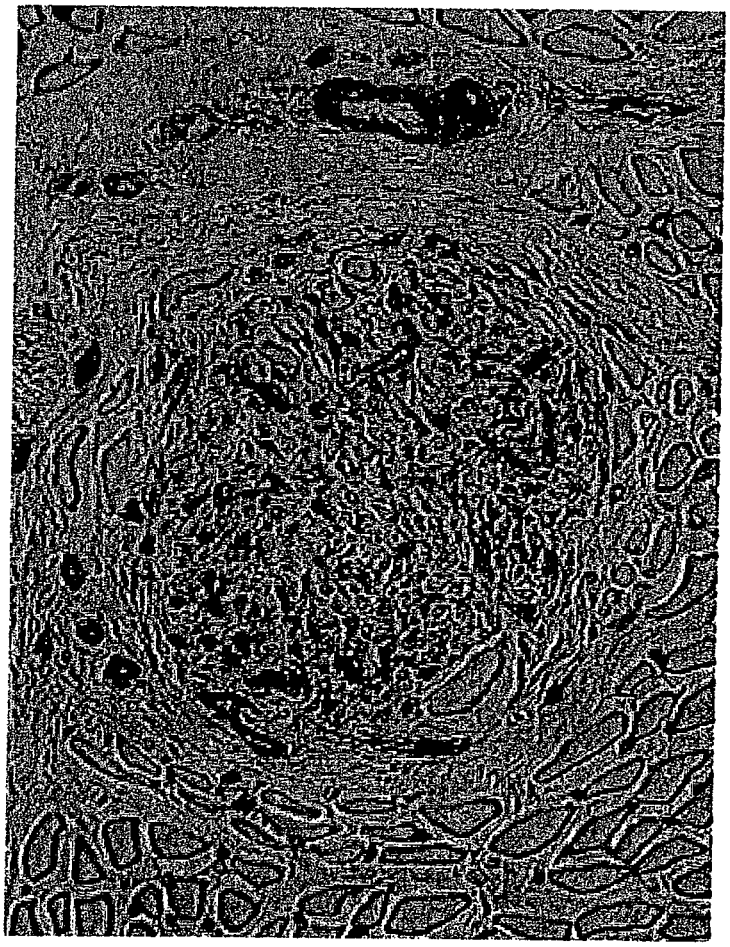
Figure 50:
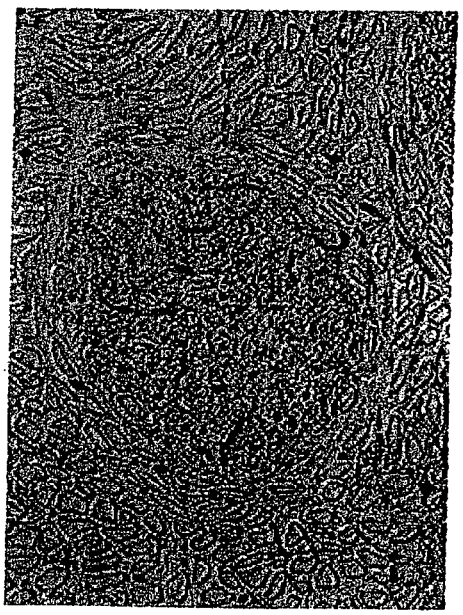

FIG. 50 depicts muscle organogenesis by ELSCs in a hindlimb ischemia model at 2 weeks post cell transplantation.

Figure 51:
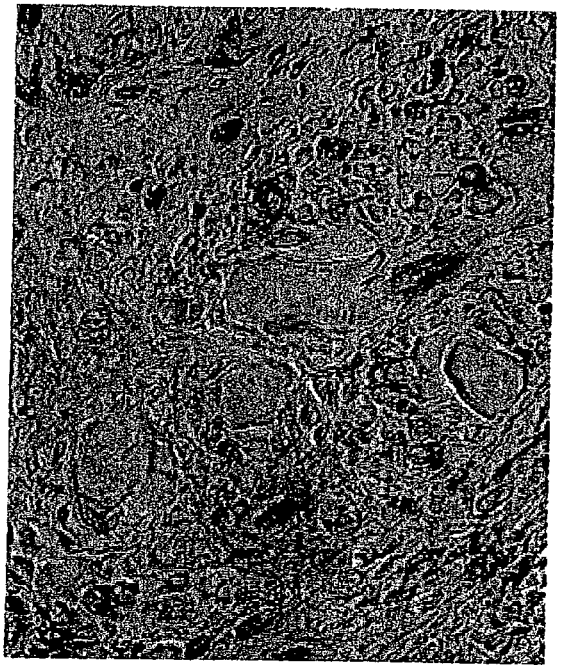
Figure 51:
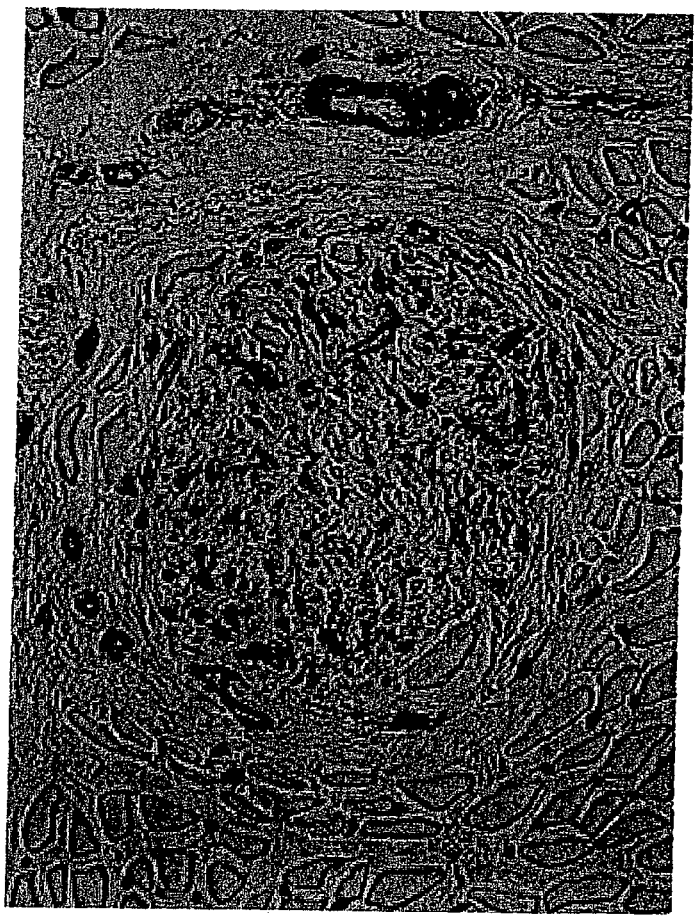

FIG. 51 depicts muscle organogenesis by ELSCs in a hindlimb ischemia model at 2 weeks post cell transplantation.

Figure 52:
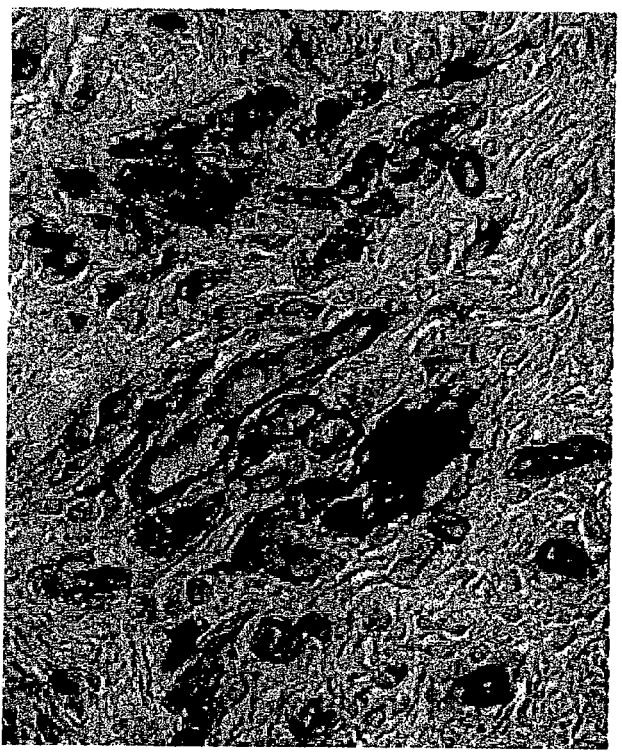
Figure 52:
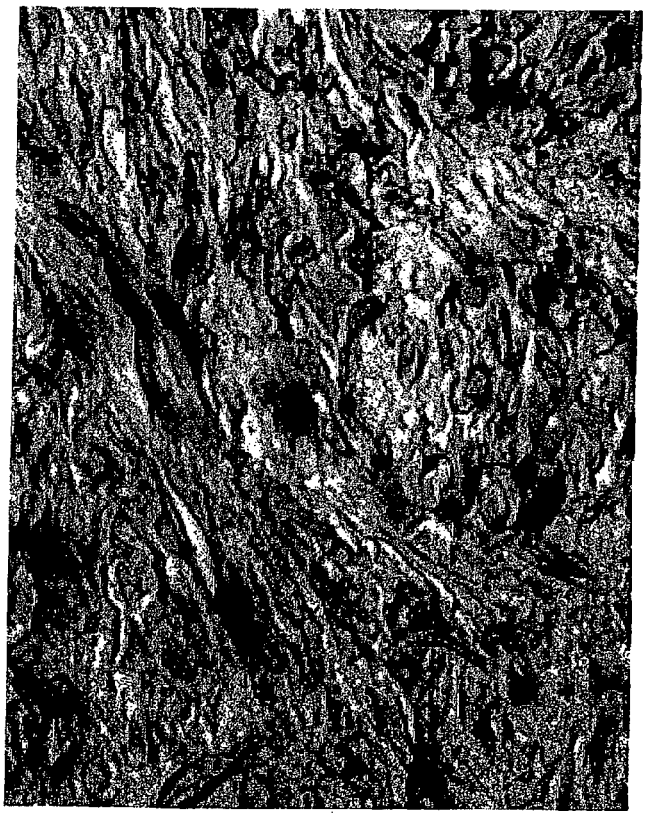

FIG. 52 depicts organogenesis with neovascularization by ELSC in hindlimb ischemia.

Figure 53:
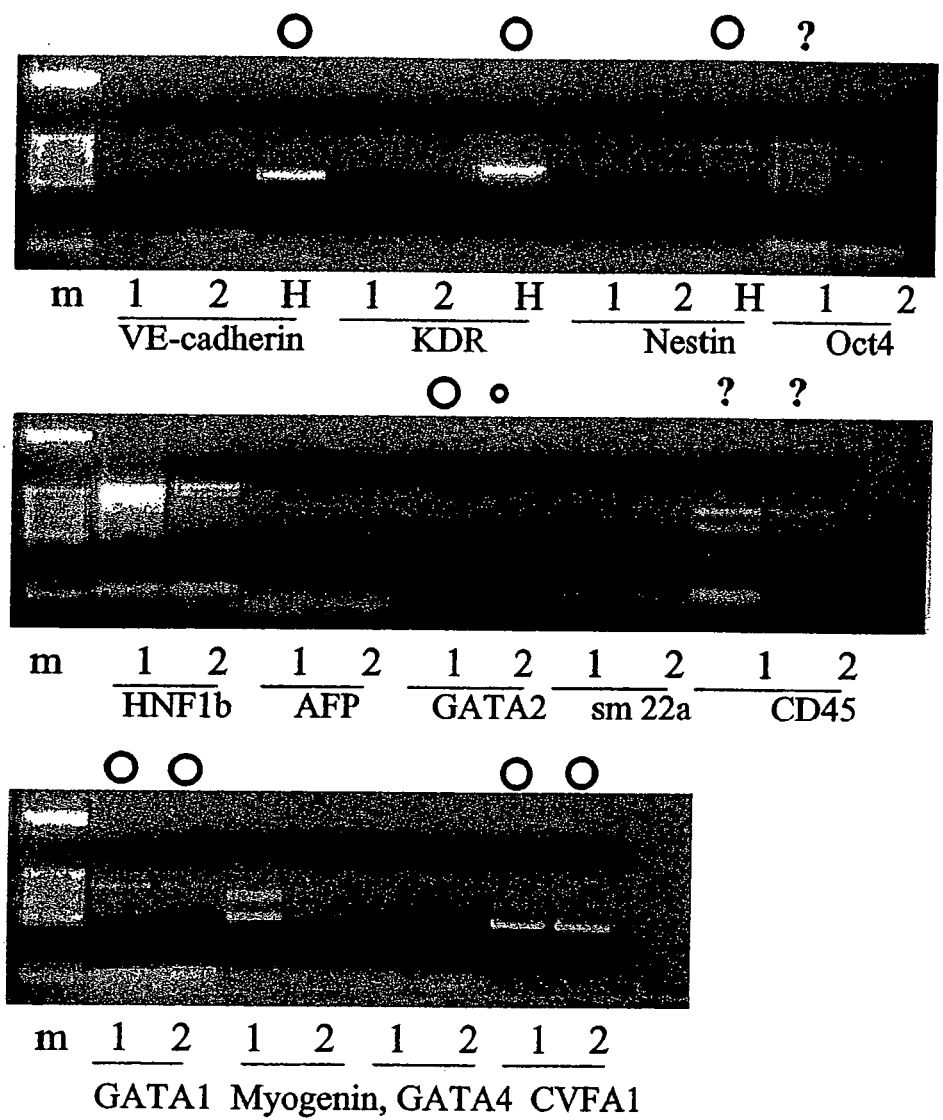

FIG. 53 depicts RT PCR results on CT3F cells. Lanes denoted 1 are of embryo body like cells reseeded for 1 week; Lanes denoted 2 are ELSCs grown in 10% HS10 serum; H are HUVEC cells.

Figure 54:
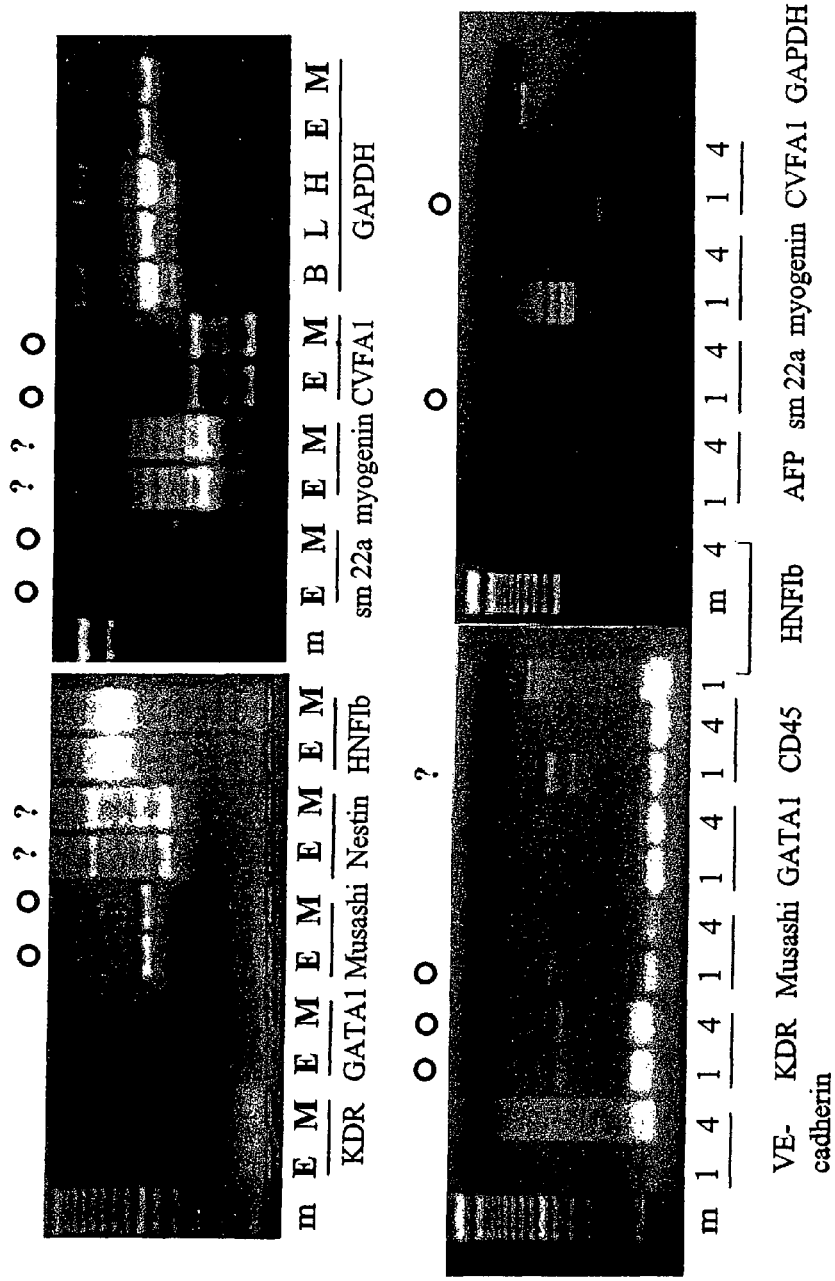

FIG. 54 depicts RT PCR results on CT3F cells. Lanes denoted 1 are of embryo body like cells reseeded for 1 day; Lanes denoted 4 are of embryo body like cells reseeded for 4 days; Lanes denoted M are ELSCs grown in 10% HS10 serum; Lanes denoted E are ELSCs grown in 1% MCSF1 serum; B indicates brain; L indicates liver; H indicates heart.

Figure 55:
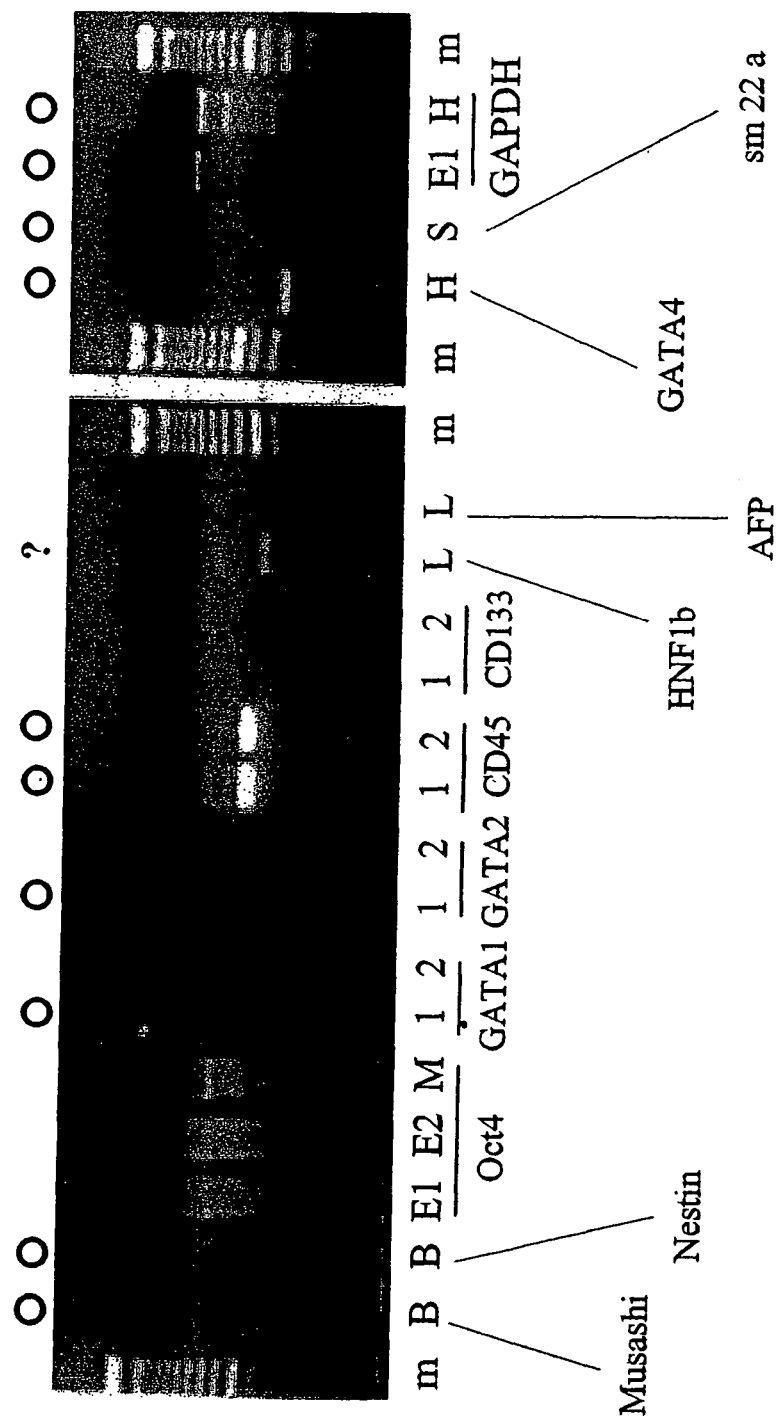

FIG. 55 depicts RT PCR results on CT3F cells. Lanes denoted 1 are of mononuclear cells from peripheral blood; Lanes denoted 2 are of EPC cells; Lanes denoted M are ELSCs grown in 10% HS10 serum; Lanes denoted E1 and E2 are ELSCs grown in 1% MCSF1 serum; B indicates brain; L indicates liver; H indicates HUVEC cells; S indicates smooth muscle cell.

Figure 56:

FIG. 56 depicts immunofluorescence of rat myocardium after MI and ELSC cell transplantation in rat 14.

Figure 57:

FIG. 57 depicts immunofluorescence of rat myocardium after MI and ELSC cell transplantation in rat 14.

Figure 58:
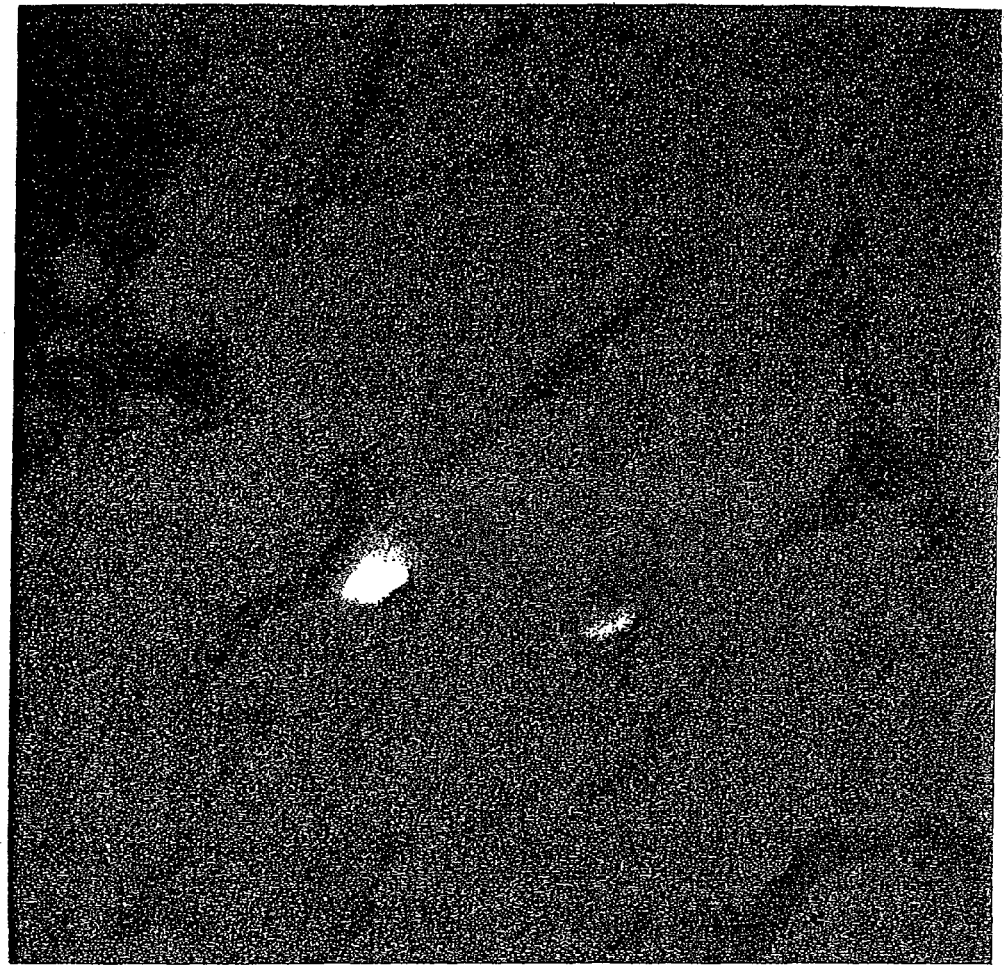

FIG. 58 depicts immunofluorescence of rat myocardium after MI and ELSC cell transplantation in rat 14.

Figure 59:

FIG. 59 depicts immunofluorescence of rat myocardium after MI and ELSC cell transplantation in rat 14.

Figure 60:
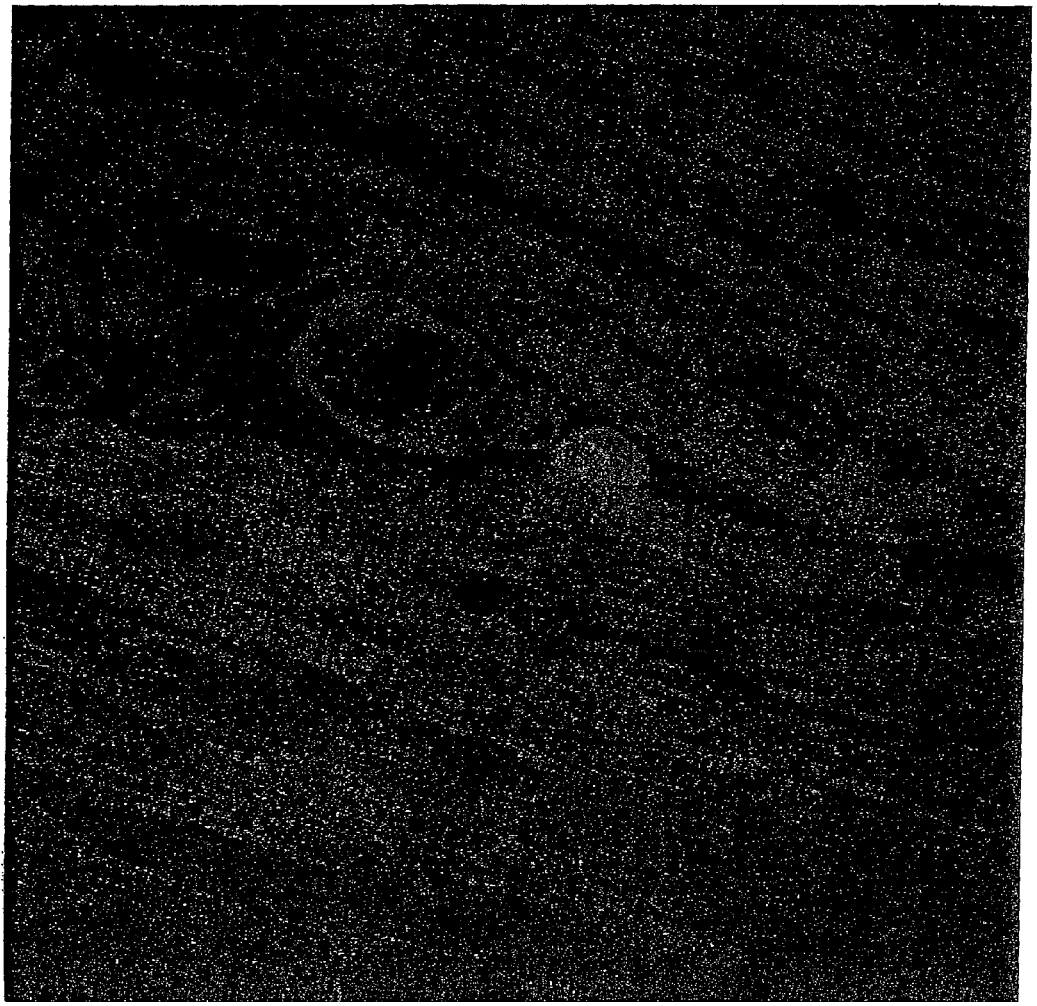

FIG. 60 depicts immunofluorescence of rat myocardium after MI and ELSC cell transplantation in rat 36.

Figure 61:

FIG. 61 depicts immunofluorescence of rat myocardium after MI and ELSC cell transplantation in rat 36.

Figure 62:

FIG. 62 depicts immunofluorescence of rat myocardium after MI and ELSC cell transplantation in rat 14.

Figure 63:

FIG. 63 depicts immunofluorescence of rat myocardium after MI and ELSC cell transplantation in rat 14.

Figure 64:
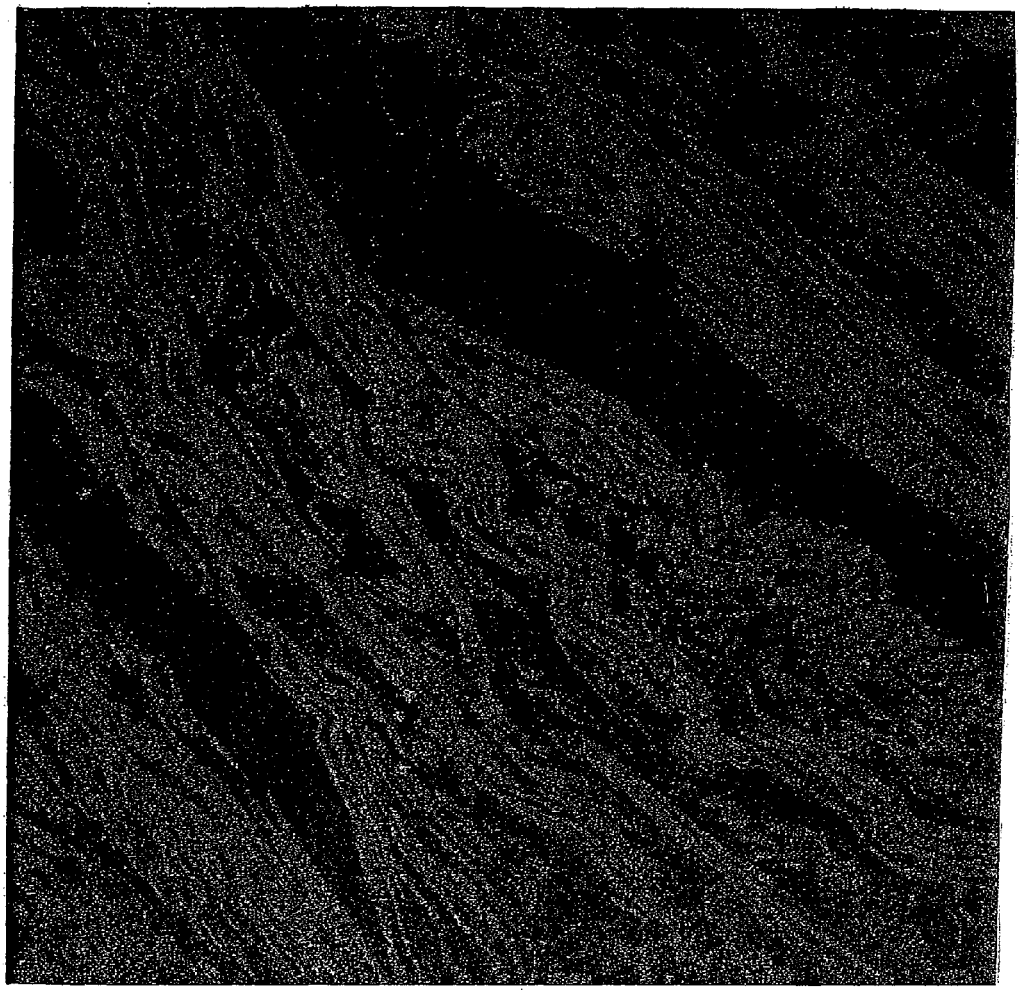

FIG. 64 depicts immunofluorescence of rat myocardium in control rat 14.

Figure 65:
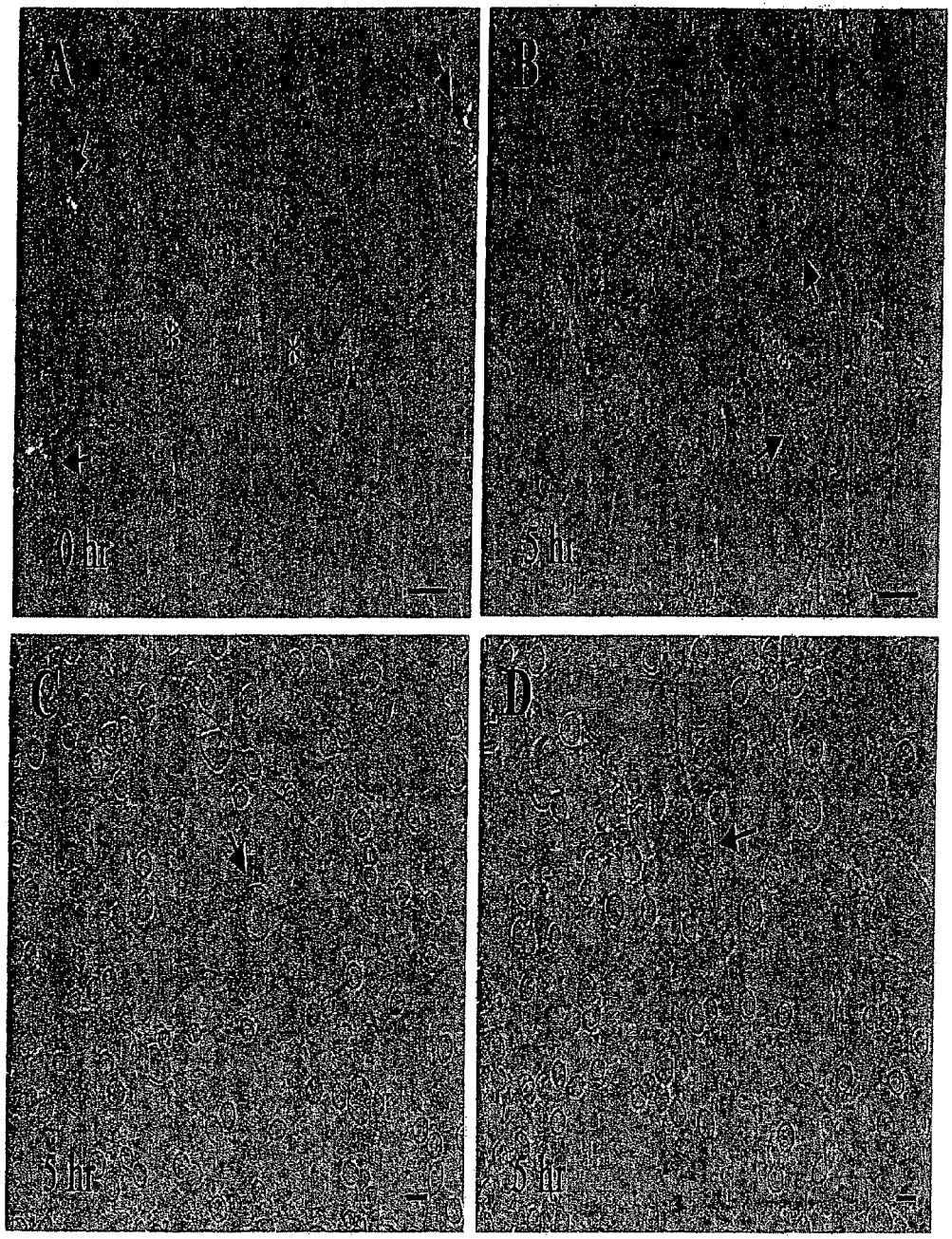

FIG. 65. Pre and post-differentiation RMSCs morphology. A: RMSCs before exposure to differentiation medium: polygonal flat cells (*) predominated, with a few cells with round or triangular cell body (arrows). B, C and D: RMSCs morphology after 5 hours in differentiation medium; most cells had round small cell bodies and processes (B: arrows). Three of the typical morphologies of differentiated cells are shown in C and D. C.: 90-95% of cells have small cell bodies an few processes whereas approximately 5-10% have a large round cell body and multipolar processes (arrow). D: Rare cell displayed large round bodies with one or two processes and direct contact to neighboring cells (arrow). Scale: 20 µm (A and B); 40 µm (C and D).

Figure 66:
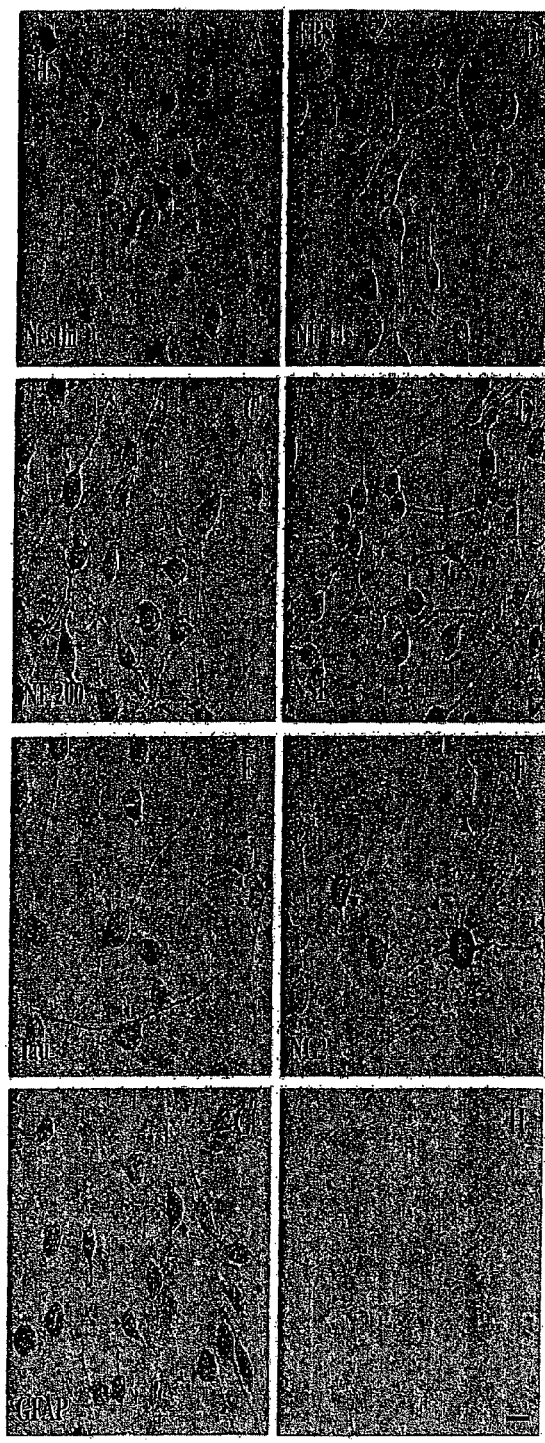

FIG. 66. Immunocytochemistry for RMSCs expanded in horse serum (A, C, E and G) or in fetal bovine serum (B, D and F) and differentiated for 5 hours. Immunolabeling for A: nestin (arrows); B: NF 145: Neurofilament MW 145 kD (arrow). Very few cells exhibited a triangular morphology (top thin arrow); C: NF 200: Neurofilament MW 200 kD (arrows); D: NSE: Neuron specific enolase (arrows); E: Tau positive cells with stained processes (arrows); F: positive (arrows) and negative (arrowheads) cells for NG2 chondroitin sulfate proteglycan; G: GFAP: Glial fibrillary acidic protein (arrows). In B, C, D, E and G, asterisks are located near flat polygonal cells that are immunonegative (5-10% of all cells). H: Representative example of cells incubated with the secondary antibody without primary antibody. Scale (bar show in H for all panels): 20 µm.

Figure 67:
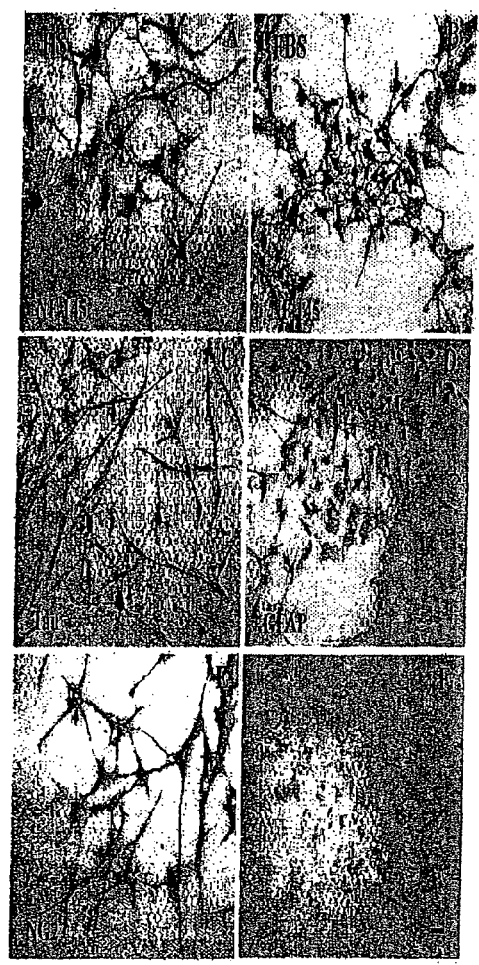
Figure 67:
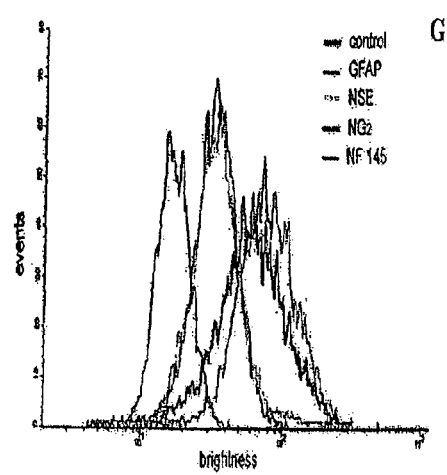

FIG. 67. Antigenic characterization of RMSCs differentiated for 24 hours. RMSCs expanded in HS and differentiated for 24 hours immunolabeled for A: NF 145: Neurofilament MW 145 kD, arrows points to stained cells with processes; C: Tau, arrows point to different positive cells with processes; E: NG2 immunolabeling was moderate in most cells (arrows). RMSCs expanded in FBS and differentiated for 24 hours immunolabeled for B: NF 145: Neurofilament MW 145 kD, groups of intensely stained cells (arrows); D: GFAP: Glial fibrillary acidic protein (arrows). In B, C and D, asterisks are located near polygonal cells that are immunonegative. F: Representative example of cells incubated with the secondary antibody without primary antibody. Scale (bar show in F for all panels): 20 µm. G: Fluorescence assisted cell sorting (FACS) of RMSCs differentiated for 24 hours. Representative example of FACs of differentiated RMSCs immunostained with polyclonal antibodies against neuron specific enolase (NSE) (yellow), glial fibrillary acidic protein (GFAP) (green), neurofilament MW 145 kDa (NF145) (blue) and NG2 chondroitin sulfate proteglycan (NG2) (red). Cells incubated with the secondary antibody without primary antibody were included in each experiment (black peak). Y-axis: Number of cells analyzed (events); x-axis: intensity of fluorescence staining (brightness).

Figure 68:
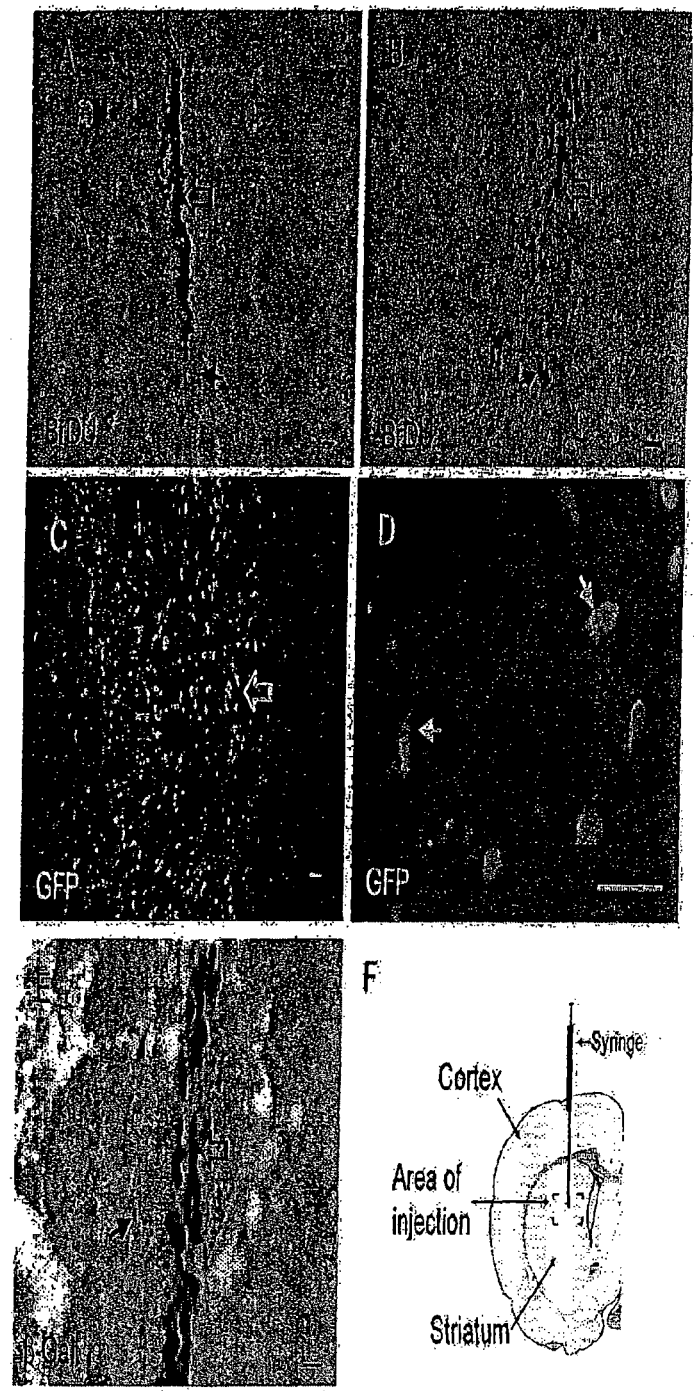

FIG. 68 shows photomicrographs from rats that were sacrificed one month (A, C, D and E) or two months (B) after transplantation. A and B: PPMSCs incubated with bromodeoxyuridine (BrDU) prior to transplantation and detected in tissue sections with an antibody against BrDU. Positively labeled cells were confined to the area of the injection (open arrows), and few cells have moved in the vicinity of the needle track (filled arrows). No labeled cells were found far from the needle track or in other brain regions. C and D: PPMSC transfected with a vector expressing Green Fluorescence Protein (GFP). C: Low magnification photomicrograph showing the transplant with numerous fluorescent cells. Some cells with processes expressing GFP were observed at high magnification (D: arrows). E: PPMSCs transfected with beta-galactosidase (β-Gal): the cells were visualized one month post-transplantation with histochemistry. The cells did not migrate from the injection area, but were localized in the needle track (open arrow) or its vicinity (filled arrow).

Figure 69:
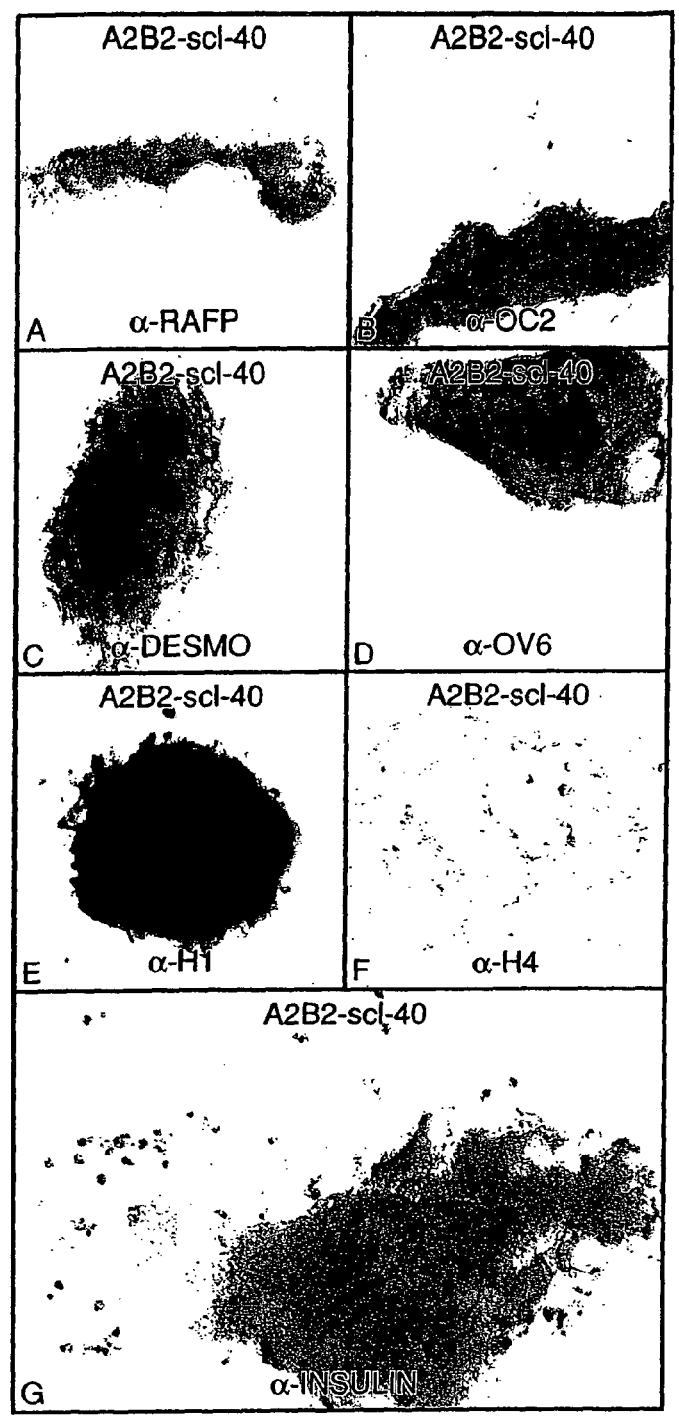

FIG. 69 depicts immunofluorescence of rat A2B2 scl-40 cells stained with various antibodies.

Figure 70:
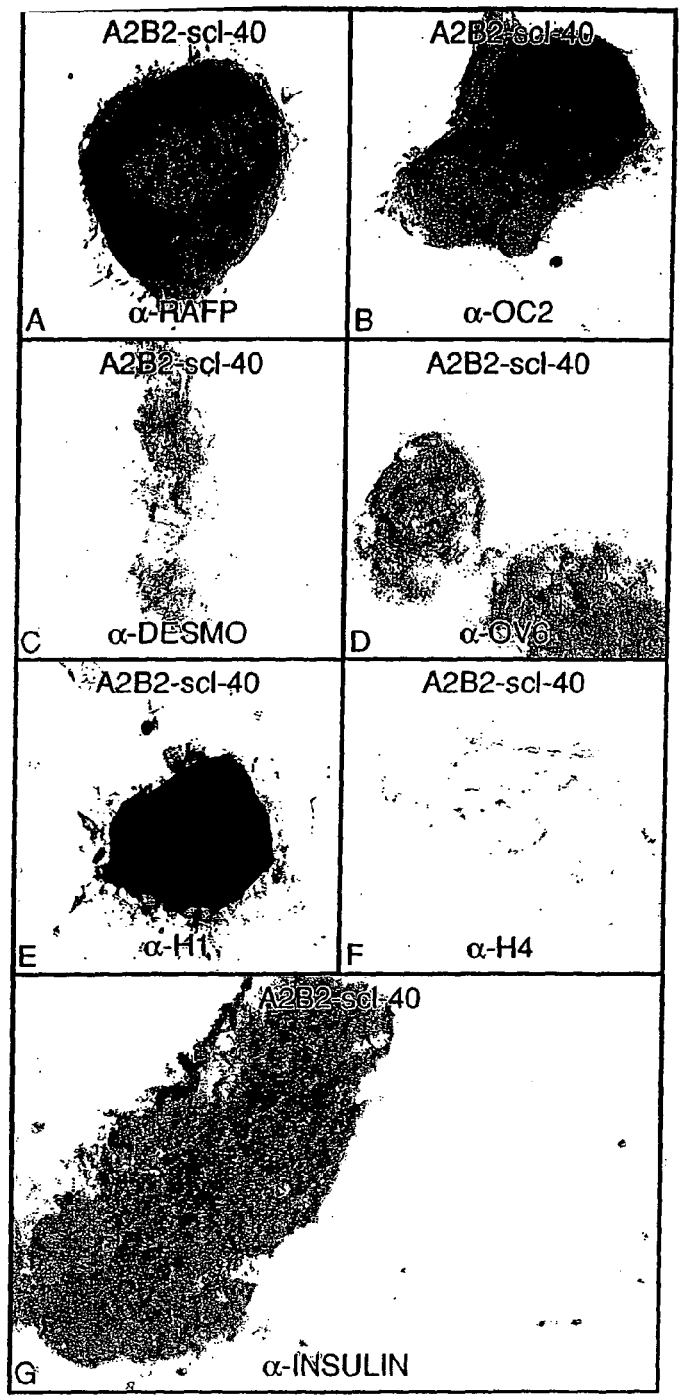

FIG. 70 depicts immunofluorescence of rat A2B2 scl-40 cells stained with various antibodies.

Figure 71:
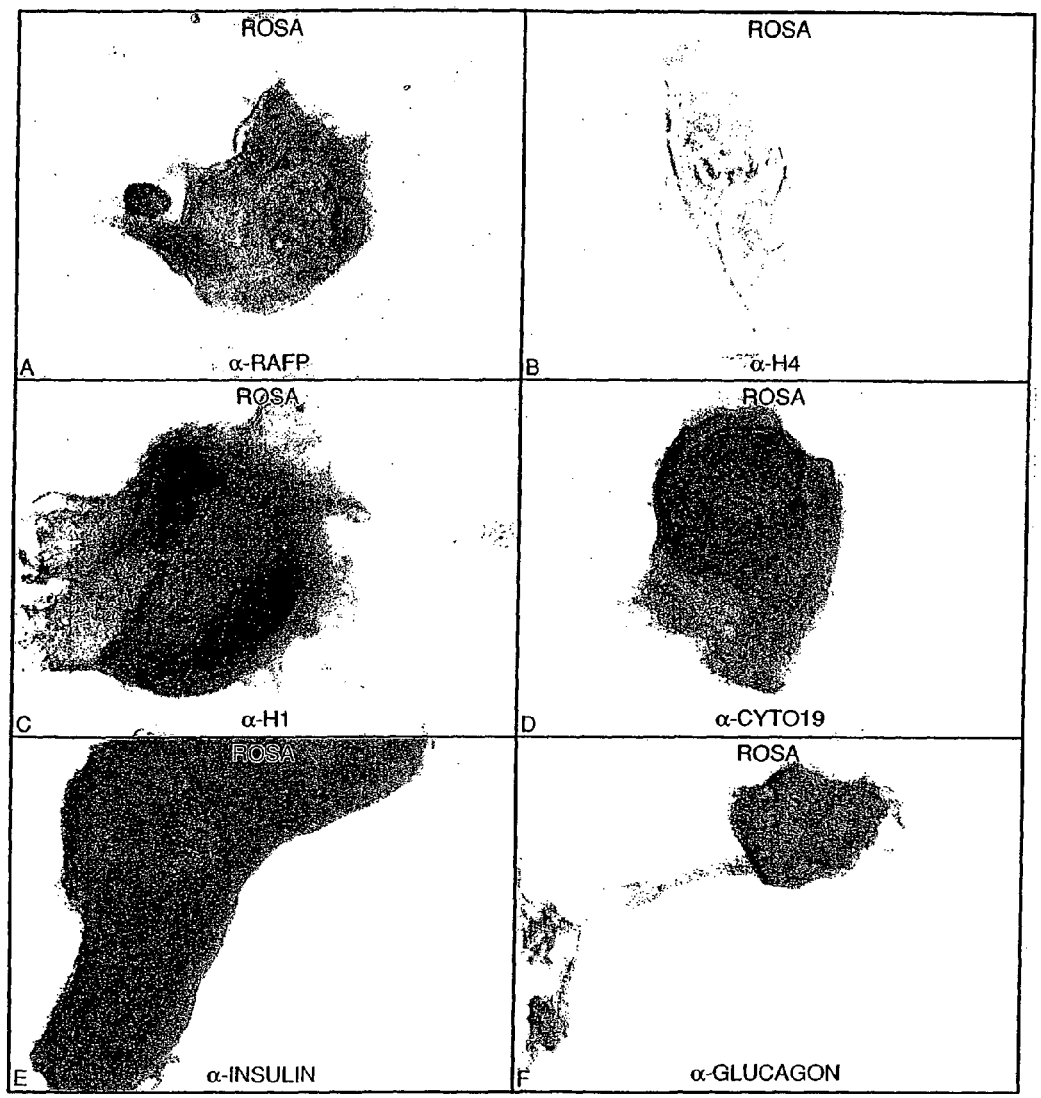

FIG. 71 depicts immunofluorescence of ROSA ELSC cells stained with various antibodies.

Figure 72:
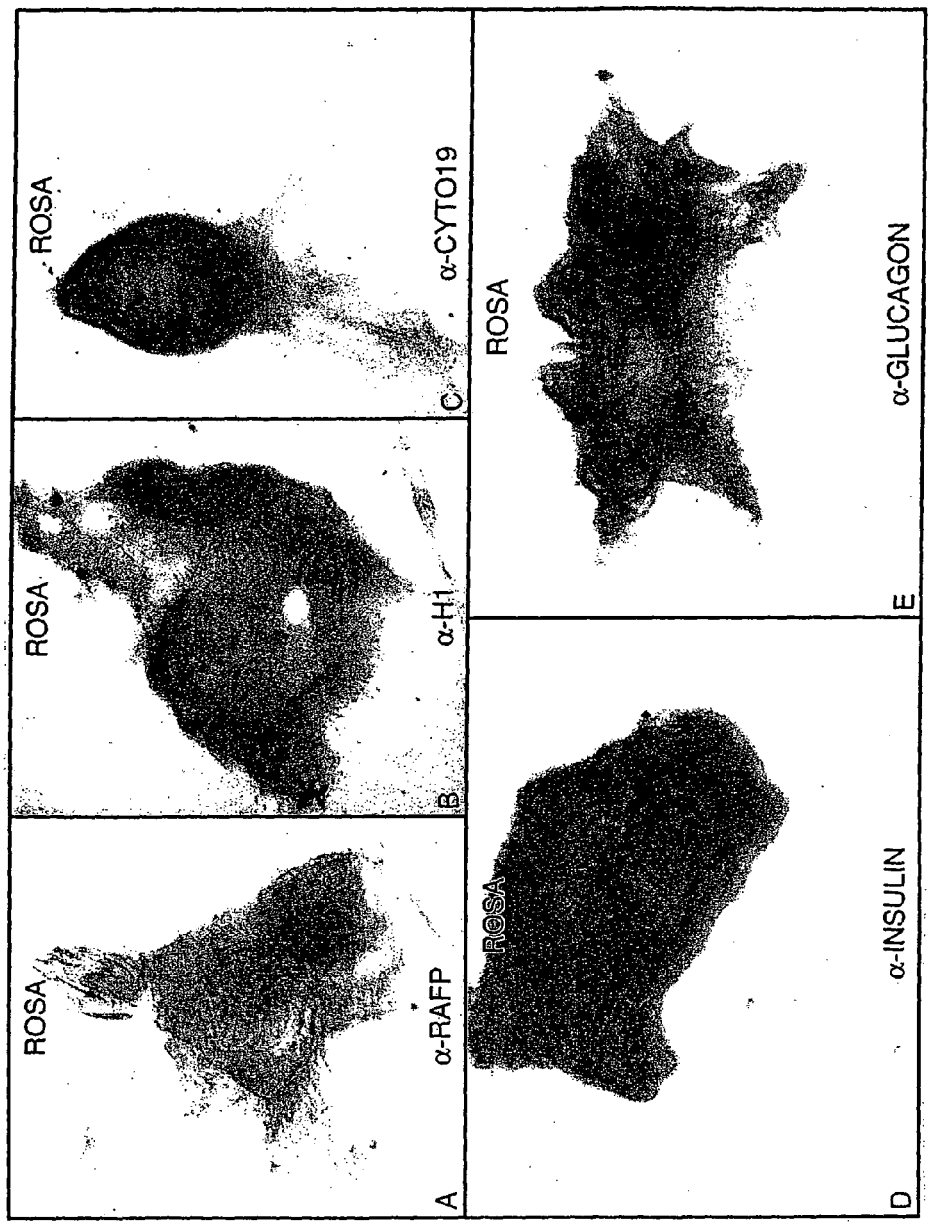

FIG. 72 depicts immunofluorescence of ROSA ELSC cells stained with various antibodies.

Figure 73:
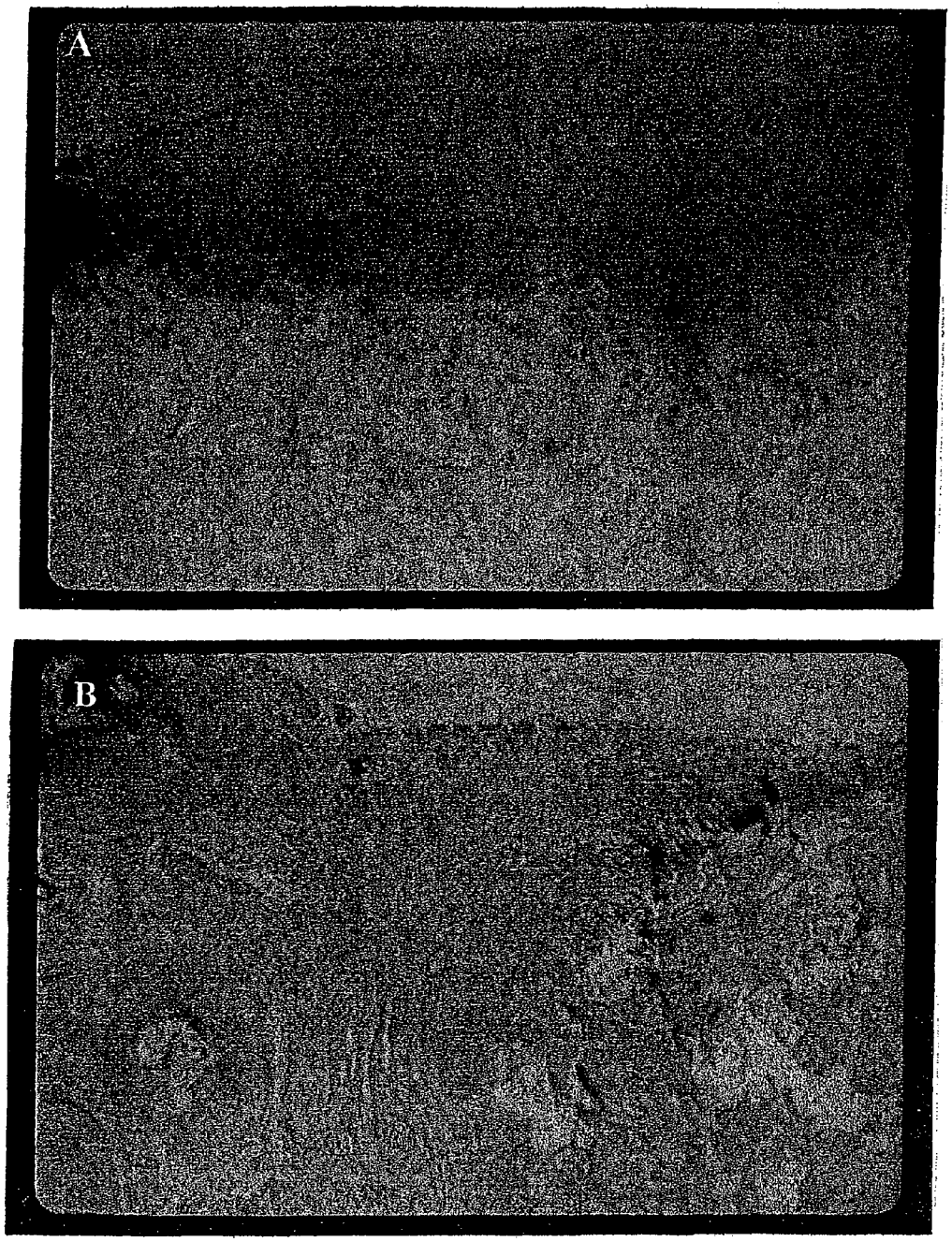

FIG. 73. Femoropatellar groove, 26 weeks post-op. Empty defects, 40×, stained with Toluidine blue. A. Animal #70. B. Animal #74.

Figure 74:
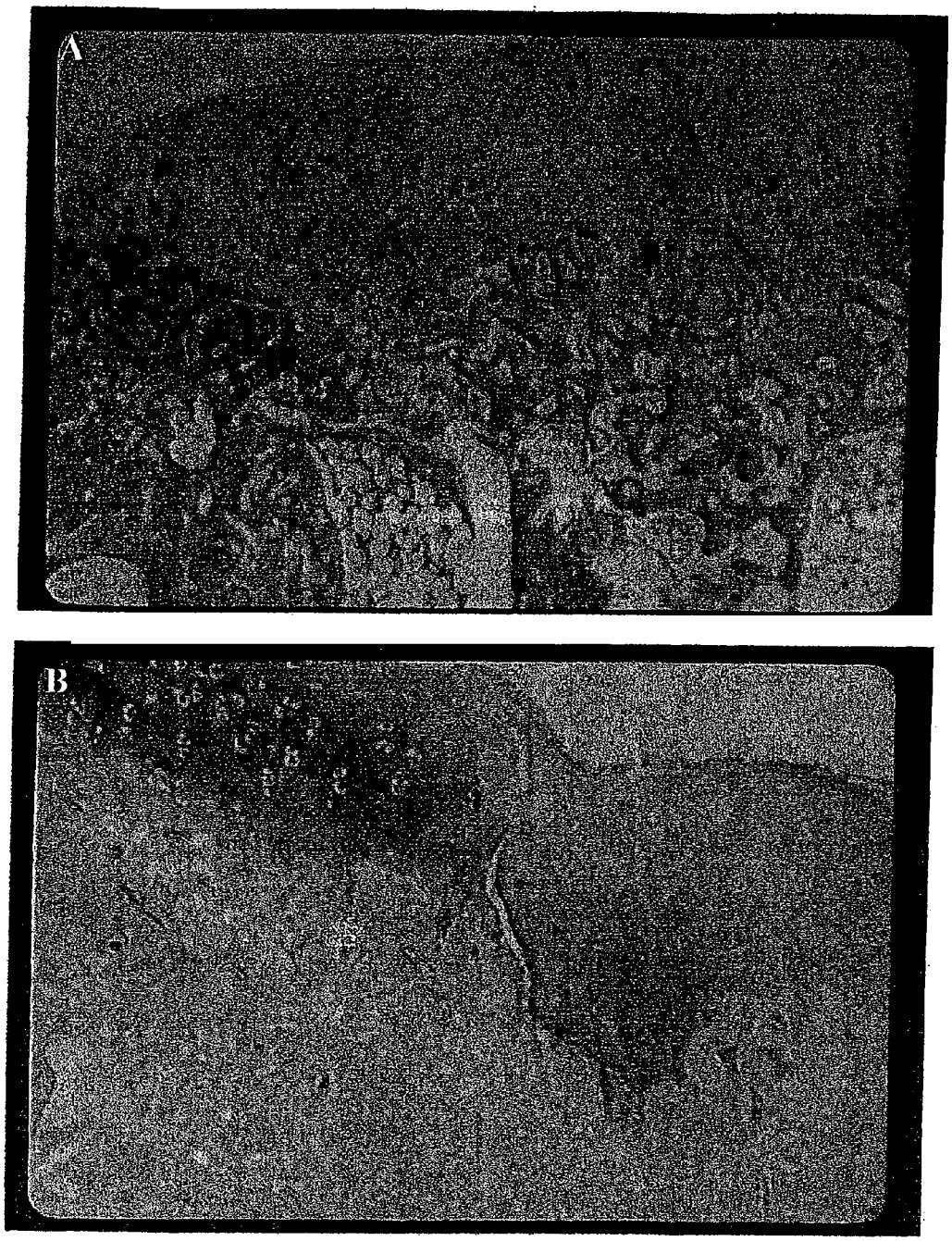

FIG. 74. Femoropatellar groove, 26 weeks post-op. Defects with polymer alone, 40×. A. Stained with Mallory-Heidenhain, animal #71. B. Stained with Toluidine blue, animal #72.

Figure 75:
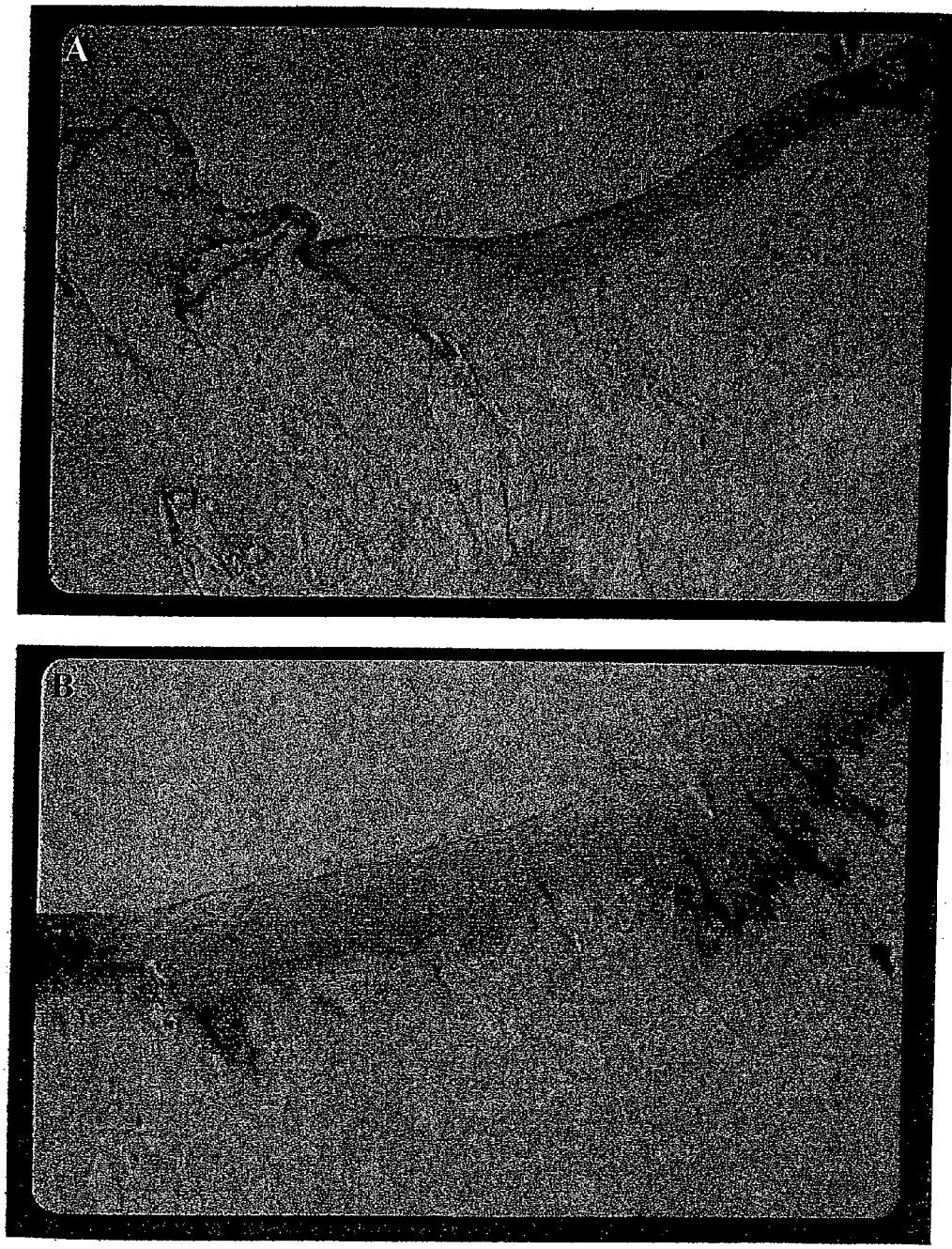

FIG. 75. Femoropatellar groove, 26 weeks post-op. Defects with PPSCs cultured in the polymer for 24 hours prior to implantation, 40×. Stained with Toluidine blue. A. Animal #71. B. Animal #79. Fat can be seen at the left hand side of panel A where the center of the defect would be.

Figure 76:
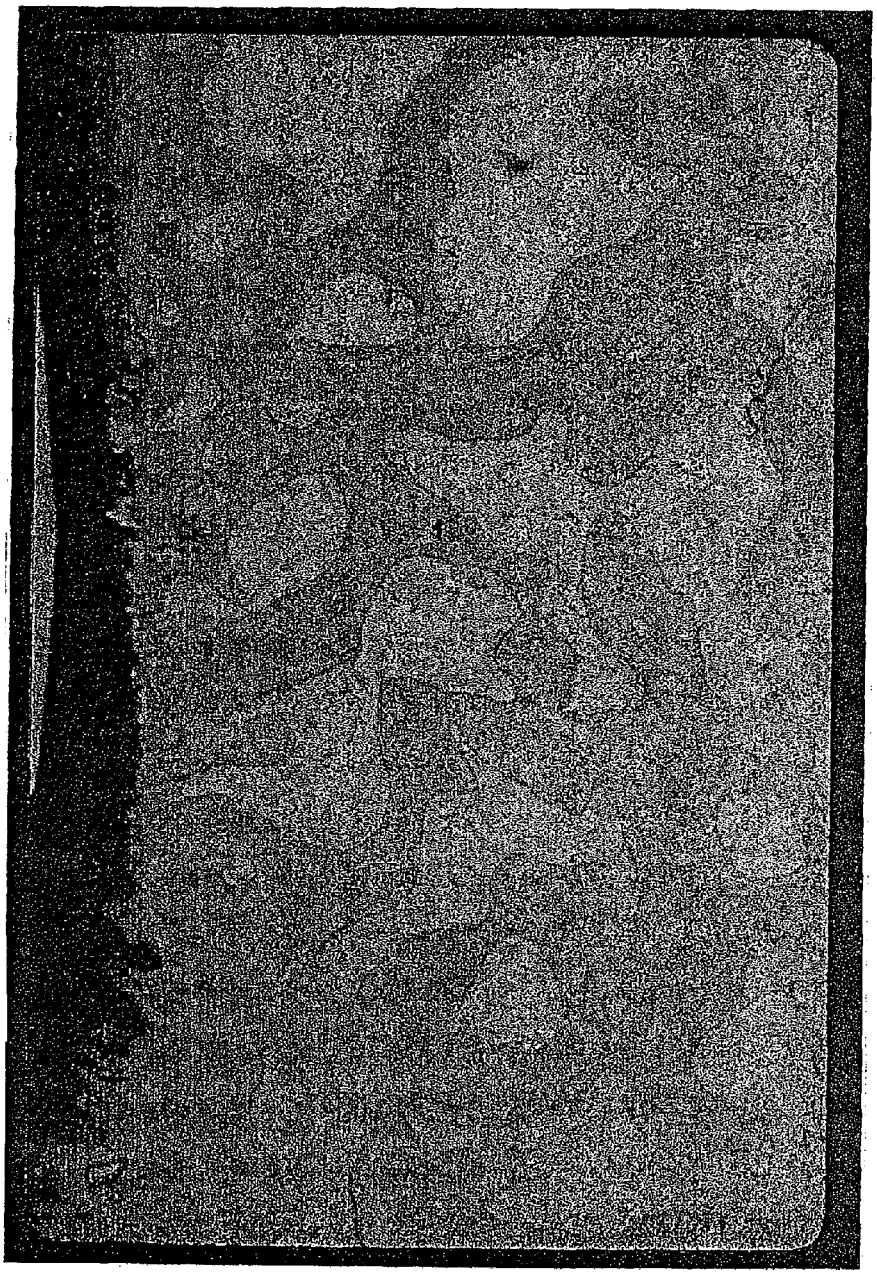

FIG. 76. Femoropatellar groove, 26 weeks post-op. Defects with PPSCs cultured in the polymer for 2 weeks prior to implantation, 40×. Stained with Toluidine blue, animal #69.

Figure 77:
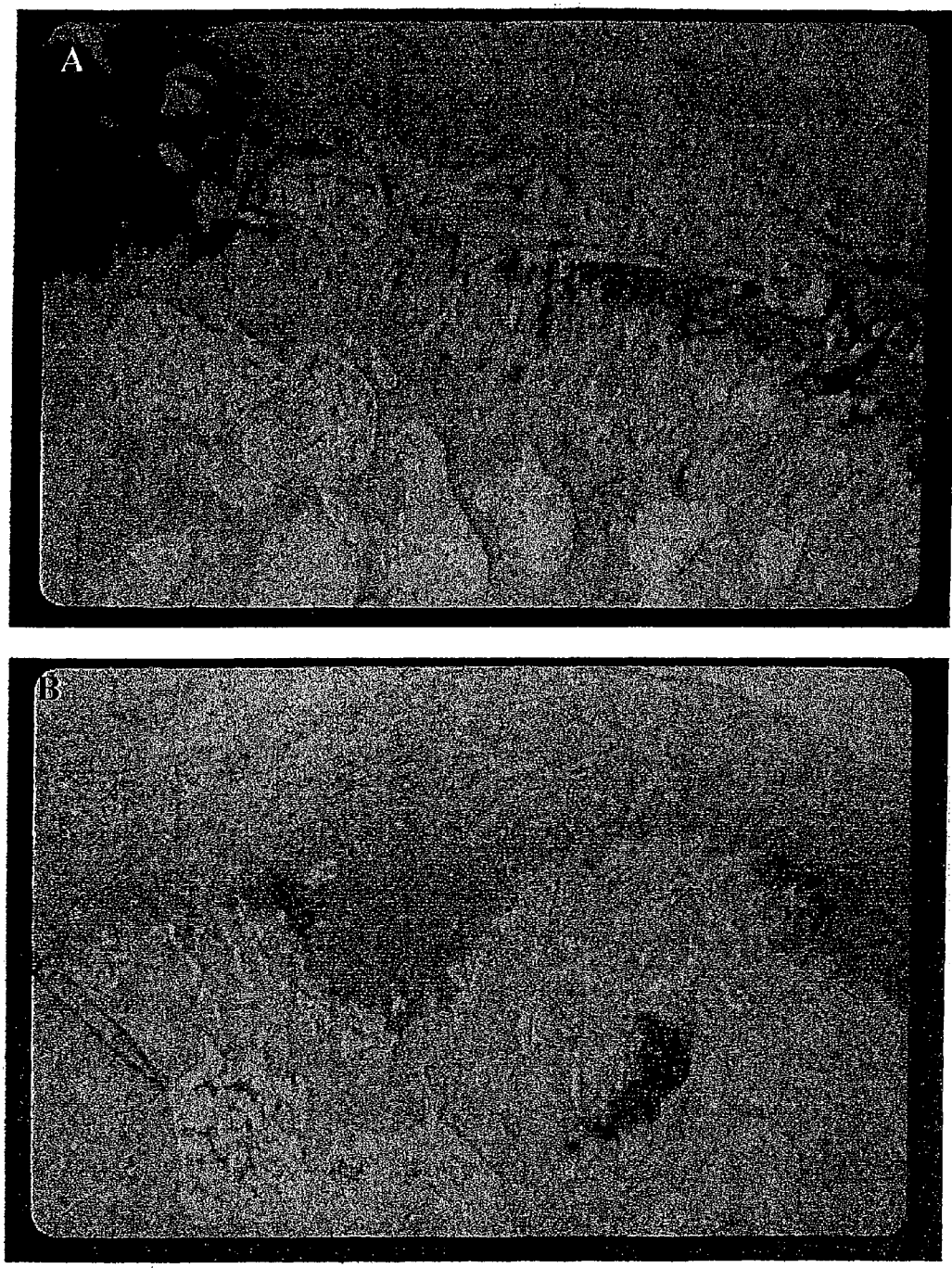

FIG. 77. Medial condyle, 26 weeks post-op. Empty defect, 40×, stained with Toluidine blue. A. Animal #70. B. Animal #75.

Figure 78:

FIG. 78. Medial condyle, 26 weeks post-op. Defect with polymer alone, 40×, stained with Toluidine blue, animal #71.

Figure 79:
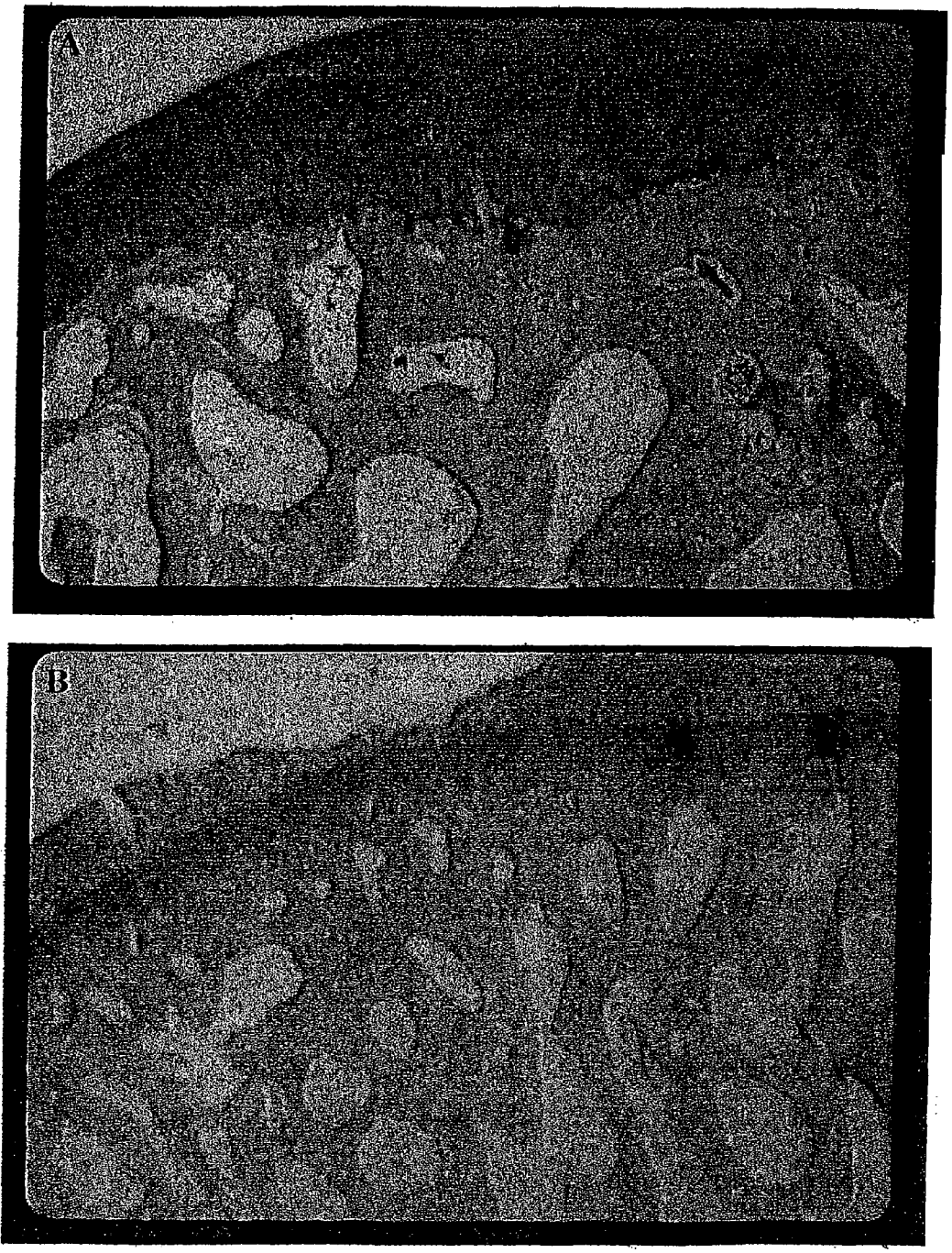

FIG. 79. Medial condyle, 26 weeks post-op. Defects with PPSCs cultured in the polymer for 24 hours prior to implantation, 40×, stained with Toluidine blue. A. Animal #71. B. Animal #79.

Figure 80:
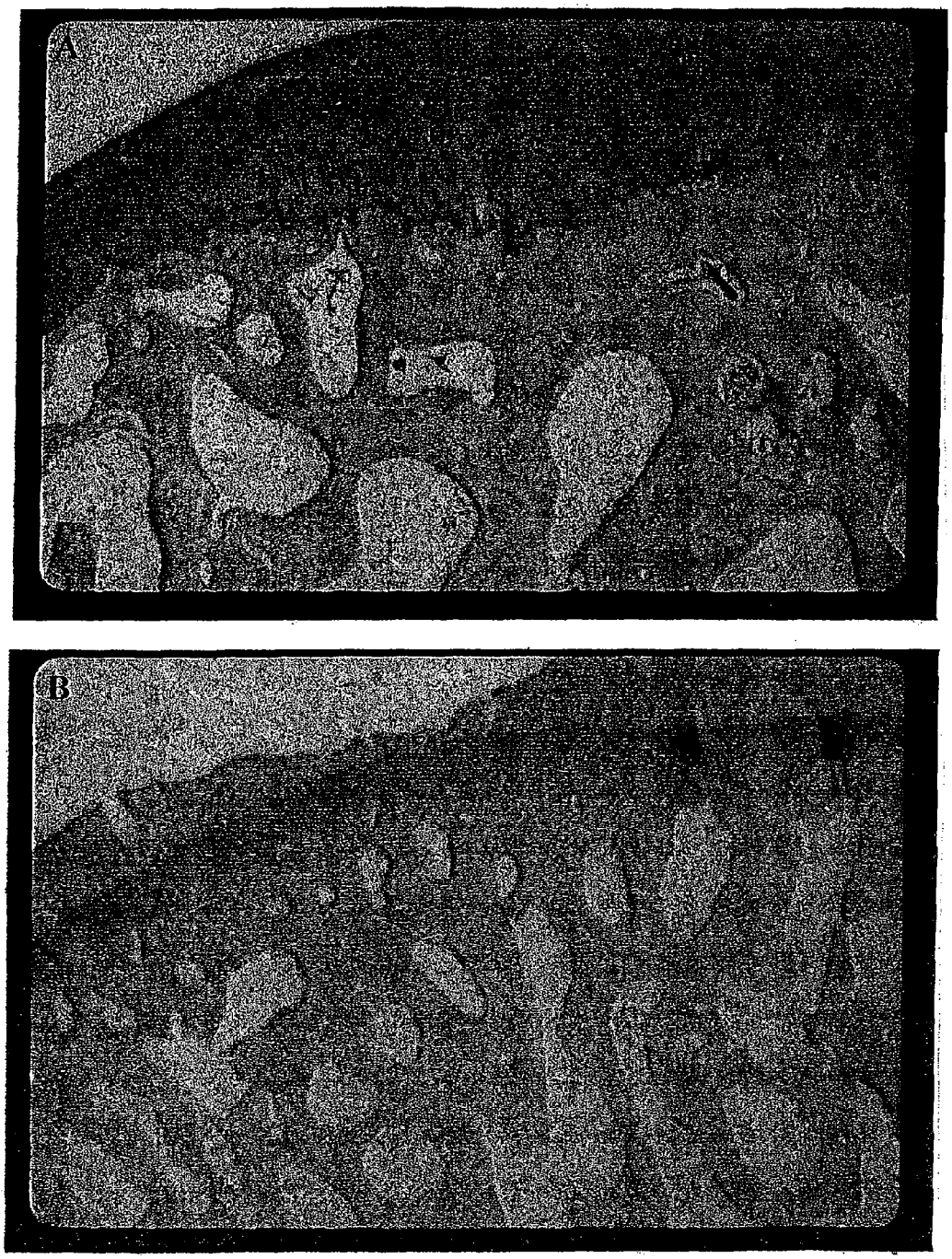

FIG. 80. Medial condyle, 26 weeks post-op. Defects with PPSCs cultured in the polymer for 2 weeks prior to implanation, 40×, stained with Toluidine blue. A. Animal #64. B. Animal #74.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984): "Nucleic Acid Hybridization" [B. D. Hames & S. J. Higgins eds. (1985)]; "Transcription And Translation" [B. D. PHames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

If appearing herein, the following terms shall have the definitions set out below.

The terms "embryonic-like pluripotent stem cell", "embryonic-like pluripotent stem cells", "embryonic-like stem cells", "pluripotent embryonic-like stem cell", "epiblastic-like stem cell", pluripotent epiblastic-like stem cell", "pluripotent stem cell", "PPELSC", "PPSC", "ELSC" and "stem cells" and any variants not specifically listed, may be used herein interchangeably, and as used throughout the present application and claims extends to those cell(s) and/or cultures, clones, or populations of such cell(s) which are derived from non-embryonic or postnatal animal cells or tissue, are capable of self regeneration and capable of differentiation to cells of endodermal, ectodermal and mesodermal lineages. The embryonic-like pluripotent stem cells have the profile of capabilities and characteristics set forth herein and in the Claims.

The embryonic-like pluripotent stem cell(s) of the present invention are lineage uncommitted, i.e., they are not committed to any particular germ layer, e.g., endoderm, mesoderm, ectoderm, or notochord. They can remain quiescent. They can also be stimulated by particular growth factors to proliferate. If activated to proliferate, embryonic-like pluripotent stem cells are capable of extended self-renewal as long as they remain lineage-uncommitted. This commitment process necessitates the use of general or specific lineage-commitment agents.

"Lineage-commitment" refers to the process by which individual cells commit to subsequent and particular stages of differentiation during the developmental sequence leading to the formation of a life form.

The term "lineage-uncommitted" refers to a characteristic of cell(s) whereby the particular cell(s) are not committed to any next subsequent stage of differentiation (e.g., germ layer lineage or cell type) of the developmental sequence.

The term "lineage-committed" refers to a characteristic of cell(s) whereby the particular cell(s) are committed to a particular next subsequent stage of differentiation (e.g., germ layer lineage or cell type) of the developmental sequence. Lineage-committed cells, for instance, can include those cells which can give rise to progeny limited to a single lineage within a germ layers, e.g., liver, thyroid (endoderm), muscle, bone (mesoderm), neuronal, melanocyte, epidermal (ectoderm), etc.

"Pluripotent endodermal stem cell(s)" are capable of self renewal or differentiation into any particular lineage within the endodermal germ layer. Pluripotent endodermal stem cells have the ability to commit within endodermal lineage from a single cell any time during their life-span. This commitment process necessitates the use of general or specific endodermal lineage-commitment agents. Pluripotent endodermal stem cells may form any cell type within the endodermal lineage, including, but not limited to, the epithelial lining, epithelial derivatives, and/or parenchyma of the trachea, bronchi, lungs, gastrointestinal tract, liver, pancreas, urinary bladder, pharynx, thyroid, thymus, parathyroid glands, tympanic cavity, pharyngotympanic tube, tonsils, etc.

"Pluripotent mesenchymal stem cell(s)" are capable of self renewal or differentiation into any particular lineage within the mesodermal germ layer. Pluripotent mesenchymal stem cells have the ability to commit within the mesodermal lineage from a single cell any time during their life-span. This commitment process necessitates the use of general or specific mesodermal lineage-commitment agents pluripotent mesenchymal stem cells may form any cell type within the mesodermal lineage, including, but not limited to, skeletal muscle, smooth muscle, cardiac muscle, white fat, brown fat, connective tissue septae, loose areolar connective tissue, fibrous organ capsules, tendons, ligaments, dermis, bone, hyaline cartilage, elastic cartilage fibrocartilage, articular cartilage, growth plate cartilage, endothelial cells, meninges, periosteum, perichondrium, erythrocytes, lymphocytes, monocytes, macrophages, microglia, plasma cells, mast cells, dendritic cells, megakaryocytes, osteoclasts, chondroclasts, lymph nodes, tonsils, spleen, kidney, ureter, urinary bladder, heart, testes, ovaries, uterus, etc.

"Pluripotent ectodermal stem cell(s)" are capable of self renewal or differentiation to any particular lineage within the ectodermal germ layer. Pluripotent ectodermal stem cells have the ability to commit within the ectodermal lineage from a single cell any time during their life-span. This commitment process necessitates the use of general or specific ectodermal lineage-commitment agents. Pluripotent ectodermal stem cells may form any cell type within the neuroectodermal, neural crest, and/or surface ectodermal lineages.

"Pluripotent neuroectodermal stem cell(s)" are capable of self renewal or differentiation to any particular lineage within the neuroectodermal layer. Pluripotent neuroectodermal stem cells have the ability to commit within the neuroectodermal lineage from a single cell any time during their life-span. This commitment process necessitates the use of general or specific neuroectodermal lineage-commitment agents. Pluripotent neuroectodermal stem cells may form any cell type within the neuroectodermal lineage, including, but not limited to, neurons, oligodendrocytes, astrocytes, ependymal cells, retina, pineal body, posterior pituitary, etc.

"Pluripotent neural crest stem cell(s)" are capable of self renewal or differentiation to any particular lineage within the neural crest layer. Pluripotent neural crest stem cells have the ability to commit within the neural crest lineage from a single cell any time during their life-span. This commitment process necessitates the use of general or specific neural crest lineage-commitment agents. Pluripotent neural crest stem cells may form any cell type within the neural crest lineage, including, but not limited to, cranial ganglia, sensory ganglia, autonomic ganglia, peripheral nerves, Schwann cells, sensory nerve endings, adrenal medulla, melanocytes, contribute of head mesenchyme, contribute to cervical mesenchyme, contribute to thoracic mesenchyme, contribute to lumbar mesenchyme, contribute to sacral mesenchyme, contribute to coccygeal mesenchyme, heart valves, heart outflow tract (aorta & pulmonary trunk), APUD (amine precursor uptake decarboxylase) system, parafollicular "C" (calcitonin secreting) cells, enterochromaffin cells, etc.

"Pluripotent surface ectodermal stem cell(s)" are capable of self renewal or differentiation to any particular lineage within the surface ectodermal layer. Pluripotent surface ectodermal stem cells have the ability to commit within the surface ectodermal lineage from a single cell any time during their life-span. This commitment process necessitates the use of general or specific surface ectodermal lineage-commitment agents. Pluripotent surface ectodermal stem cells may form any cell type within the surface ectodermal lineage, including, but not limited to, epidermis, hair, nails, sweat glands, salivary glands, sebaceous glands, mammary glands, anterior pituitary, enamel of teeth, inner ear, lens of the eye, etc.

"Progenitor cell(s)" are lineage-committed, i.e., an individual cell can give rise to progeny limited to a single lineage within their respective germ layers, e.g., liver, thyroid (endoderm), muscle, bone (mesoderm), neuronal, melanocyte, epidermal (ectoderm), etc. They can also be stimulated by particular growth factors to proliferate. If activated to proliferate, progenitor cells have life-spans limited to 50-70 cell doublings before programmed cell senescence and death occurs.

A "clone" or "clonal population" is a population of cells derived from a single cell or common ancestor by mitosis. A "cell line" is a clone of a primary cell that is capable of stable growth in vitro for many generations.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming or transfecting DNA may or may not be integrated (covalently linked) into chromosomal DNA making up the genome of the cell. In prokaryotes, yeast, and mammalian cells for example, the transforming or transfecting DNA may be maintained on an episomal element such as a plasmid. With respect to eukaryotic cells, a stably transformed or transfected cell is one in which the transforming or transfecting DNA has become integrated into a chromosome so that it is inherited by daughter cells through chromosome replication. This stability is demonstrated by the ability of the eukaryotic cell to establish cell lines or clones comprised of a population of daughter cells containing the transforming or transfecting DNA.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

TABLE OF CORRESPONDENCE

SYMBOL

| 1-Letter | 3-Letter | AMINO ACID |
|---|---|---|
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

It should be appreciated that DNA sequences encoding the same amino acid sequence, may be degenerate to one another. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations or alterations in a DNA or RNA sequence may be made such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino Acids with Nonpolar R Groups
Alanine, Valine, Leucine, Isoleucine, Proline, Phenylalanine, Tryptophan, Methionine
Amino Acids with Uncharged Polar R Groups.
Glycine, Serine, Threonine, Cysteine, Tyrosine, Asparagine, Glutamine
Amino Acids with Charged Polar R Groups (Negatively Charged at Ph 6.0)
Aspartic acid, Glutamic acid
Basic Amino Acids (Positively Charged at pH 6.0)
Lysine, Arginine, Histidine (at pH 6.0)

Another grouping may be those amino acids with phenyl groups:
Phenylalanine, Tryptophan, Tyrosine Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free NH$_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

In its primary aspect, the present invention concerns the identification and isolation of an pluripotent embryonic-like stem cell, derived from non-embryonic animal cells or tissue, capable of self regeneration and capable of differentiation to cells of endodermal, ectodermal and mesodermal lineages. The present invention extends to an pluripotent embryonic-like stem cell, derived from postnatal or adult animal cells or tissue, capable of self regeneration and capable of differentiation to cells of endodermal, ectodermal and mesodermal lineages.

The pluripotent embryonic-like stem cell of the present invention may be isolated from non-human cells or human cells. In a particular embodiment, the present invention relates to any human pluripotent embryonic-like stem cell and populations, including clonal populations of such cells.

The pluripotent embryonic-like stem cell of the present invention may be isolated from the non-embryonic, postnatal, or adult tissue selected from the group of muscle, dermis, fat, tendon, ligament, perichondrium, periosteum, heart, aorta, endocardium, myocardium, epicardium, large arteries and veins, granulation tissue, peripheral nerves, peripheral ganglia, spinal cord, dura, leptomeninges, trachea, esophagus, stomach, small intestine, large intestine, liver, spleen, pancreas, parietal peritoneum, visceral peritoneum, parietal pleura, visceral pleura, urinary bladder, gall bladder, kidney, associated connective tissues or bone marrow.

This invention further relates to cells, particularly pluripotent or progenitor cells, which are derived from the pluripotent embryonic-like stem cell. The cells may be lineage-committed cells, which cells may be committed to the endodermal, ectodermal or mesodermal lineage.

In a further aspect, the present invention relates to a culture comprising:
  (a) Pluripotent embryonic-like stem cells, capable of self regeneration and capable of differentiation to cells of endodermal, ectodermal and mesodermal lineages; and
  (b) a medium capable of supporting the proliferation of said stem cells.

Such stem cell containing cultures may further comprise a proliferation factor or lineage commitment factor. The stem cells of such cultures may be isolated from non-human cells or human cells.

The invention further relates to methods of isolating an pluripotent embryonic-like stem cell. In particular, a method of isolating an pluripotent embryonic-like stem cell of the present invention, comprises the steps of:
  (a) obtaining cells from a non-embryonic animal source;
  (b) slow freezing said cells in medium containing 7.5% (v/v) dimethyl sulfoxide until a final temperature of −80° C. is reached; and
  (c) culturing the cells.

In particular, a method of isolating an pluripotent embryonic-like stem cell of the present invention, comprises the steps of:
  (a) obtaining cells from a postnatal animal source;
  (b) slow freezing said cells in medium containing 7.5% (v/v) dimethyl sulfoxide until a final temperature of −80° C. is reached; and
  (c) culturing the cells.

In particular, a method of isolating an pluripotent embryonic-like stem cell of the present invention, comprises the steps of:
  (a) obtaining cells from an adult animal source;
  (b) slow freezing said cells in medium containing 7.5% (v/v) dimethyl sulfoxide until a final temperature of −80° C. is reached; and
  (c) culturing the cells.

In particular, a method of isolating an pluripotent embryonic-like stem cell of the present invention, comprises the steps of:
(a) obtaining cells from a non-embryonic animal source;
(b) incubating said cells in a collagenase/dispase solution;
(c) slow freezing said incubated cells in medium containing 7.5% (v/v) dimethyl sulfoxide until a final temperature of −80° C. is reached; and
(d) culturing the cells.

In particular, a method of isolating an pluripotent embryonic-like stem cell of the present invention, comprises the steps of:
(a) obtaining cells from a non-embryonic animal source;
(b) filtering said cells through a 20 um filter;
(c) slow freezing said filtered cells in medium containing 7.5% (v/v) dimethyl sulfoxide until a final temperature of −80° C. is reached; and
(d) culturing the cells.

In a further aspect, the methods of isolating an pluripotent embryonic-like stem cell relate to methods whereby a clonal population of such stem cells is isolated, wherein a single pluripotent embryonic-like stem cell is first isolated and then further cultured and expanded to generate a clonal population. A single pluripotent embryonic-like stem cell may be isolated by means of limiting dilution or such other methods as are known to the skilled artisan.

Thus, the present invention also relates to a clonal pluripotent embryonic-like stem cell line developed by such method.

In a particular aspect, the present invention relates to pluripotent embryonic-like stem cells or populations of such cells which have been transformed or transfected and thereby contain and can express a gene or protein of interest. Thus, this invention includes pluripotent embryonic-like stem cells genetically engineered to express a gene or protein of interest. In as much as such genetically engineered stem cells can then undergo lineage-commitment, the present invention further encompasses lineage-committed cells, which are derived from a genetically engineered pluripotent embryonic-like stem cell, and which express a gene or protein of interest. The lineage-committed cells may be endodermal, ectodermal or mesodermal lineage-committed cells and may be pluripotent, such as a pluripotent mesenchymal stem cell, or progenitor cells, such as an adipogenic or a myogenic cell.

The invention then relates to methods of producing a genetically engineered pluripotent embryonic-like stem cell comprising the steps of:
(a) transfecting pluripotent embryonic-like stem cells with a DNA construct comprising at least one of a marker gene or a gene of interest;
(b) selecting for expression of the marker gene or gene of interest in the pluripotent embryonic-like stem cells;
(c) culturing the stem cells selected in (b).

In a particular aspect, the present invention encompasses genetically engineered pluripotent embryonic-like stem cell(s), including human and non-human cells, produced by such method.

The possibilities both diagnostic and therapeutic that are raised by the existence and isolation of the pluripotent embryonic-like stem cells of the present invention, derive from the fact that the pluripotent embryonic-like stem cells can be isolated from non-embryonic, postnatal or adult animal cells or tissue and are capable of self regeneration on the one hand and of differentiation to cells of endodermal, ectodermal and mesodermal lineages on the other hand.

Thus, cells of any of the endodermal, ectodermal and mesodermal lineages can be provided from a single, self-regenerating source of cells obtainable from an animal source even into and through adulthood. As suggested earlier and elaborated further on herein, the present invention contemplates use of the pluripotent embryonic-like stem cells, including cells or tissues derived therefrom, for instance, in pharmaceutical intervention, methods and therapy, cell-based therapies, gene therapy, various biological and cellular assays, isolation and assessment of proliferation or lineage-commitment factors, and in varied studies of development and cell differentiation.

As previously noted herein, the ability to regenerate most human tissues damaged or lost due to trauma or disease is substantially diminished in adults. Every year millions of Americans suffer tissue loss or end-stage organ failure. Tissue loss may result from acute injuries as well as surgical interventions, i.e., amputation, tissue debridement, and surgical extirpations with respect to cancer, traumatic tissue injury, congenital malformations, vascular compromise, elective surgeries, etc. Options such as tissue transplantation and surgical intervention are severely limited by a critical donor shortage and possible long term morbidity. Three general strategies for tissue engineering have been adopted for the creation of new tissue: (1). Isolated cells or cell substitutes applied to the area of tissue deficiency or compromise. (2). Cells placed on or within matrices, in either closed or open systems. (3). Tissue-inducing substances, that rely on growth factors (including proliferation factors or lineage-commitment factors) to regulate specific cells to a committed pattern of growth resulting in tissue regeneration, and methods to deliver these substances to their targets.

A wide variety of transplants, congenital malformations, elective surgeries, diseases, and genetic disorders have the potential for treatment with the pluripotent embryonic-like stem cells of the present invention, including cells or tissues derived therefrom, alone or in combination with proliferation factors, lineage-commitment factors, or genes or proteins of interest. Preferred treatment methods include the treatment of tissue loss where the object is to provide cells directly for transplantation whereupon the tissue can be regenerated in vivo, recreate the missing tissue in vitro and then provide the tissue, or providing sufficient numbers of cells suitable for transfection or transformation for ex vivo or in vivo gene therapy.

As described above, the embryonic-like cells of the present invention have the unique capacity to differentiate into cells of any of the ectodermal, mesodermal, and endodermal lineage. The capacity for such differentiation in vitro (in culture) and in vivo, even to correct defects and function in vivo is demonstrated herein in the Examples provided. Thus, the cells of the present invention may be utilized in transplantation, cell replacement therapy, tissue regeneration, gene therapy, organ replacement and cell therapies wherein cells, tissues, organs of mesodermal, ectodermal and/or endodermal origin are derived in vivo, ex vivo or in vitro. Endoderm cell, tissue or organ therapy and/or regeneration and/or therapy utilizing the PPSCs of the invention or their derived differentiated or progenitor cells may useful as the cell source for epithelial linings of the respiratory passages and gastrointestinal tract, the pharynx, esophagus, stomach, intestine and to many associated glands, including salivary glands, liver, pancreas and lungs. In particular and as non-limiting examples, liver transplantation and pancreas cell replacement for diabetes is thereby contemplated. Mesoderm cell, tissue or organ therapy and/or regeneration and/or therapy utilizing the PPSCs of the invention or their derived differentiated or progenitor cells may useful as the cell source for smooth muscular coats, connective tissues, and vessels associated with tissues and organs and for replacement/therapy of the cardiovascular system, heart, cardiac muscle, cardiac vessels, other vessels, blood cells, bone marrow, the skeleton, striated muscles, and the reproductive and excretory organs. Ectoderm cell, tissue or organ therapy and/or regeneration and/or therapy utilizing the PPSCs of the invention or their derived differentiated or progenitor cells may useful as the cell source for the epidermis (epidermal layer of the skin), the sense organs, and the entire nervous system, including brain, spinal cord, and all the outlying components of the nervous system. A significant benefit of the pluripotent embryonic-like stem cells of the present invention are their potential for self-regeneration prior to commitment to any particular tissue lineage (ectodermal, endodermal or mesodermal) and then further proliferation once committed. These proliferative and differentiative attributes are very important and useful when limited amounts of appropriate cells and tissue are available for transplantation.

The isolation of pluripotent embryonic-like stem cells as tissue source for transplantation therapies, that (a) can be isolated and sorted; (b) has unlimited proliferation capabilities while retaining pluripotency; (c) can be manipulated to commit to multiple separate tissue lineages; (d) is capable of incorporating into the existing tissue; and (e) can subsequently express the respective differentiated tissue type, may prove beneficial to therapies that maintain or increase the functional capacity and/or longevity of lost, damaged, or diseased tissues.

In a further embodiment, the present invention relates to certain therapeutic methods which would be based upon the activity of the pluripotent embryonic-like stem cells of the present invention, including cells or tissues derived therefrom, or upon agents or other drugs determined to act on any such cells or tissues, including proliferation factors and lineage-commitment factors. One exemplary therapeutic method is associated with the prevention or modulation of the manifestations of conditions causally related to or following from the lack or insufficiency of cells of a particular lineage, and comprises administering the pluripotent embryonic-like stem cells of the present invention, including cells or tissues derived therefrom, either individually or in mixture with proliferation factors or lineage-commitment factors in an amount effective to prevent the development or progression of those conditions in the host.

In a further and particular aspect the present invention includes therapeutic methods, including transplantation of the pluripotent embryonic-like stem cells of the present invention, including lineage-uncommitted populations of cells, lineage-committed populations of cells, tissues and organs derived therefrom, in treatment or alleviation of conditions, diseases, disorders, cellular debilitations or deficiencies which would benefit from such therapy. These methods include the replacement or replenishment of cells, tissues or organs. Such replacement or replenishment may be accomplished by transplantation of the pluripotent embryonic-like stem cells of the present invention or by transplantation of lineage-uncommitted populations of cells, lineage-committed populations of cells, tissues or organs derived therefrom.

Thus, the present invention includes a method of transplanting pluripotent embryonic-like stem cells in a host comprising the step of introducing into the host the pluripotent embryonic-like stem cells of the present invention.

In a further aspect this invention provides a method of providing a host with purified pluripotent embryonic-like stem cells comprising the step of introducing into the host the pluripotent embryonic-like stem cells of the present invention.

In a still further aspect, this invention includes a method of in vivo administration of a protein or gene of interest comprising the step of transfecting the pluripotent embryonic-like stem cells of the present invention with a vector comprising DNA or RNA which expresses a protein or gene of interest.

The present invention provides a method of preventing and/or treating cellular debilitations, derangements and/or dysfunctions and/or other disease states in mammals, comprising administering to a mammal a therapeutically effective amount of pluripotent embryonic-like stem cells.

In a further aspect, the present invention provides a method of preventing and/or treating cellular debilitations, derangements and/or dysfunctions and/or other disease states in mammals, comprising administering to a mammal a therapeutically effective amount of a endodermal, ectodermal or mesodermal lineage-committed cell derived from the pluripotent embryonic-like stem cells of the present invention.

The therapeutic method generally referred to herein could include the method for the treatment of various pathologies or other cellular dysfunctions and derangements by the administration of pharmaceutical compositions that may comprise proliferation factors or lineage-commitment factors, alone or in combination with the pluripotent embryonic-like stem cells of the present invention, or cells or tissues derived therefrom, or other similarly effective agents, drugs or compounds identified for instance by a drug screening assay prepared and used in accordance with a further aspect of the present invention.

Also, antibodies including both polyclonal and monoclonal antibodies that recognize the pluripotent embryonic-like stem cells of the present invention, including cells and/or tissues derived therefrom, and agents, factors or drugs that modulate the proliferation or commitment of the pluripotent embryonic-like stem cells of the present invention, including cells and/or tissues derived therefrom, may possess certain diagnostic or therapeutic applications and may for example, be utilized for the purpose of correction, alleviation, detecting and/or measuring conditions such as cellular debilitations, cellular deficiencies or the like. For example, the pluripotent embryonic-like stem cells of the present invention, including cells and/or tissues derived therefrom, may be used to produce both polyclonal and monoclonal antibodies to themselves in a variety of cellular media, by known techniques such as the hybridoma technique utilizing, for example, fused mouse spleen lymphocytes and myeloma cells. Likewise, agents, factors or drugs that modulate, for instance, the proliferation or commitment of the cells of the invention may be discovered, identified or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761;

4,399,121; 4,427,783; 4,444,887; 4,451,570; 4,466,917; 4,472,500; 4,491,632; 4,493,890.

Panels of monoclonal antibodies produced against the pluripotent embryonic-like stem cells, including cells or tissues derived therefrom, or against proliferation or lineage-commitment factors that act thereupon, can be screened for various properties; i.e., isotype, epitope, affinity, etc. Of particular interest are monoclonal antibodies that neutralize the activity of the proliferation or lineage-commitment factors. Such monoclonals can be readily identified in activity assays, including lineage commitment or proliferation assays as contemplate or described herein. High affinity antibodies are also useful when immunoaffinity-based purification or isolation or identification of the Pluripotent embryonic-like stem cells, including cells or tissues therefrom, or of proliferation or lineage-commitment factors is sought.

Preferably, the antibody used in the diagnostic or therapeutic methods of this invention is an affinity purified polyclonal antibody. More preferably, the antibody is a monoclonal antibody (mAb). In addition, it is preferable for the antibody molecules used herein be in the form of Fab, Fab', F(ab')$_2$ or F(v) portions of whole antibody molecules.

As suggested earlier, the diagnostic method of the present invention may, for instance, comprise examining a cellular sample or medium by means of an assay including an effective amount of an antibody recognizing the stem cells of the present invention, including cells or tissues derived therefrom, such as an anti-embryonic-like pluripotent stem cell antibody, preferably an affinity-purified polyclonal antibody, and more preferably a mAb. In addition, it is preferable for the antibody molecules used herein be in the form of Fab, Fab', F(ab')$_2$ or F(v) portions or whole antibody molecules. As previously discussed, patients capable of benefitting from this method include those suffering from cellular debilitations, organ failure, tissue loss, tissue damage, congenital malformations, cancer, or other diseases or debilitations. Methods for isolating the antibodies and for determining and optimizing the ability of antibodies to assist in the isolation, purification, examination or modulation of the target cells or factors are all well-known in the art.

Methods for producing polyclonal anti-polypeptide antibodies are well-known in the art. See U.S. Pat. No. 4,493, 795 to Nestor et al. See Niman et al., *Proc. Natl. Acad. Sci. USA*, 80:4949-4953 (1983). A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference.

Splenocytes are typically fused with myeloma cells using polyethylene glycol (PEG) 6000. Fused hybrids are selected by their sensitivity to HAT. Hybridomas producing a monoclonal antibody useful in practicing one aspect of this invention are identified, for instance, by their ability to immunoreact with the pluripotent embryonic-like stem cells of the present invention. Hybridomas producing a monoclonal antibody useful in practicing a further aspect of this invention are identified, for instance, by their ability to inhibit the proliferation or lineage-commitment activity of a factor, agent or drug on pluripotent embryonic-like stem cells, including cells or tissues derived therefrom.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

The present invention further contemplates therapeutic compositions useful in practicing the therapeutic methods of this invention. A subject therapeutic composition includes, in admixture, a pharmaceutically acceptable excipient (carrier) or media and one or more of the pluripotent embryonic-like stem cells of the present invention, including cells or tissues derived therefrom, alone or in combination with proliferation factors or lineage-commitment factors, as described herein as an active ingredient.

The pluripotent embryonic-like stem cells of the present invention, including cells or tissues derived therefrom, alone or in combination with proliferation factors or lineage-commitment factors, may be prepared in pharmaceutical compositions, with a suitable carrier and at a strength effective for administration by various means to a patient experiencing cellular or tissue loss or deficiency.

It is a still further object of the present invention to provide pharmaceutical compositions for use in therapeutic methods which comprise or are based upon the pluripotent embryonic-like stem cells of the present invention, including lineage-uncommitted populations of cells, lineage-committed populations of cells, tissues and organs derived therefrom, along with a pharmaceutically acceptable carrier or media. Also contemplated are pharmaceutical compositions comprising proliferation factors or lineage commitment factors that act on or modulate the pluripotent embryonic-like stem cells of the present invention and/or the cells, tissues and organs derived therefrom, along with a pharmaceutically acceptable carrier or media. The pharmaceutical compositions of proliferation factors or lineage commitment factors may further comprise the pluripotent embryonic-like stem cells of the present invention, or cells, tissues or organs derived therefrom.

The pharmaceutical compositions of the present invention may comprise the pluripotent embryonic-like stem cells of the present invention, or cells, tissues or organs derived therefrom, alone or in a polymeric carrier or extracellular matrix.

Suitable polymeric carriers include porous meshes or sponges formed of synthetic or natural polymers, as well as polymer solutions. One form of matrix is a polymeric mesh or sponge; the other is a polymeric hydrogel. Natural polymers that can be used include proteins such as collagen, albumin, and fibrin; and polysaccharides such as alginate and polymers of hyaluronic acid. Synthetic polymers include both biodegradable and non-biodegradable polymers. Examples of biodegradable polymers include polymers of hydroxy acids such as polylactic acid (PLA), polyglycolic acid (PGA), and polylactic acid-glycolic acid (PLGA), polyorthoesters, polyanhydrides, polyphosphazenes, and combinations thereof. Non-biodegradable polymers include polyacrylates, polymethacrylates, ethylene vinyl acetate, and polyvinyl alcohols.

Polymers that can form ionic or covalently crosslinked hydrogels which are malleable are used to encapsulate cells. A hydrogel is a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazines, and polyacrylates, which are crosslinked ionically, or block copolymers such as Pluronics™ or Tetronics™, polyethylene oxide-polypropylene glycol block copolymers which are crosslinked by temperature or pH, respectively. Other materials include proteins such as fibrin, polymers such as polyvinylpyrrolidone, hyaluronic acid and collagen.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups. Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

This invention also provides pharmaceutical compositions for the treatment of cellular debilitation, derangement and/or dysfunction in mammals, comprising:
A. a therapeutically effective amount of the pluripotent embryonic-like stem cells of the present invention; and
B. a pharmaceutically acceptable medium or carrier.

Pharmaceutical compositions of the present invention also include compositions comprising endodermal, ectodermal or mesodermal lineage-committed cell(s) derived from the pluripotent embryonic-like stem cells of the present invention, and a pharmaceutically acceptable medium or carrier. Any such pharmaceutical compositions may further comprise a proliferation factor or lineage-commitment factor.

The present invention naturally contemplates several means or methods for preparation or isolation of the pluripotent embryonic-like stem cells of the present invention including as illustrated herein, and the invention is accordingly intended to cover such means or methods within its scope.

A variety of administrative techniques may be utilized, among them parenteral techniques such as subcutaneous, intravenous and intraperitoneal injections, catheterizations and the like. The therapeutic factor-containing compositions are conventionally administered intravenously, as by injection of a unit dose, for example. Average quantities of the stem cells or cells may vary and in particular should be based upon the recommendations and prescription of a qualified physician or veterinarian.

The preparation of cellular or tissue-based therapeutic compositions as active ingredients is well understood in the art. Such compositions may be formulated in a pharmaceutically acceptable media. The cells may be in solution or embedded in a matrix.

The preparation of therapeutic compositions with factors, including growth, proliferation or lineage-commitment factors, (such as for instance human growth hormone) as active ingredients is well understood in the art. The active therapeutic ingredient is often mixed with excipients or media which are pharmaceutically acceptable and compatible with the active ingredient. In addition, if desired, the composition can contain minor amounts of auxiliary substances such as wetting or emulsifying agents, pH buffering agents which enhance the effectiveness of the active ingredient.

A factor can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, media, or vehicle.

The compositions are administered in a manner compatible with the dosage formulation, and in a therapeutically effective amount. The quantity to be administered depends, for instance, on the subject and debilitation to be treated, capacity of the subject's organ, cellular and immune system to utilize the active ingredient, and the nature of the cell or tissue therapy, etc. Precise amounts of active ingredient required to be administered depend on the judgment of the practitioner and are peculiar to each individual. However, suitable dosages of a factor may range from about 0.1 to 20, preferably about 0.5 to about 10, and more preferably one to several, milligrams of active ingredient per kilogram body weight of individual per day and depend on the route of administration. Suitable regimes for initial administration and follow on administration are also variable, but can include an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions, for instance with a proliferation factor or lineage-commitment factor as active ingredient, may further include an effective amount of the factor, and one or more of the following active ingredients: an antibiotic, a steroid. Exemplary formulations are given below:

| Ingredient | mg/ml |
|---|---|
| *Formulations* | |
| Intravenous Formulation I | |
| cefotaxime | 250.0 |
| Factor | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II | |
| ampicillin | 250.0 |
| Factor | 10.0 |
| sodium bisulfite USP | 3.2 |
| disodium edetate USP | 0.1 |
| water for injection q.s.a.d. | 1.0 ml |
| Intravenous Formulation III | |
| gentamicin (charged as sulfate) | 40.0 |
| Factor | 10.0 |
| sodium bisulfite USP | 3.2 |
| disodium edetate USP | 0.1 |
| water for injection q.s.a.d. | 1.0 ml |
| Intravenous Formulation IV | |
| Factor | 10.0 |
| dextrose USP | 45.0 |
| sodium bisulfite USP | 3.2 |
| edetate disodium USP | 0.1 |
| water for injection q.s.a.d. | 1.0 ml |

As used herein, "pg" means picogram, "ng" means nanogram, "ug" or "µg" mean microgram, "mg" means milligram, "ul" or "µl" mean microliter, "ml" means milliliter, "l" means liter.

Another feature of this invention is the expression of the DNA sequences of a gene or protein of interest, including as disclosed herein. As is well known in the art, DNA sequences may be expressed by operatively linking them to an expression control sequence in an appropriate expression vector and employing that expression vector to transform an appropriate unicellular host. Such operative linking of a DNA sequence to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences. Useful expression vectors, for example, may consist of segments of chromosomal, non-chromosomal and synthetic DNA sequences. Suitable vectors include derivatives of SV40 and known bacterial plasmids, e.g., E. coli plasmids col El, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2µ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences. These hosts may include well known eukaryotic and prokaryotic hosts, such as strains of E. coli, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), human cells and plant cells in tissue culture.

It will be understood that not all vectors, expression control sequences and hosts will function equally well to express the DNA sequences. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors a person skilled in the art will be able to construct a variety of vector/expression control sequence/host combinations that will express the DNA sequences of this invention on fermentation or in large scale animal culture.

A DNA sequence can be prepared synthetically rather than cloned. The DNA sequence can be designed with the appropriate codons for the amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984).

Synthetic DNA sequences allow convenient construction of genes which will express analogs or "muteins". Alternatively, DNA encoding muteins can be made by site-directed mutagenesis of native genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science*, 244:182-188 (April 1989). This method may be used to create analogs with unnatural amino acids.

The present invention also relates to a variety of diagnostic applications, including methods for detecting the presence of proliferation factors or particular lineage-commitment factors, by reference to their ability to elicit proliferation or particular lineage commitment of pluripotent embryonic-like stem cells, including cells or tissues derived therefrom. The diagnostic utility of the pluripotent embryonic-like stem cells of the present invention extends to the use of such cells in assays to screen for proliferation factors or particular lineage-commitment factors, by reference to their ability to elicit proliferation or particular lineage commitment of pluripotent embryonic-like stem cells, including cells or tissues derived therefrom. Such assays may be used, for instance, in characterizing a known factor, identifying a new factor, or in cloning a new or known factor by isolation of and determination of its nucleic acid and/or protein sequence.

As described in detail above, antibody(ies) to the pluripotent embryonic-like stem cells, including cells and tissues derived therefrom, can be produced and isolated by standard methods including the well known hybridoma techniques. For convenience, the antibody(ies) to the pluripotent embryonic-like stem cells will be referred to herein as $Ab_1$ and antibody(ies) raised in another species as $Ab_2$.

The presence of pluripotent embryonic-like stem cells can be ascertained by the usual immunological procedures applicable to such determinations. A number of useful procedures are known. Three such procedures which are especially useful utilize either the pluripotent embryonic-like stem cell labeled with a detectable label, antibody $Ab_1$ labeled with a detectable label, or antibody $Ab_2$ labeled with a detectable label. The procedures may be summarized by the following equations wherein the asterisk indicates that the particle is labeled, and "stem cell" stands for the pluripotent embryonic-like stem cell:

A. stem cell*+$Ab_1$=stem cell*$Ab_1$
B. stem cell+$Ab_1$*=stem cell$Ab_1$*
C. stem cell+$Ab_1$+$Ab_2$*=stem cell$Ab_1$$Ab_2$*

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, the stem cell forms complexes with one or more antibody(ies) or binding partners and one member of the complex is labeled with a detectable label. The fact that a complex has formed and, if desired, can then be isolated or the amount thereof can be determined by known methods applicable to the detection of labels. Procedures, for instance, for flourescence activated cell sorting are known in the art and provided herein in the Examples. Cells can also be isolated by adherence to a column to which the antibody has been previously bound or otherwise attached to.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-stem cell antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The stem cell or its binding partner(s) can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

The invention includes an assay system for screening of potential agents, compounds or drugs effective to modulate the proliferation or lineage-committment of the pluripotent embryonic-like stem cells of the present invention, including cells or tissues derived therefrom. These assays may also be utilized in cloning a gene or polypeptide sequence for a factor, by virtue of the factors known or presumed activity or capability with respect to the pluripotent embryonic-like stem cells of the present invention, including cells or tissues derived therefrom.

The assay system could importantly be adapted to identify drugs or other entities that are capable of modulating the pluripotent embryonic-like stem cells of the present invention, either in vitro or in vivo. Such an assay would be useful in the development of agents, factors or drugs that would be specific in modulating the pluripotent embryonic-like stem cells to, for instance, proliferate or to commit to a particular lineage or cell type. For example, such drugs might be used to facilitate cellular or tissue transplantation therapy.

Thus the present invention contemplates to methods for detecting the presence or activity of an agent which is a lineage-commitment factor comprising the steps of:
 A. contacting the pluripotent embryonic-like stem cells of the present invention with a sample suspected of containing an agent which is a lineage-commitment factor; and
 B. determining the lineage of the so contacted cells by morphology, mRNA expression, antigen expression or other means;
 wherein the lineage of the contacted cells indicates the presence or activity of a lineage-commitment factor in said sample.

The present invention also relates to methods of testing the ability of an agent, compound or factor to modulate the lineage-commitment of a lineage uncommitted cell which comprises
 A. culturing the pluripotent embryonic-like stem cells of the present invention in a growth medium which maintains the stem cells as lineage uncommitted cells;

B. adding the agent, compound or factor under test; and
C. determining the lineage of the so contacted cells by morphology, mRNA expression, antigen expression or other means.

In a further such aspect, the present invention relates to an assay system for screening agents, compounds or factors for the ability to modulate the lineage-commitment of a lineage uncommitted cell, comprising:
A. culturing the pluripotent embryonic-like stem cells of the present invention in a growth medium which maintains the stem cells as lineage uncommited cells;
B. adding the agent, compound or factor under test; and
C. determining the lineage of the so contacted cells by morphology, mRNA expression, antigen expression or other means.

The invention also relates to a method for detecting the presence or activity of an agent which is a proliferation factor comprising the steps of:
A. contacting the pluripotent embryonic-like stem cells of the present invention with a sample suspected of containing an agent which is a proliferation factor; and
B. determining the proliferation and lineage of the so contacted cells by morphology, mRNA expression, antigen expression or other means;
wherein the proliferation of the contacted cells without lineage commitment indicates the presence or activity of a proliferation factor in said sample.

In a further aspect, the invention includes methods of testing the ability of an agent, compound or factor to modulate the proliferation of a lineage uncommitted cell which comprises
A. culturing the pluripotent embryonic-like stem cells of the present invention in a growth medium which maintains the stem cells as lineage uncommited cells;
B. adding the agent, compound or factor under test; and
C. determining the proliferation and lineage of the so contacted cells by mRNA expression, antigen expression or other means.

The invention further relates to an assay system for screening agents, compounds or factors for the ability to modulate the proliferation of a lineage uncommitted cell, comprising:
A. culturing the pluripotent embryonic-like stem cells of the present invention in a growth medium which maintains the stem cells as lineage uncommited cells;
B. adding the agent, compound or factor under test; and
C. determining the proliferation and lineage of the so contacted cells by mRNA expression, antigen expression or other means.

In a further embodiment of this invention, commercial test kits suitable for use by a medical specialist may be prepared to isolate or determine the presence or absence of pluripotent embryonic-like stem cells, or of a proliferation factor or lineage commitment factor. In accordance with the testing techniques discussed above, one class of such kits will contain at least the labeled stem cell or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the isolation of or demonstration of the presence of pluripotent embryonic-like stem cells, comprising:
(a) a predetermined amount of at least one labeled immunochemically reactive component obtained by the direct or indirect attachment of the pluripotent embryonic-like stem cells or a specific binding partner thereto, to a detectable label;
(b) other reagents; and
(c) directions for use of said kit.

More specifically, the test kit may comprise:
(a) a known amount of the pluripotent embryonic-like stem cells as described above (or a binding partner) generally bound to a solid phase to form an immunosorbent, or in the alternative, bound to a suitable tag, or plural such end products, etc. (or their binding partners) one of each;
(b) if necessary, other reagents; and
(c) directions for use of said test kit.

In a further variation, the test kit may be prepared and used for the purposes stated above, which operates according to a predetermined protocol (e.g. "competitive," "sandwich," "double antibody," etc.), and comprises:
(a) a labeled component which has been obtained by coupling the pluripotent embryonic-like stem cells to a detectable label;
(b) one or more additional immunochemical reagents of which at least one reagent is a ligand or an immobilized ligand, which ligand is selected from the group consisting of:
(i) a ligand capable of binding with the labeled component (a);
(ii) a ligand capable of binding with a binding partner of the labeled component (a);
(iii) a ligand capable of binding with at least one of the component(s) to be determined; and
(iv) a ligand capable of binding with at least one of the binding partners of at least one of the component(s) to be determined; and
(c) directions for the performance of a protocol for the detection and/or determination of one or more components of an immunochemical reaction between the pluripotent embryonic-like stem cells and a specific binding partner thereto.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Preliminary Considerations

The proposed investigation is part of a long term research effort directed at ascertaining the particular identities of a tripartite system necessary for the restoration of histo-architecture and tissue function, i.e., stem cells, bio-active factors, and bio-matrices, and their use for tissue regeneration and transplantation therapies. The goals of these efforts are to isolate human pluripotent stem cells and to identify the molecular machinery specific for particular lineage-commitments. Complimentary to this goal will be the characterization of these cells using antibodies to cell surface markers and then devising an isolation protocol based on the antibody binding.

We have shown in previous studies the following: (a) clonal populations of pluripotent mesenchymal stem cells can be derived from a variety of organs and tissues of mesodermal origin; (b) pluripotent mesenchymal stem cells have a virtually unlimited doubling capacity without loss of differentiative capabilities; and (c) particular bio-active factors can regulate cell kinetics, proliferation and lineage-progression, as well as commitment of pluripotent mesenchymal stem cells into various mesodermal lineages, i.e., muscle, cartilage, bone, fat, and fibrous connective tissue.

Example 1

Phylogenetic Distribution

At least five species have been examined to date to determine phylogenetic distribution of mesenchymal stem cells (TABLE 1). All species examined, e.g., pre-natal avians (Young et al., 1991, 1992a,b, 1993, 1995, 1998a; Bowerman et al., 1991), pre-natal mice (Klausmeyer et al., 1994; Rogers et al., 1995; Young et al., 1998b), pre- and post-natal rats (Lucas et al., 1994, 1995; Davis et al., 1995; Warejcka et al., 1996), post-natal rabbits (Pate et al., 1993), and pre- and post-natal humans (Young et al., 1999) have resident populations of mesenchymal stem cells. These stem cells have the capability of forming multiple mesodermal phenotypes when incubated in the presence of dexamethasone and/or insulin. To date, 16 separate and readily identifiable cell/tissue phenotypes have been obtained, i.e., skeletal muscle, smooth muscle, cardiac muscle, articular cartilage, growth plate cartilage, hyaline cartilage, elastic cartilage, fibrocartilage, endochondral ossification, intramembranous ossification, scar tissue, dermis, adipocytes, tendon/ligament, periosteum/perichondrium, and endothelial cells.

Age of Donor

Studies are ongoing to determine the optimal age for harvesting progenitor and pluripotent stem cells for transplantation therapies. To date no differences have been found with respect to number of (pluripotent) stem cells present per species, proliferative abilities, or differentiative capabilities when comparing the age of the donor or gender (humans only) (TABLE 1) (Young et al., 1993, 1995, 1998(a), 1998(b), 1999, unpublished observations; Pate et al., 1993; Troum et al., 1993; Lucas et al., 1994, 1995; Davis et al., 1995; Rogers et al., 1995; Warejcka et al., 1996; Calcutt et al., 1998). In all five species examined (chick, mouse, rat, rabbit and human), no age-related differences have been found with respect to the number pluripotent stem cells present per species. No influence of age on the ability to proliferate or on the ability to differentiate has been found. No influence of gender has been found in prenatal in geriatric (human) stem cells.

Stem Cell Location

Analysis of donor sites from the five animal species revealed that any tissue or organ in stasis or undergoing repair and having a connective tissue compartment, has resident populations of mesenchymal stem cells. Organs, tissues and their associated connective tissue components assayed to date include whole embryo, whole fetus, skeletal muscle, dermis, fat, tendon, ligament, perichondrium, periosteum, heart, aorta, endocardium, myocardium, epicardium, large arteries and veins, granulation tissue, peripheral nerves, peripheral ganglia, spinal cord, dura, leptomeninges, trachea, esophagus, stomach, small intestine, large intestine, liver, spleen, pancreas, parietal peritoneum, visceral peritoneum, parietal pleura, visceral pleura, urinary bladder, gall bladder, kidney associated connective tissues and bone marrow (Young et al., 1993, 1995; Pate et al., 1993; Troum et al., 1993; Lucas et al., 1994, 1995; Davis et al., 1995; Rogers et al., 1995; Warejcka et al., 1996; Calcutt et al., 1998; unpublished observations).

An interesting note, while the associated connective tissues of a particular tissue type had its requisite complement of fibrocytes, tissue-specific lineage-committed progenitor stem cells, and pluripotent stem cells, it also contained progenitor stem cells for other tissue lineages (Young et al., 1993, 1995, unpublished observations). For example, the perichondrium surrounding (hyaline) cartilage appeared to be segregated into three zones based on stem cell composition. The inner ⅓ (or cambial layer) contained predominantly chondrogenic progenitor cells and a few pluripotent cells; the middle ⅓ contained predominantly pluripotents, but with a few chondrogenic progenitor cells and a few non-chondrogenic progenitor cells; and the outer ⅓ contained predominantly non-chondrogenic progenitor cells (e.g., myogenic, adipogenic, fibrogenic, and osteogenic progenitor cells), fibrocytes, and a few pluripotent cells. We found similar types of regional stem cell distributions with respect to pluripotent cells, tissue-specific progenitor cells, and non-tissue-specific progenitor cells in skeletal muscle connective tissue (e.g., endomysium, perimysium, epimysium), periosteum, endocardium, and epicardium.

Clonogenic Analysis

Clonogenic analysis by serial limiting dilution was undertaken to determine the composition of cells within the identified populations of mesenchymal stem cells. Clonal analysis of mesenchymal stem cells from avians (Young et al., 1993) and mice (Rogers et al., 1995; Young et al., 1998b) consistently demonstrate two categories of stem cells, e.g., lineage-committed progenitor stem cells and lineage-uncommitted pluripotent stem cells. Five tissue lineages have been induced with general and lineage-specific inductive agents in pre-natal and post-natal pluripotent stem cell clones, e.g., myogenic, chondrogenic, adipogenic, fibrogenic, and osteogenic, with subsequent expression of differentiated phenotypes (Grigoriadis et al., 1988; Young et al., 1993, 1998b, this study; Rogers et al., 1995).

Stem Cell Characteristics

Each category of stem cell, progenitor and pluripotent, have shared characteristics and their own unique characteristics. Both progenitor and pluripotent mesenchymal stem cells prefer a type I collagen substratum for attachment and prefer cryopreservation and storage at −70 to −80° C. in medium containing 10% serum and 7.5% DMSO (Young et al., 1991).

Progenitor stem cells (i.e., precursor stem cells, immediate stem cells, and forming [−blast] cells) are lineage-committed. They will only form tissues within their respective lineage regardless of inductive agents for any other lineage that may be present in the medium (Young et al., 1998a). They can remain quiescent or be activated to proliferate and/or differentiate. They demonstrate contact inhibition at confluence. If activated to proliferate, progenitor stem cells have a 50-70 doubling life span before senescence (Young et al., 1993, 1998b). If activated to differentiate, progression factors are necessary to stimulate phenotypic expression (Young et al., 1998a).

Pluripotent stem cells are lineage-uncommitted, i.e., they are not committed to any particular mesodermal tissue lineage. They can remain quiescent or be activated to proliferate and/or commit to a particular tissue lineage. They have the potential to be induced (by general or lineage-specific inductive agents) to form progenitor stem cells for any tissue lineage within the mesodermal line any time during their life span (Young et al., 1993, 1998a,b, this study; Rogers et al., 1995). If activated to proliferate, they are capable of extended self-renewal as long as they remain lineage-uncommitted. For example, a pre-natal pluripotent mouse stem cell clone retained pluripotency after undergoing 690 cell doublings (Young et al., 1998b). Once pluripotent cells are induced to commit to a particular lineage they assume the characteristics of lineage-specific progenitor cells, i.e., a limited (approx. 50-70) doubling life-span before senescence, contact inhibition at confluence, and the assistance of progression factors to stimulate phenotypic expression (Young et al., 1993, 1998a,b). For example, the 690+ cell doubled pre-natal pluripotent mouse stem cell clone (Young et al., 1998b) was induced to form lineage-specific progenitor cells that formed morphologies exhibiting phenotypic expression markers for skeletal muscle, fat, cartilage, and bone.

Northern Analysis of Expressed mRNAs

We have used Northern blot analysis in studies thus far to examine MMP-induced myogenesis in pluripotent cells. MMP induced the transcription of mRNAs for myogenin and MyoD1 gene expression in pre-natal mouse pluripotent stem cells (Rogers et al., 1995; Young et al., 1998b).

In summary, progenitor and pluripotent mesenchymal stem cells are present in both pre- and post-natal animals. Mesenchymal stem cells can be found in any tissue or organ with a connective tissue component. There is no detectable difference in mesenchymal stem cells from any age or gender. Mesenchymal stem cells are composed of both lineage-committed progenitor stem cells and lineage-uncommitted pluripotent stem cells. Pluripotent mesenchymal stem cells can be extensively propagated without loss of pluripotency. That once committed to a particular tissue lineage as progenitor stem cells, that these stem cells will not revert back to a more primitive differentiative state. That progenitor stem cells have a finite 50-70 doubling life-span before programmed cell senescence. And that particular bioactive factors (either endogenous or exogenously supplied) can genetically regulate the processes of proliferation, lineage-commitment, and lineage-progression.

From these studies we would propose that autologous pluripotent mesenchymal stem cells could be used as HLA-matched donor tissue for mesodermal tissue transplantation, regeneration, and gene therapies, particularly in instances where large numbers of cells are needed and transplant tissues are in short supply.

TABLE 1

AGE OF DONOR TISSUE

| | | | | Human | |
|---|---|---|---|---|---|
| | Avian | Mouse | Rabbit | Rat Male | Female |
| Fetal | + | + | | 22 wk(2) 25 wk | 25 wk |
| New Born | | + | | 7 days, 18 mo. | |
| Adolescent | | + | | 8 yo, 19 yo | 15 yo, 19 yo |
| Adult | + | + | + | + 34 yo, 36 yo, 37 yo, 39 yo, 48 yo | 25 yo, 36 yo, 40 yo |
| Geriatric | | + | | 67 yo | 77 yo |

Materials and Methods

Cell Harvest and Culture

For rat cells, one day-old Sprague-Dawley rat pups were euthanized using $CO_2$ inhalation. The rats were soaked in 70% ethanol for 2 min., brought to a sterile hood, skinned, and the fleshy muscle bellies of the gluteus maximus, gluteus medius, biceps femoris, semimembranosus, semitendinosus, sartorius, quadriceps femoris, soleus, and gastrocnemius muscles were removed. Care was taken to exclude tendons, major blood vessels, and nerves. The muscle tissues, including associated endomysial, perimysial, and epimysial connective tissue compartments, were placed in 10 ml of complete medium and carefully minced. Complete medium consisted of 89% (v/v) Eagle's Minimal Essential Medium with Earle's salts (EMEM) (GIBCO, Grand Island, N.Y.) supplemented with 10% pre-selected horse serum (lot #'s 17F-0218 or 49F-0082, Sigma Chemical Co., St. Louis, Mo.), 1% antibiotic solution (10,000 units/ml penicillin and 10,000 mg/ml streptomycin, GIBCO), pH 7.4 (22). After mincing, the tissue suspension was centrifuged at 50×g for 20 min. The supernatant was discarded and an estimate made of the volume of the cell pellet. The cell pellet was resuspended in 7 volumes of EMEM, pH 7.4, and 2 volumes of collagenase/dispase solution to release the cells by enzymatic action (Lucas et al., 1995). The collagenase/dispase solution consisted of 37,500 units of collagenase (CLS-I, Worthington Biochemical Corp., Freehold, N.J.) in 50 ml of EMEM added to 100 ml dispase solution (Collaborative Research, Bedford, Mass.). The final concentrations were 250 units/ml collagenase and 33.3 units/ml dispase (Young et al., 1995). The resulting suspension was stirred at 37° C. for 1 hr to disperse the cells and centrifuged at 300×g for 20 min. The supernatant was discarded, and the tissue pellet resuspended in 20 ml of MSC-1 medium. The cells were sieved through 90 mm and 20 mm Nitex filters (Tetco Inc., Elmsford, N.Y.) to obtain a single cell suspension. The cell suspension was centrifuged at 150×g for 10 min., the supernatant discarded, and the cell pellet resuspended in 10 ml of complete medium. Cell viability was determined by Trypan blue exclusion (Young et al., 1991). Cells were seeded at $10^5$ cells per 1% gelatinized (EM Sciences, Gibbstown, N.J.) 100 mm culture dish (Falcon, Becton-Dickinson Labware, Franklin Lakes, N.J.). Cell cultures were propagated to confluence at 37° C. in a 95% air/5% $CO_2$ humidified environment. At confluence the cells were released with trypsin and cryopreserved. Cells were slow frozen (temperature drop of 1 degree per minute) in complete medium containing 7.5% (v/v) dimethyl sulfoxide (Sigma) until a final temperature of −80° C. was reached (Young et al., 1991). Comparable procedures were used for isolation of human, rabbit, avian and mouse, with the origin material differing according to the species.

Clonogenic Analysis

Aliquots of frozen cells were thawed and resuspended in complete medium. The cell suspension was centrifuged, the supernatant discarded, and the cell pellet resuspended in complete medium. The viability of the cells was determined by Trypan blue exclusion. The cells were then seeded at $10^5$ cells per gelatinized 100 mm dish and grown to confluence. Cells were released with trypsin and cryopreserved to −80° C. in complete medium containing 7.5% (v/v) dimethyl sulfoxide (DMSO, Morton Thiokol, Danvers, Mass.).

Preconditioned Medium

Previous cloning studies with prenatal chicks (Young et al., 1993) and prenatal mice (Rogers et al., 1995; Young et al., 1998b) revealed that a higher efficacy of cloning could be achieved if individual cells were grown in medium "pre-conditioned" by highly proliferating cells of the same parental line. Therefore, each time the stem cells were harvested at confluence, during log-phase growth, the culture medium was pooled, filtered twice through 0.2 mm filters, divided into aliquots, and stored at 4° C. The resulting "preconditioned medium" was used during the cloning portion of this study.

Propagation Past 50 Cell Doublings

Previous cloning studies in prenatal mice (Rogers et al., 1995; Young et al., 1998b) revealed that a higher efficacy of cloning could be achieved if cells were propagated past 50 cell doublings prior to cloning. When such stem cells were incubated with insulin less than 1% of the cells displayed phenotypic markers for differentiated cells of the various mesodermal lineages. These observations suggested that a majority of the progenitor stem cells were removed from the population by propagating the cells for more than 50 cell doublings prior to cloning. Presumably propagating the cells past the 50 cell doubling Hayflick's limit caused the lineage-committed stem cells to undergo programmed cell senescence and death (Hayflick, 1963, 1965; Young, 1999a).

The standard protocol of thawing cryopreserved cells, culturing to confluence, collecting pre-conditioned medium during log-phase growth, releasing the cells with trypsin, and subjecting them to cryopreservation was repeated until the stem cell population had undergone a minimum of 50 cell doublings. In this study larger-sized cells (with high ratios of cytoplasm to nuclei) were observed to undergo apoptosis between 40 and 50 cell doublings. The majority of the cells remaining after 50 cell doublings were of smaller size, with smaller ratios of cytoplasm to nuclei. Aliquots of cells propagated for more than 50 doublings were cryopreserved for cloning.

Cloning

Frozen aliquots of cells propagated for more than 50 doublings were thawed, grown to confluence, released with trypsin, and centrifuged. The supernatants were discarded, cell pellets resuspended, and the viability of the cells determined. Cells were diluted to clonal density (1 cell per 5 ml) with cloning medium (Young et al., 1993, 1998b; Rogers et al., 1995). Cloning medium was prepared by mixing equal volumes of complete medium and preconditioned medium. Five microliters of cell suspension was placed into the center of each well of gelatinized 96-well plates (Costar, Curtain-Matheson Scientific, Atlanta, Ga.) and incubated at 37° C. After six hr an additional 200 ml of cloning medium were added to each well. Eighteen hr after initial seeding the number of cells per well was determined. Only those wells having a single cell were allowed to propagate further. The medium was removed from all other wells. These wells were incubated with 70% (v/v) ethanol for 5 min., and dried in room air. 200 ml of sterile Dulbecco's Phosphate Buffered Saline (DPBS, GIBCO), pH 7.4, containing 0.03% (w/v) sodium azide were added to retard contaminant growth (Rogers et al., 1995; Young et al., 1998b).

For those wells allowed to propagate further, the initial cloning medium was replaced with fresh cloning medium after 10 or more cells appeared within the wells. Cloning medium replacement thereafter was dependent on the percentage of confluence of the cultures, with a maximum of a five day lapse between feedings. Cultures were allowed to grow past confluence. Each culture was released with trypsin, plated in toto into a well of gelatinized 6-well plates (Falcon), fed complete medium every other day, and allowed to grow past confluence. Cultures were released with trypsin and cryopreserved for a minimum of 24 hr. The process of seeding at clonal density in 96-well plates in cloning medium, propagation through confluence, trypsin release, propagation through confluence in 6-well plates in complete medium, culture selection, trypsin release, and cryopreservation was repeated three times after initial cloning to ensure that each isolated clone was derived from a single cell. The resultant clones were propagated, released with trypsin, aliquoted, and cryopreserved (Young et al., 1993, 1998b; Rogers et al., 1995).

Insulin-Dexamethasone Analysis for Phenotypic Expression

Clones were examined using insulin and dexamethasone to determine their identity, i.e., either lineage-committed progenitor cells or lineage-uncommitted pluripotent cells. Progression factors, such as insulin, accelerate phenotypic expression in progenitor cells but has no effect on the induction of phenotypic expression in pluripotent stem cells. By contrast, lineage-induction agents, such as dexamethasone, induce lineage-commitment and expression in pluripotent cells, but does not alter phenotypic expression in progenitor cells. Therefore, if progenitor cells alone are present in the culture there will be no difference in either the quality or quantity of expressed phenotypes for cultures incubated in insulin compared with those incubated with dexamethasone. If the culture is mixed, containing both progenitor and pluripotent cells, then there will be a greater quality and/or quantity of expressed phenotypes in cultures treated with dexamethasone compared with those treated with insulin. If the culture contains pluripotent cells alone, there will be no expressed phenotypes in cultures treated with insulin. Similar cultures treated with dexamethasone will exhibit multiple expressed phenotypes. Thus comparing the effects of treatment with dexamethasone and insulin can identify specific types of progenitor and pluripotent cells within an unknown group of cells (Young et al., 1992, 1993, 1995, 1998a,b, 1999a-c; Lucas et al., 1993, 1995; Pate et al., 1993; Rogers et al., 1995; Warejcka et al., 1996).

Cryopreserved clones were thawed and plated in complete medium at 5, 10, or $20 \times 10^3$ cells per well of gelatinized 24-well plates or 0.5 or $1.0 \times 10^3$ cells per well of 96 well plates following the standard protocol. Twenty-four hours after initial plating the medium was changed to testing medium (TM) 1 to 4 (TM-1, TM-2, TM-3, TM-4) or 5 (TM-5). TM-1 to TM-4 consisted of Ultraculture (cat. no. 12-725B, lot. nos. OMO455 [TM-1], 1M1724 [TM-2], 2M0420 [TM-3], or 2M0274 [TM-4], Bio-Whittaker, Walkersville, Md.), EMEM1, and 1% (v/v) antibiotic solution (10,000 units/ml of penicillin, and 10,000 mg/ml of streptomycin, GIBCO), pH 7.4. TM-5 consisted of 98% (v/v) EMEM, 1%, 3%, 5% or 10% (v/v) HS (HS4, HS7, or HS9), and 1% (v/v) antibiotic solution, pH 7.4. Testing medium containing ratios of Ultraculture: EMEM: antibiotics which maintained both avian progenitor and pluripotent cells in "steady-state" conditions for a minimum of 30 days in culture, and as long as 120 days in culture. Four testing media (TM#'s 1-4), each containing various concentrations of Ultraculture, were used as noted in the Experimental Procedures. The ratios of Ultraculture to EMEM to antibiotics present in each testing medium was determined empirically for each lot of Ultraculture, based on its ability to maintain steady-state culture conditions in both populations of avian progenitor and pluripotent cells. The four Ultraculture-based testing media were: TM#1=15% (v/v) Ultraculture (Lot no. OMO455): 84% (v/v) EMEM: 1% (v/v) antibiotics; TM#2=15% (v/v) Ultraculture (Lot no. 1M1724): 84% (v/v) EMEM: 1% (v/v) antibiotics; TM#3=50% (v/v) Ultraculture (Lot no. 2M0420): 49% (v/v) EMEM: 1% (v/v) antibiotics; and TM#4=75% (v/v) Ultraculture (Lot no. 2M0274): 24% (v/v) EMEM: 1% (v/v) antibiotics.

Pre-incubation for 24 hr in testing medium alone was used to wash out any potential synergistic components in the complete medium. Twenty-four hours later the testing medium was changed to one of the following. For controls, testing medium alone was used. To identify clones of progenitor cells, the medium was replaced with testing medium (TM-1 to TM-5) containing 2 µg/ml insulin (Sigma), an agent that accelerates the appearance of phenotypic expression markers in progenitor cells (Young et al., 1998a). To identify clones of pluripotent cells, the medium was replaced with testing medium (TM-1 to TM-5) containing $10^{-10}$ to $10^{-6}$ M dexamethasone (Sigma), a general non-specific lineage-inductive agent (Young et al., 1993, 1998a). Control and treated cultures were propagated for an additional 30-45 days with medium changes every other day. Four culture wells were used per concentration per experiment. During the 0-45 day time period the cultures were examined (subjectively) on a daily basis. Alterations in phenotypic expression (see below) were correlated with the days of treatment, and associated insulin or dexamethasone concentrations. The experiment was then repeated utilizing these parameters to (objectively) confirm the phenotypic expression markers using established immunochemical and histochemical procedures (Young et al., 1992a,b, 1993, 1995, 1998a, b, 1999). The cells were photographed using a Nikon TMS inverted phase contrast/brightfield microscope.

Cultures that displayed multinucleated linear and branched structures that spontaneously contracted were further evaluated using a myosin-enzyme linked immunoculture assay (myosin-ELICA) to verify the presence of sarcomeric myosin within putative skeletal muscle cells (Young et al., 1992a,b, 1999). Cultures that exhibited multiple refractile vesicles were further evaluated using Sudan black-B (Roboz Surgical Co., Washington, D.C.) staining to verify the presence of saturated neutral lipids within putative adipocytes (Young et al., 1993, 1995; Young, 1999a). Cultures that displayed aggregates of rounded cells containing pericellular matrix halos were further evaluated using Alcian Blue (Alcian Blau 8GS, Chroma-Gesellschaft, Roboz Surgical Co.) at pH 1.0 coupled with chondroitinase-AC (ICN Biomedicals, Cleveland, Ohio)/keratanase (ICN Biomedicals) digestions to verify the presence of chondroitin sulfate/keratan sulfate glycosaminoglycans located in the pericellular and/or extracellular matrix surrounding putative chondrocytes (Young et al., 1989a, 1993, 1995; Young, 1999). Cultures that exhibited cells embedded within and/or overlain with a three-dimensional matrix were further evaluated using von Kossa (Silber Protein, Chroma-Gesellschaft) staining coupled with EGTA (Ethyleneglycol-bis-[b-Aminoethyl ether]N, N, N',N'-tetraacetic acid, Sigma) pre-treatment to verify the presence of calcium phosphate within putative mineralized bone spicules (Young et al., 1989a, 1993, 1995). Cultures displaying confluent layer(s) of cells embedded within either a granular or fibrillar extracellular matrix were further evaluated using Alcian Blue pH 1.0 staining coupled with chondroitinase-ABC (ICN Biomedicals) digestion to verify the presence of extracellular chondroitin sulfate/dermatan sulfate glycosaminoglycans surrounding putative fibroblasts (Young et al., 1989a, 1993, 1995; Young, 1999).

Example 2

Isolation of a Population of Pluripotent Mesenchymal Stem Cells from Adult Rat Marrow It is known that marrow stroma contains cells capable of differentiating into osteoblasts and chondrocytes. Marrow stroma has also been postulated to contain a population of pluripotent cells capable of forming other phenotypes. We have shown that cells capable of differentiating into a number of mesenchymal phenotypes, which we call mesenchymal stem cells (MSCs), can be isolated from rat skeletal muscle. We have applied these same techniques to determine if MSCs also reside in the stromal tissue of adult rat bone marrow. Bone marrow from 7 weeks old male rats was harvested and the adherent cells were cultured to confluence in EMEM+10% pre-selected horse serum, then trypsinized, filtered, and slowly frozen in 7.5% DMSO to $-80°$ C. The cells were thawed, plated in the above media and treated with concentrations of dexamethasone ranging from $10^{-10}$ to $10^{-6}$ M for up to 5 weeks. Phenotypes observed included skeletal myotubes (anti-myosin), smooth muscle (anti-smooth muscle $\alpha$-actin), bone (Von Kossa's stain), cartilage (Alcec blue, pH 1.0), and fat (Sudan black B). Marrow contains stem cells other than osteoprogenitor cells.

The first individual to discover osteogenic stem cells in marrow stroma was Friedenstein (Friedenstein, 1976). Subsequent work by a number of labs confirmed the existence of committed osteogenic precursor cells in marrow (Urist, 1989; Beresford, 1989; Beresford et al., 1994; Johnson et al., 1998; Bab et al., 1984) and their use in the repair of orthotopic defects (Ohgushi et al., 1989; Paley et al., 1986; Grundel et al., 1991). However, later Friedenstein described two populations of osteogenic cells in marrow stroma (Friedenstein, 1995). One population Friedenstein termed Determined Osteogenic Precursor Cells (DOPCs) and the second were Induced Osteogenic Precursor Cells (IOPCs). The DOPCs were committed to becoming osteoblasts, but the IOPCs were not so committed and had to be induced by some exogenous signal to differentiate into osteoblasts. Experiments using demineralized bone matrix to supply the osteogenic signal supported the the existence of IOPCs in marrow stroma (Bleiberg, 1985; Burwell, 1985; Lindhold et al., 1982; Lindholm, 1980; Green et al., 1986; Paley et al., 1986; Grundel et al., 1991; strates et al., 1989; Kataoka et al., 1993; Theis et al., 1992).

Subsequent cloning experiments of marrow stromal cells by Owen and others (Ashton, et al., 1984; Owen et al., 1987; Vitamitjana et al., 1993; Gronthos et al., 1994) led to the the discovery that there were cells in marrow stroma that could differentiate into fibroblasts, adipocytes, chondrocytes, and osteoblasts. Owen then proposed that marrow stroma contained pluripotent mesenchymal stem cells (Locklin et al., 1995; Owen et al., 1988; Owen, 1988).

We have isolated a population of cells from embryonic chick skeletal muscle (Young et al., 1991; Young et al., 1992a), neonatal rat skeletal muscle (Lucas et al., 1995], neonatal rat heart and adult rabbit skeletal muscle that is capable of differentiating into several mesodermal phenotypes in culture: skeletal muscle, adipocytes, chondrocytes, osteoblasts, fibroblasts, smooth muscle cells, and endothelial cells. We have termed these cells pluripotent mesenchymal stem cells. The present study was undertaken to determine if a similar population of cells is present in adult rat marrow.

Materials and Methods

Cell Culture:

The procedures used for isolating cells from whole marrow are essentially identical to those first described by Friedenstein (Friedenstein, 1976). Long bones were removed from 6-8 week old rats, the ends cut off, and the marrow flushed out by injecting Eagle's Minimal Essential Media with Earle's salts (EMEM) (GIBCO, Grand Island, N.Y.) supplemented with 10% pre-selected horse serum and 1% antibiotics (Fungizone, GIBCO) through an 18 gauge needle. The marrow cells were dissociated by repeated trituration through successively smaller needles, culminating in a 22 gauge needle.

The dissociated cells were filtered through 20 μM Nitex filters to obtain a preparation of single cells. The cell number was determined with a hemocytometer and the cells, which included hematopoietic as well as stromal cells, were plated at $10^7$ cells per 100 mm culture dish. The dishes had been precoated with 1% bovine gelatin (EM Sciences, Cherry Hills N.J.)

After 24 hr. in culture, the non-adherent cells were removed and the media replaced with culture media described above. From this point forward procedures used were indentical to the isolation and assay previously described. Briefly, adherent marrow cells were cultured until confluent. The cells were The cultures were released from the dish with 0.025% trypsin in Dulbecco's Phosphate Buffered Saline (DPBS) with 0.01% ethylenediaminetetraacetic acid (EDTA) and filtered through a 20 µm filter. These cells were then frozen in aliquots of 1 ml containing $10^6$ cells in EMEM+10% horse serum and 7.5% DMSO (Sigma). Cryopreservation was performed in freezing chambers (Fisher Scientific, Norcross, Ga.) to slow freeze the cells to $-80°$ C.

After being frozen for at least 24 hours, aliquots of the frozen cells were thawed and plated at a density of 20,000 cells per 16 mm well in 24-well gelatin-coated culture plates (Corning Glass Works, Corning, N.Y.) in EMEM+10% horse serum and antibiotics. These cells were designated as secondary cultures. Some wells were maintained in the same media to allow for a control group, while the experimental wells, beginning on day 1 in culture, were treated with the media supplemented with dexamethasone (Sigma) at concentrations ranging from $10^{-10}$M to $10^{-6}$M for up to 5 weeks. At one week intervals during culture, cultures were fixed and assayed for phenotypes as described below.

Assays for Phenotypes:
1. Mineralized Tissue. The presence of calcified tissue was assayed by Von Kossa's staining of calcium phosphate essentially as described by Humason (Humason, 1972). Briefly the culture medium was removed and the plates rinsed twice with DPBS. The cells were fixed with 0.5 ml of 10% formalin (Sigma) for 3 to 5 minutes, then rinsed four times with distilled water. Then 0.5 ml of freshly prepared 2% silver nitrate (Sigma) solution was added and the cells were incubated in the dark for ten minutes. Following incubation, the silver nitrate solution was removed and the cells rinsed five times with distilled water. Approximately 0.5 ml of distilled water was left on each well. The plate was exposed to bright light for 15 minutes with a white background underneath it to reflect light. The plates were again rinsed five times with distilled water and then dehydrated quickly with 100% ethanol. The plates were made permanent with glycerine jelly (Young et al., 1991). Confirmation of the presence of calcium phosphate was performed by pre-treating selected cultures with 1% w/v [ethylene bis(oxyethylenenitrilo)]-tetraacetic acid (EGTA) (Sigma), a specific calcium chelator, in $Ca^{2+}$, $Mg^{2+}$-free buffer for 1 hr prior to incubation in the silver nitrate solution.
2. Cartilage. Cultures were stained with Alcian blue (Roboz Surgical Instrument, Rockville, Md.), pH 1.0. The fixed wells were stained with 0.5 ml Alcian blue, pH 1.0, for 30 minutes, then removed from the wells. Unbound stain was removed by rinsing the wells seven times with tap water or distilled water. The cultures were preserved under glycerine jelly.
3. Fat. Sudan black B (Asbey Surgical Co., Washington, D.C.) staining for saturated neutral lipid (Humason, 1972) was performed in the following manner: All media was aspirated from the culture wells and each well was washed twice with one ml of DPBS. Then 0.5 ml of 70% ETOH was added to break cell membranes. After one minute, the alcohol was aspirated and the wells washed twice with DPBS. The cells were then incubated twice for 5 minutes in 100% propylene. Next, the cells were incubated twice for 10 minutes with 0.5 ml of Sudan black B per well. Stain differentiation was performed by rinsing the cells repeatedly with 0.5 ml of each of the following solutions until each solution was clear: Propylene:Water 90:10, 85:15, and 70:30. The cells were washed twice for one minute using distilled water, then made permanent with glycerine jelly.
4. Muscle. The cells were stained with the MF-20 antibody to skeletal muscle myosin (Hybridoma Bank, Ames, Iowa) using a modified procedure of Young et al (Young et al., 1992b). Each step is preceded by 2 rinses with DPBS unless noted. After another rinse, 0.5 ml of cold methanol ($-20°$ C.) was applied for 5 minutes to fix the cells. This was followed by a 5 minute incubation with 0.5 ml of 1% v/v Triton-X100/0.05% w/v sodium azide in DPBS to solubilize cell membranes and inhibit endogenous peroxidases, respectively. A primary blocker of 20% goat serum was applied for 30 minutes in a 37° C. incubator. The primary IgG at 1:200 dilution of MF-20 (0.4 ml/well) was then incubated for 1 hour. A secondary blocker of 0.5 ml of 20% goat serum was applied for 30 min and was followed by 0.4 ml of 1:7500 dilution of biotinylated goat anti-mouse IgG (Leinco, St. Louis, Mo.), also incubated for 30 minutes at 37° C. A tertiary blocker, consisting of 20% goat serum, was applied for 30 min and removed, then 0.4 ml of 1:3750 dilution of Streptavidin-horseradish peroxidase (Leinco) was added and incubated at 37° C. for 30 minutes. At this point the cells were rinsed and 0.5 ml of ABTS-peroxidase substrate (Kirkegaard and Perry Labs, Gaithersburg, Md.) was added for 30 minutes incubation at ambient temperature in the dark. After incubation, 200 µl of ABTS solution was removed from the cells and placed in a well of a 96-well ELISA plate (Falcon) containing 10 µl of 0.03% sodium azide. The ELISA plate was read on a Titer Tek spectrophotometric plate reader using a 405 nm filter.

After the aliquot of ABTS solution had been removed, the cells were rinsed twice with 0.5 ml DPBS, then twice with 0.5 ml distilled water Chromagen (Sigma) was added as per the instructions in the staining kit to selected wells for future photography. Once the color developed, 25 µl of 0.05% sodium azide was added per well to stop the reaction. The wells were then rinsed and made permanent with glycerine jelly.

The ABTS was removed from the remaining wells and DNA content analyzed using the in situ diaminobenzoic acid (DABA) procedure of Johnson-Wint and Hollis (Johnson-Wint and Hollis, 1982) as previously described. Thus, the absorbance for the myosin content and the DNA content were obtained on the same wells.
6. Smooth Muscle. Smooth muscle was assayed by staining with an antibody to smooth muscle a-actin using a kit from Sigma.
7. Endothelial Cells. Endothelial cells were identified by their ability to take up low density lipoprotein as described by Voyta et al. (Voyta et al., 1984). Cells were washed 5 times with Dulbecco's Minimal Essential Medium (high glucose) (DMEM) (GIBCO) supplemented with antibiotics. The cells were incubated for 4 hr. at 37° C. with 10 µg per ml of 1,1'-dioctadecyl-3, 3,3',3'-tetramethyl-indocarbocyanine perchlorate (DiI-Acyl-LDL) (Biomedical Technology, Stoughton, Mass.). The wells were then washed 6 times with EMEM+10% horse serum and viewed on a Nikon Diaphot with fluorescent attachment.

Results

Figure 1A:
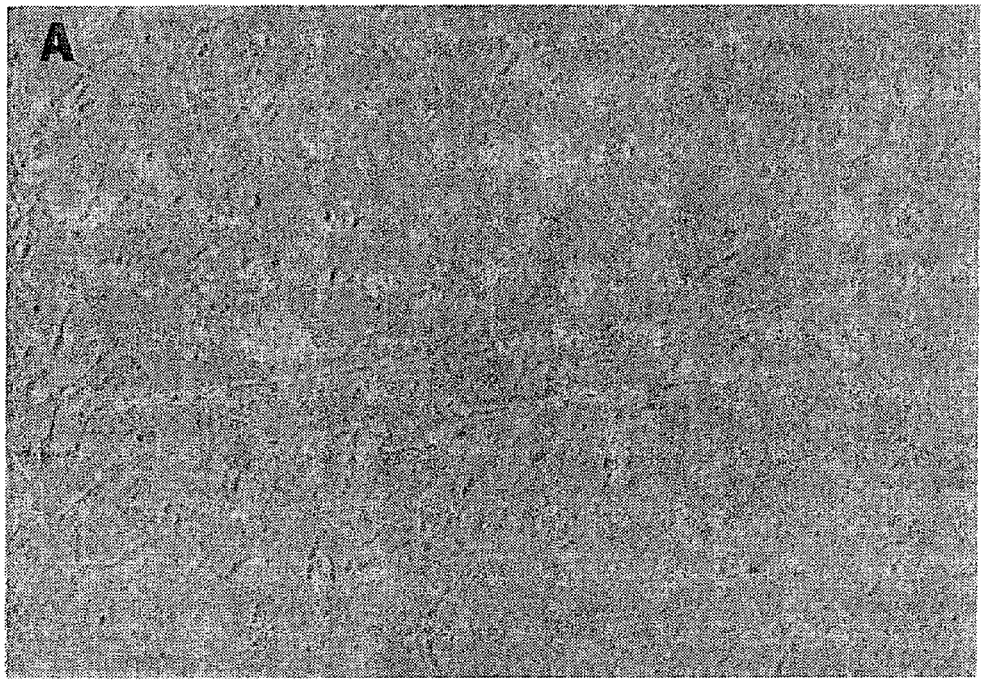
FIGS. 1A and B A. Cells isolated from adult rat marrow in primary culture 6 days after isolation. Phase contrast, 100×. Note cells in straight lines. B. Same as A. Phase contrast, 200×.
Figure 1B:
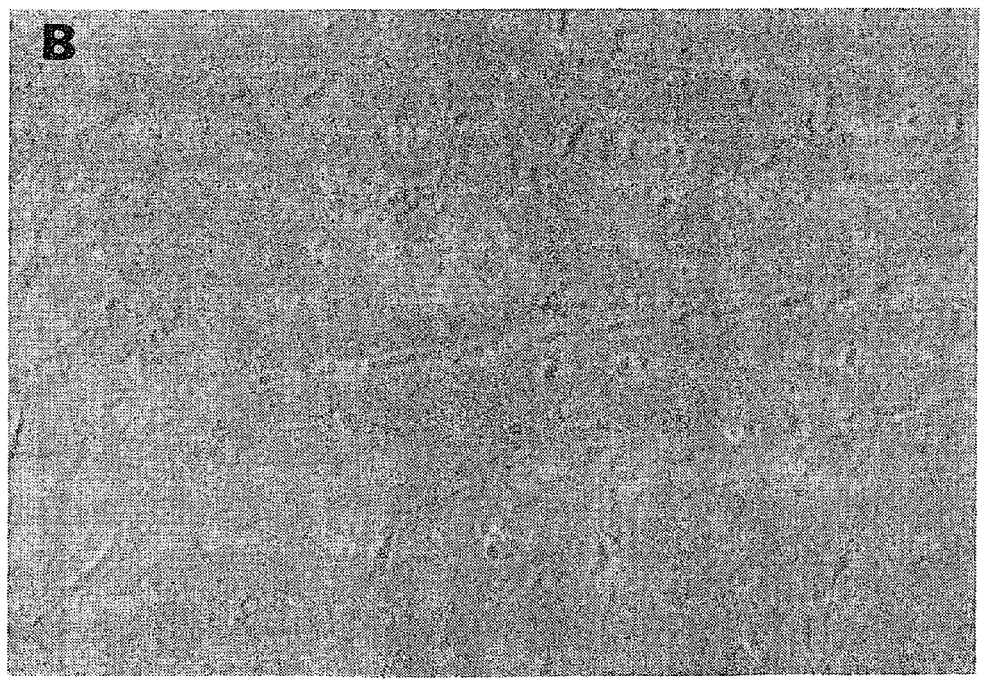

Most of the cells isolated from whole marrow were hematopoietic cells that did not adhere to the culture dish. These were removed on day 1 of culture when the media was changed. By day 6 the cultures consisted of mostly adherent cells with a stellate shape (FIGS. 1A and 1B). There were occasional clumps of cells where small, round, very refractile cells seemed to be attached to stellate cells that were, in turn, attached to the culture dish. However, the most striking feature of the cultures were the cells that were arranged in straight lines. The lines often were measured at greater than 60 mm long, nearly spanning the 100 mm culture dishes. Since the collagen was applied with a brush in a circular pattern, it is unlikely that the cells are following lines of dried collagen. The cells in a straight line appeared to have other cells attached to them. It was noted that there was a continual supply of floating cells in the media of the primary marrow cell cultures. This is in contrast to cultures from skeletal muscle and heart, where there are no floating cells after first attachment.

Figure 2A:
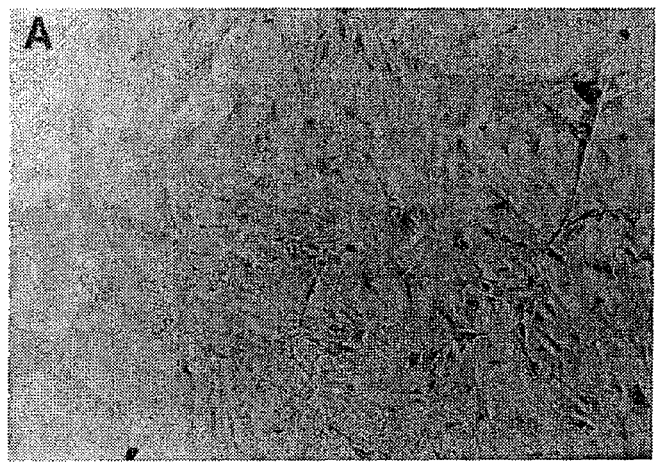
FIG. 2A-C A. Cells isolated from adult rat marrow, secondary culture, 35 days in culture. Controls. Stained with an antibody to α-myosin. Phase contrast, 100×. B. Cells isolated from adult rat marrow, secondary culture, 35 days in culture treated with $10^{-7}$ M dexamethasone. Stained with an antibody to α-myosin. Phase contrast, 200×. Arrows point to multinucleated myotubes. C. Cells isolated from adult rat marrow, secondary culture, 35 days in culture treated with $10^{-8}$ M dexametasone. Stained with an antibody to α-smooth muscle actin. Bright field, 200×. sm=smooth muscle.

After trypsin release, filtration, freezing, thawing, and replating into secondary cultures, the lines of cells were no longer present. On average, 80% of the cells survived the freeze-thaw, which is in accord with the data obtained for cells isolated from skeletal muscle and heart (Lucas et al., 1995; Warejecka et al., 1996). The cells in the secondary culture that do not receive dexamethasone are nearly uniformly stellate-shaped cells (FIG. 2A). These cells did not exhibit any phenotype even after 5 weeks in secondary culture and were negative for all the phenotypic assays.

Figure 2B:
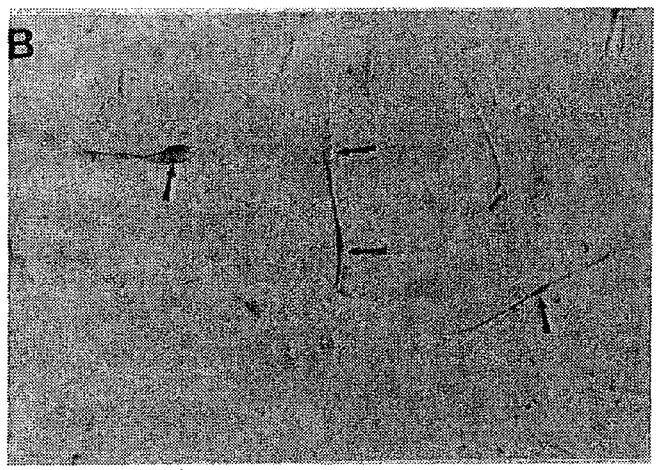
Figure 2C:
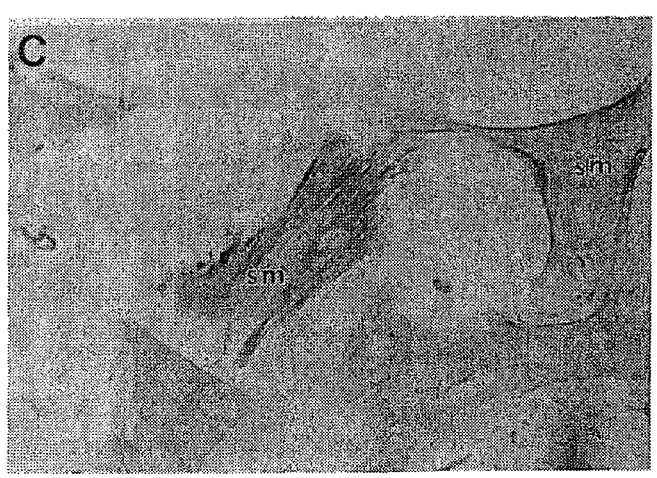
Figure 3A:
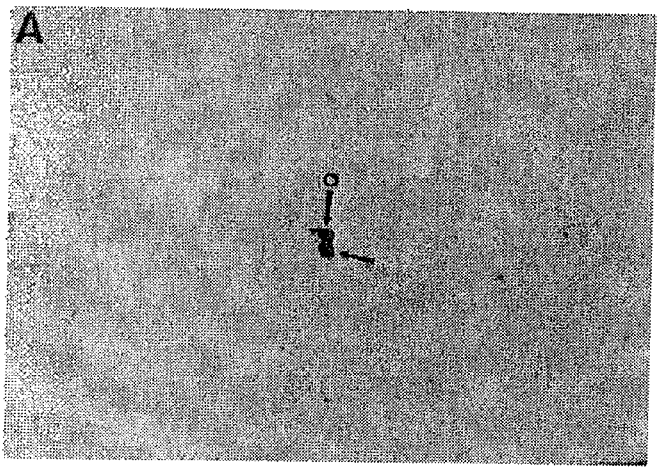
FIG. 3A-C A. Cells isolated from adult rat marrow, secondary culture, 35 days in culture treated with $10^{-8}$ M dexamethasone. Stained with Alcian blue, pH 1.0. Bright field, 100×. Arrows point to cartilage nodules. B. Cells isolated from adult rat marrow, secondary culture, 35 days in culture treated with $10^{-8}$ M dexamethasone. Stained with Alcian blue, pH 1.0. Bright field, 200×. c=cartilage. A small myotube can be seen just below the cartilage nodule. C. Cells isolated from adult rat marrow, secondary culture, 35 days in culture treated with $10^{-9}$ M dexamethasone. Stained with Von Kossa's. Bright field, 200×. Arrow points to mineral in the cartilage nodule.
Figure 3B:
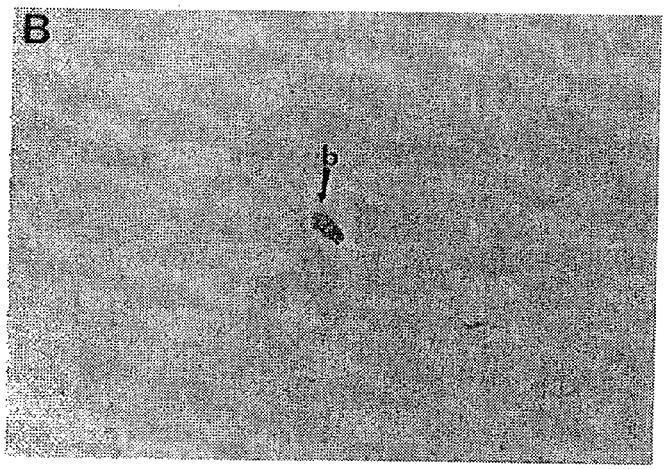
Figure 3C:
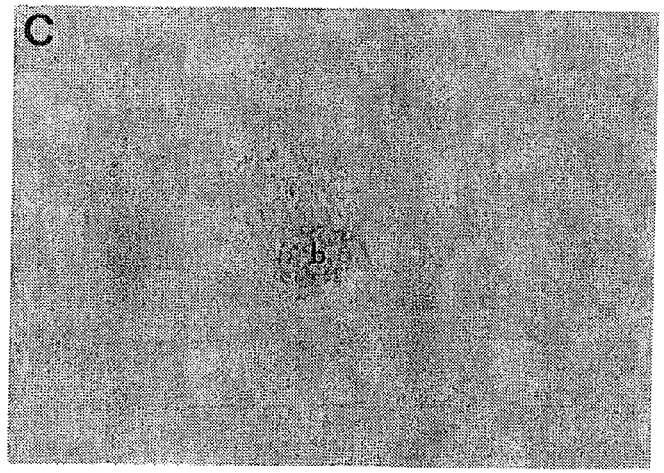

However, treatment with dexamethasone elicited the expression of a number of phenotypes. As in the cultures isolated from skeletal muscle and heart, there was a definite order of appearance of phenotypes in time and in the various dexamethasone concentrations. Multinucleated cells that spontaneously contracted in culture also appeared between one and two weeks in culture at dexamethasone concentrations ranging from $10^{-9}$ to $10^{-6}$ M. The multinucleated cells stained with an antibody to myosin, confirming their identity as myotubes (FIG. 2B). By 4 weeks of treatment with dexamethasone, cells of roughly parallelogram shape containing fibers were observed. These cells were most numerous at $10^{-7}$ and $10^{-6}$ M dexamethasone. The fibers stained with an antibody to smooth muscle α-actin and were identified as smooth muscle cells (FIG. 2C). After three weeks in culture small collections of very rounded cells, all of similar size, with a refractile extracellular matrix appeared in the wells treated with $10^{-9}$ to $10^{-6}$ M dexamethasone. These aggregates, which stained with Alcian blue at pH 1.0, were tentatively identified as chondrocytes (FIG. 3A-C). Some of the cartilage nodules had very dark areas when viewed under phase contrast. These dark areas stained with Von Kossa's, indicating the presence of mineral. These nodules may represent calcified cartilage.

Figure 4A:
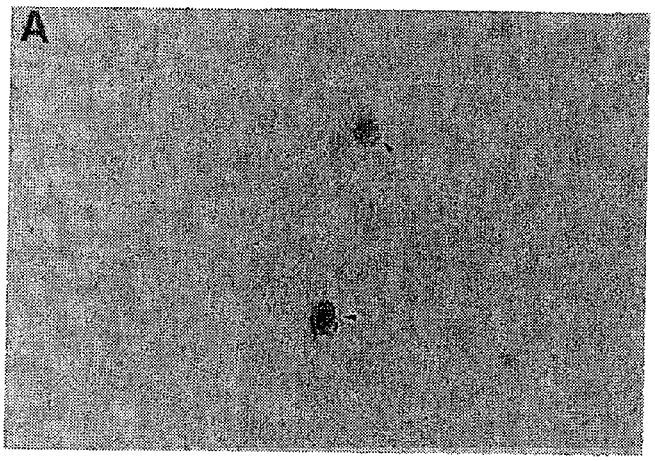
FIG. 4A-C A. Cells isolated from adult rat marrow, secondary culture, 35 days in culture treated with $10^{-8}$ M dexamethasone. Stained with Sudan Black B. Bright field, 200×. a=adipocyte. B. Cells isolated from adult rat marrow, secondary culture, 35 days in culture treated with $10^{-10}$ M dexamethasone. Stained with Von Kossa's. Bright field, 200×. b=bone. C. Cells isolated from adult rat marrow, secondary culture, 35 days in culture treated with $10^{-9}$ M dexamethasone. Stained with Von Kossa's but pretreated with EGTA. Bright ield, 200×. b=bone.
Figure 4B:
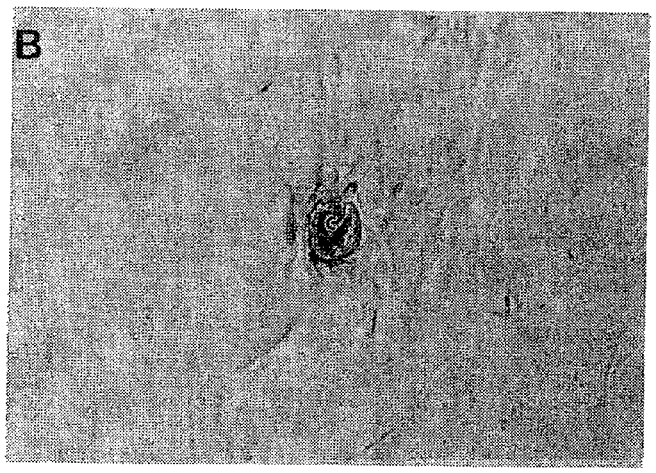
Figure 4C:
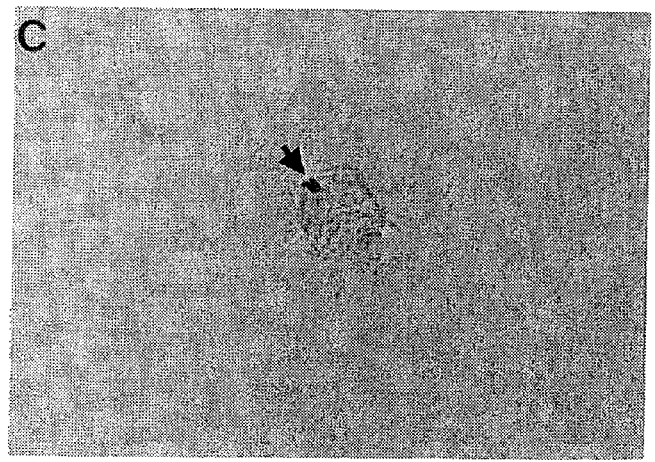
Figure 5A:
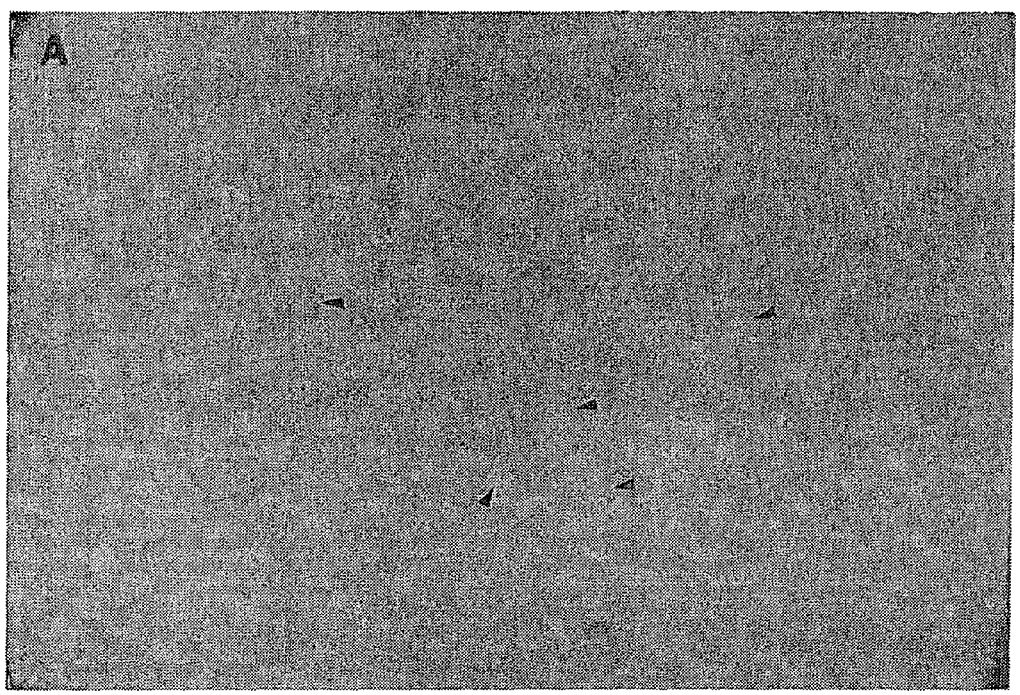
FIGS. 5A and B A. Cells isolated from adult rat marrow, secondary culture, 35 days in culture treated with $10^{-6}$ M dexamethasone. Cells incubated with rhodamine-labeled acylated low density lipoprotein. Phase contrast, 100×. Arrows point to cells stained in B. B. Same cells as A photographed under fluorescence.
Figure 5B:
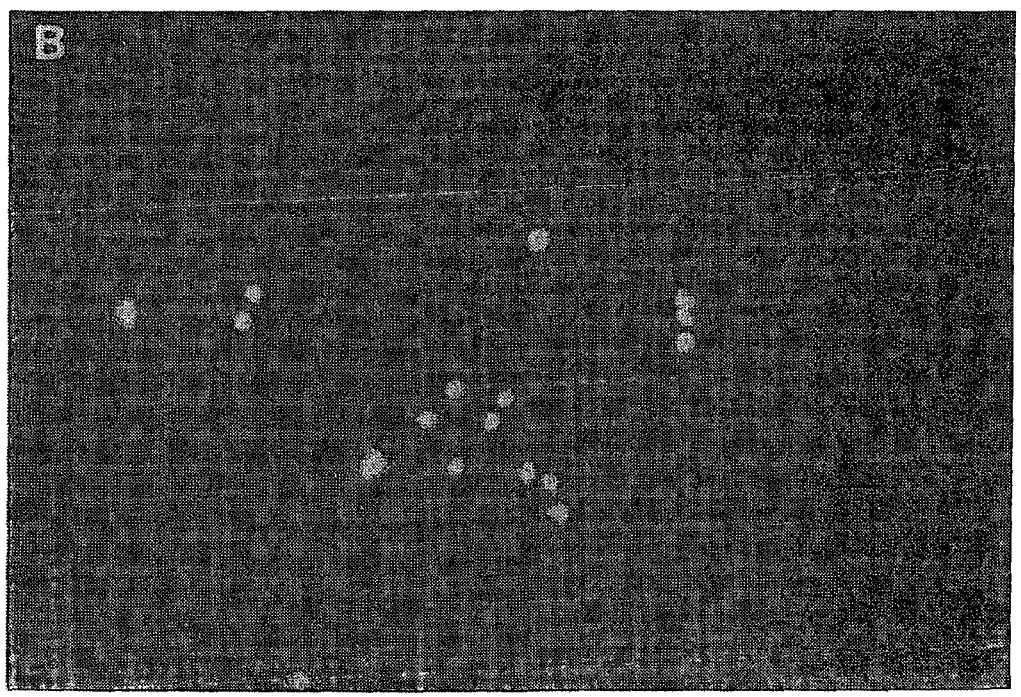

From approximately two weeks, cultures treated with $10^{-8}$ through $10^{-6}$ M dexamethasone contained cells with large vesicles of varying sizes which were refractile in appearance under phase contrast microscopy. These cells stained with Sudan black B stain, indicating the presence of saturated neutral lipids, and have thus been identified as adipocytes (FIG. 4A). These cells did not stain with antibodies to myosin or smooth muscle α-actin. However, in general the number of adipocytes was less in marrow cultures than in cultures isolated from skeletal muscle. Cell aggregates of polygonal cells appeared after four weeks in culture. They were most common in the wells treated with $10^{-9}$ to $10^{-10}$ M dexamethasone but appeared in small numbers at all concentrations of dexamethasone. These cells had a dense extracellular matrix that appeared quite dark under phase contrast microscopy, and the matrix stained with Von Kossa's stain (FIG. 4B). The staining could be prevented by pre-treatment with EGTA (FIG. 4C). All of this indicated a calcified extracellular matrix. Therefore these cells were identified as osteoblasts. Also by 4 weeks of treatment with dexamethasone, cells of polygonal shape but without discernible extracellular matrix appeared in the $10^{-7}$ and $10^{-6}$ M dexamethasone cultures. These cells took up DiI-Acyl-LDL into cytoplasmic vesicles (FIGS. 5A and B) and have thus been identified as endothelial cells. The incubation period with DiI-Acyl-LDL was limited to 4 hr., and the smooth muscle cells did not exhibit staining (data not shown). Finally, areas of spindle-shaped cells that grew in swirl patterns and had agranular matrix that stained lightly with Alcian blue, pH 1.0 appeared at $10^{-10}$ to $10^{-8}$ M dexamethasone treatment (data not shown). On the basis of the morphology and staining pattern, the cells were tentatively identified as fibroblasts.

Discussion

We were able to isolate a population of cells from bone marrow that responded to dexamethasone treatment by differentiating into a number of phenotypes in a manner nearly identical to cells obtained from skeletal muscle and heart. The primary cultures were not identical to primary cultures isolated from muscle and heart, however. This is not surprising, since each tissue contains a unique complement of differentiated cells and their immediate precursors. Primary cultures from skeletal muscle contained differentiated multinucleated myotubes while primary cultures from heart contained cardiac myocytes (Lucas et al., 1995; Warejecka et al., 1996). Both these phenotypes were absent from primary marrow cultures [FIG. 1]. However, primary marrow cultures had a unique feature, the long, straight lines of cells. These have never been reported before in the literature and we are somewhat at a loss to explain their appearance in these cultures. However, they were reproducible over several independent preparations. One possibility could be that the cells aligned along lines of dried collagen since the plates were pre-coated with collagen. This appears unlikely, however, given that the collagen was applied with a brush that was used in a circular motion. Changes in collagen application had no effect upon the formation of the straight lines of cells (data not shown). Another possibility is that the lines represent the differentiated stromal cells in the culture attempting to form a hematopoietic environment. The culture conditions and the use of pre-selected horse serum may favor this. We have already seen that most lots of serum cause the cells to differentiate into fibroblasts and be unresponsive to dexamethasone treatment (Lucas et al., 1995). Perhaps prevention of fibroblast differentiation allows the differentiated stromal cells to more explicitly express their phenotype for easier observation. The continual renewal of floating cells in the media is also different from primary cultures from skeletal muscle and heart but would be consistent with a differentiated hematopoietic tissue. The nature of the cells within the lines and the floating cells needs to be investigated further.

Whereas the primary cultures differed from those obtained from skeletal muscle and heart, the secondary cultures appeared identical to those from the other tissues and behaved identically to treatment with dexamethasone. Control secondary cultures consisted of stellate-appearing cells that did not demonstrate any differentiation over the 5 weeks of culture. Treatment with dexamethasone elicited the appearance of fully differentiated phenotypes in a typical temporal sequence and a typical range of dexamethasone concentrations. The first fully differentiated phenotype to be recognized was multinucleated myotubes which appeared from 1 to 2 weeks in culture, followed by adipocytes at 3 weeks in culture and then chondrocytes, osteoblasts, smooth muscle cells, and endothelial cells at 4 weeks. Different concentrations of dexamethasone elicited the differentiation of different phenotypes: smooth muscle cells and endothelial cells were most abundant at $10^{-7}$ and $10^{-6}$ M dexamethasone, adipocytes were present in dexamethasone concentrations ranging from $10^{-8}$ to $10^{-6}$ M, chondrocytes and skeletal myotubes were present at $10^{-9}$ to $10^{-6}$ M dexamethasone, while osteoblasts were present in small amounts at all concentrations of dexamethasone. From this it can be seen that one culture could have several phenotypes present, and indeed it is common to see all the phenotypes in cultures treated with $10^{-7}$ M dexamethasone. Both the time of appearance of the different phenotypes and the concentrations of dexamethasone used to induce the phenotypes correspond to the results obtained in secondary cultures isolated from rat skeletal muscle and heart.

However, the effects of dexamethasone on the secondary cultures of marrow cells differ from that previously reported. In most cases, treatment of marrow stromal cells with dexamethasone in vitro results in the differentiation of osteoblasts (Vilamitjana-Amedee et al., 1993; Beresford et al., 1994; Klein et al., 1994; Gronthos et al., 1994; Owen et al., 1987) although some studies have also reported the differentiation of adipocytes (Beresford et al., 1994; Klein et al., 1994; Grontos et al., 1994; Owen et al., 1987). However, no one has reported the differentiation of skeletal muscle myotubes, chondrocytes, or endothelial cells. The absence of the differentiation of chondrocytes in vitro is unusual in that several in vivo studies of marrow stromal cells in diffusion chambers report the appearance of cartilage in the chambers (Bab et al., 1984; Bab et al., 1988; Zipori, 1989). The previous studies may have been looking at the differentiation potential of committed precursors, as indeed has been the case of some of the studies on osteogenesis and adipogenesis. However, culture conditions may again account for the difference. One, the isolation procedure used here is designed to eliminate precursor cells by allowing them to differentiate in the primary cultures. The differentiated cells are then preferentially killed during the freeze-thaw process (Young et al., 1991), demonstrated here again with the complete absence of differentiated phenotypes in the control cultures. Two, without exception, previous studies have used fetal bovine serum in the culture medium. Our experience is that fetal bovine serum differentiates the uncommitted cells in the secondary cultures to fibroblasts, eliminating any response to dexamethasone (Lucas et al., 1995). While the exact mechanism of action of dexamethasone is not known, it appears that it stimulates the differentiation of all possible pathways of the cell (Lucas et al., 1995). In the case of committed precursor cells, this will result in terminal differentiation of that phenotype, but in the case of multipotential cells dexamethasone will induce the committment and differentiation of each of the possible phenotypes (Lucas et al., 1995). Thus previous studies detected the differentiation of osteoblasts because they did not attempt to eliminate committed progenitor cells, i.e. pre-osteoblasts, and uncommitted cells in the culture were committed to the fibrogenic lineage by the serum.

Example 3

Granulation Tissue Contains Cells Capable of Differentiating into Multiple Mesodermal Phenotypes Previously, we have isolated cells from neonatal rat skeletal muscle capable of differentiating into a number of mesenchymal phenotypes when treated with a non-specific differentiating agent such as dexamethasone. We have termed these cells mesenchymal stem cells and have postulated they may be present in granulation tissue. In order to test this hypothesis cells were isolated from granulation tissue and assayed for their ability to form multiple mesodermal phenotypes. Stainless steel wound chambers were implanted subcutaneously into 7 week old male rats. They were removed 7 or 14 days post-implantation and scraped of adhering tissue. The cells were isolated by digestion with collagenase/dispase and cultured in gelatin-coated dishes in media with pre-selected horse serum until confluent. The cells were released with trypsin and frozen in 7.5% dimethylsulfoxide (DMSO) at $-80°$ C., then thawed and cultured in the same media supplemented with $10^{-6}$ to $10^{-10}$ M dexamethasone. Cells from both time points behaved similarly in culture. Control cultures contained cells with a stellate morphology and were similar in appearance to cells isolated from skeletal muscle. However, the following phenotypes were observed upon treatment with dexamethasone: long, multinucleated cells that spontaneously contracted in culture and stained with an antibody to myosin (skeletal myotubes), nodules of rounded cells whose extracellular matrix stained with Alcian blue, pH 1.0 (cartilage), rounded cells whose extracellular matrix stained with Von Kossa's stain for mineral (bone), round cells with large vesicles that stained with Sudan black B (adipocytes), large cells with intracellular fibers that stained with an antibody to smooth muscle α-actin (smooth muscle), round cells that incorporated acylated low density lipoprotein (endothelial cells), and granulated and fibrillar cells (connective tissue). These results suggest the presence of mesenchymal stem cells within granulation tissue capable of forming multiple mesodermal tissues rather than solely fibrous connective tissue scar. If these cells can be appropriately manipulated in vivo, actual tissue regeneration could be achieved as opposed to the formation of scar tissue.

The cellular events associated with cutaneous wound healing have been extensively studied (for recent reviews, see Clark, 1993; Bennett, 1993a, 1993b; Hunt and LaVan, 1989; Falanga, 1993; Orgill and Demling, 1988; Springfield, 1993). First, trauma causes the rupture of capillary beds which releases blood into the perivascular tissue spaces where it clots to form a hematoma. During the hematoma formation platelets aggregate and degranulate, releasing a number of growth factors into the clot. Components of the clot and the released growth factors attract macrophages that migrate to and degrade the clot. The macrophages also synthesize and release numerous growth factors which act on the capillary endothelial cells and fibroblasts in the surrounding undamaged tissues. Some of the growth factors, notably basic fibroblast growth factor (bFGF), cause the proliferation and migration of endothelial cells (Folkman and Klagsbrun, 1987; Connolly et al., 1987). These cells form new capillary loops just behind the macrophages and restore circulation to the wound. Meanwhile, the fibroblasts proliferate and also migrate into the wound, following the macrophages. The fibroblasts begin secreting an extracellular matrix composed principally of type I collagen, proteoglycans, and fibronectin. This eventually becomes a very dense matrix and, as the collagen molecules undergo cross linking, a fairly strong matrix. This combination of fibroblasts and associated extracellular matrix composes the scar tissue.

While scar tissue inevitably forms in subcutaneous tissue following trauma in the absence of exogenous agents, studies using demineralized bone matrix and proteins purified from that matrix have, shown the de novo induction of cartilage and bone in a subcutaneous site (Urist, 1989; Reddi and Huggins, 1972; Weiss and Reddi, 1981; Reddi, 1981; Lucas et al., 1990; Weiss and Reddi, 1980; Reddi and Anderson, 1976; and Wang et al., 1990). The cellular events of this induction have been studied and consist of tissue trauma leading to formation of a hematoma, infiltration of macrophages followed by "mesenchymal cells", and new capillaries. The mesenchymal cells differentiate into chondrocytes which then hypertrophy. The hypertrophic chondrocytes are replaced by bone through classic endochondral bone formation (Reddi, 1981; Reddi and Anderson, 1976). The early cellular events of this sequence are identical with wound healing with the exception of the appearance of mesenchymal cells in place of fibroblasts. This data implies the existence of cells in wounds with the capability to differentiate into tissues other than a fibrogenic scar.

Previous studies have demonstrated the existence of a population of cells located within the connective tissues surrounding skeletal muscle (Lucas et al., 1995) with dexamethasone, a non-specific differentiating agent, these cells differentiated not only into fibroblasts but also into other mesodermal phenotypes such as skeletal muscle, smooth muscle, endothelial cells, cartilage, bone, and fat. These cells were thus designated as "mesenchymal stem cells" (MSCs). Additional studies demonstrated that MSCs are resident within the connective tissue compartments of various organs (Young et al., 1995). Since these cells are normally present within connective tissues of various organs and, thus, may contribute to the wound healing response after tissue trauma, we conducted the following experiments to determine if these cells are also present in the granulation tissue of healing wounds.

Materials and Methods

Cell Culture:

Wound chambers were constructed from stainless steel mesh fashioned into cylinders 3.5 cm long as described by Schilling (Schilling et al., 1959, 1969) and modified by Goodson (Goodson et al., 1976). The wound chambers were cleaned by soaking them in benzene then ethanol, washed in soapy water, and then thoroughly rinsed. They were sterilized in an autoclave.

Seven week old rats were anesthetized with intraperitoneal pentobarbital. The abdomen was shaved and cleaned with providone-iodine solution. The wound chambers were inserted into the abdominal panniculus by the method of Hunt et al. (Hunt et al., 1966) and the wound closed with stainless steel wound clips.

The wound chambers were removed either 7 or 14 days post-implantation and putative stem cells were isolated using a previously described two-step procedure for the isolation of mesenchymal stem cells (Lucas et al., 1995). First, all the adhering tissue was removed from the wound chamber under sterile conditions. The chamber was then opened, the volume of tissue in the chamber estimated visually, and the chamber transferred to a 100 ml media bottle containing a magnetic stir bar. Seven volumes of Eagle's Minimal Essential Media with Earle's salts (EMEM) (GIBCO, Grand Island, N.Y.) containing 250 units/ml collagenase (CLS-I Worthington Biochemicals, Freehold, N.J.), 33.3 units/ml dispase Collaborative Research, Bedford, Mass.) were added and the mixture was stirred at 37° C. for 1½ hr until the tissue in the wound chamber was digested. The mixture was transferred to centrifuge tubes and centrifuged at 300×g for 20 min. The supernatant was discarded, 20 ml of EMEM supplemented with 10% pre-selected horse serum and penicillin-streptomycin, pH 7.4 was added, and the cells filtered through a 20 µm filter to obtain a single cell suspension. Again the cells were centrifuged at 150×g for 10 min., the supernatant discarded, and 10 ml of EMEM+10% horse serum added. The cells were counted on a hemocytometer and plated at 100,000 cells per 100 mm culture dish coated with 1% bovine gelatin (EM Sciences, Cherry Hills, N.J.). Cultures were maintained in EMEM supplemented with 10% pre-selected horse serum and antibiotics.

After approximately 8 days, the cells had reached confluence and the cultures consisted of mononucleated cells with a few multinucleated myotubes. The cells were released with 0.05% trypsin and the cells filtered through a 20 µm filter that removed the myotubes, leaving the mononucleated cells. The cells were then frozen in EMEM+10% horse serum+7.5% DMSO at −80° C. Aliquots of the cells were thawed and plated at a density of 5,000 cells per 16 mm well in a 24 well gelatin-coated culture plate (Corning Glass Works, Corning, N.Y.). Cultures were maintained in the same media for controls, but experimental dishes were treated with media containing dexamethasone in concentrations ranging from $10^{-10}$M to $10^{-6}$M. At 4 or 5 weeks, cultures were fixed and assayed for phenotypes as described below.

Assays for Phenotypes:

1. Muscle. Skeletal muscle myotubes were observed morphologically as multinuclear linear and branched structures that spontaneously contracted in culture (Young et al., 1992a). Confirmation of the skeletal muscle phenotype was obtained immunochemically by staining the cells with the MF-20 antibody to sacromeric myosin (Hybridoma Bank, Ames, Iowa) using a modified procedure of Young et al (Young et al., 1992b). Each step is preceded by 2 rinses with DPBS unless noted. After rinsing the cell layer with DPBS, 0.5 ml of cold methanol (−20° C.) was applied for 5 minutes to fix the cells. This was followed by a 5 minute incubation with 0.5 ml of 1% v/v Triton-X100/ 0.05% w/v sodium azide in DPBS to solubilize cell membranes and inhibit endogenous peroxidases, respectively. A primary blocker of 20% goat serum was applied for 30 minutes in a 37° C. incubator. The primary IgG of 1:200 dilution of MF-20 (0.4 ml/well) was then incubated for 1 hour. A secondary blocker of 0.5 ml of 20% goat serum was applied for 30 min. and was followed by 0.4 ml of 1:7500 dilution of biotinylated goat anti-mouse IgG (Leinco, St. Louis, Mo.), also incubated for 30 minutes at 37° C. A tertiary blocker, consisting of 20% goat serum, was applied for 30 min. and removed, then 0.4 ml of 1:3750 dilution of Streptavidin-horseradish peroxidase (Leinco) was added and incubated at 37° C. for 30 minutes. At this point the cells were rinsed twice with 0.5 ml DPBS, then twice with 0.5 ml distilled water. Chromagen (Sigma) was added as per the instructions in the staining kit to selected wells for future photography. Once the color developed, 25 μl of 0.05% sodium azide was added per well to stop the reaction. The wells were then rinsed and made permanent with glycerine jelly.

2. Cartilage. Cultures were stained with Alcian blue (Roboz Surgical Instrument, Rockville, Md.), pH 1.0. Cells were fixed in 10% formalin then stained with 0.5 ml Alcian blue, pH 1.0, for 30 minutes, then removed from the wells. Unbound stain was removed by rinsing the wells seven times with tap water or distilled water. The cultures were preserved under glycerine jelly.

3. Mineralized Tissue. Possible mineralized tissue was distinguishable as aggregates of polygonal cells surrounded by a very dense extracellular matrix. Confirmation of the calcified nature of the extracellular matrix was done by histochemical staining for calcium phosphate using the Von Kossa procedure as described by Humason (Humason, 1972). Briefly, the culture medium was removed and the plates rinsed twice with DPBS. The cells were fixed with 0.5 ml of 10% formalin (Sigma) for 3 to 5 minutes, then rinsed four times with distilled water. Then 0.5 ml of freshly prepared 2% silver nitrate (Sigma) solution was added and the cells were incubated in the dark for ten minutes. Following incubation, the silver nitrate solution was removed and the cells rinsed five times with distilled water. Approximately 0.5 ml of distilled water was left on each well. The plate was exposed to bright incandescent light for 15 minutes with a white background underneath it to reflect light. The plates were again rinsed five times with distilled water and then dehydrated quickly with 100% ethanol. The plates were made permanent with glycerin jelly. Confirmation of the presence of calcium phosphate was performed by pre-treating selected cultures with 1% w/v [ethylene bis(oxyethylenenitrilo)]-tetraacetic acid (EGTA) (Sigma), a specific calcium chelator, in $Ca^{2+}$, $Mg^{2+}$-free buffer for 1 hr prior to incubation in the silver nitrate solution (Humason, 1972).

4. Fat. Sudan black B (Asbey Surgical Co., Washington, D.C.) staining for saturated neutral lipid (Humason, 1972) was performed in the following manner: All media was aspirated from the culture wells and each well was washed twice with one ml of DPBS. Then 0.5 ml of 70% ethanol was added to break cell membranes. After one minute, the alcohol was aspirated and the wells washed twice with DPBS. The cells were then incubated twice for 5 minutes in 100% propylene. Next, the cells were incubated twice for 10 minutes with 0.5 ml of Sudan black B per well. Stain differentiation was performed by rinsing the cells repeatedly with 0.5 ml of each of the following solutions until each solution was clear: Propylene:Water 90:10, 85:15, and 70:30. The cells were washed twice for one minute using distilled water, then made permanent with glycerine jelly.

5. Smooth Muscle. Smooth muscle was assayed by staining with an antibody to smooth muscle α-actin using a kit from Sigma.

6. Endothelial Cells. Endothelial cells were identified by their ability to take up low density lipoprotein as described by Voyta et al. (Voyta, 1984). Cells were washed 5 times with Dulbecco's Minimal Essential Medium (high glucose) (DMEM) (GIBCO) supplemented with antibiotics. The cells were incubated for 4 hr. at 37° C. with 10 μg per ml of 1,1'-dioctadecyl-3,3,3',3'-tetramethyl-indocarbocyanine perchlorate (DiI-Acyl-LDL) (Biomedical Technology, Stoughton, Mass.). The wells were then washed 6 times with EMEM+10% horse serum and viewed on a Nikon Diaphot with fluorescent attachment.

Results

Figure 6A:
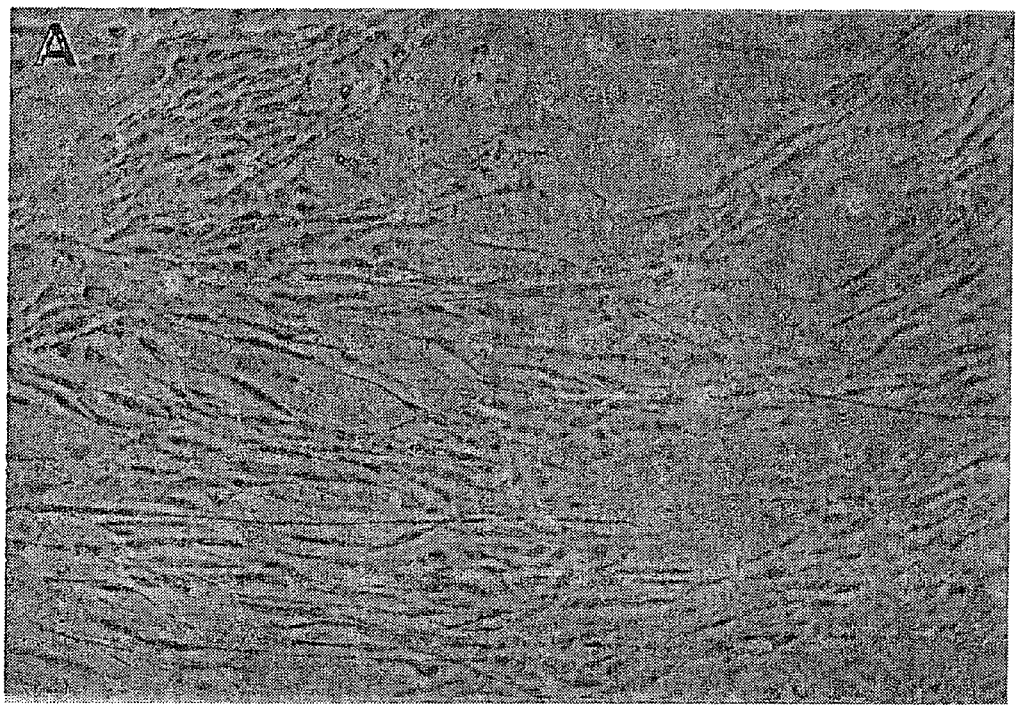
FIG. 6A-B Phase contrast photomicrographs of primary cultures of cells isolated from day 7 wound chambers. Original magnification=200×. A. Cells after 4 days in culture. B. Cells after 8 days in culture. Arrows point to stellate-shaped cells.
Figure 6B:
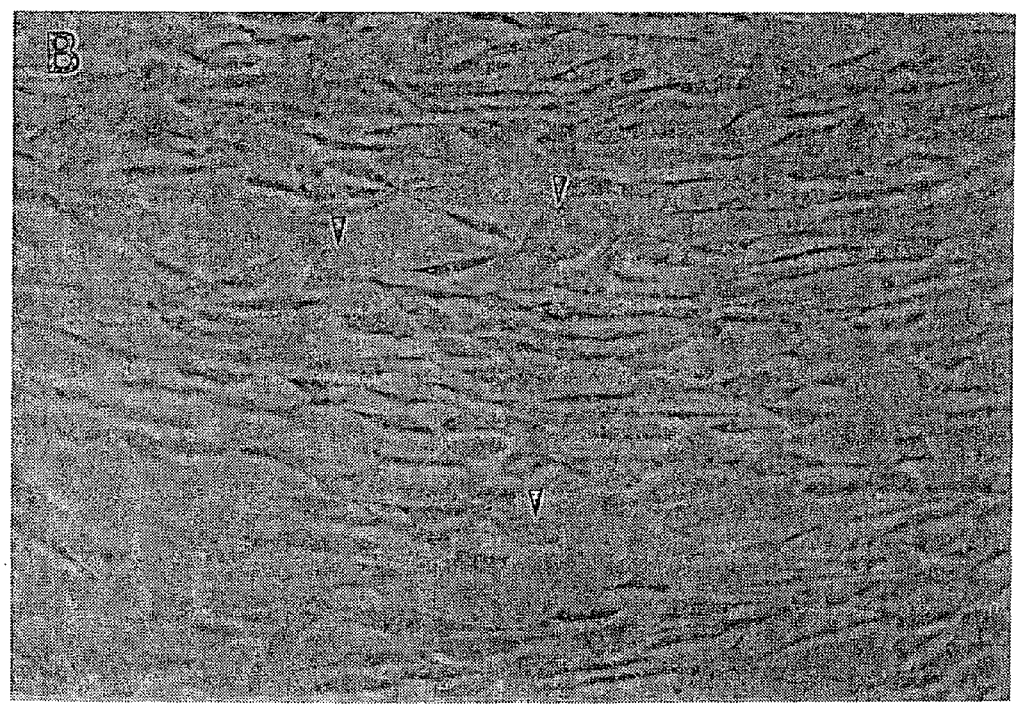
Figure 7A:
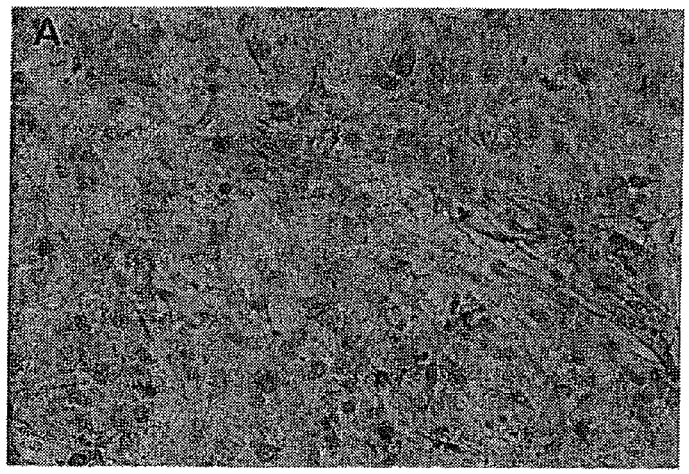
FIG. 7A-C Secondary cultures of cells after 4 weeks in culture. A. Phase contrast photomicrograph of a control culture from a 7 day wound chamber stained with Alcian blue, pH 1.0. Original magnification=200×. B. Phase contrast photomicrograph of an unstained culture from a day 7 wound chamber treated with $10^{-7}$ M dexamethasone showing multinucleated cells. Arrows point to clusters of nuclei. Original magnification=100×. C. Light photomicrograph of a culture from a day 14 wound chamber treated with $10^{-7}$ M dexamethasone and stained with an antibody to sarcomeric myosin. Arrows point to nuclei. Original magnification=200×.
Figure 7B:
Figure 7C:
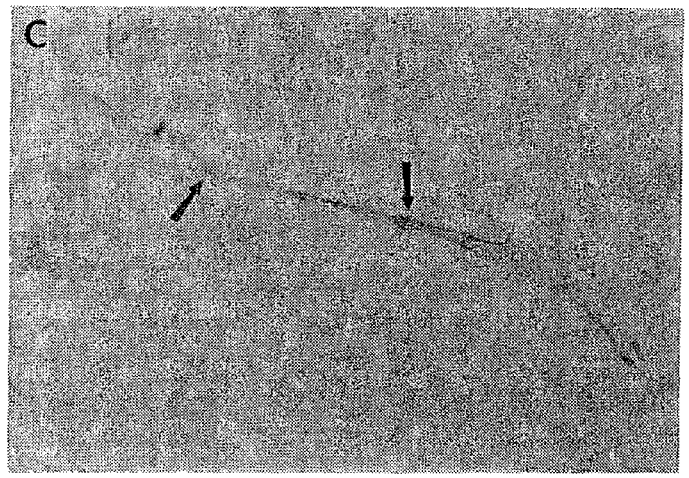

Primary cultures grew as mononucleated stellate-shaped cells until the cells reached confluence (FIGS. 6A and B). After release of the cells with trypsin, filtration, and cryopreservation, the cells remained stellate-shaped when plated. At 4 weeks, the control cultures still consisted of stellate-shaped cells (FIG. 7A). However, cultures treated with dexamethasone demonstrated several morphologies. Beginning about one week in culture both linear and branched multinucleated cells that spontaneously contracted appeared in all dexamethasone concentrations, but appeared to be more numerous at $10^{-8}$ and $10^{-7}$ M dexamethasone (FIG. 7B). These cells stained with an antibody to skeletal sarcomeric myosin (FIG. 7C) and were identified as skeletal muscle myotubes.

Figure 8A:
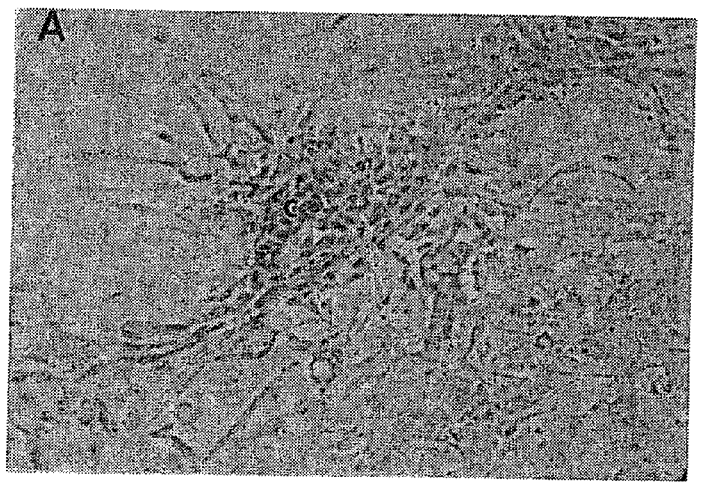
FIG. 8A-C Secondary cultures of cells after 5 weeks in culture. Original magnification=200×. A. Phase contrast photomicrograph of a culture from a day 14 wound chamber treated with $10^{-7}$ M dexamethasone stained with Alcian blue, pH 1.0. c=cartilage. B. Phase contrast photomicrograph of a culture from day 7 wound chamber treated with $10^{-7}$ M dexamethasone stained with Alcian blue, pH 1.0. c=cartilage; a=adipocyte. C. Light photomicrograph of a culture from day 7 wound chamber treated with $10^{-6}$ M dexamethasone and stained with Von Kossa's. b=bone.
Figure 8B:
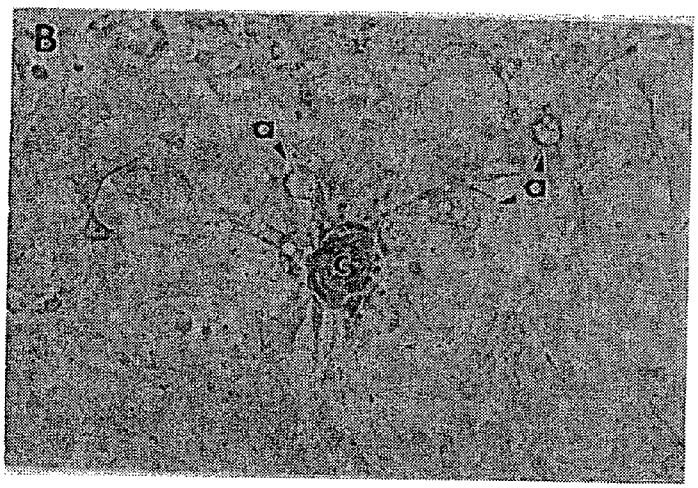

Cultures treated with $10^{-9}$-$10^{-6}$ M dexamethasone contained nodules of round cells with a refractile pericellular matrix when observed with phase contrast microscopy. Two morphologies of these nodules were identified. One morphology had mounded cell aggregates without a distinct border but with the cell aggregates merging with the stellate-shaped cell layer (FIG. 8A). The second morphology consisted of mounded cell aggregates containing a sharp boundary with the stellate-shaped cell layer (FIG. 8B). The pericellular matrix of both nodular morphologies stained with Alcian blue, pH 1.0, indicating the presence of sulfated glycosaminoglycans (FIGS. 8A and B). Based on particular cellular morphology and histological staining patterns, these cells were identified as chondrocytes in cartilage nodules.

Figure 8C:
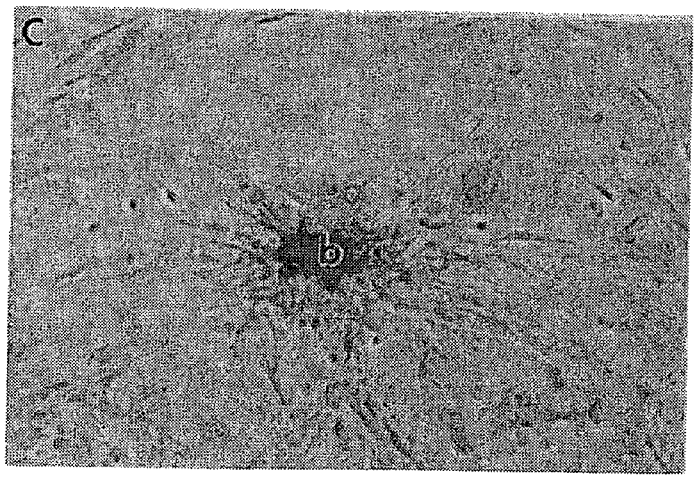

Cell aggregates of polygonal cells appeared after four weeks in culture. They were most common in the wells treated with $10^{-9}$ to $10^{-10}$ M dexamethasone but appeared in small numbers at all concentrations of dexamethasone. These cells had a dense extracellular matrix that appeared quite dark under phase contrast microscopy, and the matrix stained with Von Kossa's stain (FIG. 8C). It was found that the staining could be prevented by pre-treatment with EGTA (data not shown). All of this indicated a calcified extracellular matrix. Therefore these cells were tentatively identified as osteoblasts.

Figure 9A:
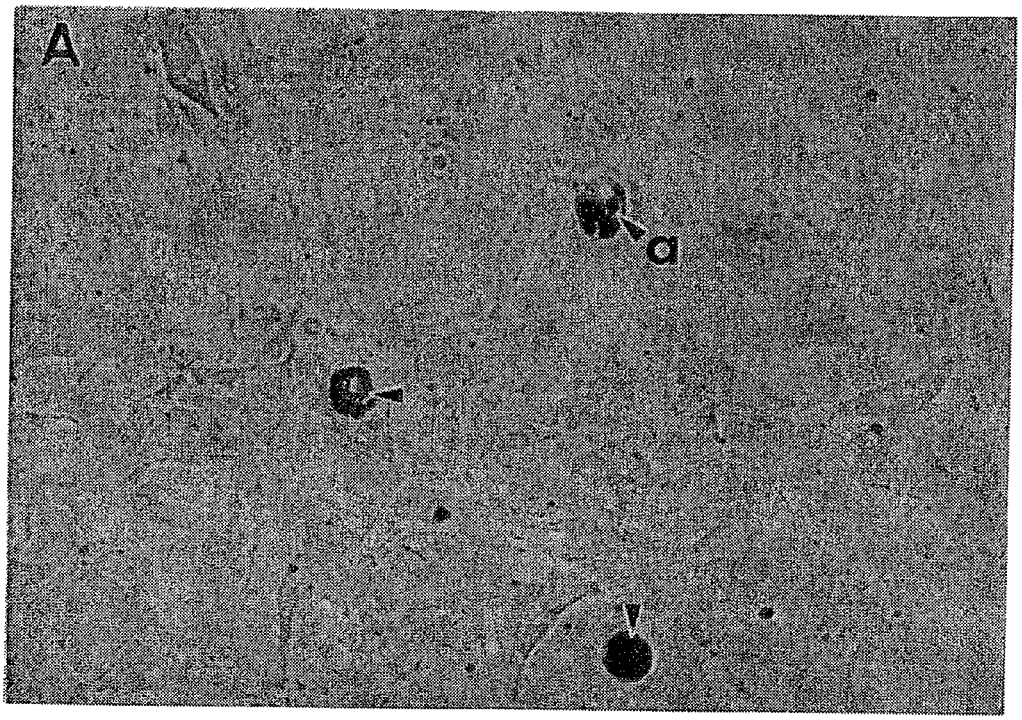
FIGS. 9A and B Secondary cultures of cells after 5 weeks in culture. A. Phase contrast photomicrograph of a culture from a day 7 wound chamber treated with $10^{-9}$ M dexamethasone and stained with Sudan black B. a=adipocytes. Original magnification=200×. B. Light photomicrograph of a culture treated from a day 14 wound chamber with $10^{-6}$ M dexamethasone and stained with an antibody to smooth muscle α-actin. sm=smooth muscle. Original magnification=100×.

Cultures treated with $10^{-8}$-$10^{-6}$ M dexamethasone contained cells with intracellular vesicles that first appeared at 2 weeks of culture. The intracellular vesicles stained black with Sudan Black B, indicating the presence of neutral lipids (FIG. 9A). Based on the particular morphology and the histochemical staining pattern, these cells were identified as adipocytes. In FIG. 9A adipocytes with their characteristic intracellular vesicles/lipid droplets can be seen in proximity to the cartilage nodule. This highlights two characteristics of the culture system: 1) dexamethasone can non-specifically induce multiple mesodermal phenotypes and 2) multiple phenotypes appeared at each dexamethasone concentration in each culture well.

Figure 9B:
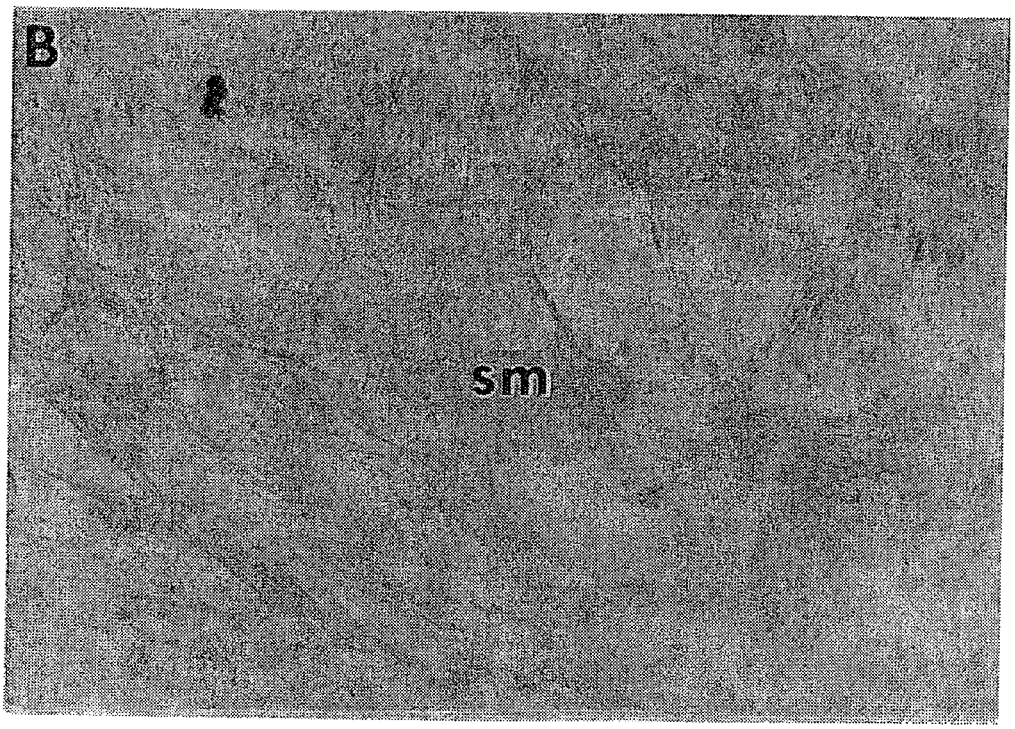
Figure 10A:
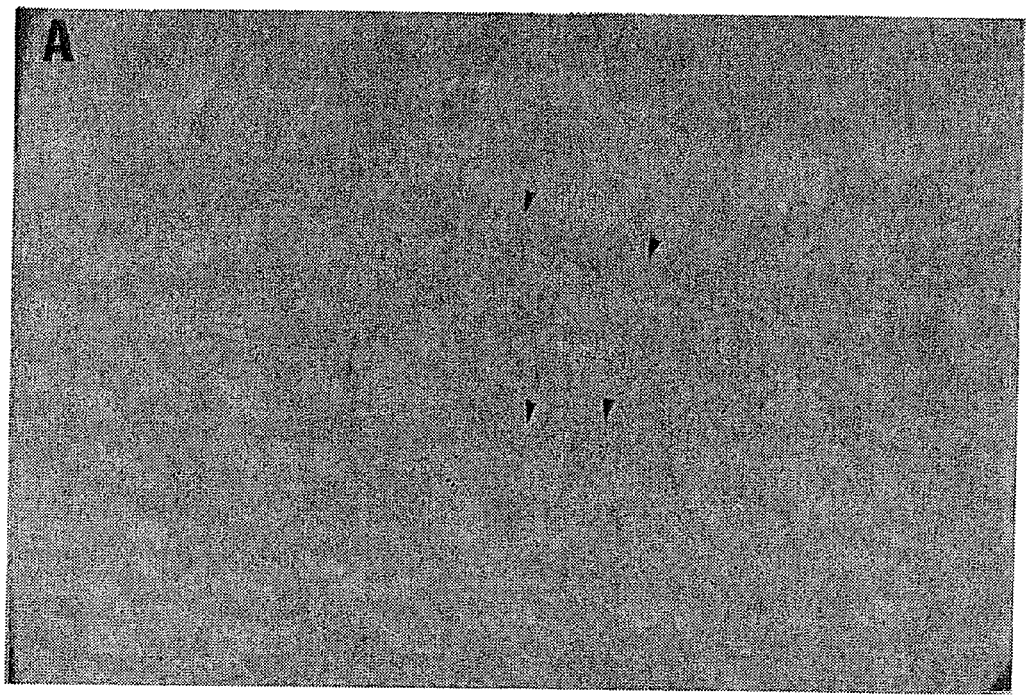
FIGS. 10A and B Secondary culture of cells after 5 weeks in culture from a day 7 wound chamber treated with $10^{-6}$ M dexamethasone and incubated with acetylated low density lipoprotein. Original magnification=200× A. Phase contrast photomicrograph. Arrows point to cells stained in B. B. Fluorescent photomicrograph of field shown in A. Arrows point to the same cells as in A.
Figure 10B:
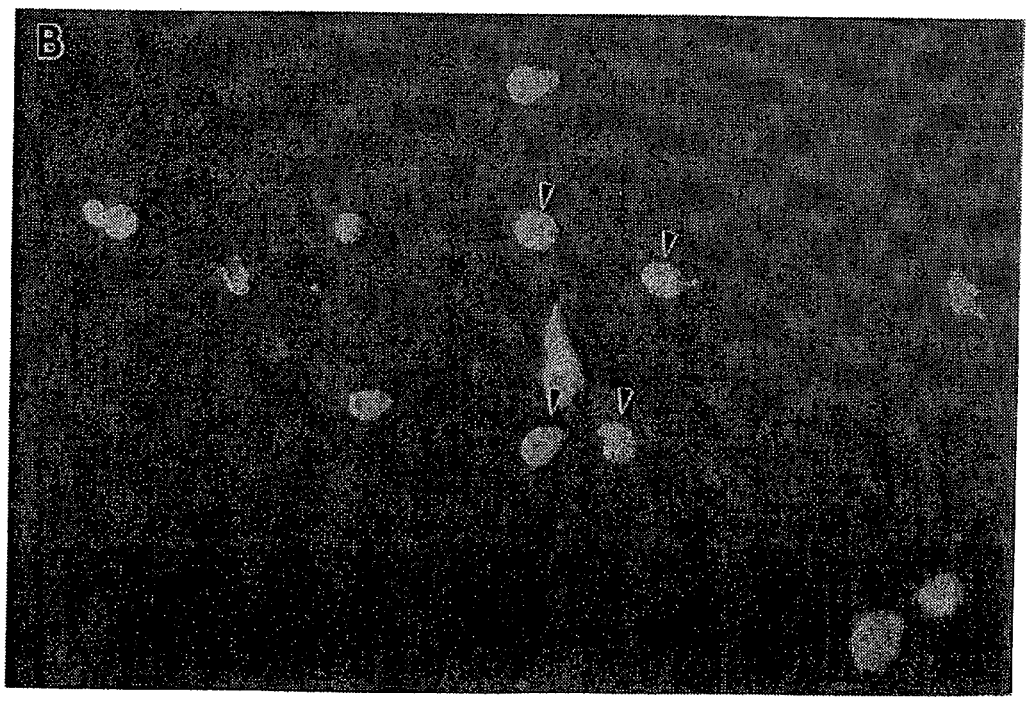

At dexamethasone concentrations of $10^{-7}$ and $10^{-6}$ M and after 3 weeks in culture, cells appeared that were extremely large, stellate or quadrilateral in shape, and contained distinguishable intracellular fibers. These cells stained with an antibody to smooth muscle α-actin (FIG. 9B). The staining was especially intense in intracellular fibers. We have therefore identified these cells as smooth muscle cells. At the same concentrations of dexamethasone ($10^{-7}$ and $10^{-6}$ M) and also after 3 weeks in culture, individual non-aggregating polygonal to round mononucleated cells appeared. These cells incorporated fluorescent labeled acyl-low density lipoprotein into the cytoplasm (FIGS. 10A and B). The staining was perinuclear with the nucleus being conspicuous in several cells. We have thus identified these cells as endothelial cells.

At $10^{-9}$-$10^{-7}$ M concentrations of dexamethasone, aggregations of confluent spindle-shaped cells in swirl patterns with non-refractile granular extracellular matrices were recognized in the cultures after 3 weeks. These extracellular matrices of these cells stained with Alcian blue pH 1.0 in a pattern indicative of fibroblastic cells (data not shown). We have thus tentatively identified these cells as fibroblasts.

There were only minor differences between cultures obtained from wound chambers removed 7 days post-implantation from those removed on day 14 post-implantation. Cultures from both time points demonstrated the same phenotypes at the same dexamethasone concentrations.

Discussion

Previous work from our laboratory has demonstrated the existence of a population of cells located in the skeletal muscle of chicks, rats, and rabbits capable of differentiating into several mesodermal phenotypes (Lucas et al., 19995; Young et al., 1992a; Pate et al., 1993). A similar population of cells has been found in several connective tissues of the embryonic chick (Young et al., 1995) and in newborn rat heart (Warejcka, 1996). Following the terminology of Owen (Owen, 1987) we have termed these cells mesenchymal stem cells for their apparent unlimited proliferation potential (Lucas et al., 1995; Young et al., 1993) and their ability to differentiate into cells of the mesodermal (mesenchymal) developmental lineage. In this study we have applied the same isolation and testing procedure to granulation tissue obtained from Hunt-Schilling wound chambers implanted for 7 or 14 days subcutaneously into 7 week old rats.

The isolation procedure for the cells in the current study was identical to that used for rat muscle and heart (Lucas et al., 1995; Warejcka, 1996). Care was taken to scrape adhering tissue from the wound chambers so that only the granulation tissue that had grown into either the mesh or interior of the chamber was used. Isolated cells were grown in primary culture until confluent in order to allow any contaminating progenitor cells to differentiate into phenotypically recognizable morphologies. In these primary cultures only a few skeletal myotubes appeared, with no other discernible differentiated phenotypes present. The primary cultures were then released with trypsin, slow frozen to $-80°$ C. in 7.5% DMSO, and thawed and plated into secondary culture. The freeze-thaw step is designed to eliminate differentiated phenotypes while allowing survival of the mesenchymal stem cells.

When grown in medium alone, the secondary cultures maintain a stellate morphology and do not differentiate (FIG. 7A). Differentiation must be stimulated by an exogenous agent and dexamethasone is used to accomplish this. In this system dexamethasone acts as a non-specific differentiating agent. Although its exact mechanism of action is unknown, dexamethasone has been used in a number of culture systems to stimulate differentiation of stem cells (Ball and Sanwal, 1980; Owen and Joyner, 1987; Bellows et al., 1990; Greenberger, 1979; Houner et al, 1987; Schiwek and Loffler, 1987; Bernier and Goltzman, 1993; Zimmerman and Cristae, 1993; Grigo uncommitted pluripotent stem cells. Previous examples of the existence of lineage-committed progenitor stem cell populations include the unipotent progenitor myosatellite stem cell of skeletal muscle (Mauro, 1961; Snow, 1978; Grounds, 1990, 1991), the unipotent progenitor chondrogenic and osteogenic stem cells of the perichondrium and periosteum, respectively (Bloom and Fawcett, 1994), and the bipotent progenitor chondrogenic, osteogenic stem cells in marrow (Owen, 1988; Beresford, 1989). The existence of lineage-uncommitted pluripotent MSCs is based on the results from clonally isolated stem cells. Individual clonal cell lines derived from embryonic rat periosteum (Grigoriadis, 1988) and embryonic chick skeletal muscle, dermis, and heart (Young et al., 1993) have demonstrated multiple phenotypes when treated with dexamethasone, suggesting the existence of lineage-uncommitted pluripotent stem cells in these tissues. In addition, preliminary data from clonal cell lines generated from cells isolated from neonatal rat skeletal muscle have also shown individual clones that can differentiate into multiple mesodermal phenotypes (Davis et al., 1995), suggesting continuance of pluripotent stem cells into post-partum life.

In the present study the culture medium allows differentiation of lineage-committed progenitor cells in the primary cultures, where skeletal muscle myotubes were observed. However, secondary cells cultured in the same medium did not exhibit differentiation into the mesodermal phenotypes assayed (FIG. 8A). It seems unlikely that dermis would contain lineage-committed progenitor cells for chondrocytes or osteoblasts. Therefore, it appears likely that at least some of the cells in the secondary cultures obtained from granulation tissue are lineage-uncommitted pluripotent MSCs.

Of additional interest to this study is the potential origin of the MSCs isolated from the wound chambers and the age of the animals examined. As described in the Methods section, only cells within the wound chambers were used for the analysis. This suggests a migratory ability for the mesenchymal stem cells and that they originated from tissue surrounding the wound chamber. The MSCs apparently migrate into a wound concurrently with the other cell types described in wound healing: fibroblasts and vascular cells. The animals used in this study were 7 weeks old at the time of implantation of the wound chambers. The existence of MSCs in the granulation tissue indicates that MSCs persist into adult life (Pate et al., 1993).

Mesenchymal stem cells isolated from wound chambers that had been implanted for 7 or 14 days had identical responses to dexamethasone treatment. Previous studies have shown that granulation tissue is present in wound chambers at 7 days and reaches a maximum at 14 days (Schilling et al., 1969). After 14 days the granulation tissue is gradually remodeled to form a connective tissue scar. The current results indicate that mesenchymal stem cells are present throughout the granulation phase of wound healing and therefore may be capable of participating in the wound healing response. However, it is impossible to estimate the absolute number of mesenchymal stem cells present in the wound chambers. The isolation procedure of primary culture followed by freeze-thawing and growth in secondary culture does not permit comparisons in the number of mesenchymal stem cells present in the original tissue. In addition, the proliferative capabilities of both subpopulations of stem cells, lineage-committed and pluripotent, render such calculations difficult. Previous studies have shown that lineage-committed progenitor cells have an approximate life span of fifty cell doublings before programmed cell senescence (Hayflick, 1965), whereas pluripotent MSCs are essentially proliferation immortal as long as they stay uncommitted to a particular lineage (Lucas et al., 1995; Young et al., 1993). Comparisons of the relative abundance of MSCs in granulation tissue must wait until a marker for mesenchymal stem cells is available.

The presence of mesenchymal cells in granulation tissue challenges the current view of wound healing. This view states that the cells that migrate into wounds are thought to be vascular cells (smooth muscle and endothelial cells) and fibroblasts. The implication is that formation of a fibrous connective tissue scar is inevitable. Based on our studies, we propose that at least a portion of the cells that migrate into the wound site are mesenchymal stem cells with the potential to form multiple mesodermal phenotypes. As shown, MSCs are present in the surrounding connective tissues, can migrate in conjunction with other cells constituting the "granulation tissue", and have the capability of differentiating into a number of mesodermal phenotypes including fibroblasts, endothelial cells, and smooth muscle cells. Previous studies have demonstrated that MSCs placed into full-thickness articular cartilage defects differentiate into cartilage and bone under the influence of local, endogenous factors (Grande et al., 1995). We would therefore propose that one or more local factors present at a wound site have the potential to influence the commitment and subsequent differentiation of MSCs into the observed phenotypes in connective tissue scar, i.e. fibroblasts, endothelial cells, and smooth muscle cells. A large number of growth factors released by degranulating platelets, macrophages, lymphatic cells, and present in the systemic circulation during wound healing have been identified and their functions with respect to lineage-committed progenitor cells have been characterized (Clark, 1993; Bennett, 1993a, 1993b; Hunt and LaVan, 1989; Falanga, 1993; Orgill and Demling, 1988; Springfield, 1993; Adolph et al., 1993). However, a number of unknown factors remain for identification, characterization, and functional analysis for their effects on both progenitor stem cells and pluripotent mesenchymal stem cells. This view is supported by the presence in most lots of serum of an activity that causes the in vitro differentiation of MSCs to spindle-shaped cells that form swirl patterns (fibroblasts) (Lucas et al., 1995).

We would postulate that, if the local environment is altered, the resident MSCs present at the wound site may form tissues other than fibrous connective tissue scar. This view is supported by the studies where bone morphogenetic is placed at an extraskeletal subcutaneous wound site. This results in the appearance of first cartilage which subsequently undergoes endochondral ossification to form bone (Urist, 1989; Reddi and Huggins, 1972; Reddi, 1981; Wang et al., 1990). Separate studies have indicated that the respondent cells are resident at the site of implantation (Weintroub et al., 1990). Implantation of another morphogenetic protein, muscle morphogenetic protein, in a subcutaneous site results in the differentiation of skeletal myotubes in the dermal tissue (Lucas et al., 1996). Finally, levels of transforming growth factor-β (TGF-β) have also been manipulated by the addition of antibodies to TGF-β1 or the addition of exogenous TGF-β3 to effect cutaneous wound healing (Ferguson, 1994; Shah et al., 1992, 1994, 1995). These studies revealed that antibodies to TGF-β1 or exogenous TGF-β3 reduced scarring and resulted in normal appearing dermis. We would speculate that alteration of the levels of TGF-β isoforms at the wound site resulted in a shift in differentiation of MSCs away from scar fibroblasts and towards normal fibroblasts resulting in the normal appearing dermis.

The presence of a population of mesenchymal stem cells in granulation tissue opens the possibility of true tissue regeneration as opposed to scar tissue formation. Regeneration would require that the mesenchymal stem cells be appropriately and specifically manipulated to differentiate into desired tissues. We are currently testing bioactive factors for their ability to 1) inhibit fibrogenesis and 2) stimulate specific phenotypes.

Example 4

Mesenchymal Stem Cells Isolated from Adult Human Skeletal Muscle

Wound healing is the response to injury, but results in nonfunctional scar tissue. A more desirable result would be tissue regeneration. We hypothesized the existence of a mesenchymal stem cell which was capable of differentiating into the tissue normally found in the limb—bone, muscle, fat, dermis, etc. and have found such a cell population in fetal and adult rat skeletal muscle. These experiments were designed to isolate these cells from adult human tissue. Skeletal muscle was harvested from an amputated leg of a 75-year old diabetic female and a 35-year old male. Mononucleated cells were enzymatically isolated and cultured in Minimal Essential Media with Earle's salts (EMEM) supplemented with 10% pre-selected horse serum. This preparation contained committed myogenic cells which were allowed to differentiate into myotubes. The cultures were then trypsinized, filtered, frozen in 7.5% DMSO at −80 degrees C., thawed, and plated, where they were cultured in the same media as above supplemented with dexamethasone (a non-specific differentiation agent) at concentrations ranging from $10^{-10}$-$10^{-6}$ M for 2-6 weeks. Control cultures exhibited the stellate morphology typical of mesenchymal stem cells. Cultures treated with dexamethasone contained the following phenotypes: long, multinucleated cells that stained with an antibody to myosin (skeletal muscle), round cells with lipid droplets that stained with Sudan Black B (adipocytes), round cells with extracellular matrix that stained with Alcian Blue, pH 1.0 (cartilage), cells that stained with an antibody to smooth muscle a-actin (smooth muscle), cells that incorporated acetylated-low density lipoprotein (endothelial cells), and cells with an extracellular matrix that stained with Von Kossa's stain for mineral (osteoblasts). The experiments establish the existence of human mesenchymal stem cells with the capability to differentiate into mesenchymal phenotypes. This raises the possibility of manipulating the cells to achieve appropriate regeneration of mesenchymal tissues in the injured patient.

Mesenchymal cells gives rise to many different tissues including: connective tissue, muscle, bone, fat, cartilage, and blood cells. Injury to mesenchymally derived tissues of the body is not an uncommon occurance. Often the injury is caused by trauma, pathologic breakdown, so called "wear and tear" on the tissues, or a congenital defect. This is especially true with the pathologic processes involved with bone fractures, osteoarthritis, or skeletal muscle injury. Although the body has mechanisms for repair of the damaged or lost mesenchymal tissues, the regeneration of normal functioning tissue seems to be ineffecient or inadequate. Instead, healing usually leaves an area consisting primarily of non functional fibrous scar tissue.

When an injury does occur, the process of wound healing begins. The first step involves the formation of a hematoma, followed by an inflammatory response and subsequent migration of granulation tissue to fill the defect caused by the damage. As the wound heals, remodeling and fibrous scarring occurs. Although this usually is adequate to repair the void of cells, there is a limited capacity of the adult body to regenerate an identical match of functionally optimal cells. There is also evidence that the inflow of proteins and growth factors are signals for the migration of cells to the sight of injury (Postelthwaite et al., 1976, 1978, 1981; Seppa et al., 1982; Grotendorst et al., 1982; Dueul et al., 1982). Although this may be true, regeneration of a large defect cannot simply be explained by migration of cells into the wound alone. Therefore, the hypothesis that there exists a resident population of pluripotent cells residing in the connective tissue matrices, was proposed. The growth factors seem to be important signals for the initiation and repair, with possible regeneration by these resident mesenchymal stem cells. If the direction of differentiation regarding the multipotent properties of these mesenchymal stem cells can be altered by specific signals, regeneration could be initiated and non functional scar tissue may be avoided.

Although scar formation does manage to stabilize the injury, it is not functionally optimal. There are numerous problems that may arise at the sight of an injury healed with scarring. Scar tissue in the areas of mesenchymal tissue such as tendon, muscle and cartilage injury show is a marked decrease in functionality, especially with respect to resilience, compressive, tensile and shear strength. For example, problems due to non functional scar formation include: non-union or malunion in bone after fracture, tendons that are predisposed to reinjury at the sight of scarring, arthritis due to the changes at the articular cartilage surface, and hypertrophic scars in the skin connective tissue. Mesenchymal cells are very important in the healing process, and are known characteristically for their property of differentiating into a number of mesenchymal tissues present in the wound.

Stem cells are defined as cells which have unlimited proliferation ability and are therefore not bound to Hayflick's theory of a limited amount of cell doublings. (Hayflick, 1965). These cells are able to produce daughter cell progeny that can differentiate into cell lineages that making up multiple tissue types in the body (Hall & Watt, 1989). It is known that in the developing mammalian embryo there exists mesenchymal stem cells, which are pluripotent cells whose daughter cells give rise to the skeletal tissues of the organism (Gilbert, 1997). The skeletal tissues derived from these cells include: bone, muscle, cartilage, connective tissue, and marrow stroma.

In adults, there is also evidence that cells with similar multipotential abilities to the mesenchymal stem cells of the embryo have been identified in epidermis, gastrointestinal epithelium, and the hematopoietic compartment of bone marrow. The multipotent cells seem to be important factors in repair and maintenance of adult tissues. The stem cells derived from the hematopoietic compartment have been the most studied. The cells referred to as hematopoietic stem cells, were noted to have the ability to differentiate into many various phenotypes. (Lemischka et al 1986, Sachs, etc) Another similar but entirely separate population of cells was hypothesized and subsequently found in adult bone marrow, termed mesenchymal stem cells (MSCs). The MSCs were also studied extensively, and shown to give rise to various tissue phenotypes such as: bone and cartilage (Owen, Beresford, Caplan), tendon (Caplan), muscle (Wakatani, Saito), fat (Dennis) and marrow stromal connective tissue capable of supporting hematopoeisis (Dexter, Majumdar). These properties have also been observed during studies involving demineralized bone matrix implants. The implants, or proteins derived from it showed de novo induction of cartilage and bone formation at an ectopic sight, namely in muscle (Urist, 1965; Reddi and Anderson, 1976; Wang et al., 1990; Urist et al., 1978; Lucas et al., 1988). This gives more evidence that there may be a population of multipotent cells within the connective tissue matrix in adult humans, which responds to the protein signals within the bone matrices.

Recent studies have previously shown that there exists a population of cells in the connective tissue surrounding embryonic avian skeletal muscle, that is capable of differentiating into numerous mesenchymal phenotypes (Young et al., 1992a). When incubated in dexamethasone of differing concentrations, the MSCs have been shown to differentiate into various phenotypes including: bone, cartilage, skeletal muscle, fat, and endothelial tissue (Young et al., 1995). Populations of these cells have also recently been shown to exist in cardiac muscle of the adult rat (Lucas et al., 1995), skeletal muscle of the neonatal rat, adult rat (Warejecka et al., 1996), and adult rabbit (Pate et al., 1993). These isolated cells have been termed mesenchymal stem cells (MSCs). The purpose of the current study is to determine whether a population of cells similar to the above mentioned mesenchymal stem cells-exists, and can be isolated from the skeletal muscle of the human adult.

Materials and Methods:

Assays for Phenotypes:

1. Mineralized Tissue. The presence of calcified tissue was assayed by Von Kossa's staining of calcium phosphate essentially described by Humason (Humason, 1972). Briefly the culture medium was removed and the plates rinced twice with DPBS. The cells were fixed with 0.5 ml of 10% formalin (Sigma) for 3 to 5 minutes, then rinsed four times with distilled water. Then 0.5 ml of freshly prepared 2% silver nitrate (Sigma) solution was added and the cells were incubated in the dark for ten minutes. Following incubation, the silver nitrate solution was removed and the cells rinsed five times with distilled water. Approximately 0.5 ml of distilled water was left on each well. The plate was exposed to bright light for 15 minutes with a white background underneath it to reflect light. The plates were again rinsed five times with distilled water and then dehydrated quickly with 100% ethanol. The plates were made permanent with glycerine jelly (Young et al., 1991). Confirmation of the presence of calcium phosphate was preformed by pre-treating selected cultures with 1% w/v [ethylene bis(oxyethylenenitrilo)]-tetraacetic acid (EGTA) (Sigma), a specific calcium chelator, in Ca2+, Mg2+-free buffer for 1 hr prior to incubation in the silver nitrate solution (Humason, 1972).

2. Cartilage. Cultures were stained with Alcian blue (Roboz Surgical Instrument, Rockville, Md.), pH 1.0. The fixed wells were stained with 0.5 ml Alcian blue, pH 1.0, for 30 minutes, then removed from the wells. Unbound stain was removed by rinsing the wells seven times with tap water or distilled water. The cultures were preserved under glycerine jelly.

3. Fat. Sudan black B (Asbey Surgical Co., Washington, D.C.) staining for saturated neutral lipid (Humason, 1972) was performed in the following manner: All media was aspirated from the culture wells and each well was washed twice with one ml of DPBS. Then 0.5 ml of 70% ETOH was added to break cell membranes. After one minute, the alcohol was aspirated and the wells washed twice with DPBS. The cells were then incubated twice for 5 minutes in 100% propylene. Next, the cells were incubated twice for 10 minutes with 0.5 ml of Sudan black B per well. Stain differentiation was performed by rinsing the cells repeatedly with 0.5 ml each of the following solutions until each solution was clear: Propylene:Water 90:10, 85:15, and 70:30. The cells were washed twice for one minute using distilled water, then made permanent with glycerine jelly.
4. Muscle. The cells were stained with the MF-20 antibody to sarcomeric myosin (Hybridoma Bank, Ames, Iowa) using a modified procedure of Young et al. (Young et al., 1992b). Each step is preceded by two rinces with DPBS unless noted. After another rinse, 0.5 ml of cold methanol (−20 degrees C.) was applied for 5 minutes to fix the cells. This was followed by a 5 minute incubation with 0.5 ml of 1% v/v Triton-X100/0.05% w/v sodium azide in DPBS to solubilize cell membranes and inhibit endogenous peroxidases, respectively. A primary blocker of 20% goat serum was applied for 30 minutes in a 37 degree C. incubator. The primary IgG of 1:200 dilution of MF-20 (0.4 ml/well) was then incubated for 1 hour. A secondary blocker of 0.5 ml of 20% goat serum was applied for 30 min and was followed by 0.4 ml of 1:7500 dilution of biotinylated goat anti-mouse IgG (Leinco, St. Louis, Mo.), also incubated for 30 minutes at 37 degrees C. A tertiary blocker, consisting of 20% goat serum, was applied for 30 min and removed, then 0.4 ml of 1:3750 dilution of Streptavidin-horseradish peroxidase (Leinco) was added and incubated at 37 degrees C. for 30 minutes. At this point the cells were rinced and 0.5 ml of ABTS-peroxidase substrate (Kirkegaard and Perry Labs, Gaithersburg, Md.) was added for 30 minutes incubation at ambient temperature in the dark. After incubation, 200 ul of ATBS solution was removed from the cells and placed in a well of a 96-well ELISA plate (Falcon) containing 10 ul of 0.03% sodium azide. The ELISA plate was read on a Titer Tek spectrophotometric plate reader using a 405 nm filter.

After the aliquot of ATBS solution had been removed, the cells were rinsed twice with 0.5 ml DPBS, then twice with 0.5 ml distilled water. Chromagen (Sigma) was added as per the instructions in the staining kit to selected wells for future photography. Once the color developed, 25 ul of 0.05% sodium azide was added per well to stop the reaction. The wells were then rinced and made permanent with glycerine jelly.

The ABTS was removed from the remaining wells and DNA content analyzed using the in situ diaminobenzoic acid (DABA) procedure of Johnson-Wint and Hollis as previously described (Johnson-Wint et al., 1982). Thus, the absorbance for the myosin content and the DNA content were obtained on the same wells.
5. Smooth Muscle. Smooth muscle was assayed by staining with an antibody to smooth muscle a-actin using a kit from Sigma.
6. Endothelial Cells. Endothelial cells were identified by their ability to take up low density lipoprotein by Voyta et al. (Yoyta et al., 1984). Cells were washed 5 times with Dulbecco's Minimal Essential Medium (high glucose) (DMEM) (GIBCO) supplemented with antibiotics. The cells were incubated for 4 hr. at 37 degrees C. with 10 ug per ml of 1,1'-dioctadecyl-3,3,3',3'-tetramathyl-indocarbocyanine perchlorate (DiI-Acyl-LDL) (Biomedical Technology, Stoughton, Mass.). The wells were then washed 6 times with EMEM+10% hoese serum and viewed on a Nikon Diaphot with fluorescent attachment.
7. Hematopoietic Cells. Hematopoietic cells were identified by the presence of marker for CD-34. Cells were washed in the culture dish twice with DPBS-Ca-Mg. Next, DPBS-Ca2+Mg2+ and EDTA solution was added. 40 minutes later, the samples were gently triturated to remove the cells. The dislodged cells were then removed and transferred to a 15 ml centrifuge tube. EMEM 10% HS-3 was then added to the culture dish and the sample was re-incubated. The cell suspension was centrifuged at 150 g for 12 minutes. The supernatant was aspirated, and the pellet resuspended in 1.95 ml DPBS-$Ca^{2+}$—$Mg^{2+}$. Cells were then counted using a hemocytometer. Next, cells were washed with DPBS-$Ca^{2+}$—$Mg^{2+}$. We then incubated 0.5 ml of the primary IgG in EMEM 10% HS-3 at 4 degrees C. IgG was at 40 ul/10 6 cells CD-34 A isotope. In two microfuge tubes 20 ul/$10^6$ cells CD-34 B isotope. The samples were then centrifuged in the microfuge for 4 minutes at 150 g. The supernatant was aspirated, and the pellet resuspended and washed in DPBS. The samples were then centrifuged again and blocked in 1% BSA, 0.5% TW for 20 minutes. The samples were then centrifuged again. The secondary IgG was then added and incubated for 20 minutes. The sample was then centrifuged on 3 speed for 4 minutes. The supernatant was aspirated and pellet washed with 0.5 ml media. The solution was centrifuged again and supernatant aspirated. 100 ml of media PBS was added to the pellet, and the sample was then plated utilizing 10 ul per slide. The samples were fixed with acetone, ETOH, heat and formalin. The samples were then viewed under a fluorescent microscope with a blue filter.

Results and Discussion

Figure 11A:
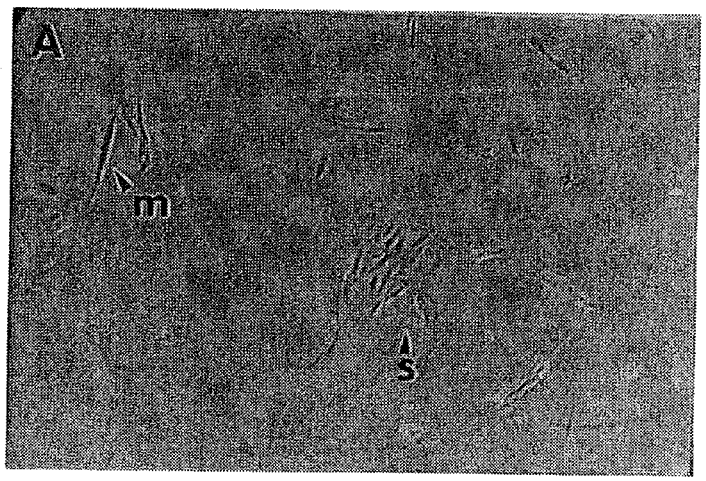
FIG. 11A-C A. Primary culture from 77 year old female, 5 days in culture. Phase contrast 100×. s=stellate cell m=myoblast. B. Primary culture from 77 year old female, 14 days in culture. Phase contrast 100× stained with antibody to myosin. s=stellate (putative PPMSC), m=myotubes. C. Secondary culture (PPMSCs) from 77-year-old female, 35 days in culture. Phase contrast 200×.
Figure 11B:
Figure 11C:
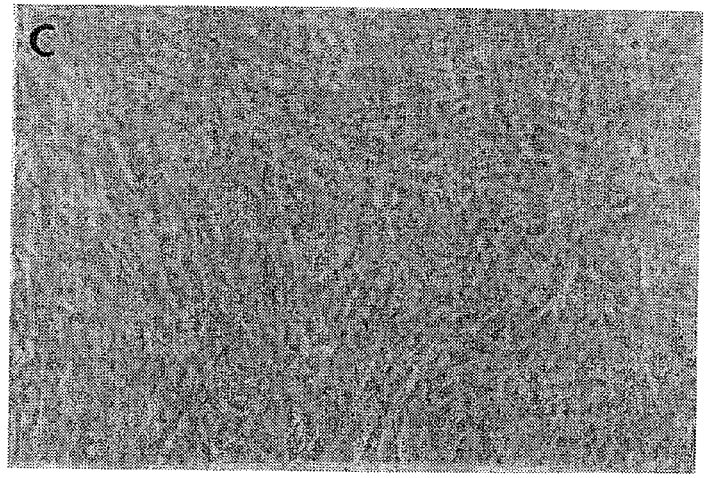

Mesenchymal stem cells were isolated from skeletal muscle obtained from surgical samples from a 77 year old female and a 37 year old male. The primary cultures showed mononucleated stellate-shaped cells (putative pluripotent mesenchymal stem cells) as well as myoblasts (FIG. 11A, 11B). After release of the cells with trypsin, filtration, and cryopreservation, the cells in this secondary culture remained stellate-shaped when plated (FIG. 11C).

Figure 12A:
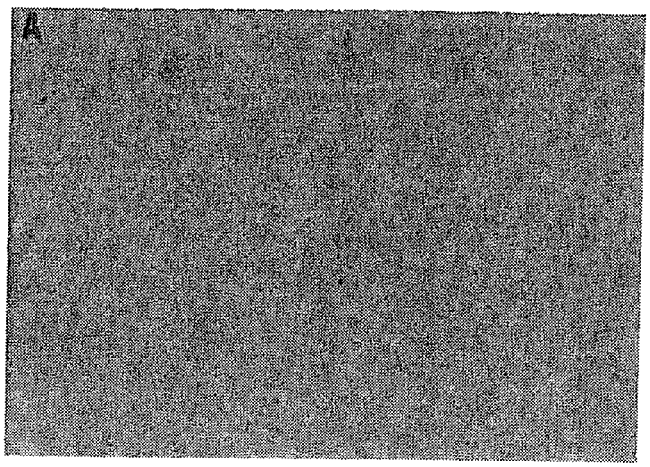
FIG. 12A-B A. Secondary culture of cells derived from 37-year-old male, 35 days in culture. Bright field 200× stained with an antibody to myosin. B. Secondary culture of cells derived from 37-year-old male 35 days in culture and treated with $10^{-10}$ M dexamethasone. Bright field 200× stained with an antibody to myosin. Arrows point to nuclei.
Figure 12B:
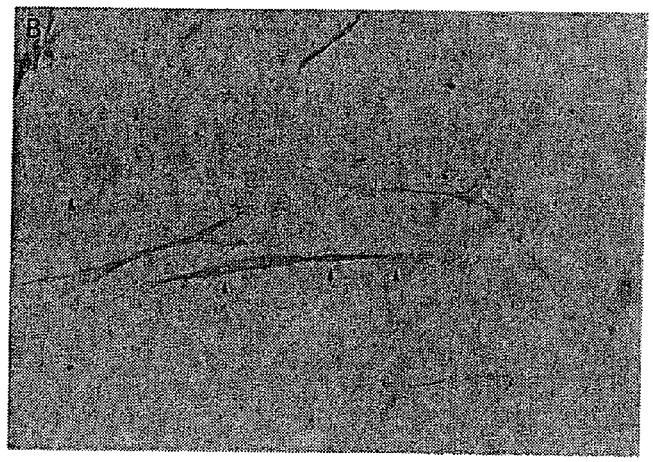
Figure 12C:
Figure 13C:
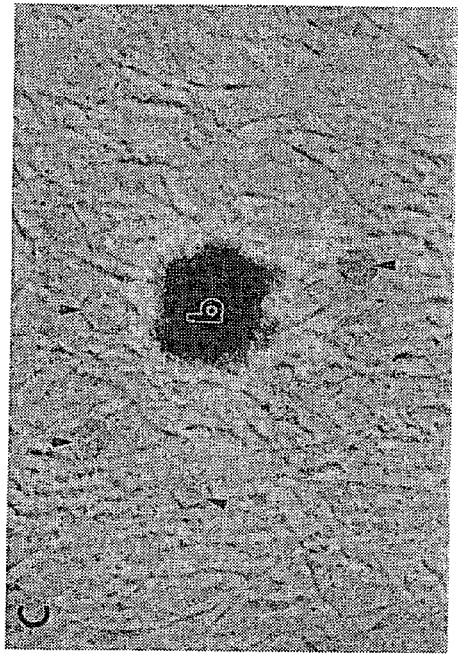
FIG. 13A-D A. Secondary culture derived from 77-year-old female, 28 days in culture and treated with $10^{-8}$ M dexamethasone. Phase contrast, 200×. Spindle shaped cells in swirl patterns. B. Secondary culture of cells derived from 37-year-old male, 35 days in culture, and treated with $10^{-8}$ M dexamethasone. Bright field, 200× stained with Alcian Blue, pH 1.0. c=cartilage. C. Secondary culture of cells derived from 37-year-old male, 35 days in culture, and treated with $10^{-8}$ M dexamethasone. Bright field, 200× stained with Von Kossa's stain. b=bone. Arrows point to adipocytes in the same culture. D. Secondary culture of cells derived from 37-year-old male, 35 days in culture, and treated with $10^{-7}$ M dexamethasone. Bright field, 200× stained with Von Kossa's stain but pretreated with EGTA. b=bone.
Figure 13D:
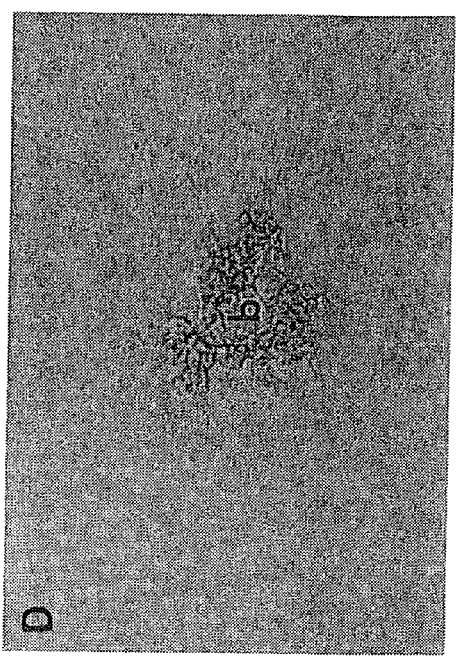
Figure 13A:
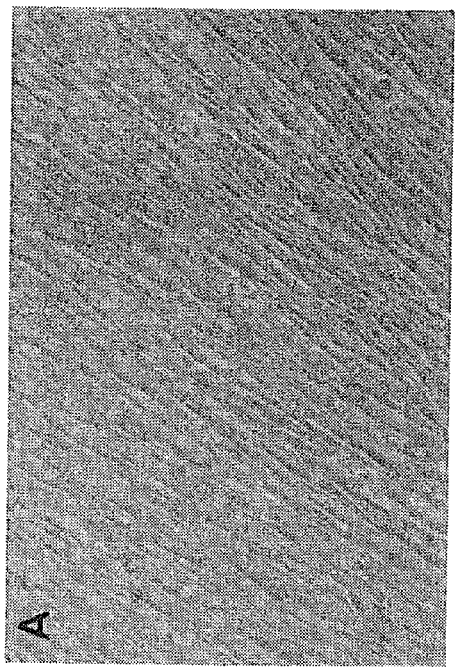
Figure 13B:
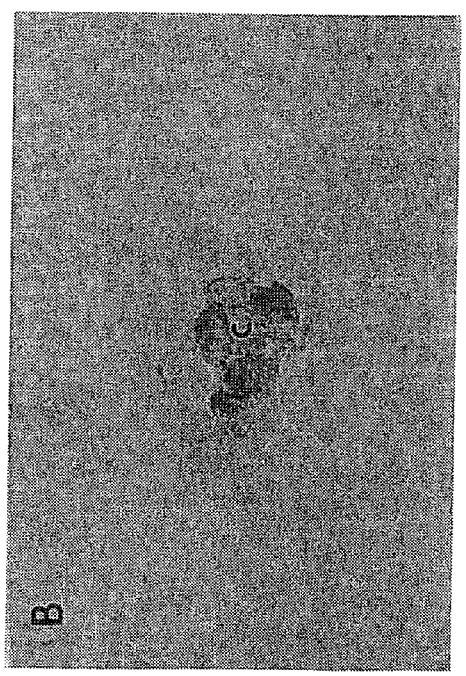
Figure 14A:
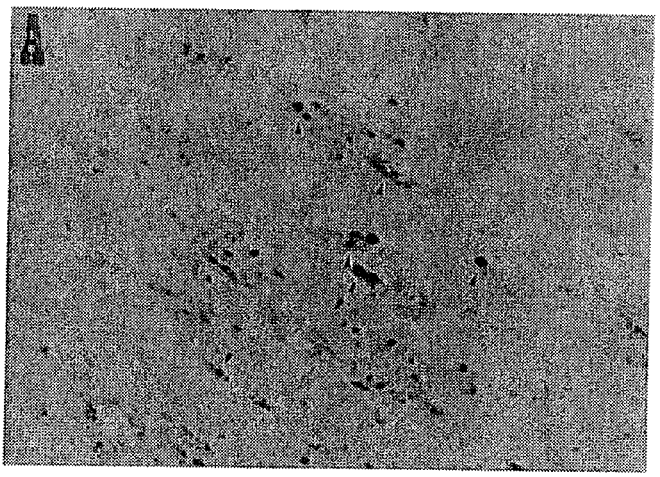
FIG. 14A-C A. Secondary culture of cells derived from 37-year-old male, 35 days in culture, and treated with $10^{-7}$ M dexamethasone. Bright field, 100× stained with Sudan Black B. Arrows point to adipocytes. B. Secondary culture of cells derived from 37-year-old male, 35 days in culture, and treated with $10^{-6}$ M dexamethasone. Bright field, 100× and stained with antibody to smooth muscle α-actin. sm=smooth muscle. C. Same as B but shown at 200×.
Figure 14B:
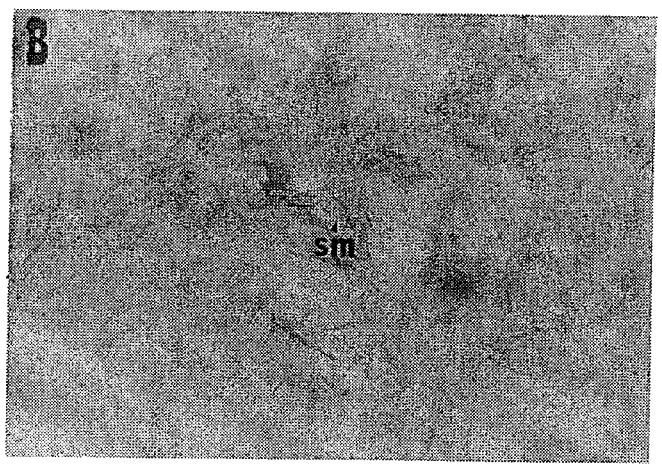
Figure 14C:
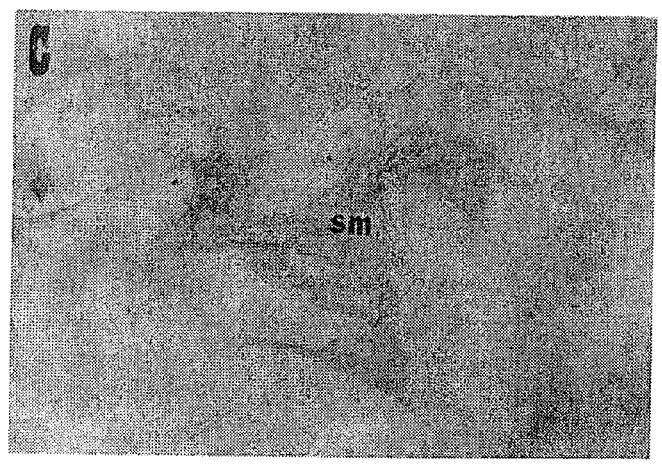
Figure 15A:
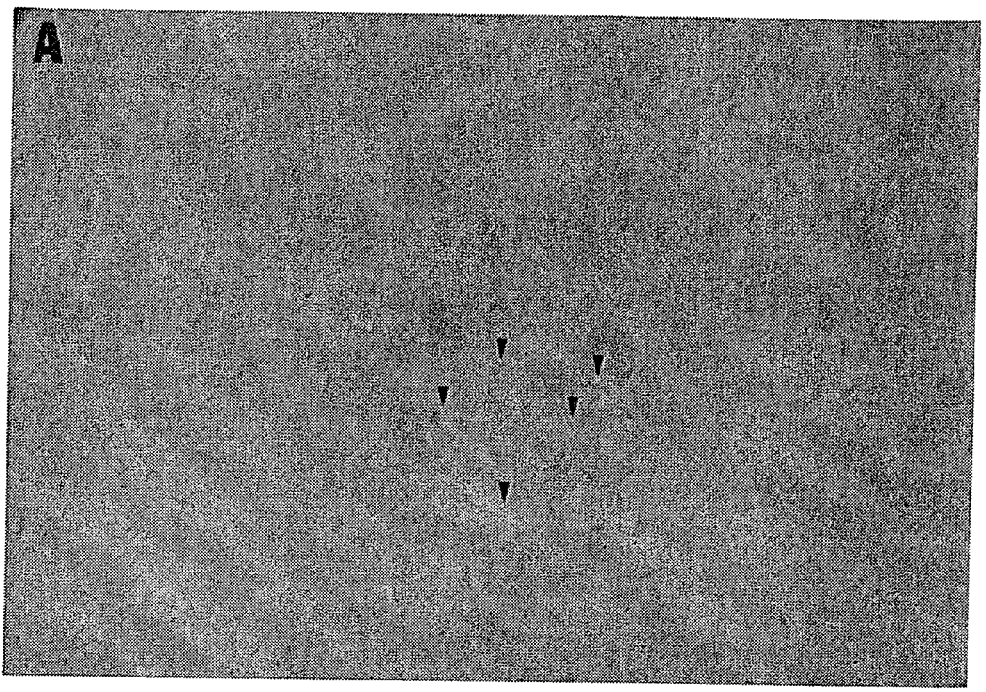
FIGS. 15A and B A. Secondary culture of cells derived from 37-year-old male, 35 days in culture, and treated with $10^{-7}$ M dexamethasone. Phase contrast, 200× but cells incubated with acetylated LDL. Arrows point to cells that fluoresce in B. B. Same field as A but under fluorescent light. Arrows point to endothelial cells.
Figure 15B:
Figure 16A:
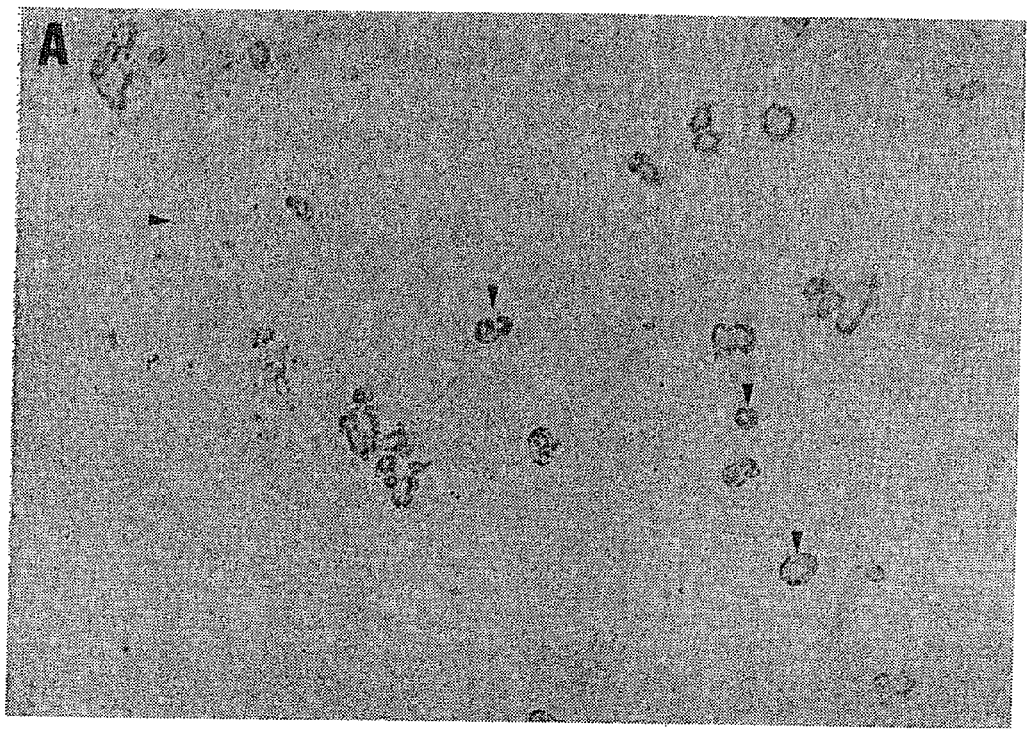
FIG. 16A-B A. Secondary culture of cells derived from 37-year-old male, 2 days in culture, and not treated with dexamethasone (Controls). Bright field, 200×. Cells have been fixed with ethanol, are in suspension, and have been stained with an antibody to CD34. Arrows point to cells in B. B. Same field as A but under fluorescent light. Arrows point to cells that are CD34 positive.
Figure 16B:
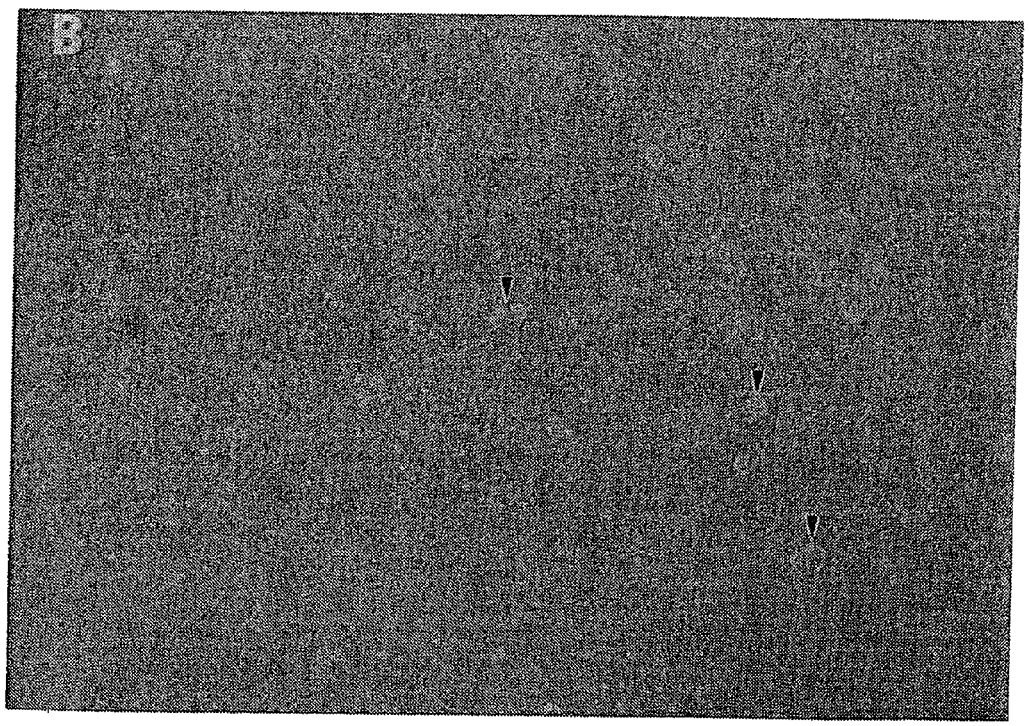

Secondary cultures treated with dexamethasome demonstrated several morphologies, including adipocytes, cartilage and bone (FIG. 13B-D; FIG. 14A-C). Cells in these cultures stained positive with antibody to myosin (FIG. 12A-B) and were identified as skeletal muscle myotubes. Other cells were identified as endothelial cells, by virtue of their morphology and their ability to incorporate fluorescent labeled acyl-low density lipoprotein into the cytoplasm (FIG. 15A-B). Cells staining with antibody to smooth muscle α-actin were also identified (FIG. 14). The secondary cultures were also evaluated for expression of CD34, and fixed cells shown to stain positive with antibody to CD34 (FIG. 16A-B).

These results demonstrate that pluripotent mesenchymal stem cells, capable of differentiation in culture to smooth muscle, adipocytes, cartilage, bone and endothelial cells can be isolated from adult, even geriatric (77 year old), human skeletal muscle.

Example 5

3T3 Cells Differentiate into Multiple Phenotypes In Vitro

Connective tissue is thought to be composed only of fibroblasts. 3T3 cells are a cell line derived from embryonic mouse tissue that appear fibroblastic. We have cultured 3T3 cells according to a protocol we developed for isolating cells from rat tissues capable of differentiating into multiple phenotypes. Swiss 3T3 cells (American Type Culture Collection) were cultured in Minimal Essential Media with Eule's salts (EMEM)+10% pre-selected horse serum. The cells were treated with a nonspecific differentiating agent, dexamethasone, in concentrations ranging from $10^{-10}$ to $10^{-6}$ M for 4-8 weeks. The controls did not receive dexamethasone. Several mesenchymal phenotypes developed in culture: adipocytes (Sudan Black B staining), chondrocytes (Alcian Blue staining, pH 1.0), osteoblasts (Von Kossa's stain for mineral), smooth muscle cells (antibody against a-smooth muscle actin), endothelial cells (uptake of acyllow density lipoprotein), and skeletal myotubes (linear multinucleated cells and antibodies against sarcomeric myosin). Some cultures also demonstrated a binucleated beating cell, whose beat rate increased with isoproterenol treatment and reversed with propanolol treatment. We tentatively identified this cell as a cardiac myocyte. 3T3 cells are capable of differentiating into multiple mesenchymally-derived phenotypes, characteristic of stem cells but not of fibroblasts. Therefore, they can be an invaluable tool in exploring the cell biology of stem cells and providing a simple, convenient assay system to study the differentiation of specific tissue types directed by growth and differentiation factors. The ability to specifically direct cell differentiation offers tremendous possibilities in tissue repair.

Swiss-3T3 cells were originally generated by Todaro and colleagues (Todaro and Green, 1963; Todara et al., 1964) from embryonic Swiss mice using long term culture methods. The cell line was selected for contact inhibition of cell growth at confluence after its apparent immortality in culture. This was attributed to a loss of conformation to Hayflick's number (Hayflick, 1965) with respect to cell senescence after approximately 50 cell doublings. The cell line appeared fibroblast-like and was designated Swiss-3T3 cells. Since their origin the 3T3 cell line and its derivatives have been used in over 13,000 studies to investigate various aspects of the control of cell growth, including viral transformation, (Denhardt et al., 1991; Green and Olaniyi, 1974), cell surface receptors (Eldar et al., 1990; Friedman et al., 1990; Maher, 1993; Satoh et al., 1990), growth factor regulation (campbell et al., 1993; Corps and Brown, 1991; Powis et al., 1990; Satoh et al., 1990; Yates et al., 1993), cellular physiology (Corps and Brown, 1992; Domin and Rozengurt, 1993; Pang et al., 1993), and factors regulating differentiation (Evans et al., 1993; Sparks et al., 1993). With the advent of molecular biological techniques, Swiss-3T3 cells have been utilized to study genetic regulatory mechanisms (Battey et al., 1991; Linder et al., 1991; Miyazawa et al., 1993; yan and Hung, 1993; Yang et al., 1993).

Subpopulations of 3T3 cells have been shown to differentiate into adipocytes when treated with glucocorticoids in culture (Green and Meuth, 1974; Kuri-Harcuch, 19978; Nixon and Green, 1984; Morikaua, et al., 1982; Ringold et al., 1991; Wier and Scott, 1986). A clone of 3T3, the 3T3-10 T½ cell has been shown to differentiate into adipocytes, chondrocytes, osteoblasts, and myotubes when treated with 5'-azacytidine (Taylor and Jones, 1979).

Recently, (Young et al., 1995) it was found that both lineage committed progenitor mesenchymal stem cells and lineage uncommitted pluripotent mesenchymal stem cells are located within connective tissue compartments associated with multiple organs and organ systems in the chick embryo. Lucas et al (Lucas et al, 1995), isolated mesenchymal stem cells from fetal and newborn rat skeletal muscle. These cells were capable of differentiating into skeletal muscle, cartilage, bone, smooth muscle, endothelial cells, and fibroblasts. Warejcka et al. (Warejcka et al., 1996), isolated a population of stem cells from 3-5 day old rat hearts. After treatment with dexamethasone these were also noted to develop into skeletal muscle, smooth muscle, adipocytes, bone and cartilage.

In this study we evaluated the ability of Swiss-3T3 cells to form multiple phenotypes in culture.

Materials and Methods

Cell Culture

Swiss-3T3 cells at passage 125 were acquired from American Type Culture Collection (Bethesda, Md.). Upon arrival, the cells were thawed and initially seeded at 100,000 cells per dish onto 100 mm dishes (Falcon, Lincoln Park, N.J.), precoated with 1% bovine gelatin (EM Sciences, Cherry Hills, N.J.), in medium containing 89% Eagle's minimal essential medium with Earl's salts (EMEM GIBCO, Grand Island, N.Y.), 10% pre-selected horse serum, and 1% penicillin/streptomycin (10,000 u penicillin/10,000 microgram streptomycin sulfate, GIBCO) at pH 7.4. Cultures were placed in an incubator containing humidified 95% air/5% CO2 at 37° C. until the cells were confluent.

The cells reached confluence in approximately 8 days and were released from the plates with a solution of 0.025% trypsin and 0.01% EDTA in Ca, Mg-Free Phosphate buffered saline (PBS), filtered through a 20 µm Nitex filter, diluted to $1\times10^6$ cells/ml in EMEM+10% horse serum containing 7.5% dimethylsulfoxide (Sigma, Salom, Mo.), and frozen slowly to −80° C. in freezing chambers (Fisher Scientific, Norcross, Ga.).

Frozen 3T3 cells were then thawed, cell viability was determined using 0.4% Typan Blue in PBS with a hemocytometer (Denhardt et al., 1991; Domin and Rozengurt, 1993), and the cells were plated in 24 well plates (Corning Glassworks, Corning, N.Y.), precoated with 1% gelatin at a density of 5000 cells/well. Cells were cultured in EMEM containing 10% horse serum and varying concentrations of dexamethasone (Sigma, Salom, Mo.). Four wells served as controls and received medium without dexamethasone. Four wells each received medium containing $10^{-10}$ M, $10^{-9}$ M, $10^{-8}$ M, $10^{-7}$ M, $10^{-6}$ M dexamethasone. The medium was changed every other day and cultures were examined using phase contrast microscopy for the appearance of different phenotypes.

Assay of Phenotypes

Bone—The presence of calcified tissue was assayed by Von Kossa's staining of calcium phosphate as described by Humason. Briefly, the culture medium was removed, and the plates were rinsed twice with the DPBS. The cells were fixed with 0.5 ml of 10% formalin for 3-5 minutes, then rinsed four times with distilled water. One half of a milliliter of freshly prepared 2% silver nitrate solution was then added, and the cells were incubated in the dark for 10 minutes. After incubation, the silver nitrate solution was removed and the cells were rinsed five times with distilled water. Approximately 0.5 ml of distilled water was left on each well. The plate was exposed to bright light for 15 minutes against a white background to reflect light. The plates were again rinsed five times with distilled water and quickly dehydrated with 100% ethanol. The plates were made permanent with glycerin jelly. Confirmation of the presence of calcium phosphate was performed by pretreating selected cultures with 1% weight/volume [ethylene bis(oxyethylenenitrilo)]-tetraacetic acid, a specific calcium chelator, in Ca, MG-free buffer for 1 hour before incubation in the silver nitrate solution.

Muscle—The cells were stained with the MF-20 antibody to sarcomeric myosin (Hybridoma Bank, Ames Iowa)

by means of a modified procedure of Young et. al., 1992b. Each step is preceded by two rinses with DPBS unless otherwise noted. After another rinse, 0.5 ml of cold methanol (−20° C.) was applied for 5 minutes to fix the cells. This procedure was followed by a 5 minute incubation with 0.5 ml of 1% v/v Triton-X100/0.05% w/v sodium azide (Sigma) in DPBS to solubilize cell membranes and inhibit endogenous peroxidases, respectively. A primary blocker of 20% goat serum (Sigma) was applied for 30 minutes in a 37° C. incubator. The primary immunoglobulin G of 1:200 dilution of MF-20 (0.4 ml/well) was then incubated for 1 hour. A secondary blocker of 0.5 ml of 20% goat serum was applied for 30 minutes and was followed by 0.4 ml of 1:7500 dilution of biotinylated goat antimouse anti-globulin G (Leinco, St. Louis, Mo.). This was incubated for 30 minutes at 37° C. A tertiary blocker consisting of 20% goat serum, was applied for 30 minutes and removed. Next, 0.4 ml of 1:3750 dilution of Streptavidin-horseradish peroxidase (Leinco) was added and incubated at 30° C. for 30 minutes. The cells were rinsed twice with 0.5 ml. distilled water. Chromagen (Sigma) was added as per the instructions in the staining kit to selected wells for future photography. Once the color developed, 25 microliters of 0.05% sodium azide was added per well to stop the reaction. The wells were then rinsed and made permanent with glycerin jelly.

Cartilage—Cultures were stained with Alcian blue solution (Roboz Surgical Instrument, Rockville, Md.) at pH 1.0. The fixed wells were stained for 30 minutes with 0.5 ml Alcian blue solution, pH 1.0, then removed from the wells. Unbound stain was removed by rinsing the wells seven times with tap water or distilled water. The cultures were preserved under glycerin jelly.

Smooth muscle—The cells were identified by staining with an antibody to smooth muscle α-actin (Sigma, St. Louis, Mo.).

Endothelial cells—Endothelial cells were identified by their ability to take up low-density lipoprotein as described by Voyta et. al. (Voyta et al., 1984). The cells were washed five times with Dulbecco's minimal essential medium (high glucose) (GIBCO) supplemented with antibiotics. The cells were incubated for 4 hours at 37° C. with 10 μg per ml of 1,1'-dioctadecyl-3,3,3',3'-tetramethyl-indocarbocyanine perchlorate (DiI-Acyl-LDL) (Biomedical Technology, Stoughton, Mass.). The wells were then washed six times with EMEM+10% horse serum and viewed on a Nikon Diaphot with fluorescent attachment.

Cardiac muscle—Cardiac myocytes were identified based on their large binucleated nuclei and their reactions to inotropic and chronotropic agents.

Results

Figure 17A:
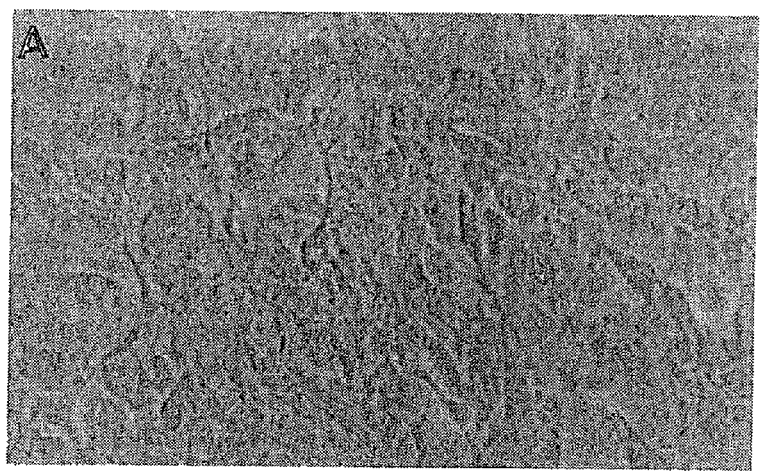
FIG. 17A-C shows 3T3 cells in secondary culture after 35 days. A. Control cultures, phase contrast. B. Culture treated with $10^{-10}$ M dexamethasone, phase contrast. a=adipocytes, arrows point to lipid droplets. C. Culture treated with $10^{-7}$ M dexamethasone stained with Sudan black B, bright field. a=adipocytes. Original magnification=200×.

The 3T3 cells received from ATCC, when thawed and cultured, had mostly a stellate or triangular morphology. Confluence was reached in approximately a week to ten days in culture. The cells were frozen, thawed, and replated as described. The control cultures, without dexamethasone, continued to exhibit a uniformly stellate morphology throughout the culture period (FIG. 17A).

Figure 17B:
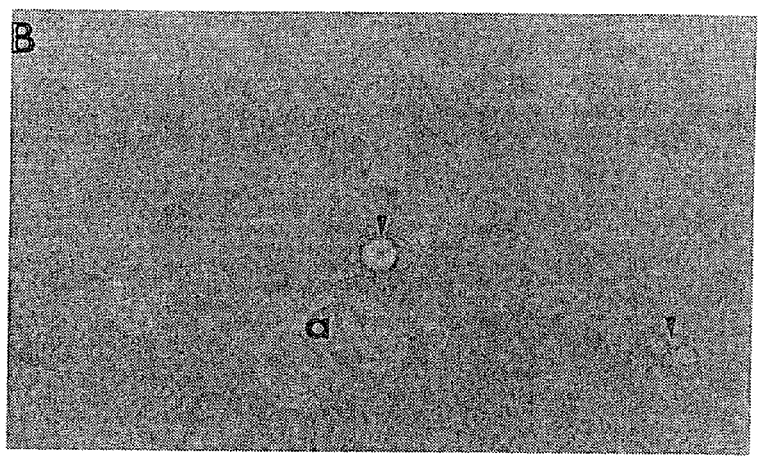
Figure 17C:
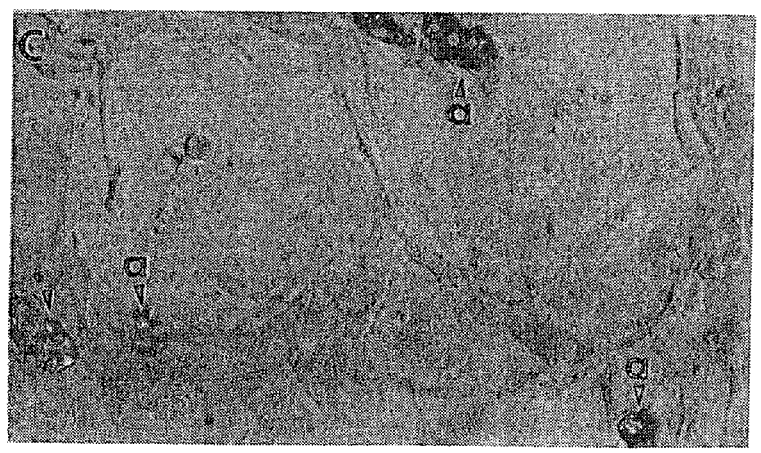

The cultures treated with dexamethasone exhibited a number of phenotypes. Dexamethasone was used as a non-specific inductive agent in order to test for differentiation in vitro (Grig., aubin, Heersche). One phenotype that appeared after two weeks treatment with dexamethasone contained cells with round droplets that were refractile in phase contrast (FIG. 17B). These cells stained with Sudan Black B (FIG. 17C) and were thus identified as adipocytes. Most of these adipocytes appeared at $10^{-8}$-$10^{-6}$ M dexamethasone concentration.

Figure 18A:
FIG. 18A-C shows 3T3 cells in secondary culture. A. Culture treated with $10^{-8}$ M dexamethasone for 14 days, phase contrast. Myotube, arrows point to nuclei. B. Culture treated with $10^{-7}$ M dexamethasone for 14 days stained with a monoclonal antibody to sarcomeric myosin, bright field. Arrow points to myotube. C. Culture treated with $10^{-7}$M dexamethasone for 14 days, phase contrast. cm=cardiac myocyte.
Figure 18B:
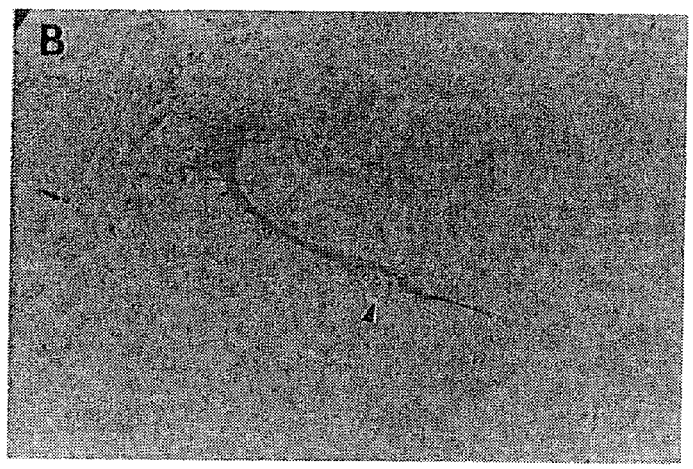

At 14 days, at a concentration of $10^{-9}$-$10^{-6}$ M dexamethasone, elongated cells containing several nuclei appeared (FIG. 18A). These cells contracted spontaneously in culture and stained with a monoclonal antibody to sarcomeric myosin (FIG. 18B). Therefore the cells were identified as myotubes.

Figure 18C:
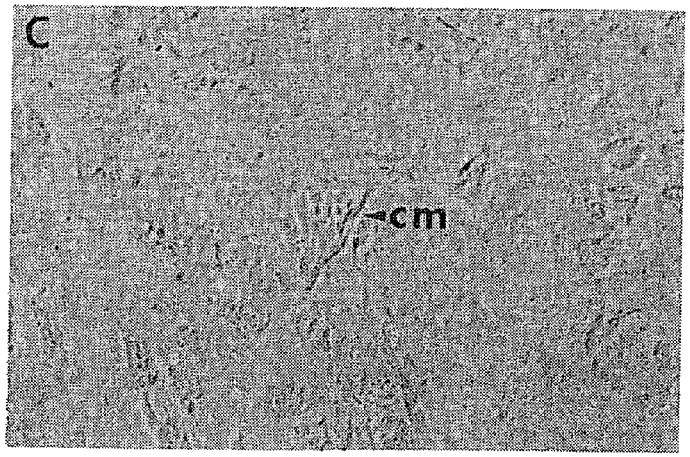

At 4 weeks in culture, A few binucleated cells appeared at a concentration of $10^{-7}$-$10^{-6}$ M dexamethasone (FIG. 18C). These cells beat rhythmically in culture at about 65 beats per minute (TABLE 2). The beat rate increased to 85 beats per minute when the cells were treated with $10^{-6}$ M isoproterenol. Isoproterenol is a potent selective B adrenergic agonist that has positive inotropic and chronotropic effects on cardiac muscle (Goodman and Gilman, 1996). In contrast, propanolol is a B-adrenergic antagonist that slows the heart rate. When the cells were pretreated with $10^{-6}$ M propanolol and then exposed to isoproterenol, the cells maintained their beat rate. Based on these criteria, positive chronotropic reaction to isoproterenol and negative reaction to propanolol, we tentatively identified these cells as cardiac myocytes.

TABLE 2

| Treatment | Beats per minute n = 5 |
|---|---|
| Control | 66.25± |
| Isoproterenol 10-6M | 87.4±* |
| Propanolol 10-6M | 36.8± |
| Propanolol + Isoproteronal | 30.8± |

Different from Controls at $p < 0.05$

Table 2. Comparison of exposure of cardiac myocytes and control cells to isoproterenol and propanolol and change in beat rate.

Figure 19A:
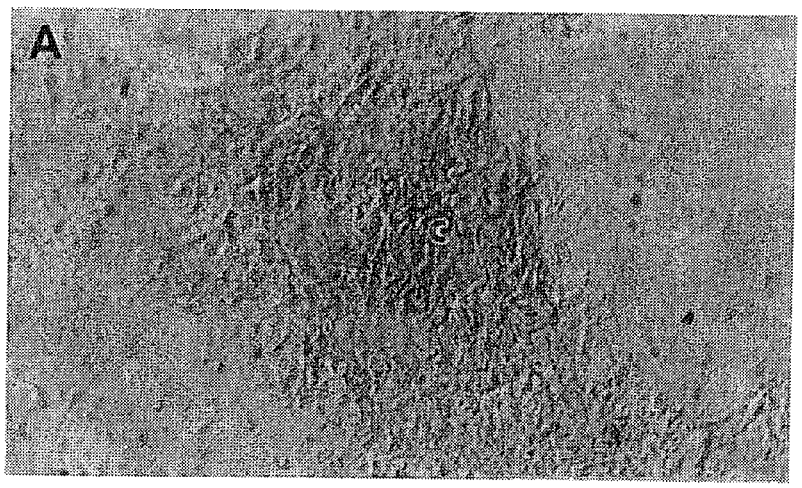
FIG. 19A-C shows 3T3 cells in secondary culture after 35 days. A. Culture treated with $10^{-7}$ M dexamethasone stained with Alcian blue, bright field. c=cartilage nodule. Original magnification=100×. B. Culture treated with $10^{-9}$ M dexamethasone stained with Alcian blue, bright field. c=cartilage nodule. Original magnification=200×. C. Culture treated with $10^{-7}$ M dexamethasone stained with Von Kossa's stain, bright field. b=bone. Original magnification=200×.
Figure 19B:
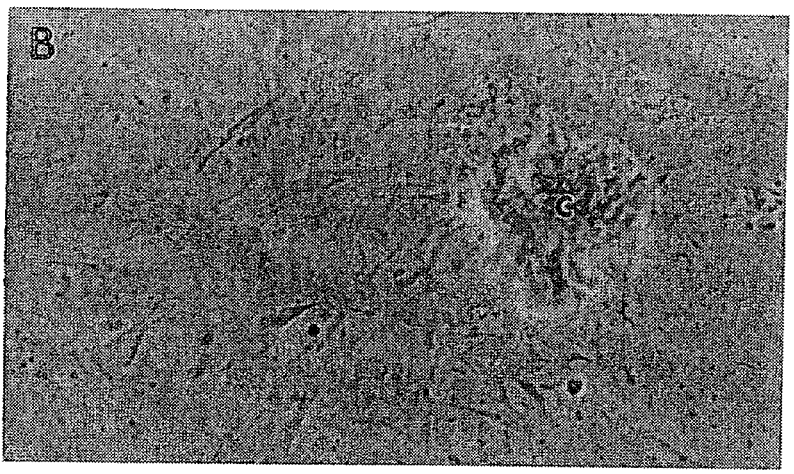
Figure 19C:
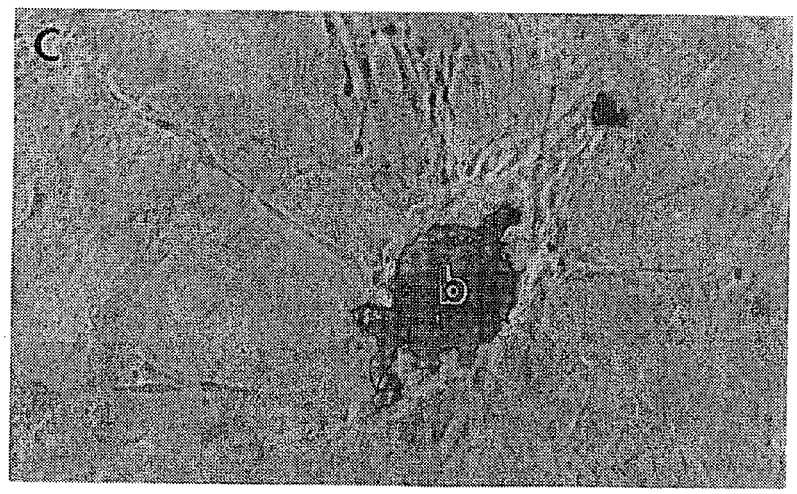

At 35 days in culture, at a concentration of $10^{-7}$ to $10^{-9}$ M dexamethasone, round cells that grew in nodules and had a refractile extracellular matrix appeared (FIGS. 19A and B). The extracellular matrix stained with Alcian blue at pH 1.0. These nodules were identified as cartilage. Two distinct morphologies were observed. In one, the cartilage nodule had irregular borders where the cells merged with the surrounding stellate cells (FIG. 19C). The other consisted of nodules with very clearly defined borders distinct from the background stellate cells (FIG. 19B).

Polygonal cells appeared after 28 days in culture in small numbers in all concentrations of dexamethasone (FIG. 19). These cells formed a dense extracellular matrix that stained with Von Kossa's stain (FIG. 19). Pre-treatment of the cultures with EGTA prevented staining with Von Kossa's stain (data not shown). Based on their ability to make a calcified matrix, these cells were identified as osteoblasts.

Figure 20A:
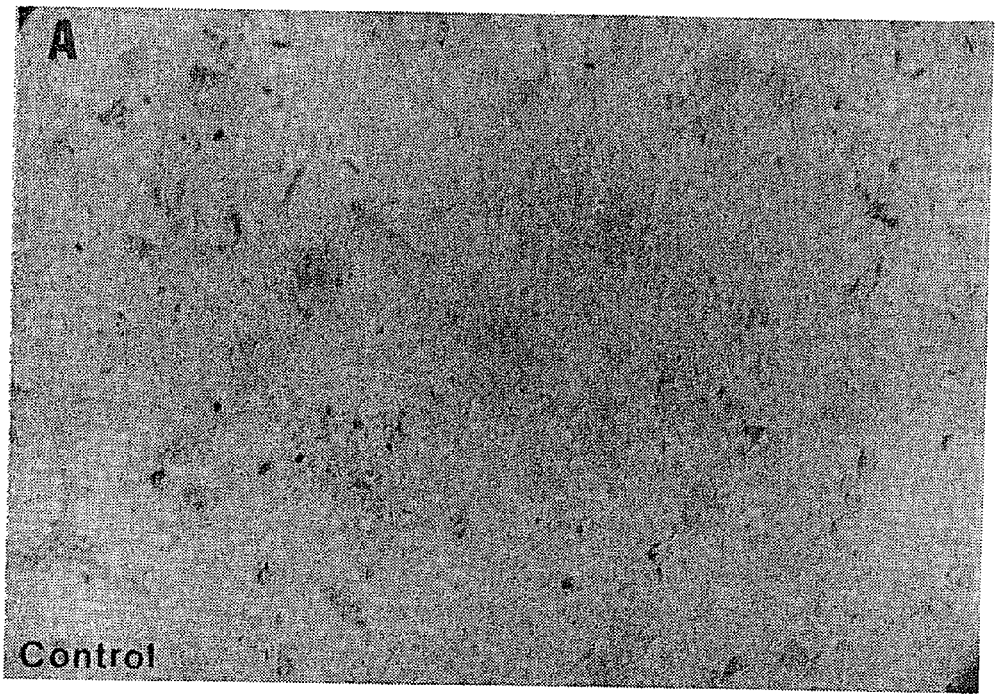
FIGS. 20A and B shows 3T3 cells in secondary culture after 35 days stained with a monoclonal antibody to smooth muscle α-actin. A. Control culture, no dexamethasone. B. Culture treated with $10^{-6}$ M dexamethasone, bright field. sm.=smooth muscle cells. Original magnification=200×.
Figure 20B:
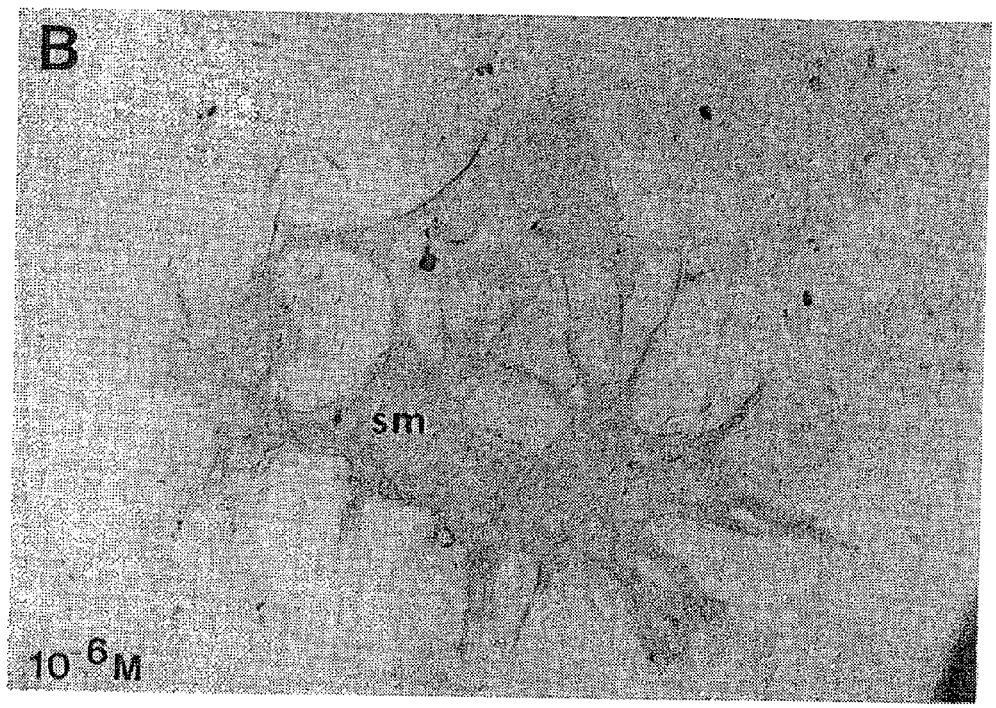

At 35 days of treatment with dexamethasone, parallelogram shaped cells containing fibers were observed. These cells were most numerous at $10^{-7}$ and $10^{-6}$ M dexamethasone concentration. The fibers stained with an antibody to smooth muscle α-actin. Therefore, the cells were identified as smooth muscle cells (FIG. 20).

Figure 21A:
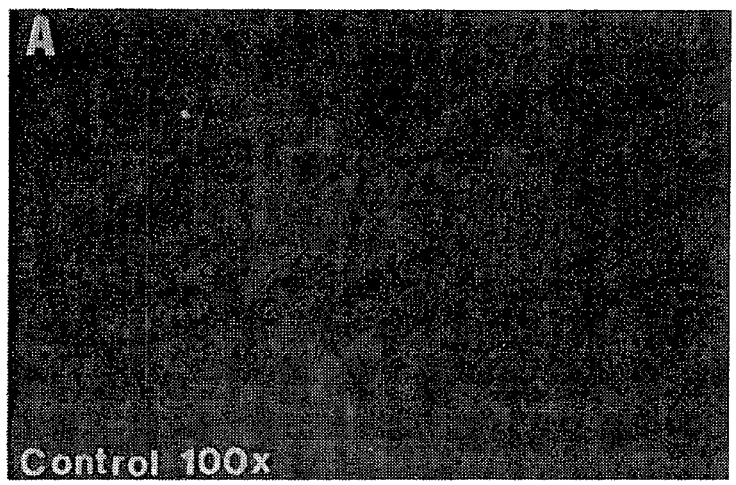
FIG. 21A-C shows 3T3 cells in secondary culture after 35 days, incubated with acetylated-LDL and viewed with fluorescent microscopy. A. Control culture, no dexamethasone. Original magnification=100×. B. Culture treated with $10^{-6}$ M dexamethasone. Original magnification=100×. C. Culture treated with $10^{-7}$ M dexamethasone. Original magnification=200×.
Figure 21B:
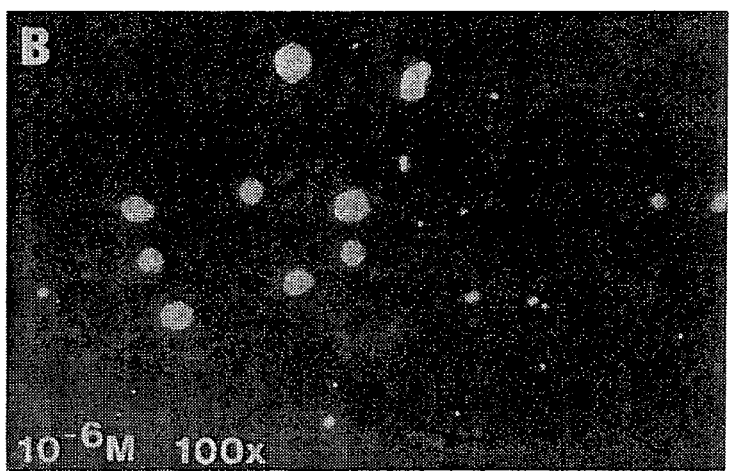
Figure 21C:
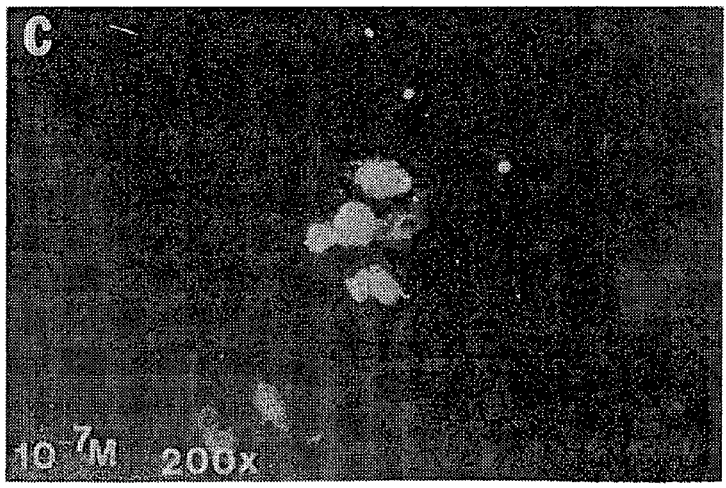

Polygonal cells without a discernible extracellular matrix appeared at 35 days, at a concentration of $10^{-7}$ and $10^{-6}$ M dexamethasone. The cells incorporated DiI-Acyl-LDL into cytoplasmic vesicles and were identified as endothelial cells (FIG. 21).

Discussion

Tissue growth in culture has tremendous promise for understanding cellular biology that can later be translated to development of biologic tissues for in vivo use. Swiss 3T3 cells have generally been referred to as fibroblasts in the literature (Eldar et al, 1990; Linder et al., 1991). However, when 3T3 cells are cultured according to the protocol developed for isolating mesenchymal stem cells, the 3T3 cells were able to develop into several mesodermal phenotypes when treated with dexamethasone.

In this study, the cultures at two weeks treatment, at a concentration of $10^{-8}$ M dexamethasone, exhibited cells with round droplets that were refractile in phase contrast. These cells stained with Sudan Black B and were identified as adipocytes. At 14 days at a concentration of $10^{-9}$-$10^{-8}$ M dexamethasone elongated, multinucleated cells that contracted spontaneously in culture appeared. These were identified as myotubes based on staining with monoclonal antibody to sarcomeric myosin. At a concentration of $10^{-7}$-$10^{-6}$M dexamethasone, on day 28, binucleated cells that beat rhythmically in culture were seen. These cells behaved as cardiac myocytes when exposed to a selective B agonist and antagonist. At 35 days in culture, at a concentration of $10^{-9}$-$10^{-7}$ M dexamethasone, cartilage cells appeared in two distinct morphologies, one had irregular borders and the other clearly defined borders from the background stellate cells. After 28 days in culture, in all concentrations of dexamethasone, polygonal cells appeared. These cells were identified as osteoblasts based on their ability to make a calcified matrix. At 35 days of dexamethasone treatment, at a concentration of $10^{-6}$ M dexamethasone, parallelogram shaped cells were observed. These cells were identified as smooth muscle cells based on their staining with an antibody to smooth muscle $\alpha$-actin. At 35 days, at a concentration of $10^{-7}$ M dexamethasone, polygonal cells without an extracellular matrix that incorporated Dil-Acyl-LDL into cytoplasmic vesicles were identified as endothelial cells.

While most reports do not discuss the ability of 3T3 cells to differentiate, there are several studies in the literature that show the cells can differentiate into other phenotypes. Murine fibroblastic mesenchymal cells C3H10T ½, a clone of 3T3, lost their original fibroblastic nature after permanent transfection with BMP 2 and 4 (Aherns et al., 1993). These cells were shown to differentiate into three distinct phenotypes similar to; osteoblasts, chondroblasts, and adipocytes. Taylor and Jones (Taylor and Jones, 1979), showed that 5'-azacytidine (5-AZA-CR) induces the formation of biochemically differentiated functional striated muscle, adipocytes and chondrocytes in the mouse embryo cell lines C3H/10 T½ CL8 and Swiss 3T3. In 1982, the same group showed that muscle and adipocyte phenotypes are maximal when cells are treated during early S phase (Taylor and Jones, 1982).

Two distinct characteristics of stem cells are their unlimited differentiation potential, and their ability to be quiescent. The 3T3 cells in this study were obtained from ATCC at 125 passages or 625 cell doublings. This is past Hayflick's limit of 50 cell doublings for committed cells (Hayflick, 1965). During the study, we observed at least five more cell doublings. The control studies demonstrate that the 3T3 cells are quiescent and undifferentiated unless stimulated.

Sparks and Scott (Sparks et al., 1991) examined the effects of TGFB on 3T3 cells. They noted that TGFB was a specific inhibitor of differentiation of 3T3 cells into adipocytes. Proliferation however, was not affected. Therefore, prior to expression of the differentiated adipocyte phenotype 3T3 stem cells must first stop growth at a distinct stage in the cell cycle. Further, differentiation can be initiated non-specifically by highly mitogenic agents that prevent growth arrest In another study on the differentiation of stem cells, (Scott and Maercklein 1984), low dose UV irradiation was found to stably and selectively inhibit the differentiation of proadipocyte 3T3 cells without altering their ability to regulate cellular proliferation in growth factor deficient or nutrient-deficient culture conditions. This effect may be an early event in the initiation of carcinogenesis. The irradiated cells were also more likely to transform than non-irradiated cells.

The original isolation by Todaro and Green did not involve intentional transformation. It has often been asserted that 3T3 cells are spontaneously transformed, accounting for their unlimited proliferation potential. However, the studies by Scott and co-workers indicate that cellular proliferation is not effected despite exposure to UV radiation.

In addition, in studies where the 3T3 cells are transformed by viral transfection, the untransfected cells do not form tumors (Sparks et al., 1991). Therefore, it is possible that the ability of the 3T3 cells to exceed Hayflick's number is because they are stem cells.

Mesoderm, a tissue of embryonic origin, gives rise to appendicular skeleton and muscle (dosral mesoderm), connective tissue and endothelium of blood vessels and heart (splanchnic mesoderm), and other organs (intermediate mesoderm). The phenotypes observed in this study derive from dorsal and splanchnic mesoderm. Future studies will look to phenotypes from intermediate mesoderm.

BMP and CDMP are agents that have been noted to direct differentiation of these various tissues. BMP induced differentiation of C3H10T½ into adipocytes, chondrocytes and osteoblasts in the presence of azacytidine (Aherns et al., 1993). Extracts from calf articular cartilage have been found to induce cartilage and bone formation when subcutaneously implanted in rats (Chang et al., 1994). These cartilage derived morphological proteins (CDMP) are thought to have a role in chondrocyte differentiation and growth of long bones.

3T3 cells are thus showing a multipotent differentiation potential and are behaving as stem cells. This makes the 3T3 cells a potential assay system for studying the genetic steps of differentiation.

Example 6

Hematopoietic Cytokines Induce Hematopoietic Expression in Human Pluripotent Stem Cells Human pluripotent stem cells (geriatric, PAL#3 cell line at 150 cell doublings post harvest) were seeded at $75 \times 10^3$ cells per 1% gelatinized T-25 flask in Opti-MEM medium containing 10% HS & 1% antibiotic/antimycotic. After 24 hr, media was replaced with (controls) same medium or (experimentals) same medium containing hematopietic cytokines: 2.5 U/ml erythropoietin, 10 ng/ml granulocyte/macrophage-colony stimulating factor, 10 ng/ml granulocyte-colony stimulating factor, 10 ng/ml macrophage-colony stimulating factor, 50 ng/ml interleukin-3, 50 ng/ml interleukin-6, 50 ng/ml stem cell factor, and 2 µg/ml insulin. Cultures were fed biweekly in their respective media. Compared to controls, experimental treatment for three weeks induced the expression of GM-CSF-receptor, as indicated by Northern RNA/cDNA analysis.

Example 7

Human Mesenchymal Stem Cells Display Cell Surface Cluster Differentiation Markers CD10, CD13, CD56, and MHC Class-I

Each year millions of people suffer tissue loss or end-stage organ failure. While allogeneic therapies have saved and improved countless lives, they remain imperfect solutions. These therapies are limited by critical donor shortages, long-term morbidity, and mortality. A wide variety of transplants, congenital malformations, elective surgeries, and genetic disorders have the potential for treatment with autologous stem cells as a source of HLA-matched donor tissue. Our current research is aimed at characterizing cell surface cluster differentiation (CD) markers on human progenitor and pluripotent mesenchymal stem cells to aid in isolating comparatively purified populations of these cells. This study examined human pluripotent and progenitor cells isolated from fetal, mature, and geriatric individuals for the possible presence of 15 CD markers. The response to insulin and dexamethasone revealed that the cell isolates were composed of lineage-committed progenitor cells and lineage-uncommitted pluripotent cells. Flow cytometry showed cell populations positive for CD10, CD13, CD56, and MHC Class-I markers and negative for CD3, CD5, CD7, CD11b, CD14, CD15, CD16, CD19, CD25, CD45, and CD65 markers. Northern analysis revealed that CD13 and CD56 were actively transcribed at time of cell harvest. We report the first identification of CD10, CD13, CD56, and MHC Class-I cell surface antigens on these human mesenchymal stem cells.

Numerous studies have shown the existence of mesenchymal stem cells distributed widely throughout the connective tissue compartments of many animals. These cells provide for the continued maintenance and repair of tissues throughout the life-span of the individual. Examples of these cells include the unipotent myosatellite myoblasts of muscle (Mauro, 1961; Campion, 1984; Grounds et al., 1992); the unipotent adipoblast cells of adipose tissue (Aihaud et al., 1992); the unipotent chondrogenic and osteogenic stem cells of the perichondrium and periosteum, respectively (Cruess, 1982; Young et al., 1995); the bipotent adipofibroblast cells of adipose tissue (Vierck et al., 1996); the bipotent chondrogenic/osteogenic stem cells of marrow (Owen, 1988; Beresford, 1989; Caplan et al., 1997); and the multipotent hematopoietic stem cells of bone marrow and peripheral blood (Palis and Segel, 1998; McGuire, 1998; Ratajczak et al., 1998).

Recent studies utilizing serial dilution clonogenic analysis (Young et al., 1993, 1998a, b; Rogers et al., 1995), have shown that mesenchymal stem cells consist of two uniquely different categories of cells: progenitor cells committed to a variety of phenotypic lineages (see above), and pluripotent cells that are not committed to any particular lineage. Further analysis (Young et al., 1993, 1995) revealed that multiple lineage-specific progenitor cells as well as pluripotent cells were also present in the connective tissue compartments of various tissues. For example, the connective tissues of skeletal muscle contain not only myosatellite cells (the precursor cells for skeletal muscle) and fibroblasts (the precursor cells for connective tissues) but also adipoblasts (the precursor cells for fat), chondrogenic progenitor cells (the precursor cells for cartilage), osteogenic progenitor cells (the precursor cells for bone), as well as lineage-uncommitted pluripotent stem cells.

Lineage-committed progenitor cells conform to Hayflick's limit (Hayflick, 1965), having life-spans limited to 50-70 cell doublings before programmed cell senescence and death occur. Progenitor cells differentiate into cell types limited to the lineage to which they are committed (see above). By contrast, pluripotent cells have the capacity for extended self-renewal beyond Hayflick's limit as long as they remain lineage-uncommitted. Pluripotent cells can commit to any tissue lineage within the embryonic mesodermal line. Once committed to a particular lineage, these cells assume all the attributes of progenitor cells.

We propose that progenitor and pluripotent cells could be of value in transplantation and/or gene therapies where donor tissue is in short supply. Indeed, Grande et al. (1995) used rabbit pluripotent cells in the rabbit full thickness cartilage defect model. Dramatic results were reported in the resurfacing of articular cartilage as well as the reconstitution of adjacent subchondral and trabecular bone.

Previous studies (Young et al., 1993, 1998, Rogers et al., 1995) have shown that extended time periods are necessary to isolate and separate progenitor and pluripotent cells, either by limiting serial dilution clonogenic analysis (18-24 months) or propagation past Hayflick's limit (5-9 months). Improvements in the ease of isolation and induction of lineage commitment must be made for these cells to be useful in the clinical setting. Therefore, our current research is aimed at characterizing the cell surface antigens of human progenitor and pluripotent cells in order to shorten the time required for their isolation and separation.

Antibodies to cell surface cluster differentiation (CD) markers have been used in conjunction with flow cytometry to characterize cell surface antigens on hematopoietic cells. To date, more than 180 CD markers have been used to 'fingerprint' hematopoietic cell lineages (Kishimoto et al., 1997). The experiments reported in this paper involved characterizing 15 cell surface CD marker antigens on human male and female progenitor and pluripotent stem cells isolated from fetal, adult, and geriatric donors. We report the first identification of CD10, CD13, CD56, and MHC Class-I on human progenitor and pluripotent mesenchymal stem cells. Negative results were obtained for CD3, CD7, CD11b, CD14, CD15, CD16, CD19, CD25, CD45, and CD65 antigens. RNAs were extracted from the cells, electrophoresed, and probed with 32P-labeled cDNAs to CD10, CD13, and CD56 using Northern analysis. CD13 and CD56 were being actively transcribed at time of cell harvest.

Materials and Methods (Materials and Methods are as above in Example 1, except as noted below).

Human Mesenchymal Stem Cells

Five populations of human cells, adult (female), fetal (male and female), and geriatric (male and female), were used for this study. Adult female cells were purchased as a subconfluent culture of 25 year-old human dermal fibroblasts [NHDF, catalog # CC-0252, lot #6F0600, Clonetics, San Diego, Calif.]. Fetal male cells were purchased as a subconfluent culture of 22 week-old fetal skeletal muscle cells derived from the thigh muscle [CM-SkM, catalog # CC-0231, lot #6F0604, Clonetics]. Fetal female cells were purchased as a subconfluent culture of 25 week-old fetal skeletal muscle cells derived from the triceps muscle [CF-SkM, catalog # CC-2561, lot #14722, Clonetics]. Upon arrival, the cells were transferred to plating medium-A (PM-A). PM-A consisted of 89% (v/v) Eagle's Minimal Essential Medium with Earle's salts [EMEM, GIBCO BRL, Grand Island, N.Y.], 10% (v/v) pre-selected horse serum [lot nos. 17F-0218 (HS7) or 49F-0082 (HS4), Sigma Chemical Co., St. Louis, Mo.], and 1% (v/v) Penicillin/Streptomycin [10,000 units/ml penicillin and 10,000 mg/ml streptomycin, GIBCO], pH 7.4. Cells were incubated at 37° C. in a 95% air/5% CO2 humidified environment. After expansion, cells were released with 0.05% (w/v) trypsin [DIFCO, Detroit, Mich.] in $Ca^{+2}$-, $Mg^{+2}$-free Dulbecco's phosphate buffered saline [GIBCO] containing 0.0744% (w/v) ethylenediamine tetraacetic acid [EDTA, Sigma], centrifuged at 100×g for 20 min., and the supernatant aspirated. The cell pellet was resuspended in PM-A and the cell suspension cryopreserved by slow freezing for storage at −70 to 80° C. in PM-A containing 7.5% (v/v) dimethyl sulfoxide [DMSO, Morton Thiokol, Danvers, Mass.] (Young et al., 1991).

Geriatric cells were isolated from specimens of skeletal muscle obtained from a 67 year-old male patient and a 77 year-old female patient following standard protocols for the isolation of mesenchymal stem cells (Young et al., 1995; Lucas et al., 1995). The male cells were designated "PAL#3", and the female cells "PAL#2". In brief, cells were liberated from the connective tissue compartment of skeletal muscle with collagenase [CLS-I, Worthington Biochemical Corp., Freehold, N.J.] and dispase [catalog #40235, Collaborative Research Inc., Bedford, Mass.]. Single cell suspensions were obtained by sequential filtration through 90-mm and 20-mm Nitex [Tetco Inc., Elmsford, N.Y.]. Cells were seeded at $10^5$ cells/1% (w/v) gelatin-coated [EM Sciences, Gibbstown, N.J.] T-75 flasks [Falcon, Becton-Dickinson Labware, Franklin Lakes, N.J.] in PM-A and allowed to expand and differentiate prior to cryopreservation. Cells were incubated at 37° C. in a 95% air/5% $CO_2$ humidified environment. After expansion, cells were released with trypsin, sieved as above to separate mononucleated cells from differentiated phenotypes (i.e., multinucleated myotubes, adipocyte colonies, cartilage nodules, bone nodules), and cryopreserved at −70 to −80° C. in PM-A containing 7.5% (v/v) DMSO. Using the procedures outlined above, each subsequent cryopreservation step effectively removes more than 98% of contaminating fibroblasts and differentiated phenotypes from the stem cell preparation (Young et al., 1991).

Further purification of progenitor and pluripotent cells was obtained by multiple expansion and cryopreservation steps utilizing 1% gelatin coated flasks with plating medium-B (PM-B). PM-B consisted of 89% (v/v) Opti-MEM based medium [catalog #22600-050, GIBCO] containing 0.01 mM W β-mercaptoethanol [Sigma], 10% (v/v) horse serum [HS3, lot number 3M0338, BioWhittaker, Walkersville, Md.], and 1% (v/v) antibiotic-antimycotic solution [GIBCO], pH 7.4. Cells were then propagated to 30 cell doublings, released with trypsin, and aliquoted for insulin/dexamethasone analysis, flow cytometry and molecular analysis.

Insulin/Dexamethasone Analysis to Identify Progenitor and Pluripotent Cells

Aliquots of CM-SkM, CF-SkM, NHDF, PAL#3, and PAL#2 cells were thawed and plated individually at 10,000 cells per well in 1% gelatin-coated 24-well plates [Corning, Corning, N.Y.] utilizing PM-B. After 24 hr PM-B was removed and replaced with either control medium, insulin testing medium, or dexamethasone testing medium. Control medium consisted of 98% (v/v) Opti-MEM containing 0.01 mM β-mercapto-ethanol, 1% (v/v) HS3, and 1% antibiotic-antimycotic solution. Insulin testing medium consisted of control medium containing 2 μg/ml insulin [Sigma]. Dexmethasone testing medium was composed of 98% Opti-MEM, 0.01 mM β-mercaptoethanol, 1% serum [HS3, HS9 (horse serum, lot number 90H-0701, Sigma) or FBS (fetal bovine serum, lot no. 3000L, Atlanta Biologicals, Norcross, Ga.)] and 1% antibiotic-antimycotic solution. This solution was made $10^{-10}$, $10^{-9}$, $10^{-8}$, $10^{-7}$ or $10^{-6}$ M with respect to dexamethasone [Sigma]) (Young et al., 1995; Young, 1999; Young et al., 1998). Media were changed three times per week for six weeks. Cultures were viewed twice per week for changes in phenotypic expression and photographed.

Figure 22A:
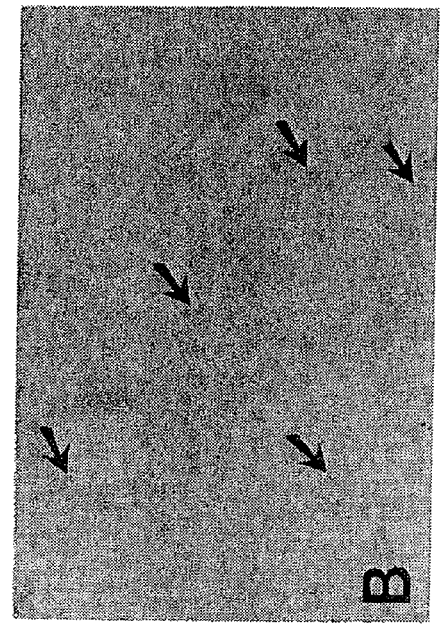
FIG. 22A-D. CF-SkM propagated to 30 cell doublings and incubated with insulin or dexamethasone for 0 to six weeks. Morphologies as noted. A. Cells treated for one week with 2 μg/ml insulin. Note presence of four nuclei (arrows) within linear structure, indicative of a multinucleated myotube, MT. Orig. mag., 10×. B. Cells treated for two weeks with $10^{-6}$ M dexamethasone. Note presence of clusters of cells (arrows) containing intracellular refractile vesicles indicative of adipogenic cells. Orig. mag., 10×. C. Cells treated for four weeks with $10^{-6}$ M dexamethasone. Note presence of nodular mass of cells with pericellular matrix halos, indicative of cartilage nodule (CN) overlying multiple multinucleated linear structures indicative of myotubes (MTs). Orig. mag., 10×. D. Cells treated for six weeks with 2 μg/ml insulin. Note presence of three-dimensional matrix (delineated by arrows) overlying cell cluster, indicative of bone nodule (BN). Orig. mag., 10×.
Figure 22B:
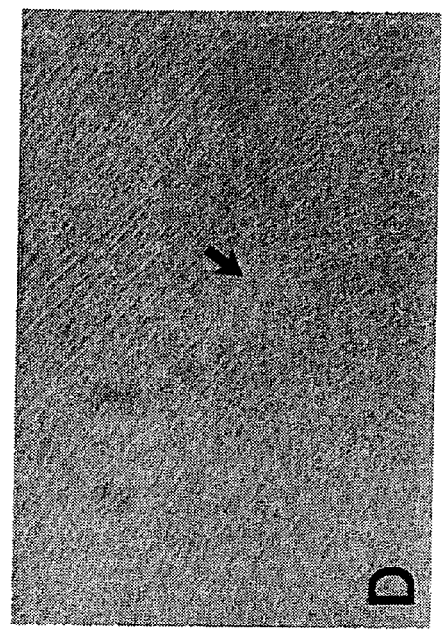
Figure 22C:
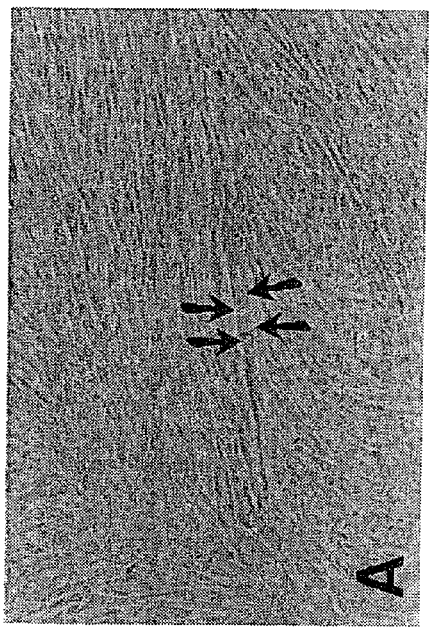
Figure 22D:
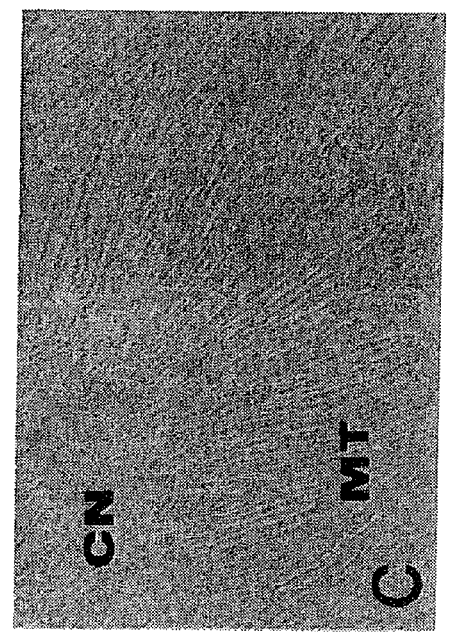
Figure 23A:
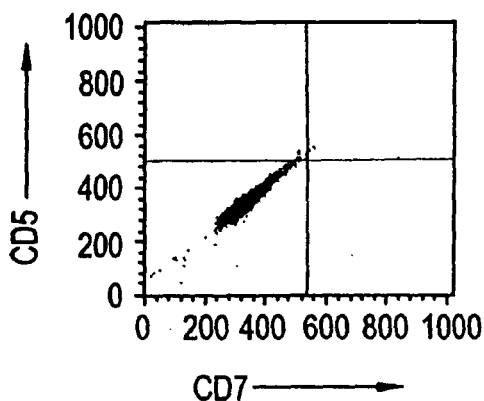
FIG. 23. Flow cytometry of cluster differentiation markers. "X"-axis and "Y"-axis as noted on figure. NHDF propagated to 30 cell doublings and analyzed with antibodies to cell surface cluster differentiation markers.
Figure 23D:
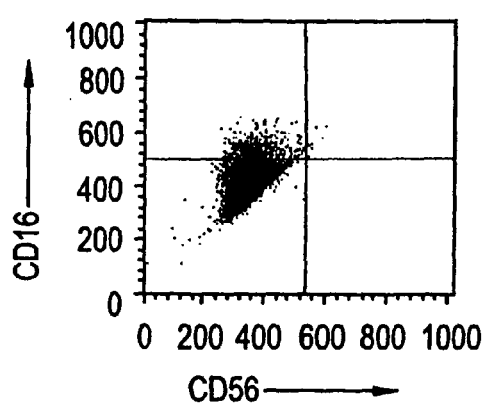
Figure 23B:
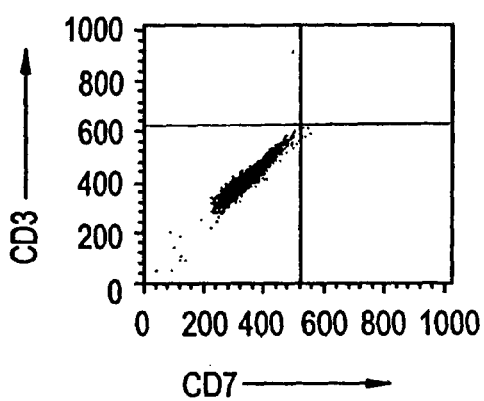
Figure 23E:
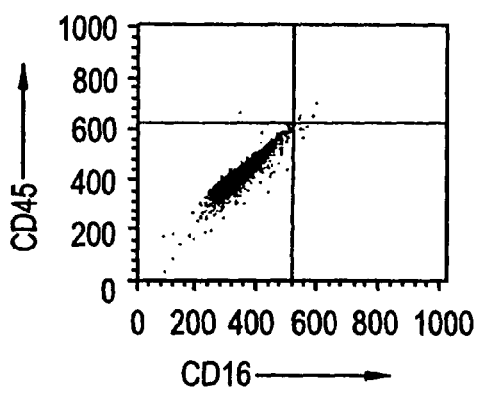
Figure 23C:
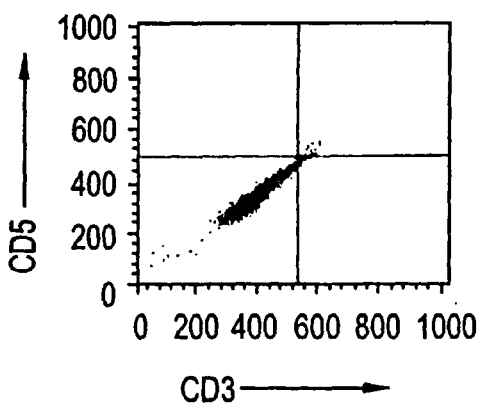
Figure 23F:
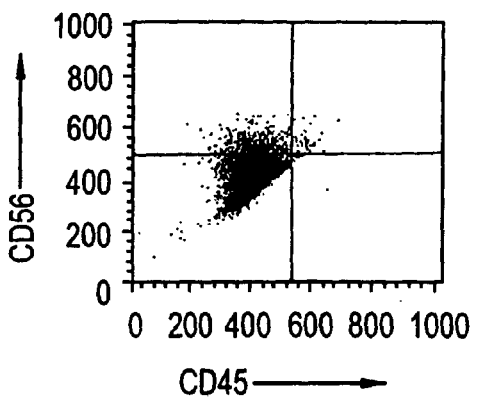
Figure 23G:
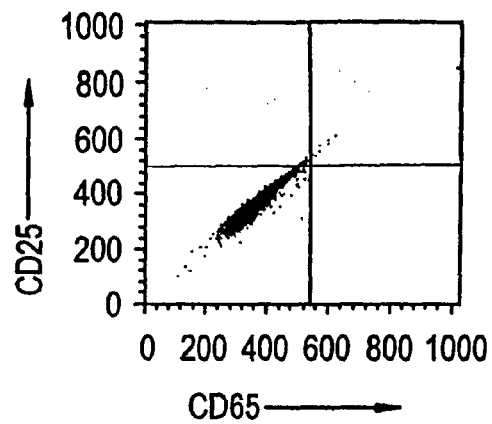
Figure 23H:
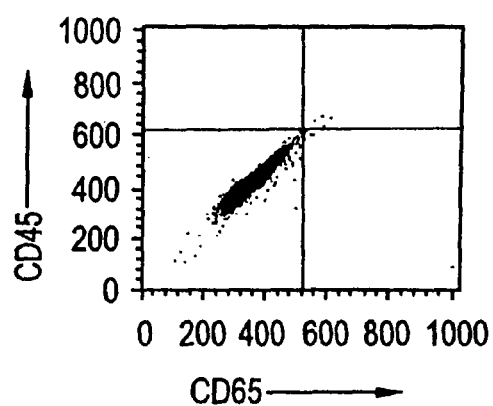
Figure 23I:
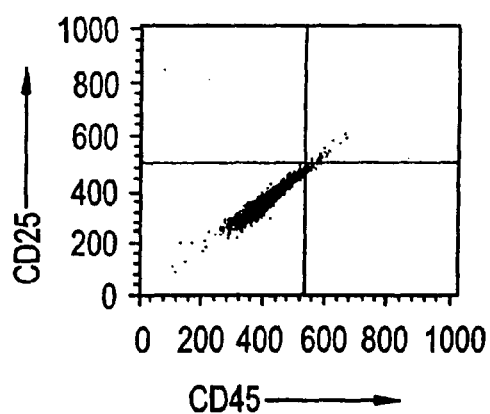
Figure 24A:
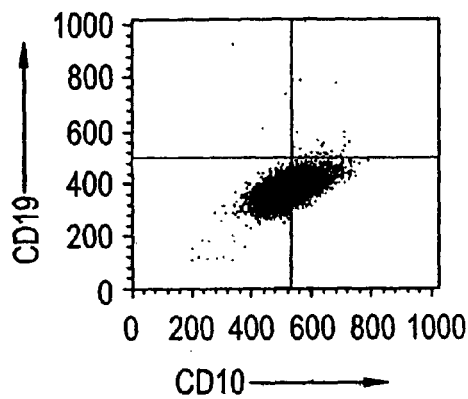
FIG. 24. Flow cytometry of cluster differentiation markers. "X"-axis and "Y"-axis as noted on figure. NHDF propagated to 30 cell doublings and analyzed with antibodies to cell surface cluster differentiation markers.
Figure 24C:
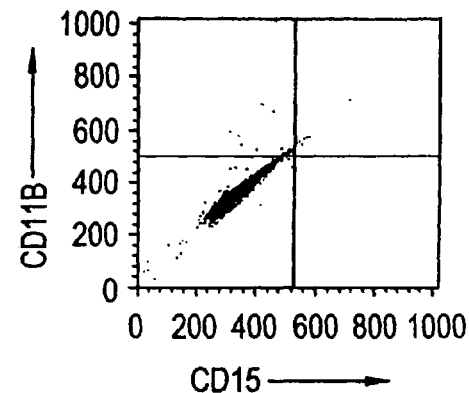
Figure 24B:
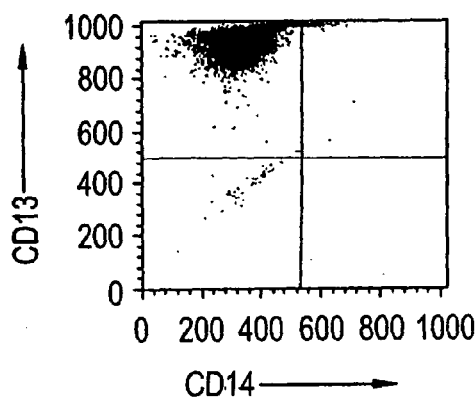
Figure 24D:
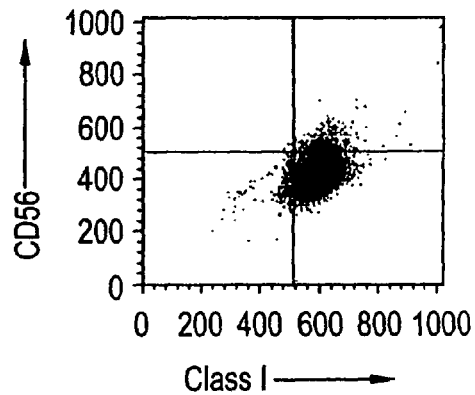
Figure 25:
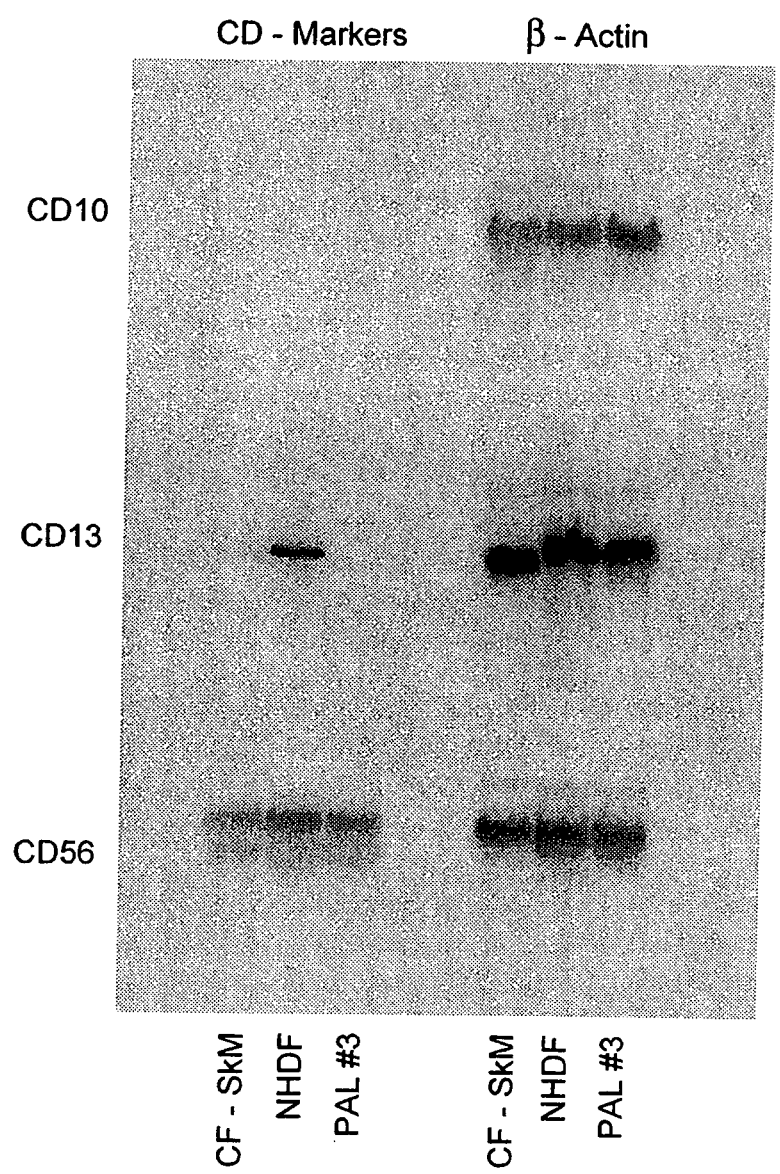
FIG. 25. Northern analysis of cluster differentiation markers CD10, CD13, and CD56 for cell lines CF-SkM, NHDF, and PAL#3. Cells were propagated to 30 cell doublings, harvested, total RNAs extracted, electrophoresed, and probed with 32P-labeled cDNAs to CD10, CD13, CD56, and b-actin (control). As shown, mRNAs for CD13, CD56, and b-actin were being actively transcribed at time of cell harvest.
Figure 26B:
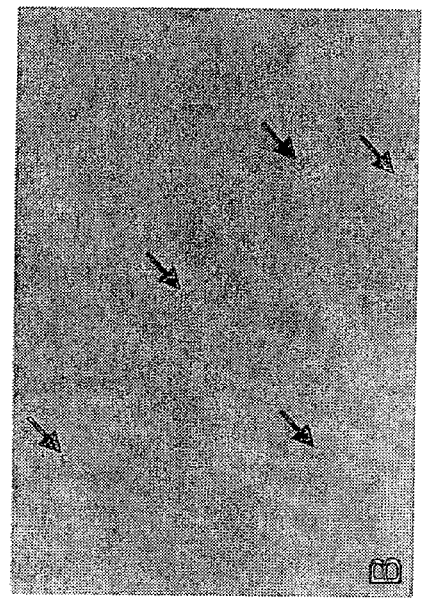
FIG. 26A-D. NHDF propagated as noted and incubated with insulin or $10^{-10}$ to $10^{-6}$ M dexamethasone for 0 to six weeks. Morphologies as noted. A. Cells at 30 cell doublings post harvest treated for one week with 2 mg/ml insulin. Note presence of five nuclei (arrows) with linear structure, indicative of a multinucleated myotube, MT. Mag. 125×. B. Cells at 80 cell doublings after harvest treated for two weeks with $10^{-6}$ M dexamethasone. Note presence of cells (arrows) containing intracellular refractile vesicles indicative of adipogenic cells. Mag., 125×. C. Cells at 80 cell doublings after harvest treated for four weeks with $10^{-6}$ M dexamethasone. Note presence of nodular mass of cells with pericellular matrix halos, indicative of cartilage nodule (CN). Mag., 25×. D. Cells at 80 cell doublings after harvest treated for six weeks with $10^{-6}$ M dexamethasone. Note presence of three-dimensional matrix (delineated by arrow) overlying cell cluster, indicative of bone nodule (BN). Mag., 40×.
Figure 26D:
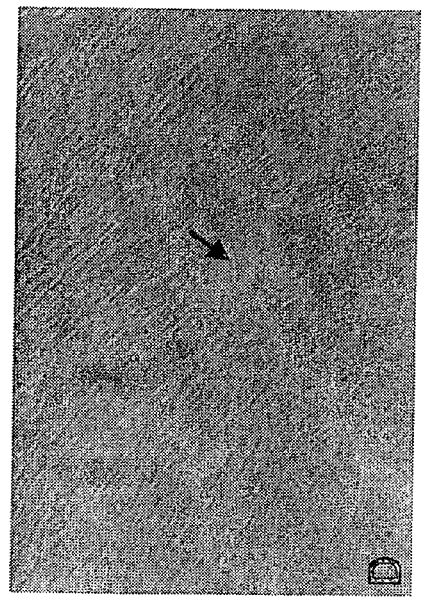
Figure 26A:
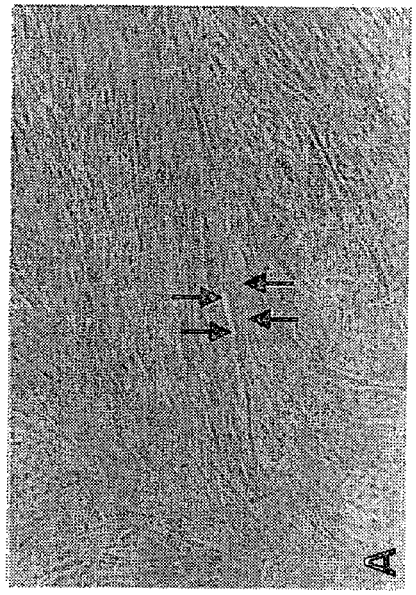
Figure 26C:
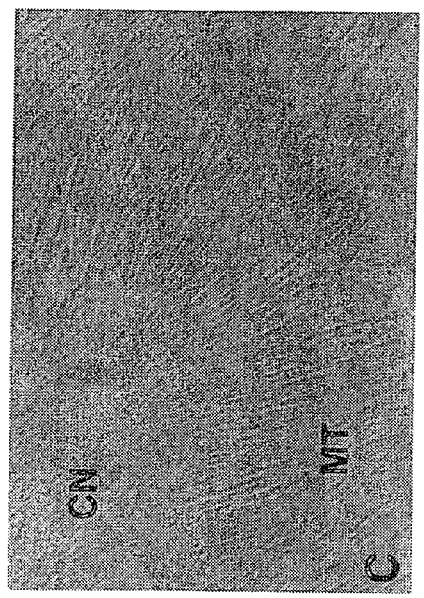

Discernible changes in phenotypic expression of the cells were assayed morphologically. These morphological tissue cellular types were identical to those previously noted in avian and mouse mesenchymal stem cells incubated with insulin or dexamethasone and extensively analyzed by histochemical and immunochemical procedures (Young et al., 1995; Rogers et al., 1995; Young et al., 1993; Young, 1999; Young et al., 1998). Myogenic structures were identified at one week by their elongated multinucleated appearance (FIG. 22A). Adipogenic cells were identified at two weeks as polygonal cells containing multiple intracellular refractile vesicles (FIG. 22B). Chondrogenic cells were identified at four weeks as aggregations of round cells (either as sheets or discrete nodules) with refractile pericellular matrix halos (FIG. 22C). Osteogenic cells were identified at six weeks as three-dimensional extracellular matrices overlying cellular aggregations (FIG. 22D).

Flow Cytometry

Aliquots of CM-SkM, CF-SkM, NHDF, PAL#3, and PAL#2 cells were thawed and seeded at $10^5$ cells/1% gelatin-coated T-75 flasks in PM-B, and allowed to expand at 37° C. in a 95% air/5% $CO_2$ humidified environment. After expansion, cells were released with trypsin and resuspended in PM-B. The cells were then centrifuged and resuspended in wash buffer at a concentration of 1×106 cells/ml. Wash buffer consisted of phosphate buffer supplemented with 1% (v/v) FBS and 1% (w/v) sodium azide, $NaN_3$ [Sigma]. Cell viability was >95% by the Trypan blue dye [GIBCO] exclusion technique (Young et al., 1993; Young et al., 1991). One hundred microliters of cell preparation (1×$10^5$ cells) were stained with saturating concentrations of fluorescein isothiocyanate—(FITC), phycoerythrin—(PE), or perdinin chlorophyll protein—(PerCP) conjugated CD3, CD5, CD7, CD10, CD11b, CD13, CD14, CD15, CD16, CD19, CD25, CD45, CD56, CD65, MHC Class-I, or isotype matched controls [Becton-Dickinson, Inc., San Jose, Calif.]. Briefly, cells were incubated in the dark for 30 min. at 4° C. After incubation, cells were washed three times with wash buffer and resuspended in 0.5 ml of wash buffer for analysis on the flow cytometer. Flow cytometry was performed on a FACScan™ (Becton-Dickinson). Cells were identified by light scatter. Logarithmic fluorescence was evaluated (4 decade, 1024 channel scale) on 10,000 gated events. Analysis was performed using LYSYS II™ software (Becton-Dickinson) and the presence or absence of each antigen was determined by comparison to the appropriate isotype control. An antigenic event was gated if the fluorescence was greater than 25% above its isotype control. Statistical analysis was performed on the pooled flow cytometric data from the five mesenchymal stem cell lines. Thus, a sample size of five was used for each CD marker. Absolute numbers of cells per 10,000 gated events are shown in TABLE 4. A mean value above 1000 cells is considered positive for any CD marker.

Molecular Analysis

Aliquots of CF-SkM, NHDF, and PAL#3 cells were thawed and seeded at 105 cells/1% gelatin-coated T-75 flasks in PM-B, and allowed to expand at 37° C. in a 95% air/5% $CO_2$ humidified environment. After expansion, cells were released with trypsin and centrifuged. The resulting supernatants were aspirated, and cell pellets frozen and stored at 80° C. Cell pellets were thawed on ice and total RNA was extracted from CF-SkM, NHDF, and PAL#3 cells using the Qiagen QIAshredder [catalog #79654, Qiagen, Chatsworth, Calif.] and RNeasy Total RNA Kits [catalog #74104, Qiagen] according to the manufacturer's instructions. I.M.A.G.E. Consortium (LLNL) cDNA clones (Lennon et al., 1996) for CD10, CD13, CD56 and beta-actin (I.M.A.G.E. Consortium Clone ID: 701606, 713961, 468885, and 586736, respectively, Research Genetics, Huntsville, Ala.) were obtained. The cDNA insert was excised from the plasmid by restriction digestion and separated by agarose gel electrophoresis according to standard procedures (Sambrook et al., 1989). The cDNA band was purified using the Qiaex II Gel Extraction Kit [catalog #20021, Qiagen] according to the manufacturer's instructions. The cDNA was labeled by incorporation of 3,000 Ci/mM alpha-[$^{32}$P]-dCTP [catalog number AA0005, Amersham, Arlington Heights, Ill.] using the Prime-It Random Primer Labeling Kit [catalog #300385, Stratagene, La Jolla, Calif.].

Northern Analysis: Total RNA (30 μg/lane/cell line) was electrophoresed through formaldehyde/agarose gels [formaldehyde, catalog #F79-500, and agarose, catalog #BP164-100, Fisher, Norcross, Ga.] and transferred to a nylon membrane [catalog #NJ0HYB0010 Magnagraph, Fisher] according to standard procedures (Sambrook et al., 1989). Hybridization was carried out in roller bottles at 68° C. overnight in QuikHyb hybridization solution [catalog #201220, Stratagene]. Washing was performed according to the manufacturer's instructions. Autoradiography [Fuji film, catalog #04-441-95, Fisher] was carried out at −70° C. to −80° C., using an intensifying screen.

Results

Identification of Cells

The identity of the cells present within the human fetal, mature, and geriatric cell populations were examined using insulin and dexamethasone in a comparison/contrast analysis. Morphologies consistent with skeletal muscle myotubes, adipocytes, cartilage nodules, and bone nodules were produced by treatment with both insulin or dexamethasone in all five human cell populations. However, a greater percentage of morphologies were induced with dexamethasone than with insulin (TABLE 3, FIG. 22A-D). The data suggest that both progenitor cells (insulin accelerated morphologies) and pluripotent cells (dexamethasone induced morphologies) are present in human cells derived from 25 year-old female dermis, 22 week-old fetal male and 25 week-old fetal female (pre-natal) skeletal muscle connective tissues, and 67 year-old male and 77 year-old female skeletal muscle connective tissues.

TABLE 3

Induction of the Expression of Different Mesodermal Morphologies by Dexamethasone and Insulin in Human Mesenchymal Stem Cells

| | Insulin (2 μg/ml) | | | | Dexamethasone ($10^{-10} - 10^{-6}$M) | | | |
|---|---|---|---|---|---|---|---|---|
| | MT[a] | Adip | CN | BN | MT | Adip | CN | BN |
| Weeks | 1 | 2 | 4 | 6 | 1 | 2 | 4 | 6 |
| CF-SkM | +[c] | + | + | + | ++[d] | ++ | ++ | ++ |
| CM-SkM | + | + | + | + | ++ | ++ | ++ | ++ |
| NHDF | + | + | + | + | ++ | ++ | ++ | ++ |

TABLE 3-continued

Induction of the Expression of Different Mesodermal Morphologies by Dexamethasone and Insulin in Human Mesenchymal Stem Cells

| | Insulin (2 μg/ml) | | | | Dexamethasone ($10^{-10} - 10^{-6}$M) | | | |
|---|---|---|---|---|---|---|---|---|
| | MT[a] | Adip | CN | BN | MT | Adip | CN | BN |
| PAL#2 | + | + | + | + | ++ | ++ | ++ | ++ |
| PAL#3 | + | + | + | + | ++ | ++ | ++ | ++ |

[a]MT, myotubes; Adip, adipocytes; CN, cartilage nodule; BN, bone nodule.
[b]Number of weeks of incubation for appearance of the cell type.
[c]approximately 0-5% of culture expressing each particular designated phenotype, with approximately 20% of culture exhibiting all four phenotypes after six weeks of incubation.
[d]approximately 10% of culture expressing each particular designated phenotype, with >40% of culture expressing all four phenotypes after six weeks of incubation.

Flow Cytometric Analysis

Since the cell surface antigens expressed by human progenitor and pluripotent cells were unknown, we analyzed the five cell populations for the presence of CD3, CD5, CD7, CD10, CD11b, CD13, CD14, CD15, CD16, CD19, CD25, CD45, CD56, CD65, and MHC Class-I by immunochemistry coupled with flow cytometry. This powerful technique allowed us to examine large numbers of cells relatively quickly and easily. All human cell populations examined were positive for the cell surface expression of CD10, CD13, CD56, and MHC Class-I, and negative for CD3, CD5, CD7, CD11b, CD14, CD15, CD16, CD19, CD25, CD45, and CD65 (TABLE 4, FIGS. 23 and 24). The data demonstrate that CD10 (neutral endopeptidase), CD13 (aminopeptidase), CD56 (neural cell adhesion molecule, 140 kDa isoform), and major histocompatibility Class-I antigens are located on the cell surface of these human cells at fetal (male and female), adult (female), and geriatric (male and female) ages.

TABLE 4

CD MARKER EXPRESSION*

| | CM-SkM | CF-SkM | NHDF | PAL#3 | PAL#2 |
|---|---|---|---|---|---|
| CD3 | 150 | 140 | 13 | 19 | 0 |
| CD5 | 23 | 38 | 26 | 26 | 0 |
| CD7 | 29 | 66 | 2 | 2 | 0 |
| CD10 | 4700 | 200 | 4676 | 4627 | 66 |
| CD11b | 4 | 126 | 31 | 31 | 0 |
| CD13 | 9280 | 9638 | 9900 | 9976 | 8260 |
| CD14 | 27 | 205 | 104 | 182 | 750 |
| CD15 | 75 | 89 | 168 | 8 | 0 |
| CD16 | 71 | 67 | 12 | 12 | 0 |
| CD19 | 8 | 68 | 14 | 29 | 151 |
| CD25 | 1 | 57 | 21 | 21 | 52 |
| CD45 | 5 | 74 | 30 | 32 | 43 |
| CD56 | 1120 | 2952 | 488 | 474 | 3980 |
| CD65 | 210 | 87 | 8 | 10 | 0 |
| Class-1 | 542 | 9556 | 9542 | 8420 | 8416 |

*CD Marker expression detected by immuno-flow cytometry. Results are expressed as absolute numbers of cells exhibiting positive staining for cell surface CD markers from a gated population of 10,000 cells.

Molecular Analysis of CD10, CD13, and CD56

To determine whether CD10 (neutral endopeptidase), CD13 (aminopeptidase), and CD56 (neural cell adhesion molecule, 140 kDa isoform) were being transcribed by the cells at time of harvest, total RNA from CF-SkM, NHDF, and PAL#3 samples was analyzed by the Northern blot technique using fragments of human CD10, CD13, and CD56 $^{32}$P-labeled cDNAs as probes. A variable pattern in the transcription of the CD markers at the time of cell harvest was observed (TABLE 4, FIG. 28). Strong cDNA binding for CD56-mRNA was observed in all three cell lines, suggesting active transcription of neural cell adhesion molecule isoforms in all three cell lines. cDNA binding for CD13-mRNA was either weak (CF-SkM), strong (NHDF), or not present (PAL#3), suggesting that there are variations in the transcription of aminopeptidase within the different cell lines. No cDNA binding for CD10 mRNA was present in any of the three cell lines examined. This finding suggests two possibilities: either the mRNA for CD10 was not transcribed at the time of harvest, or the amount of mRNA for CD10 was below the limits of detection of the assay.

Discussion

Every year millions of people suffer tissue loss or end-stage organ failure (Langer and Vacanti, 1993). The total national US health care costs for these patients exceeds 400 billion dollars per year. Currently over 8 million surgical procedures requiring 40 to 90 million hospital days are performed annually in the United States to treat these disorders. Although these surgical procedures have saved and improved countless lives, they remain imperfect solutions. Options such as tissue transplantation and surgical intervention are severely limited by critical donor shortages, long-term morbidity, and mortality. Donor shortages worsen every year and increasing numbers of patients die while on waiting lists for needed organs. A wide variety of transplants, congenital malformations, elective surgeries, diseases, and genetic disorders have the potential for treatment with autologous stem cells as the source of donor tissue, either alone or in combination with other agents. A preferred treatment is the treatment of tissue loss where the object is to increase the number of cells available for transplantation, thereby replacing the missing tissues or providing sufficient numbers of cells for ex vivo gene therapy. The use of autologous cells should result in an identical HLA match, obviating the morbidity and mortality associated with allogeneic transplants and immunosuppressive therapy.

Previous studies have demonstrated the existence of mesodermal stem cells located within the connective tissue matrices of many animal species, including humans (Young et al., 1992a; Young et al., 1995; Lucas et al., 1993; Lucas et al., 1995; Pate et al., 1993; Rogers et al., 1995; Warejcka et al., 1996). The existence of two categories of these cells has been demonstrated by serial limiting dilution clonogenic analysis (Young et al., 1993, 1986; Rogers et al., 1995); Young, 1999). Lineage-committed progenitor cells are either unipotent (forming tissues of a single lineage such as the myogenic, fibrogenic, adipogenic, chondrogenic or osteogenic lineages), bipotent (forming tissues of two lineages such as the chondro-osteogenic or adipofibrogenic lineage), or multipotent (forming multiple tissues or cells within the same lineage, such as the hematopoietic lineage). Lineage-committed progenitor cells are capable of self-replication but have a life-span limited to approximately 50-70 cell doublings before programmed cell senescence occurs. Individual clones of progenitor cells demonstrate lineage restriction by giving rise to progeny of separate lineages (e.g., myogenic, fibrogenic, adipogenic, chondrogenic, and osteogenic). One unique characteristic of progenitor cells is that their phenotypic expression can be accelerated by treatment with progression factors such as insulin, insulin-like growth factor-I (IGF-I), or insulin-like growth factor-II (IGF-II) (Young, 1999; Young et al., 1998b). By contrast, pluripotent cells are capable of extended self-renewal and the ability to generate various lineage-committed progenitor cells from a single clone. For example, a prenatal pluripotent mouse clone was induced by long-term treatment with dexamethasone to form lineage-committed progenitor cells that exhibited morphological and phenotypic expression markers characteristic of skeletal muscle, fat, cartilage, and bone after more than 690 cell doublings (Young et al., 1998b). Differentiation-inducing factors, such as dexamethasone, bone morphogenetic protein (BMP), muscle morphogenetic protein (MMP), etc., are necessary to induce lineage-commitment (Young, 1999; Young et al., 1998a). Progression factors such as insulin, IGF-I, or IGF-II have no effect on pluripotent cells (Young, 1999). Once pluripotent cells commit to a particular lineage (i.e., become lineage-committed progenitor cells), theoretically their ability to replicate would be limited to approximately 50-70 cell doublings before programmed cell senescence occurs. These newly generated progenitor stem cells can proliferate (under the influence of proliferation factors, such as platelet-derived growth factors) for a maximum of 50-70 cell doublings. They can also differentiate further (under the influence of progression factors) along separate mesodermal lines (Rogers et al., 1995; Young et al., 1993, 1998a, 1998b).

Because of both the proliferative and differentiative potential of these cells, we would propose that they could be of value in various transplantation and/or gene therapies where donor tissue is in short supply. Indeed, utilizing our protocols (Lucas et al., 1995; Pate et al., 1993) for the isolation of mammalian pluripotent cells, Grande et al. (Grande et al., 1995) have demonstrated dramatic results in the reconstitution of articular cartilage as well as subchondral and trabecular bone in the treatment of full thickness articular cartilage defects in rabbits.

The time required for pluripotent cell isolation, propagation, and induction of lineage commitment must be relatively short for these cells to be used in many clinical situations in which the cells are removed, treated, and reintroduced into the patient's body. Isolation of mammalian pluripotent cells may be accomplished by alternate methods. Pluripotent cells may be obtained by means of cryopreservation at −70 to −80° C. in medium containing 7.5% (v/V) DMSO as previously described (Young et al., 1991; Young et al., 1995; Lucas et al., 1995). Alternatively, a purified population of pluripotent cells is obtained by propagating isolated cells from a primary harvest past Hayflick's limit (50-70 cell doublings) (Hayflick, 1965). This procedure requires 5 to 9 months. A further procedure is to isolate individual clones of pluripotent and progenitor cells by serial dilution clonogenic analysis. This procedure requires 18 to 24 months. We would like to minimize the time required for isolating these cells. One aspect of our current research is aimed at characterizing cell surface antigens on human progenitor and pluripotent cells. This knowledge is intended to reduce the time and manipulation required to isolate more highly purified populations of these cells.

This is the first study to demonstrate the cell surface localization of neutral endopeptidase (CD10), aminopeptidase (CD13), neural cell adhesion molecule, 140 kDa isoform (CD56), and MHC Class-I for human progenitor and pluripotent mesenchymal stem cells. We suggest that these cell surface CD antibodies could be used in conjunction with flow cytometry and fluorescence-activated cell sorting or magnetic bead technology as an initial step to isolate more purified populations of human cells from an initial cell harvest. Starting with a population enriched with these autologous cells would significantly decrease the culture time and cost required to obtain an adequate number of progenitor and pluripotent cells for various transplantation and/or gene therapies.

Positive Staining for CD Markers in Human Mesodermal Cells

The functional significance of the particular cell surface moieties CD10, CD13, CD56, and MHC Class-I expressed by the human fetal, adult, and geriatric cells utilized in this study remains unknown at this time. However, CD10, CD13, and CD56 are known to be expressed on both differentiated cells and early stem cells within the hematopoietic system (Kishimoto et al., 1997). Cell surface neutral endopeptidase (CD10) has been utilized with antibodies to cluster differentiation (CD) markers and flow cytometry as a method for the identification of common acute lymphoblastic leukemia antigen (CALLA) cells, early lymphoid progenitor cells, mature granulocytes, and neutrophils (Kishimoto et al., 1997). This membrane-associated zinc-metallopeptidase has been shown to inactivate a wide variety of regulatory peptide hormones, including enkephalin, chemotactic peptide, substance P, neurotensin, oxytocin, bradykinin, bombesin, and angiotensins I and II (Shipp et al., 1989; Shipp et al., 1991a; Llorens-Cortes et al., 1992; Casale et al., 1994).

Cell surface aminopeptidase (CD13) has been utilized with flow cytometry to identify early committed progenitors of granulocytes and monocytes (CFU-GM). It is expressed by all cells of these lineages as they mature (Kishimoto et al., 1997). CD13 is also expressed on a small proportion of large granular lymphocytes, but not other lymphocytes (Kishimoto et al., 1997). CD13 is identical in structure to aminopeptidase N (EC 3.4.11.2), a membrane bound zinc-binding metalloprotease (Look et al., 1989; Larsen et al., 1996. This enzyme is known to catalyze the removal of NH2-terminal amino acids from regulatory peptides produced by diverse cell types (Larsen et al., 1996; Weber et al., 1996).

One possible function of the cell surface enzymes, neutral endopeptidase (CD10) and aminopeptidase (CD13), on these stem cells is that they may serve to regulate the differentiation process by preferentially degrading autocrine, paracrine, and/or endocrine regulatory peptides (e.g., lineage-commitment agents, progression factors, and proliferation agents) that may affect these cells. Young et al. (1998a) demonstrated the ability of various paracrine and endocrine regulatory peptides to alter proliferation, lineage-commitment, and lineage progression in progenitor and pluripotent stem cells. These compounds included those which affected proliferation (platelet derived growth factors-AA and -BB), lineage-induction (dexamethasone, BMP and MMP), and progression (insulin, IGF-I and IGF-II). Their study suggested that the ability of stem cells to respond to specific regulatory peptides is more tightly controlled as differentiation proceeds from a lineage-uncommitted pluripotent stem cell to a lineage-committed progenitor stem cell.

The 140 kDa isoform of neural cell adhesion molecule (NCAM, CD56) has been utilized with flow cytometry as the prototypic marker to identify natural killer (NK) cells and (CD4+/CD8+) T-cells (Kishimoto et al., 1997). Although its function has not been convincingly demonstrated with hematopoietic cells, it has been suggested to be involved in homophilic adhesion for NK and T-cells due to the C2-set Ig regions and fibronectin regions within its extracellular domain (Lanier et al., 1989; Lanier et al., 1991). With respect to non-hematopoietic tissues, homophilic and heterophilic adhesion by NCAM has been proposed to regulate both cell-cell and cell-matrix interactions. This may be due in part to its ability to interact with type I collagen in its associated extracellular matrix, a key element in adhesion and migration of cells (Meyer et al., 1995). NCAM appears on early embryonic cells and is important in the formation of cell collectives and their boundaries at sites of morphogenesis (Rutishauser, 1992). Later in development it is found on various differentiated tissues.

Previous studies (Young et al., 1995; Lucas et al., 1995; Young et al., 1993; Young, 1999) demonstrated the potential for mesenchymal stem cells to form tissues of mesodermal origin such as skeletal muscle, cardiac muscle, smooth muscle, and bone (osteoblasts). These particular differentiated cell types have been shown to utilize NCAM for cell-cell and cell-matrix interactions leading to their differentiation (Knudsen et al., 1990; Peck and Walsh, 1993; Byeon et al., 1994; Lyons et al., 1992; Romanska et al., 1996; Lee and Chuong, 1992). Of particular interest is the percentage of mesenchymal stem cells within the five cell lines displaying CD56 (TABLE 4). The differences in numbers of cells exhibiting CD56 may reflect the chronological age or the functional capability of the cells at time of harvest. It is also possible that the percentage of cells exhibiting CD56 in each cell line may reflect the absolute numbers of progenitor versus pluripotent stem cells within their respective populations. Cell surface NCAM functions during normal embryological development to regulate the required cell-cell and cell-matrix interactions in preparation for further differentiation of mesenchymal stem cells along their respective tissue lineage pathways. It may also have a similar function in the adult.

Cell surface major histocompatibility complex (MHC) Class-I molecules have been shown to be present on all vertebrate species and to be expressed on almost every nucleated cell in the body (Benjamini et al., 1996). While MHC Class-I molecules play a central role in the phenomena of antigen processing and presentation (Benjamini et al., 1996; Abbas et al., 1997), they have also been studied extensively to understand the mechanisms of immune responses that discriminate between self and non-self. Mesenchymal stem cells have been proposed as a source of cells for tissue engineering, either as donor tissue for transplantation or as a delivery vehicles for gene therapy (Young et al., 1998a,b). As shown (TABLE 4), greater than 80% of the cells within the populations of stem cells isolated from fetal, adult, and geriatric-aged individuals express MHC Class-I antigens. This indicates that those particular Class-I antigen-expressing cells would be recognized as foreign in a MHC mismatched immunocompetent individual, and thus should only be used for autologous or syngeneic transplants. In contrast, there were approximately 5% of fetal and adult stem cells and approximately 15% of geriatric stem cells that did not express MHC Class-I antigens. This apparent decrease in MHC Class-I antigen expression may have been due to quantities of cell surface Class-I antigens below the limits detectable by the immunochemical/flow cytometric procedure utilized, or complete absence of these molecules from the surface of a particular subset of stem cells. The significance of this finding is unknown at this time. The presence or absence of cell surface MHC Class-I molecules on these stem cells may signify the "differentiated" state of that particular cell, i.e., the more differentiated (progenitor) stem cell exhibiting MHC Class-I antigens and the more primitive (pluripotent) stem cell not expressing these particular cell surface antigens. Alternatively, the "differentiated" state of a particular stem cell may have nothing to do with the expression of MHC Class-I antigens on its cell surface. In this instance there may be a subset of stem cells without MHC Class-I antigens that are essentially invisible to the immune system and thus may be candidates for a universal tissue transplant. Such a particular subset of cells might be useful in allograft transplant procedures. This area is currently under investigation.

Negative Staining for CD Markers in Human Mesenchymal Stem Cells

In contrast to the above four positive staining cell surface antigens, the following 11 antigens were found absent on the cell surface of fetal, adult, and geriatric human mesenchymal stem cells. These markers were CD3, CD5, CD7, CD11b, CD14, CD15, CD16, CD19, CD25, CD45, and CD65. The significance of these findings is unknown at this time. However, these particular cell surface antigens have been ascribed only to differentiated cells within the hematopoietic system (Kishimoto et al., 1997), i.e., T-cells (CD3, CD5, CD7, CD11b, CD25, CD45), B-cells (CD5, CD11b, CD19, CD25, CD45), thymocytes (CD7), granulocytes (CD11b, CD14, CD5, CD16, CD45, CD65), monocytes (CD11b, CD14, CD16, CD25, CD45), natural killer cells (CD11b, CD16, CD45), follicular dendritic cells (CD19), and mature erythrocytes (CD45).

In conclusion, this is the first study to demonstrate the cell surface localization of neutral endopeptidase (CD10), aminopeptidase (CD13), neural cell adhesion molecule isoform (CD56), and MHC Class-I for human mesenchymal stem cells. In and of itself, we would suggest that these cell surface CD markers could be used in conjunction with flow cytometry, fluorescent-activated cell sorting, magnetic bead separation, or antibody purification columns as an initial step to isolate more purified populations of human progenitor and pluripotent cells from an initial cell harvest. Starting with a population enriched for these mesodermal cells would significantly decrease both culture time and supply costs, plus improve the yield on the requisite progenitor and pluripotent cells needed for various transplantation and/or gene therapies.

Example 8

Human Mesenchymal Stem Cells Display Hematopoietic Cell Surface Cluster Differentiation Markers CD34 and CD90

This report details the profile of 13 cell surface cluster differentiation markers on human mesenchymal stem cells. Cells were isolated from fetal, mature, and geriatric individuals following standard protocols for the isolation, cryopreservation, and propagation of mesenchymal stem cells. The mesenchymal stem cell population from each individual was composed of both progenitor and pluripotent stem cells. Results from mesenchymal stem cells at 30 cell doublings revealed positive staining for CD34 and CD90 and negative staining for CD3, CD4, CD8, CD11c, CD33, CD36, CD38, CD45, CD117, glycophorin-A, and HLA-II (DR). RNAs were extracted from each cell line and probed with 32P-labeled cDNAs to CD34 and CD90 using Northern analysis. The results demonstrate that CD90 was actively transcribed at time of cell harvest. We report the first identification of CD34 and CD90 cell surface antigens on human mesenchymal stem cells.

In order for stem cells to be useful clinically, the time period required for the isolation, propagation, and induction of lineage commitment of stem cells prior to reintroducing them into the patient's body must be relatively short. Our current research is therefore focused upon characterizing cell surface antigens on human mesenchymal stem cells to facilitate the isolation of more purified populations of these cells. The identification of unique cell surface antigens to stem cells can permit the use of antibodies to these antigens to expedite the isolation of stem cells. One technique currently under investigation uses flow cytometry coupled with fluorescently labeled antibodies and fluorescence-activated cell sorting. This technique has been used with antibodies to cluster differentiation (CD) markers to characterize and isolate hematopoietic cells based on the profiles of their cell surface antigens. Indeed, more than 180 individual CD markers, have been used to characterize and isolate the individual cell types within the various lymphopoietic and erythropoietic lineages (Kishimoto et al., 1997).

The experiments reported in this paper involve characterizing the cell surface CD marker antigens of human male and female stem cells isolated from fetal, mature, and geriatric donors. The cells were obtained following standard protocols for the isolation, cryopreservation, and expansion of mesenchymal stem cells (Young et al., 1995; Lucas et al., 1995; Young et al., 1993; Young et al., 1991). The cell population from each individual contained a mixture of both progenitor cells and pluripotent cells as determined by a comparison/contrast analysis using dexamethasone and insulin (Young et al., 1998a). Thirteen CD markers were examined in each stem cell population using immunochemical fluorescence-activated flow cytometry. Positive staining was obtained for CD34 and CD90. Negative results were obtained for CD3, CD4, CD8, CD11c, CD33, CD36, CD38, CD45, CD117, glycophorin-A, and HLA-II (DR). RNAs were extracted from the cell populations, subjected to electrophoresis, and probed with 32P-labeled cDNAs to CD34 and CD90 using Northern analysis. The results showed that CD90 was being actively transcribed at time of cell harvest. We report the first identification of the presence of hematopoietic stem cell surface markers CD34 and CD90 on human progenitor and pluripotent cells.

Materials and Methods

Human Mesenchymal Stem Cells

Six populations of stem cells were used in this study. Two were drawn from fetal donors (one female and one male), two from mature donors (both female), and two from geriatric donors (one female and one male). The cells were derived from two different connective tissue compartments (dermis and connective tissues associated with skeletal muscle). The protocols for harvesting human tissues were approved by the Institutional Review Board at the Medical Center of Central Georgia, Macon, Ga.

Fetal female cells were purchased as a subconfluent culture of 25 week-old fetal skeletal muscle cells derived from the connective tissue associated with the triceps muscle [CF-SkM1, catalog # CC-2561, lot #14722, Clonetics, San Diego, Calif.]. Fetal male cells were purchased as a subconfluent culture of 22 week-old fetal skeletal muscle cells derived from the connective tissue associated with the thigh muscle [CM-SkM1, catalog # CC-0231, lot #6F0604, Clonetics]. Adult female cells were purchased as a subconfluent culture of 25 year-old human dermal cells [NHDF1, catalog # CC-0252, lot #6F0600, Clonetics] and a subconfluent culture of 36 year old human dermal cells [NHDF2, catalog # CC-0252, lot #16280, Clonetics]. Upon arrival, the cells were transferred to plating medium-A (PM-A). PM-A consisted of 89% (v/v) Eagle's Minimal Essential Medium with Earle's salts [EMEM, GIBCO BRL, Grand Island, N.Y.], 10% (v/v) pre-selected horse serum [lot no. 17F-0218 (HS7) or 49F-0082 (HS4), Sigma Chemical Co., St. Louis, Mo.] or [lot no. 3M0338 (HS3), BioWhittaker, Walkersville, Md.], and 1% (v/v) Penicillin/Streptomycin solution [10,000 units/ml penicillin and 10,000 µg/ml streptomycin, GIBCO], pH 7.4. Cells were incubated at 37° C. in a 95% air/5% $CO_2$ humidified environment. After expansion, cells were released with 0.05% (w/v) trypsin [DIFCO, Detroit, Mich.] in $Ca^{+2}$-, $Mg^{+2}$-free Dulbecco's phosphate buffered saline [GIBCO] containing 0.0744% (w/v) ethylenediamine tetraacetic acid [EDTA, Sigma] and centrifuged at 100×g for 20 min. The supernatant was aspirated, the cell pellet resuspended in plating medium-A and the cell suspension cryopreserved by slow freezing to storage at −70 to −80° C. in plating medium-A containing 7.5% (v/v) dimethyl sulfoxide [DMSO, Morton Thiokol, Danvers, Mass.] (Young et al., 1991).

Geriatric stem cells were obtained from Dr. Paul Lucas (Department of Orthopedic Surgery, New York Medical College, Valhalla, N.Y.). Geriatric cells were isolated from the endomysial, perimysial and epimysial connective tissue compartments associated with skeletal muscle pathology specimens obtained from a 77 year-old female patient and a 67 year-old male patient following standard protocols for the isolation of mesenchymal stem cells (Lucas et al., 1995; Young et al., 1999). These cells were designated as "PAL2" and "PAL3", respectively. In brief, stem cells were liberated with collagenase [CLS-1, Worthington Biochemical Corp., Freehold, N.J.] and dispase [catalog #40235, Collaborative Research Inc., Bedford, Mass.]. Single cell suspensions were obtained by sequential filtration through 90-μm and 20-μm Nitex [Tetco Inc., Elmsford, N.Y.]. Cells were seeded at $10^5$ cells/1% (w/v) gelantinized [EM Sciences, Gibbstown, N.J.] 100 mm dishes [Falcon, Becton Dickinson Labware, Franklin Lakes, N.J.] in PM-A and allowed to expand and differentiate prior to cryopreservation. Cells were incubated at 37° C. in a 95% air/5% $CO_2$ humidified environment. After expansion, cells were released with trypsin, sieved as above to separate mononucleated stem cells from fibroblasts and differentiated phenotypes (i.e., multinucleated myotybes, adipocyte colonies, cartilage nodules, bone nodules), and cryopreserved at −70 to −80° C. in PM-A containing 7.5% (v/v) DMSO (Sigma) (Lucas et al., 1995).

Further expansion of cells was obtained by repeating the propagation and cryopreservation steps, but without sieving, utilizing 1% gelatinized T-75 flasks [Falcon] and plating medium-B (PM-B). PM-B consisted of 89% (v/v) Opti-MEM basal medium (Kawamoto et al., 1983) [catalog #22600-050, GIBCO], 10% (v/v) horse serum [HS3], and 1% (v/v) antibiotic-antimycotic solution [10,000 units/ml penicillin, 10,000 μg/ml streptomycin, and 25 μg/ml amphotericin B as Fungizone, GIBCO], pH 7.4. Cells were then aliquoted for the insulin/dexamethasone bioassay and flow cytometry.

Insulin/Dexamethasone Bioassay to Identify Progenitor and Pluripotent Stem Cells Propagated cells were examined using insulin and dexamethasone to determine existence of progenitor and/or pluripotent stem cells (Young et al., 1998b). In this bioassay, insulin accelerates phenotypic expression in progenitor stem cells but has no effect on the induction of phenotypic expression in pluripotent stem cells. By contrast, dexamethasone induces lineage-commitment and expression in pluripotent stem cells, but does not alter phenotypic expression in progenitor stem cells. Therefore, if progenitor cells alone are present in the culture there will be no difference in the expressed phenotypes for cultures incubated in insulin compared with those incubated with dexamethasone. If the culture is mixed, containing both progenitor and pluripotent cells, then there will be a greater quantity of expressed phenotypes in cultures treated with dexamethasone compared with those treated with insulin. In addition, an increase in the number of phenotypes expressed may be observed. If the culture contains pluripotent cells alone, there will be no expressed phenotypes in cultures treated with insulin. Similar cultures treated with dexamethasone will exhibit multiple expressed phenotypes. Thus comparing the effects of treatment with insulin and dexamethasone permits the identification of specific types of progenitor and pluripotent stem cells within an unknown population of cells (Young et al., 1992, 1993, 1995, 1998a,b, 1999; Lucas et al., 1993, 1995; Pate et al., 1993; Rogers et al., 1995; Warejcka et al., 1996).

Aliquots of CM-SkM1, CF-SkM1, NHDF2, PAL3 and PAL2 cells were thawed and plated individually at 10,000 cells per well in 1% gelatinized 24-well plates [Corning, Corning, N.Y.] or 1,000 cells per well in 1% gelatinized 96-well plates [Falcon] utilizing PM-B, After 24 hr PM-B was removed and replaced with either control medium (CM) (98% Opti-MEM, 1% HS3, 1% antibiotic-antimycotic solution), insulin stesting medium (CM+2 μg/ml insulin [Sigma]), or dexamethasone testing medium. The dexamethasone testing medium consisted of 98%, 94%, or 89% Opti-MEM; 1, 5, or 10% serum [HS3, HS9 (horse serum, lot number 90H-0701, Sigma), respectively, or 1% FBS (fetal bovine serum, lot no. 3000L, Atlanta Biologicals, Norcross, Ga.)], 1% antibiotic-antimycotic solution and $10^{-10}$, $10^{-9}$, $10^{-8}$, $10^{-7}$, or $10^{-6}$ M dexamethasone [Sigma]) (Young et al., 1995, 1998b). Media were changed three times per week for eight weeks. Cultures were viewed twice weekly for changes in phenotypic expression and photographed.

Discernible changes in phenotypic expression of the putative mesenchymal stem cells were determined using morphological criteria. The morphological phenotypes were identical to those noted previously in avian and mouse mesenchymal stem cells incubated with insulin or dexamethasone (Young et al., 1993, 1998a). Skeletal myogenic structures were identified by their elongated multinucleated appearance, cross-striations, and spontaneous contractility (Young et al., 1993, 1995). Skeletal muscle myotubes were verified by immunochemical staining using antibodies to myogenin (F5D, Developmental Studies Hybridoma Bank, DSHB: Wright et al., 1991), sarcomeric myosin (MF-20, DSHB: Bader et al., 1982), fast-skeletal muscle myosin (MY-32, Sigma: Naumann and Pette, 1994), myosin heavy chain (ALD-58: Shafiq et al., 1984), and human fast myosin fibers (A4.74: Webster et al., 1988). Smooth muscle cells were identified as large polygonal cells containing intracellular stress filaments. The smooth muscle phenotype was verified immunocytochemically with antibodies to smooth muscle alpha-actin (1A4, Sigma Skalli et al., 1986). Cardiac myocytes were identified as binucleated cells. The cardiac muscle phenotype was verified immunochemically with co-labeling of antibodies for both smooth muscle alpha-actin (1A4) and sarcomeric myosin (MF-20) (Eisenberg and Markwald, 1997). Adipogenic cells were identified as polygonal cells containing multiple intracellular refractile vesicles. Adipocytes were verified by the presence of intracellular vesicles containing saturated neutral lipids by means of histochemical staining with Sudan Black-B (Chroma-Gesellschaft, Roboz Surgical Co., Washington, D.C.: Young et al., 1993) and Oil Red-O (Sigma: Humason, 1972). Chondrogenic structures were identified as aggregations of round cells (either as sheets or discrete nodules) with refractile pericellular matrix halos. The cartilage phenotype was verified by immunochemical staining for collagen pro type-II (C11C1m DSHB: Holmdahl et al., 1986; Johnstone et al., 1998); human-specific collagen type-II (II-4CII, ICN Biomedicals, Aurora, OH: Burgeson and Hollister, 1979; Kumagai et al. 1994); and type IX collagen (D1-9, DSHB:

Ye et al., 1991), and histochemical staining with Alcian Blue at pH 1.0 for glycosaminoglycans containing chondroitin sulfate and keratan sulfate (Chroma-Gesellschaft: Young et al., 1993; Young et al., 1998a,b) and Perfix/Alcec Blue (Fisher Scientific Co., Norcross, Ga./Alrrich Chemical Co., Milwaukee, Wis.: Lucas et al., 1991) for glycosaminolycans containing sulfate moieties. Osteogenic structures were identified as three-dimensional extracellular matrices overlying cellular aggregations. The ostogenic phenotype was verified by immunochemical staining for bone sialoprotein (WV1D1, DSHB: Kasugai et al., 1992) and osteopontine (MP111, DSHB: Gorski et al., 1990), and histochemical staining for calcium phosphate using the von Kossa procedure (Silber Protein, Chroma-Gesellschaft: Young et al., 1993, 1998a,b). Fibroblasts were identified by their morphological appearance as polygonal or spindle-shaped cells. The fibrogenic phenotype was verified immunocytochemically with antibodies directed against human fibroblast surface protein (1B10, Sigma: Ronnov-Jessen et al., 1992). Endothelial cells were identified as cobblestone-shaped cells, occurring individually or in sheets. The endothelial phenotype was verified by immunological staining for human-specific endothelial cell surface marker (P1H12, Accurate, Westbury, N.Y.: Solovey et al., 1997), peripheral endothelial cell adhesion molecule, PECAM (P2B1, DSHB), vascular cell adhesion molecule, VCAM (P8B1, DSHB: Dittel et al., 1993), and E-selectin (P2H3, DSHB). Secondary antibodies consisted of biotinylated anti-sheep IgG (Vector), biotinylated anti-mouse IgG (Vector), or antibodies contained within the Vecstatin ABC Kit (Vector). The tertiary probe consisted of avidin-HRP contained within the Vecstatin ABC Kit (Vector). The following insoluble horseradish peroxidase (HRP) substrates were used to visualize antibody binding: VIP Substrate Kit for Peroxidase (blue, Vector), DAB Substrate for Peroxidase (black, Vector), and AEC Staining Kit (red, Sigma). Different colored substrates were utilized to allow for multiple sequential staining of the same culture wells.

Flow Cytometry

Aliquots of CM-SkM, CF-SkM, NHDF1, NHDF2, PAL#3, and PAL#2 cells at 30 cell doublings after harvest were thawed and seeded at $10^5$ cells/1% gelatinized T-75 flasks in plating medium-B (PM-B), and allowed to expand at 37° C. in a 95% air/5% $CO_2$ humidified environment. After expansion, cells were released with trypsin, centrifuged, and resuspended in PM-B. The cells were then centrifuged and resuspended in wash buffer (Dulbecco's phosphate buffered saline without $Ca^{+2}$, $Mg^{+2}$ [Cellgro, MediaTech] supplemented with 1% FBS [HyClone] and 1% (w/v) sodium azide, NaN3 [Sigma]) at a concentration of $1 \times 10^6$ cells/ml. Cell viability was >95% by the Trypan blue dye [GIBCO] exclusion technique (Young et al., 1993; Young et al., 1991). One hundred microliters of cell preparation ($1 \times 10^5$ cells) were stained with saturating concentrations of fluorescine isothiocyanate—(FITC), phycoerythrin—(PE), or perdinin chlorophyll protein—(PerCP) conjugated CD3, CD4, CD8, CD11c, CD33, CD34, CD36, CD38, CD45, CD90, CD117, glycophorin-A, and HLA-IL (DR), or isotype matched controls [Becton Dickinson, Inc. San Jose, Calif.]. Briefly, cells were incubated in the dark for 30 min. at 4° C. After incubation, cells were washed three times with wash buffer and resuspended in 0.5 ml of wash buffer. Flow cytometry was performed on a FACScan™ (Becton Dickinson) flow cytometer. Cells were identified by light scatter (FIG. 29). Logarithmic fluorescence was evaluated (4 decade, 1024 channel scale) on 10,000 gated events. Analysis was performed using LYSYS II™ software (Becton Dickinson). The presence or absence of staining was determined by comparison to the appropriate isotype control. Gated events were scored for the presence of staining for a CD marker if more than 25% of the staining was above its isotype control. Statistical analysis was performed on the pooled flow cytometric data from the five mesenchymal stem cell lines. Absolute numbers of cells per 10,000 gated events are shown in TABLE 5. A mean value above 1,000 gated cells is considered positive for any given CD marker.

Statistical Analysis

The only biologically significant results were for markers CD34 and CD90. These were divided into two specimens derived from prenatal human tissues and those derived postnatal human tissues. The two groups were analyzed by One Way Analysis of Variance, using the ABSTAT computer program (Anderson-Bell Corp., Arvada, Colo.).

Molecular Analysis

Aliquots of CF-SkM, NHDF, and PAL#3 cells at 30 cell doublings after harvest were thawed and seeded at $10^5$ cells/1% gelatinized T-75 flasks in plating medium-B, and allowed to expand at 37° C. in a 95% air/5% $CO_2$ humidified environment. After expansion, cells were released with trypsin, centrifuged, supernatants aspirated, and cell pellets frozen and stored at –80° C. Cell pellets were thawed on ice and total RNA was extracted from CF-SkM, NHDF, and PAL#3 cells using the Qiagen QIAshredder [catalog #79654, Qiagen, Chatsworth, Calif.] and RNeasy Total RNA Kit [catalog #74104, Qiagen] according to the manufacturer's instructions. I.M.A.G.E. Consortium (LLNL) cDNA clones (Lennon et al., 1996) for CD34, CD90 and β-actin (I.M.A.G.E. Consortium Clone ID: 770858, 714060, and 586736, respectively, Research Genetics, Huntsville, Ala.) were obtained. The cDNA inserts were excised from their respective plasmids by restriction digestions and separated by agarose gel electrophoresis according to standard procedures (Sambrook et al., 1989). Each cDNA band was purified using the Qiaex II Gel Extraction Kit [catalog #20021, Qiagen] according to the manufacturer's instructions. The cDNA were labeled by incorporation of 3,000 Ci/mM a-[$^{32}$P]-dCTP [catalog number AA0005, Amersham, Arlington Heights, Ill.] using the Prime-It Random Primer Labeling Kit [catalog #300385, Stratagene, La Jolla, Calif.].

Northern Analysis: Total RNA (30 mg/lane/cell line) was electrophoresed through formaldehyde/agarose gels [formaldehyde, catalog #F79-500, Fisher, Norcross, Ga.; agarose, catalog #BP164-100, Fisher] and transferred to a nylon membrane [catalog #NJ0HYB0010 Magnagraph, Fisher] by capillary transfer according to standard procedures (Sambrook et al., 1989). Hybridization was carried out in roller bottles at 68° C. overnight in QuikHyb hybridization solution [catalog #201220, Stratagene]. Washing was carried out according to the manufacturer's instructions. Autoradiography [Fuji, catalog #04-441-95, Fisher] was carried out at –70° C. to –80° C., using an intensifying screen.

Results

Stem Cell Identification

The identity of the putative stem cells present within male and female human fetal, mature, and geriatric cell populations was examined by a comparison/contrast analysis utilizing insulin and dexamethasone. Small numbers of phenotypic alterations in morphological appearance consistent with skeletal muscle myotubes, adipocytes, cartilage nodules, and bone nodules were produced with insulin. Larger numbers of similar phenotypic alterations were produced by treatment with dexamethasone. Dexamethasone induced phenotypic expression markers for muscle, fat, cartilage, bone, connective tissue, and endothelial cells. Skeletal muscle, smooth muscle, and cardiac muscle phenotypes were recognized based on antibody staining. These cells also resembled skeletal muscle myotubes, adipocytes, cartilage nodules, and bone nodules. These morphological alterations occurred in all six human stem cell populations at 30 cell doublings. At 80 cell doublings insulin had no effect on the cells, whereas dexamethasone altered the phenotypic expression of the cells (FIG. 26A-D). The data support the hypothesis that both progenitor cells (insulin-accelerated morphologies) and pluripotent cells (dexamethasone-induced morphologies) were present in the populations after 30 cell doublings of putative human stem cells isolated from 22 week-old fetal (pre-natal) male and 25 week-old fetal (pre-natal) female skeletal muscle connective tissues, 25 year-old female dermis, 67 year-old male and 77 year-old female skeletal muscle connective tissues.

Flow Cytometric Analysis

Figure 27:
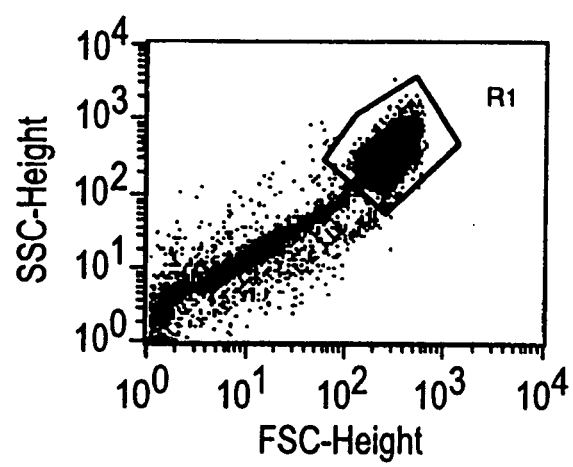
FIG. 27. Flow cytometry of FSC×SSC showing R1 gated cell population of NHDF used for analysis. A similar R1 gate was used to analyze CM-SkM, CF-SkM, PAL #2, PAL #3.
Figure 28A:
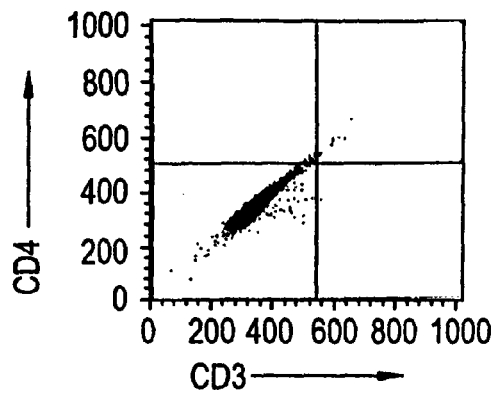
FIG. 28. Flow cytometry of cluster differentiation markers. "X"-axis denotes forward scatter (0 to 1000 linear scale) and "Y"-axis denotes side scatter, (0 to 1000 linear scale). NHDF propagated to 30 cell doublings after harvest and analyzed with antibodies to cell surface cluster differentiation markers CD4 vs. CD3, CD8 vs. CD3, CD4 vs. CD8, CD34 vs. CD33, CD45 vs. CD33, CD34 vs. CD45, CD11c vs. Glycophorin-A, HLA-II (DR) vs. Glycophorin-A, and CD11c vs. HLA-II (DR).
Figure 28D:
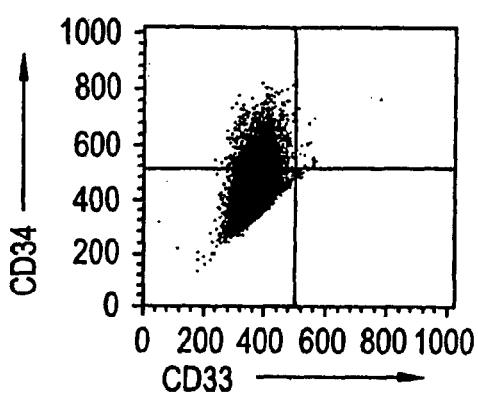
Figure 28B:
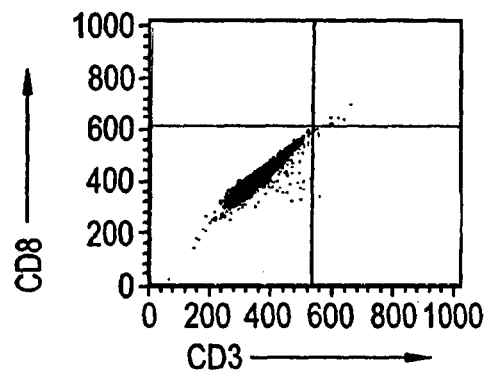
Figure 28E:
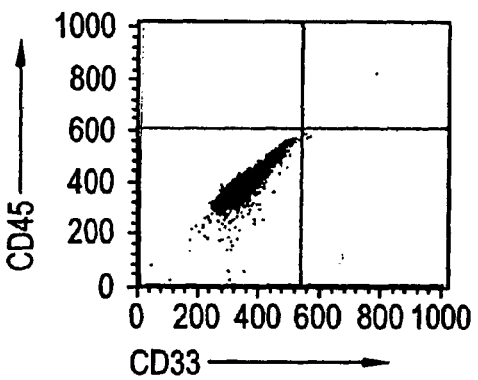
Figure 28C:
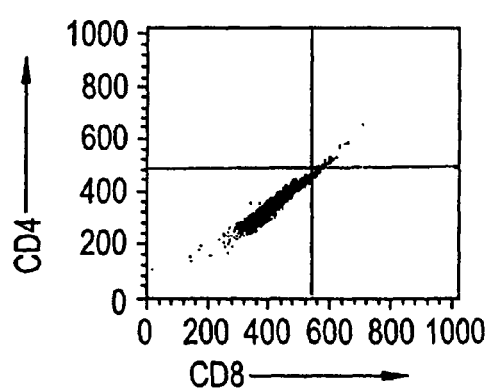
Figure 28F:
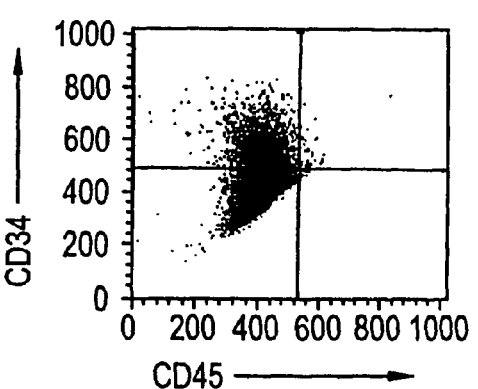
Figure 28G:
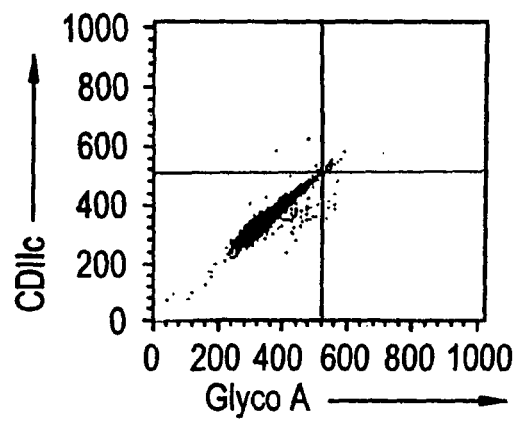
Figure 28H:
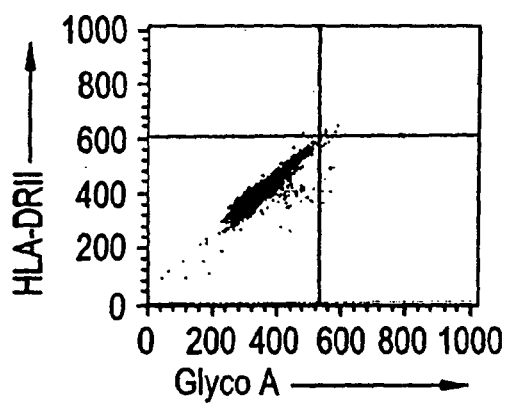
Figure 28I:
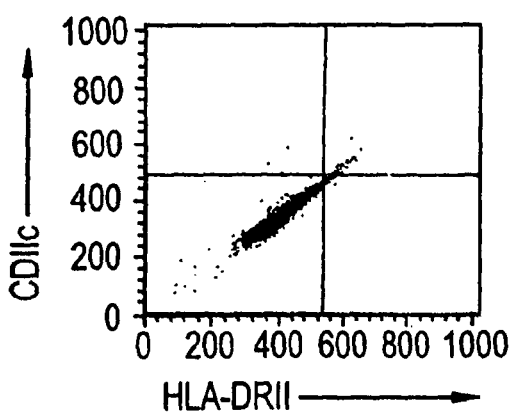
Figure 29A:
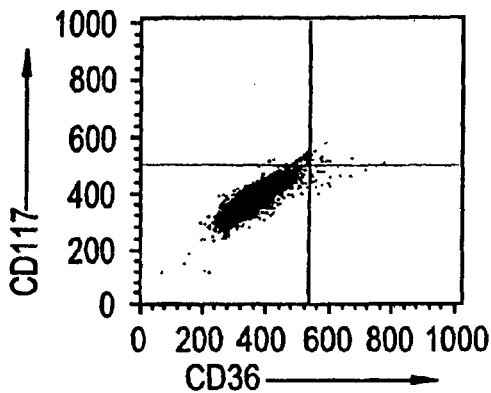
FIG. 29. Flow cytometry of cluster differentiation markers. "X"-axis denotes forward scatter (0 to 1000 linear scale) and "Y"-axis denotes side scatter (0 to 1000 linear scale). NHDF propagated to 30 cell doublings after harvest and analyzed with antibodies to cell surface cluster differentiation markers CD117 vs. CD36, CD45 vs. CD36, CD117 vs. CD45, CD34 vs. CD90, CD45 vs. CD90, CD34 vs. CD45, CD34 vs. CD38, CD45 vs. CD38, and CD34 vs. CD45.
Figure 29D:
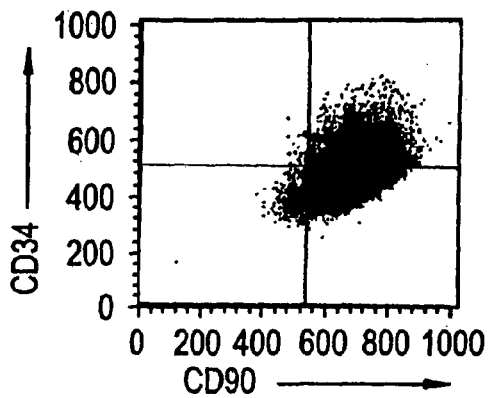
Figure 29B:
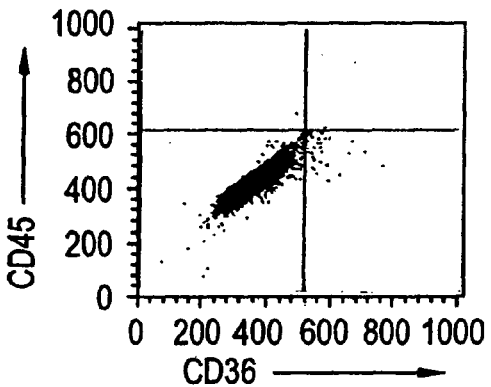
Figure 29E:
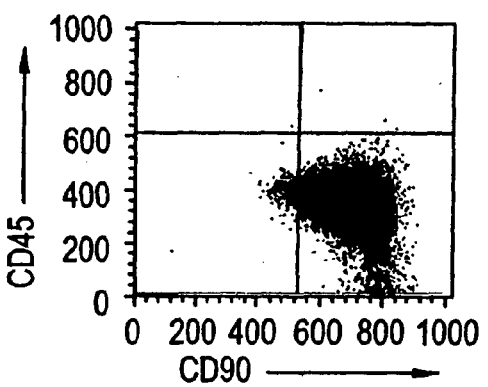
Figure 29C:
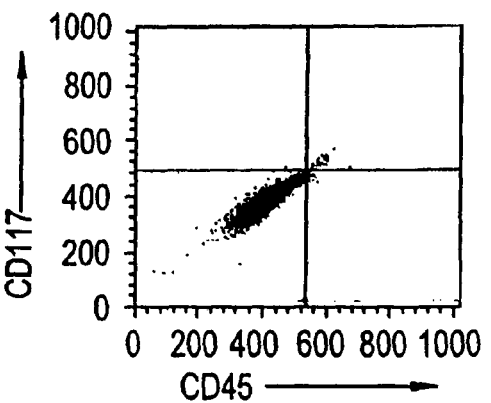
Figure 29F:
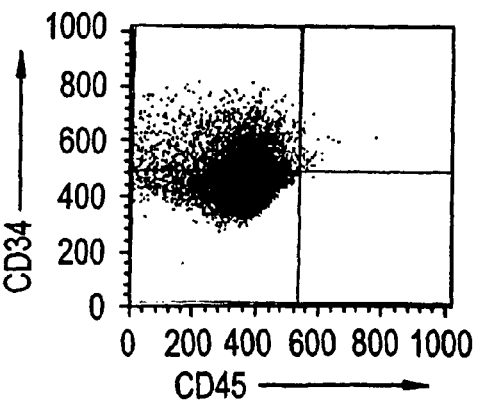
Figure 29G:
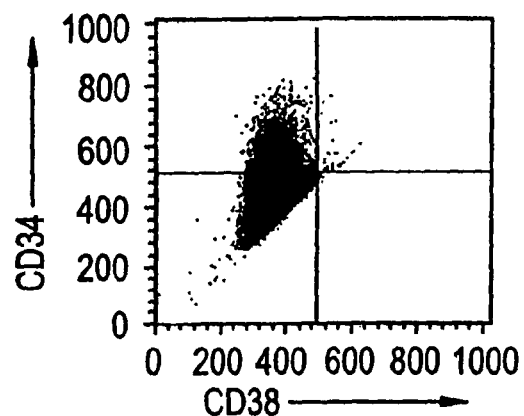
Figure 29H:
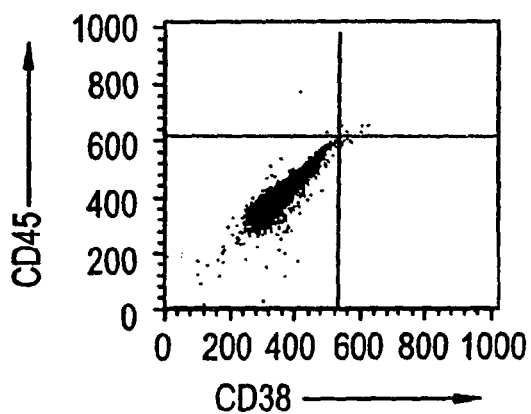
Figure 29I:
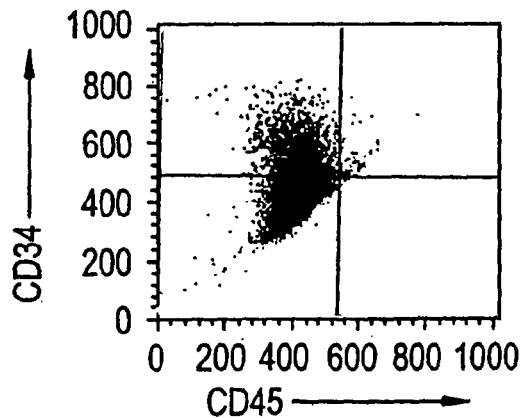

Since cluster differentiation cell surface antigens expressed by human mesenchymal stem cell populations were unknown, we analyzed the five cell populations for the presence of CD3, CD4, CD8, CD11c, CD33, CD34, CD36, CD38, CD45, CD90, CD117, glycophorin-A, and HLA-II (DR) by immunochemistry coupled with flow cytometry. This powerful technique allowed us to examine large numbers of cells relatively quickly and easily. All human stem cells exhibited positive staining for CD90. Positive staining for CD34 was exhibited by postnatal stem cells from NHDF (adult human female NHDF1 and NHDF2), PAL#3 (geriatric human male), and PAL#2 (geriatric human female). Negative staining for CD34 was exhibited by prenatal stem cells from CM-SkM (fetal human male) and CF-SkM (fetal human female). The postnatal adult NHDF1 and NHDF2 and geriatric (PAL#3 and PAL#2) cell populations expressed dual CD34/CD90 staining, whereas the fetal (CM-SkM and CF-SkM) populations only expressed CD90. When analyzed for antibodies to both CD34 and CD90, the NHDF1 population expressed 2520 cells positive for both CD34 and CD90 and 6979 cells positive for CD90 alone. NHDF2 expressed 7320 cells positive for both CD34 and CD90 and 1539 cells positive for CD90 alone. Using the same technique, PAL#3 contained 3430 cells positive for both CD34 and CD90 and 6069 cells positive for CD90 alone. PAL#2 contained 1880 cells positive for both CD34 and CD90 and 6360 cells positive for CD90 alone. CM-SkM contained 1 cell positive for both CD34 and CD90 and 9549 cells positive for CD90 alone. CF-SkM expressed 180 cells positive for both CD34 and CD90, but expressed 8680 cells positive for CD90 alone. No cells positive for CD34 but negative for CD90 were found in any population tested. Staining was negative for CD3, CD4, CD8, CD11c, CD33, CD36, CD38, CD45, CD117, glycophorin-A, and HLA-II (DR) (TABLE 5, FIGS. 27-29) in all populations examined.

TABLE 5

CD MARKER EXPRESSION*

| | CM-SkM | CF-SkM | NHDF | PAL#3 | PAL#2 |
|---|---|---|---|---|---|
| CD3 | 150 | 140 | 13 | 19 | 0 |
| CD4 | 5 | 55 | 26 | 26 | 0 |
| CD8 | 59 | 76 | 38 | 20 | 160 |
| CD11c | 43 | 120 | 24 | 24 | 0 |
| CD33 | 82 | 71 | 20 | 20 | 0 |
| CD34 | 1 | 129 | 2065 | 1812 | 1880 |
| CD36 | 135 | 154 | 36 | 36 | 0 |
| CD38 | 86 | 80 | 26 | 26 | 0 |
| CD45 | 5 | 74 | 30 | 32 | 43 |

TABLE 5-continued

CD MARKER EXPRESSION*

| | CM-SkM | CF-SkM | NHDF | PAL#3 | PAL#2 |
|---|---|---|---|---|---|
| CD90 | 9550 | 708 | 9499 | 9499 | 8240 |
| CD117 | 4 | 134 | 40 | 40 | 0 |
| GlycoA | 118 | 131 | 22 | 22 | 0 |
| HLA-DRII | 5 | 74 | 36 | 36 | 0 |

*CD Marker expression detected by immuno-flow cytometry. Results are expressed as absolute numbers of cells exhibiting positive staining for cell surface CD markers from a gated population of 10,000 cells.

Molecular Analysis of CD34 and CD90

Figure 30:
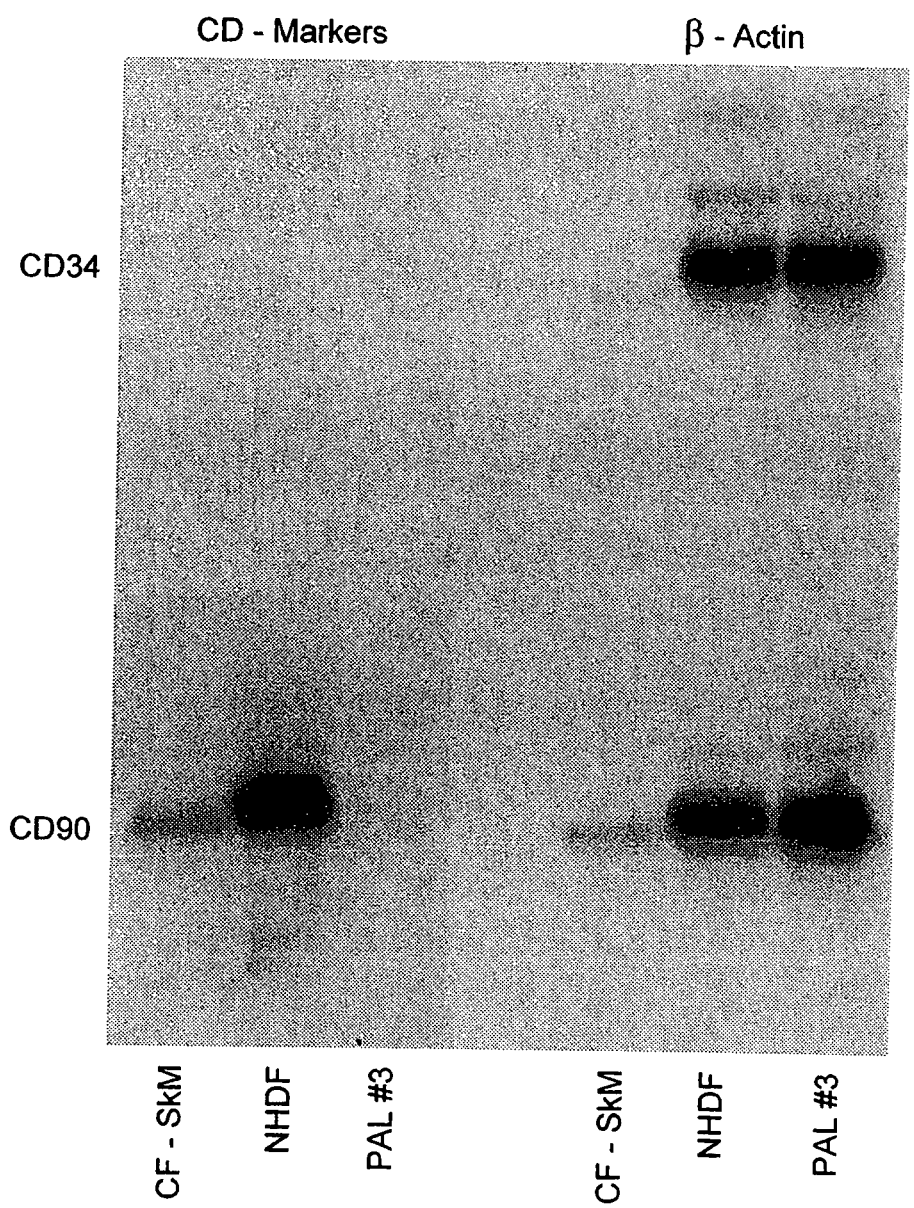
FIG. 30. Northern analysis of cluster differentiation markers CD34 and CD90 for cell lines CF-SkM, NHDF, and PAL#3. Cells were propagated to 30 cell doublings after tissue harvest and released with trypsin. Total RNAs were extracted, electrophoresed, and probed with 32P-labeled cDNAs to CD34, CD90, and b-actin (control). As shown, mRNAs for CD90 and b-actin were being actively transcribed at time of cell harvest.

To determine whether CD34 and CD90 were actively being transcribed by the cells at time of harvest, total RNA from CF-SkM, NHDF, and PAL#3 samples was analyzed by the Northern blot technique using fragments of human CD34 and CD90 cDNAs as probes. A variable pattern in transcription of the CD markers at time of cell harvest was obtained (TABLE 5, FIG. 30). No cDNA binding for CD34-mRNA was present in any of the three cell lines examined, suggesting that either no active transcription was occurring at the time of harvest, or that the amount of mRNA for CD34 was below the limits of detectability of the assay. cDNA binding for CD90-mRNA was either strong (CF-SkM and NHDF), or weak (PAL#3), suggesting similar transcription patterns for CD90 within the respective cell lines.

Discussion

Positive Staining for CD Markers in Human Mesenchymal Stem Cells

The functional significance of the cell surface cluster differentiation markers CD34 and CD90 expressed by the human fetal, adult, and geriatric mesenchymal stem cells remains unknown at this time.

However, CD34 is known to be expressed on committed and uncommitted hematopoietic precursor cells, small vessel endothelial cells and on some cells in nervous tissue (Lin et al., 1995). One group of investigators, working with a cDNA clone, characterized CD34 as a sialomucin (Simmons et al., 1992). The proposed cellular function of CD34 is thought to be the regulation of the differentiation of blood cell precursors, with some suggestion that it is a cell adhesion molecule (Lin et al, 1995). Clinicians have extensively utilized monoclonal antibodies to CD34 to purify hematopoietic stem cells and progenitor cells for use in autologous bone marrow transplantation. In addition, selection for cells expressing CD34 may be employed to isolate cells in clinical applications for hematopoietic gene therapy (Sutherland, et al. 1993).

CD90, also known as Thy-1, is expressed on hematopoietic cells (Craig et al., 1993), neuronal tissue (Tiveron et al., 1992; Morris, 1985) and some connective tissues (Morris and Beech, 1984). Craig et al. determined that CD90 was co-expressed along with CD34 on a significant number of hematopoietic cells (Craig et al., 1993). Human peripheral blood cells positive for both CD90 and CD34 were found to include hematopoietic stem cells capable of producing multiple hematopoietic lineages in immunodeficient mice (Tsukamoto et al., 1994). A function has not yet been assigned to CD90, but it may play a role in signal transduction in T lymphocytes, as it is linked to pathways involving tyrosine phosphorylation (Lancki et al., 1995). The protein is considered part of the immunoglobulin superfamily since it shares some homology with immunoglobulins. Interestingly, since Thy-1 is expressed on brain tissue as well as T lymphocytes, this protein may play a role in the development of ataxia-telangiectasia. This disorder is characterized by lesions in both neurologic and immunologic function (Gatti, 1991; Teplitz, 1978).

The adult female (NHDF), geriatric male (PAL#3), and geriatric female (PAL#2) stem cell populations expressed both CD34 and CD90 on the cell surface (as analyzed by flow cytometry), whereas the fetal male (CM-SkM) and fetal female (CF-SkM) populations expressed CD90 alone. This finding may be important for two reasons.

First, the only previously described cell population positive for both CD34 and CD90 belongs to the hematopoietic stem cell lineage. Because of their ability to express phenotypic markers from multiple mesodermal lineages, we do not believe that these cells belong solely to the hematopoietic lineage. Rather, our data suggest that we have found a unique population that share this phenotypic characteristic with hematopoietic stem cells.

Second, the CD34 marker could be detected on the cell surface of adult female (NHDF), geriatric male (PAL#3), and geriatric female (PAL#2) cells, but not on the fetal male (CM-SkM) and fetal female (CF-SkM) cells. In addition, none of the cells lines examined expressed CD34 mRNA by Northern blot analysis. There are two possible explanations for the lack of expression of CD34 mRNA. The amount of mRNA present might have been below the limits of detectability of the assay. Alternately, the active transcription of CD34 might have ceased, even though the marker was still present on the cell surface of postnatal cells. This finding could help explain why CD34 was expressed by fewer cells than CD90. The relative absence of expression of CD34 by fetal (CM-SkM and CF-SkM) cells is especially striking. However, the significance of this finding is unknown at this time.

It is possible that the cells positive for either CD34 or CD90 observed in the stem cell populations are derived from neuronal or connective tissue progenitor cells that survived in culture. The stem cell populations used for flow cytometry were at 30 cell doublings after tissue harvest. Programmed cell senescence occurs after Hayflick's limit (50-70 cell doublings) has been achieved (Hayflick, 1963, 1965). Since the stem cell populations used in this study had replicated fewer times than Hayflick's limit (i.e., were at 30 cell doublings), they could still contain progenitor and differentiated cells. However, the cells positive for both CD34 and CD90 are unlikely to be derived from neuronal or connective tissue cells as cells from these tissues are not known to coexpress these two proteins. The full characterization of the cells positive for both CD34 and CD90 remains to be accomplished.

Negative Staining for CD Markers in Human Mesenchymal Stem Cells

In contrast to the findings for CD34 and CD90, 11 antigens-were found absent on the cell surface of fetal, adult, and geriatric human mesenchymal stem cells. These markers were CD3, CD4, CD8, CD11c, CD33, CD36, CD38, CD45, CD117, glycophorin-A, and HLA-II (DR). The significance of these findings is unknown at this time. However, these particular cell surface CD antigens have been ascribed only to differentiated cells within the hematopoietic system. T-cells have exhibited the presence of CD3, CD4, CD8, CD45, and CD117 (Kishimoto et al., 1997). Monocytes/macrophages have exhibited CD11c, CD36, CD38, CD45, CD117, and HLA DR-II (Kishimoto et al., 1997). Natural killer cells have exhibited CD11c, CD38, CD45, and CD117 (Kishimoto et al., 1997). Granulocytes have exhibited CD11c, CD36, CD38, CD45, and CD117 (Kishimoto et al., 1997). Myeloid progenitor cells have exhibited CD33, CD38, CD45, and CD117 (Kishimoto et al., 1997). Erythrocytes have exhibited glycophorin-A (Kishimoto et al., 1997). Some neuronal cells have exhibited CD38 and HLA DR-II (Mizguchi et al., 1995; Rohn et al., 1996).

The absence of these eleven surface markers characteristic of differentiated hematopoietic cells on the male and female fetal, adult, and geriatric stem cells used in this study has two possible explanations. The stem cells examined may lack the capability under normal circumstances to differentiate along hematopoietic lineages. If this hypothesis is correct, these markers may never appear on differentiated lineages of these cells. Alternately, if these stem cells have the capability to differentiate along hematopoietic lines, the absence of the eleven differentiation markers may indirectly indicate that the cells studied are more primitive stem cells.

Potential for Tissue Engineering

Every year millions of people suffer tissue loss or end-stage organ failure (Langer and Vacanti, 1993). The total national US health care costs for these patients exceeds 400 billion dollars per year. Currently over 8 million surgical procedures are performed annually in the United States to treat these disorders. 40 to 90 million hospital days are required for these treatments. Although these therapies have saved and improved countless lives, they remain imperfect solutions. Options such as tissue transplantation and surgical intervention are severely limited by critical donor shortages and possible long-term morbidity. Donor shortages worsen every year and increasing numbers of patients die while on waiting lists for needed organs. A wide variety of traumas, congenital malformations, diseases, and genetic disorders have the potential for treatment with autologous mesenchymal stem cells as the source of donor tissue. In treating tissue loss, it is desirable to increase the numbers of cells available for transplantation to replace lost tissues. Procedures to increase cell numbers are also desirable for ex vivo gene therapy. One benefit of using autologous stem cells is that they can provide an identical HLA match, obviating the need for immunosuppressive therapy, with its associated morbidity and mortality. A second benefit is the potential for extended cell proliferation associated with pluripotent cells. Pluripotent stem cells can greatly increase cell numbers prior to the induction of lineage commitment. Following the induction of lineage commitment, the resulting progenitor stem cells can then proliferate an additional 50-70 cell doublings before programmed cell senescence occurs. The proliferative attributes of these two stem cell populations are very important when limited amounts of tissue are available for transplantation and/or gene therapies.

To date, progenitor stem cells have been used for site-directed repair of bone (Kadiyala et al., 1997), and pluripotent mesenchymal stem cells have been used for site-directed repair of cartilage and bone (Grande et al., 1995). For autologous stem cell therapies to have clinical relevance, relatively short time periods are needed for the isolation, propagation, and lineage induction (if necessary) prior to re-introduction of the cells into the individual. Previous work from our lab used propagation past Hayflick's limit (50-70 cell doublings) or cloning by limiting serial dilution (Rogers et al., 1995; Young et al., 1993; Young et al., 1998b) to isolate individual populations of progenitor and pluripotent cells. These techniques required from nine months to two years for isolation and/or complete separation of progenitor and pluripotent cell populations. Our current research is aimed at reducing the time required for the purification of autologous progenitor and pluripotent cells. To that end we have isolated these cells from fetal, adult, and geriatric human donors of both genders and have begun characterizing their cell surface cluster differentiation antigens. We now report the first demonstration of the expression of CD90 and varying amounts of CD34 in human progenitor and pluripotent mesenchymal stem cells. We suggest that these cell surface CD markers could be used in conjunction with flow cytometry and fluorescence-activated cell sorting as an initial step in isolating more purified populations of these cells from an initial stem cell harvest.

The clinical application we envision is as follows. A patient wanting elective surgery to repair a tissue defect or a candidate for gene therapy comes to a doctor's office. A small dermal biopsy (approximately 5 mm$^3$) is removed under local anesthetic, placed in transport fluid, and sent to the laboratory. There the tissue is digested enzymatically to release the stem cells, and the cell suspension cultured. After the cells reach confluence, they are released and the progenitor cells of choice and the pluripotent cells are isolated using antibodies to their unique cell surface antigenic profiles. The pluripotent cells are propagated to increase cell numbers and induced to commit to the tissue lineage(s) of choice. In less than 30 days the patient's autologous stem cells, both the original progenitor cells and the pluripotent cells (induced to commit to the desired lineage) are transplanted into the patient. For gene therapy, the pluripotent cells would be transfected with the desired gene prior to cell propagation. This protocol would significantly decrease both culture time and costs. It would also improve the yield of the stem cells needed for specific transplantation and gene therapies.

Example 9

Retention of Pluripotent Embryonic-Like Stem Cells in Postnatal Mammals

Figure 31A:
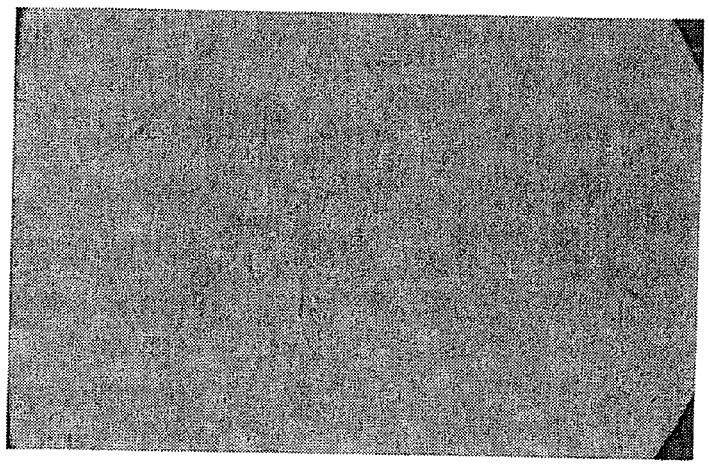
FIG. 31A-C A. Mesenchymal stem cells isolated from 37 year old male treated with $10^{-8}$ M Dexamethasone, 35 days in culture. Large cell with single nucleus. Reminiscent of macrophage in culture. Phase contrast, 200×. B. Mesenchymal stem cells isolated from 37 year old male treated with $10^{-7}$ M dexamethasone, 35 days in culture. Cell with small cell body and thin, extensive cell processes. Resembles neuron in culture. Phase contrast, 200×. C. Mesenchymal stem cells isolated from newborn rat treated with $10^{-7}$ M dexamethasone, 35 days in culture. Cell looks very similar to that seen in B. Also resembles neuron in culture. Phase contrast, 200×.
Figure 31B:
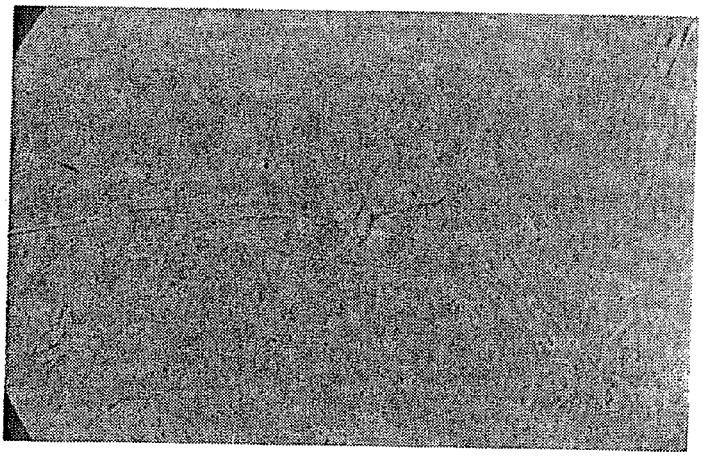
Figure 31C:
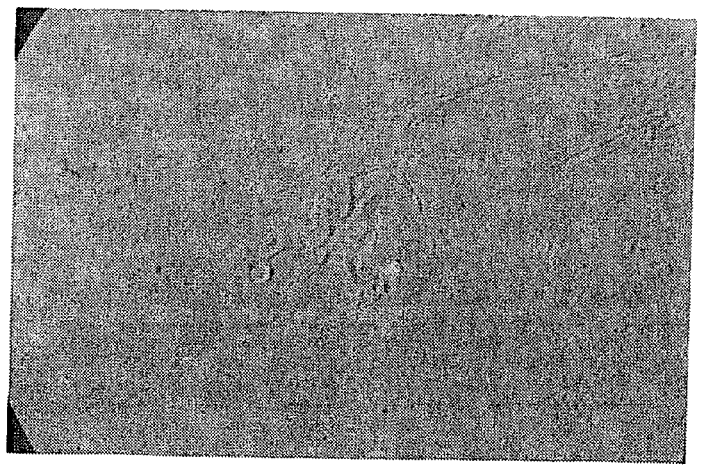

In the course of characterization of the mesodermal differentiative capacity of isolated pluripotent stem cells, we observed and noted other morphologies, indicating the presence of distinct, even non-mesodermal phenotypes. Human cells isolated by cryopreservation as described in (Young et al., 1991, 1992a; Lucas et al., 1995) were grown in $10^{-7}$ or $10^{-8}$ M dexamethasone and cells looking like osteoclasts (hematopoietic lineage) (FIG. 31A) and nerve cells (FIGS. 31B and C) were observed after 18 days in culture. Similarly, with Mouse 3T3 cells grown in $10^{-6}$ M dexamethasone a large cell looking like a macrophage was observed after 9 days in culture. Rat cells were grown in $10^{-7}$ M dexamethasone and large cells were noted.

To assess the nature and extent of additional morphologies, pluripotent stem cells, isolated from humans (CF-NHDF2 and PAL3 cells), were incubated in insulin and dexamethasone for up to 45 days and examined morphologically, immunochemically and histochemically.

Figure 34A:
FIG. 34 A-R NHDF-2 Cells incubated in CM only (A-D) or CM plus dexamethasone (E-R) for 24 hr (A) or 56 days (B-R). Cells photographed at same original magnification (100×) in either phase contrast (A,L) or bright field (B-K, M-R) microscopy. A Eight very small cells with high nuclear to cytoplasmic ratios. B Two very small cells heavily stained with antibody to stage-specifica embryonic antigen-1 (MC480). C Single very small cell (arrow) stained with antibody to stage-specific embryonic antigen-3 (MC631).
Figure 34B:
Figure 34C:
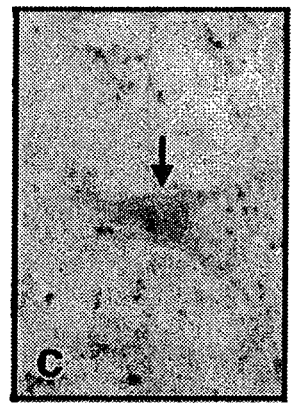
Figure 34D:
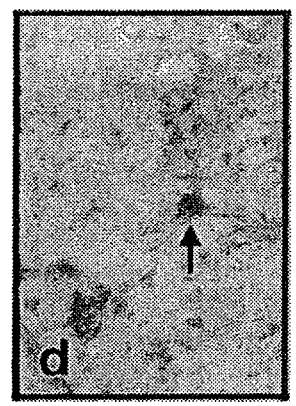

The original intent of this study was to determine if pluripotent mesenchymal stem cells were present in postnatal humans. Adult human cells, derived from the dermis of a 36-year-old female and the skeletal muscle connective tissues of a 67-year-old male, were isolated as described. The initial morphological studies of these cells showed that they were small cells, and exhibited a high ratio of nucleus to cytoplasm (FIG. 34A). This morphological appearance is consistent with that of embryonic stem cells. Subsequent immunological staining showed that individual cells expressed stage-specific embryonic antigens (SSEA)-1 (FIG. 34B), SSEA-3 (FIG. 34C), SSEA-4 (FIG. 34D), and human-specific carcinoembryonic antigens (HCEA and CD66) (data not shown). These results suggested that cells retaining cell surface embryonic antigens were present within these two cell lines.

We then used insulin and dexamethasone in a comparative/contrast bioassay to determine the identity of the cells. No change in morphology or change in antigen staining occurred when the cells were incubated with insulin, i.e., some cells still expressed SSEA-1, SSEA-3, SSEA-4, HCEA, and CD66 (data not shown). This suggested that the cells were not lineage-committed progenitor cells.

Figure 34E:
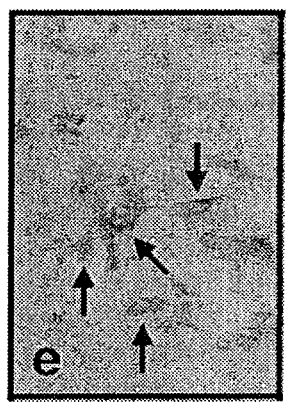
Figure 34F:
Figure 34G:
Figure 34H:
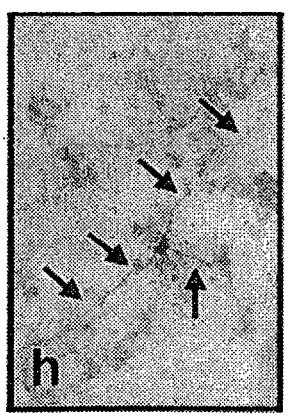
Figure 34I:
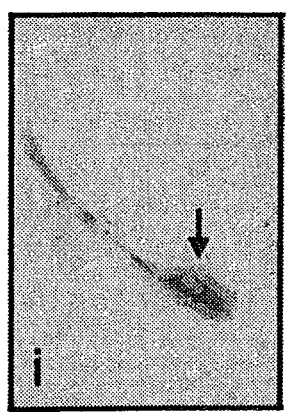
Figure 34J:
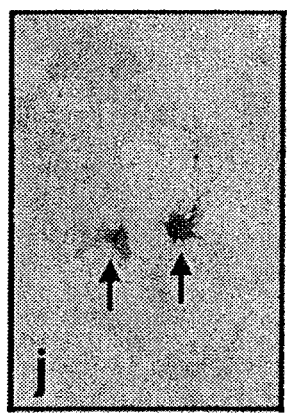
Figure 34K:
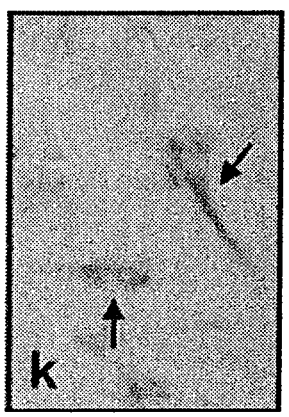
Figure 34L:
Figure 34M:
Figure 34N:
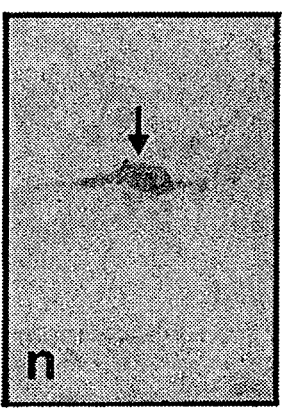
Figure 34O:
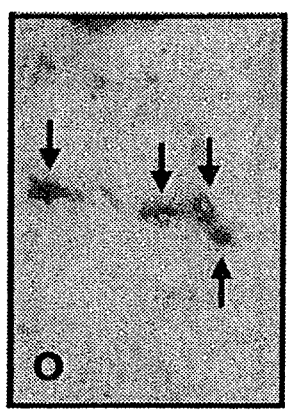
Figure 34P:
Figure 34Q:
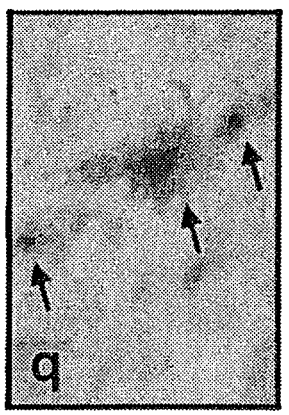
Figure 34R:
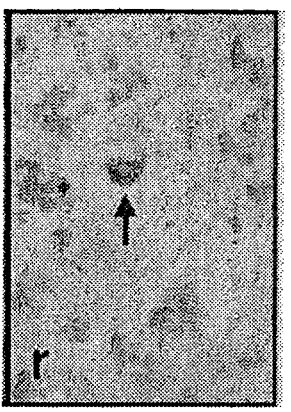

Incubation with dexamethasone caused both a loss of embryonic antigen staining and the appearance of phenotypic expression markers for cells of ectodermal, mesodermal, and endodermal origin. This suggested that the cells were lineage-unrestricted stem cells. Cells displaying ectodermal lineage markers were identified by induction of the expression markers for neural ectoderm, e.g., nestin (FIG. 34E), neurons (FIG. 34F), neurofilaments (FIG. 34H), neuroglia (FIG. 34I), and surface ectoderm, e.g., keratinocytes (FIG. 34J). Cells displaying mesodermal lineage markers were identified by induction of the expression markers for muscle, e.g., myogenin (FIG. 34K), sarcomeric myosin, fast-skeletal muscle myosin, myosin heavy chain (data not shown), skeletal muscle myotubes (FIG. 34L), smooth muscle alpha-actin (data not shown); fat, e.g., saturated neutral lipid (FIG. 34M); cartilage, e.g., type-II collagen (FIG. 34N), type-IX collagen, chondroitin sulfate and keratan sulfate proteoglycan-containing nodules (data not shown); bone, e.g., bone sialoprotein-II (FIG. 34O), osteopontine, calcium phosphate-containing nodules (data not shown); fibroblasts (data not shown); and endothelial cells, e.g., PECAM (FIG. 34P), VCAM, E-selectin, human-specific endothelial cell surface marker, and CD34 (data not shown). Cells displaying endodermal lineage markers were identified by induction of the expression markers for alpha-fetoprotein (FIG. 34Q) and gastrointestinal epithelium (FIG. 34R).

Hayflick demonstrated that diploid fibroblasts (lineage-committed fibroblastic progenitor cells) had a finite life-span limited to approximately 50 cell doublings before programmed cell senescence and death occurred. Thus the 50 cell doublings has been termed "Hayflick's Limit". Investigators working with lineage-uncommitted embryonic stem cells demonstrated that their cells have extended capabilities for self-renewal through cell division, far surpassing Hayflick's Limit. We therefore examined the proliferative capabilities of the cell lines. These cells were maintained in the pluripotent state in these experiments. Cells underwent propagation, release, and cryopreservation through 17 passages (NHDF2) and 39 passages (PAL3). Doubling time averaged 12-24 hr with approximately 4 doublings per passage. Thus the NHDF2 cells underwent more than 70 cell doublings and the PAL3 cells more than 200 cell doublings. In one group of experiments, cells were incubated in CM alone to maintain them in the pluripotent state. In these experiments cells were incubated for 30-56 days. Morphological, immunochemical, and histochemical analysis showed that these cells demonstrated staining with antibodies to embryonic-antigens. In a second group of experiments, cells were incubated in CM containing insulin for 30-56 days to determine if extended propagation would induce lineage commitment in the cells. Morphological, immunochemical, and histochemical analysis showed that these cells demonstrated the same staining pattern with antibodies to embryonic antigens. In a third group of experiments, cells were incubated in CM containing dexamethasone for 30-56 days to cause the cells to differentiate.

Morphological, immunochemical, and histochemical analysis showed that following the induction of differentiation, the cells expressed antigens characteristic of cells from the ectodermal, mesodermal, and endodermal cell lineages. These results demonstrate that the cell lines did not lose their characteristics resembling those of embryonic stem cells following propagation past Hayflick's Limit. They also did not lose their pluripotent characteristics (ability to differentiate into cells belonging to different embryonic lineages) following such treatment.

Based on a high nuclear to cytoplasmic ratio, expression of embryonic cell surface antigens, capabilities for extended self-renewal, loss of embryonic antigens concomitant with induced differentiation, and induced differentiated cell types showing phenotypic expression markers for ectodermal, mesodermal, and endodermal lineage cells, these cell lines meet the criteria for pluripotent stem cells. Their expression of embryonic antigens and their differentiative capabilities closely resembles the attributes of embryonic stem cells derived from the inner cell mass of mice, primates and humans. These findings suggest that reserve pluripotent stem cells having characteristics resembling those of embryonic stem cells are present in adult humans.

Figure 32A:
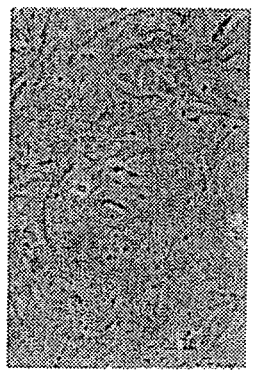
FIG. 32A-Y Human cell lines CF-NHDF2 and PAL3 incubated with insulin and/or dexamethasone for 0 to six weeks. Morphologies as noted. A, CF-NHDF2 treated in control medium for 24 hr, note presence of stellate-shaped mononucleated cells with large nuclear to cytoplasmic ratios, phase contrast, 200×; B, CF-NHDF2 treated for one week with 1% HS+$10^{-6}$ M dexamethasone+2 ug/ml insulin and then stained with antibody to myogenin (F5D), note stellate-shaped cell with intracellular cytoplasmic staining, indicative of a muscle (mesodermal) lineage, brightfield, 100×; C, CF-NHDF2 treated for two weeks with 1% HS+10' M dexamethasone+2 ug/ml insulin and then stained with antibody to myogenin (F5D), note binuclear and mononucleated cells with intracellular cytoplasmic staining, indicative of a muscle (mesodermal) lineage, brightfield, 100×; D, CF-NHDF2 treated for two weeks with 1% HS+$10^{-6}$ M dexamethasone+2 ug/ml insulin and then stained with antibody to sarcomeric myosin (MF-20), note mononucleated cells with intracellular cytoplasmic staining, indicative of a muscle (mesodermal) phenotype, brightfield, 100×; E, CF-NHDF2 treated for two weeks with 1% HS+$10^{-6}$ M dexamethasone+2 ug/ml insulin and then stained with antibody to anti-skeletal muscle fast myosin (MY-32), note mononucleated cells with intracellular cytoplasmic staining, indicative of a skeletal muscle (mesodermal) phenotype, brightfield, 100×; F, CF-NHDF2 treated for three weeks with 1% HS+$10^{-6}$ M dexamethasone+2 ug/ml insulin and then stained with antibody to anti-skeletal muscle fast myosin (MY-32), note multinucleated structure demonstrating intracellular cytoplasmic staining, indicative of a skeletal muscle (mesodermal) phenotype, brightfield, 200×; G, CF-NHDF2 treated for two weeks with 1% HS+$10^{-6}$ M dexamethasone+2 ug/ml insulin and then stained with antibody to myosin heavy chain (ALD-58), note stellate structures demonstrating intracellular cytoplasmic staining, indicative of a skeletal muscle (mesodermal) phenotype, brightfield, 100×; H, CF-NHDF2 treated for two weeks with 1% HS+$10^{-6}$ M dexamethasone+2 ug/ml insulin and then stained with antibody to myosin fast chain (A4.74), note stellate structures demonstrating intracellular cytoplasmic staining, indicative of a skeletal muscle (mesodermal) phenotype, brightfield, 100×; I, CF-NHDF2 treated for three weeks with 1% HS+$10^{-6}$ M dexamethasone+2 ug/ml insulin, note linear multinucleated structure, indicative of a skeletal muscle (mesodermal) phenotype, phase contrast, 100×; J, CF-NHDF2 treated for six weeks with 1% HS+$10^{-6}$ M dexamethasone+2 ug/ml insulin, note large linear and branched multinucleated structures, indicative of a skeletal muscle (mesodermal) phenotype, phase contrast, 100×; K, CF-NHDF2 treated for two weeks with 1% HS+$10^{-6}$ M dexamethasone+2 ug/ml insulin and then stained with, antibody to smooth muscle alpha-actin (1A4), note binuclear-stellate cell with intracellular cytoplasmic staining, alpha-actin intracellular staining of a binuclear-stellate is suggestive of a cardiac muscle phenotype, brightfield, 100×; L, CF-NHDF2 treated for two weeks with 1% HS+$10^{-6}$ M dexamethasone+2 ug/ml insulin and then stained with antibody to smooth muscle alpha-actin (1A4), note mononuclear-stellate cells with intracellular cytoplasmic staining, smooth muscle alpha-actin intracellular staining of a mononuclear-stellate is indicative of a smooth muscle (mesodermal) phenotype, phase contrast, 100×; M, PAL3 treated for four weeks with 1%, 5%, or 10% HS+$10^{-6}$ M dexamethasone+2 ug/ml insulin and then stained with Sudan Black-B for saturated neutral lipids, note mononucleated cells containing intracellular-stained vesicles, indicative of an adipogenic (mesodermal) phenotype, brightfield, 100×; N, CF-NHDF2 treated for three weeks with 5% or 10% HS+$10^{-6}$ M dexamethasone and 2 ug/ml insulin and then stained with antibody to type-II pro-collagen (CIIC1), note mononuclear-stellate cell with intracellular cytoplasmic staining, type-II procollagen intracellular staining of a mononuclear-stellate cell is indicative of a commitment to the chondrogenic (mesodermal) lineage, brightfield, 200×; O, CF-NHDF2 treated for three weeks with 5% or 10% HS+$10^{-6}$ M dexamethasone and 2 ug/ml insulin and then stained with antibody to collagen type-II (HC-II), note mononuclear-stellate cell with intracellular cytoplasmic staining, type-II collagen intracellular staining of a mononuclear-stellate cell is indicative of a commitment to the chondrogenic (mesodermal) lineage, brightfield, 100×; P, CF-NHDF2 treated for three weeks with 5% or 10% HS+$10^{-6}$ M dexamethasone and 2 ug/ml insulin and then stained with antibody to type-II collagen (D19), note mononuclear-stellate cells with intracellular cytoplasmic staining, type-II collagen intracellular staining of a mononuclear-stellate is indicative of a commitment to the chondrogenic (mesodermal) lineage, brightfield, 100×; Q, PAL3 treated for six weeks with 5% or 10% HS+10' M dexamethasone and 2 ug/ml insulin and then stained histochemically for chondroitin sulfate and keratan sulfate proteoglycans (Alcian Blue, pH 1.0), dark stained nodule indicative of chondrogenic (mesodermal) phenotype; brightfield, 100×; R, PAL3 treated for six weeks with 5% or 10% HS+$10^{-6}$ M dexamethasone and 2 ug/ml insulin and then stained histochemically for chondroitin sulfate and keratan sulfate proteoglycans (Perfix/Alcec Blue), dark stained nodule indicative of chondrogenic (mesodermal) phenotype, brightfield, 50×; S, CF-NHDF2 treated for two weeks with 5% or 10% HS+$10^{-6}$ M dexamethasone and 2 ug/ml insulin and then stained with antibody to bone sialoprotein (WV1D1), note mononuclear-stellate cells with intracellular cytoplasmic staining, bone sialoprotein intracellular staining of a mononuclear-stellate cell is indicative of commitment to the osteogenic (mesodermal) lineage, brightfield, 100×; T, CF-NHDF2 treated for two weeks with 5% or 10% HS+1106 M dexamethasone and 2 ug/ml insulin and then stained with antibody to osteopontine (MP111), note mononuclear-stellate cells with intracellular cytoplasmic staining, osteopontine intracellular staining of a mononuclear-stellate cell is indicative of commitment to the osteogenic (mesodermal) lineage, brightfield, 100×; U, PAL3 treated for six weeks with 5% or 10% HS+$10^{-6}$ M dexamethasone and 2 ug/ml insulin and then stained histochemically for calcium phosphate (von Kossa), note black-stained nodules, von Kossa-positive staining of the three dimensional matrix of multiple nodules is indicative of an osteogenic (mesodermal) phenotype, brightfield, 50×; V, CF-NHDF2 treated for two weeks with 1% or 5% HS+$10^{-6}$ M dexamethasone+2 ug/ml insulin and then stained with antibody to human-specific fibroblast specific protein (HFSP), note mononuclear-stellate cells with intracellular cytoplasmic staining, fibroblast-specific protein staining of a mononuclear-stellate is indicative of a fibrogenic (mesodermal) phenotype, brightfield, 100×; W, CF-NHDF2 treated for two weeks with 1% or 5% HS+$10^{-6}$ M dexamethasone+2 ug/ml insulin and then stained with antibody to peripheral endothelial cell adhesion molecule, PECAM (P2B1), note mononuclear-stellate cells with intracellular cytoplasmic staining, PECAM-staining of a mononuclear-stellate is indicative of an endothelial (mesodermal) phenotype, brightfield, 200×; X, CF-NHDF2 treated for two weeks with 1% or 5% HS+$10^{-6}$ M dexamethasone+2 ug/ml insulin and then stained with antibody to human-specific endothelial cell surface marker (HEndo), note mononuclear-stellate cells with intracellular cytoplasmic staining, HEndo-staining of a mononuclear-stellate is indicative of an endothelial (mesodermal) phenotype, brightfield, 40×; Y, CF-NHDF2 treated for two weeks with 1% or 5% HS+$10^{-6}$ M dexamethasone+2 ug/ml insulin and then stained with antibody to vascular endothelial cell adhesion molecule, VCAM (P8B1), note mononuclear-stellate cells with intracellular cytoplasmic staining, VCAM-staining of a mononuclear-stellate is indicative of an endothelial (mesodermal) phenotype, brightfield, 40×.
Figure 32B:
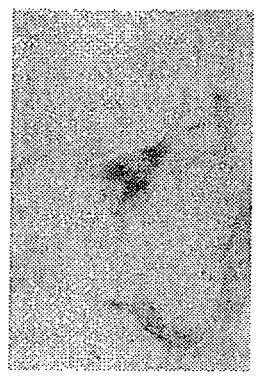
Figure 32C:
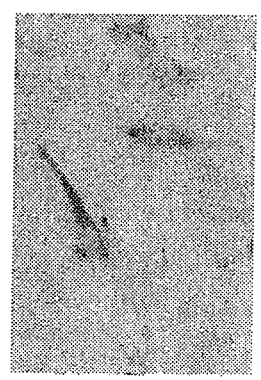
Figure 32D:
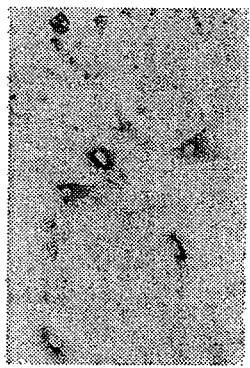
Figure 32E:
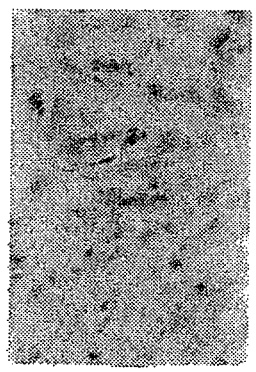
Figure 32F:
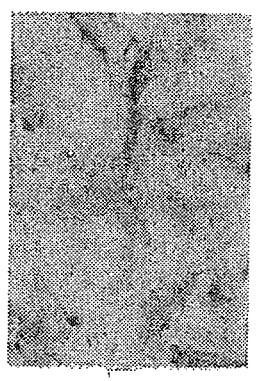
Figure 32G:
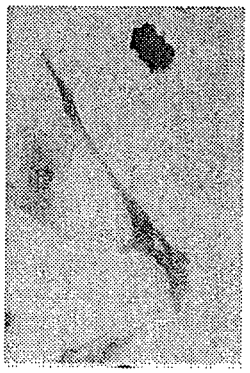
Figure 32H:
Figure 32I:
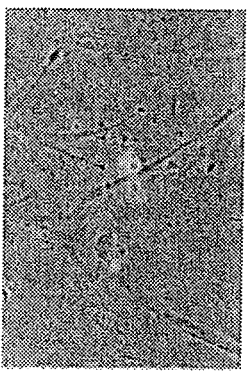
Figure 32J:
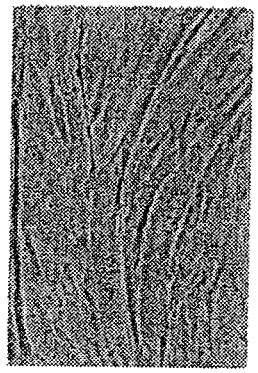
Figure 32K:
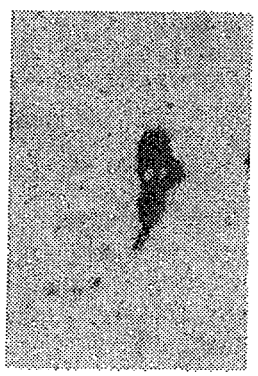
Figure 32L:
Figure 32M:
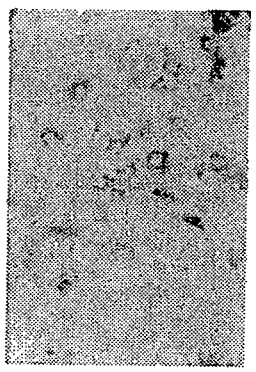
Figure 32N:
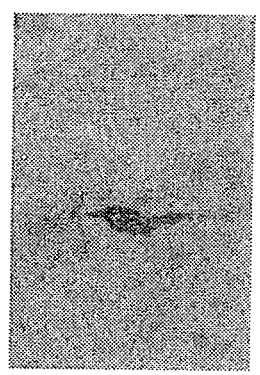
Figure 32O:
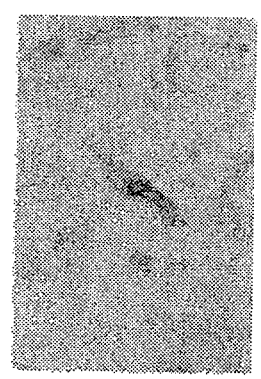
Figure 32P:
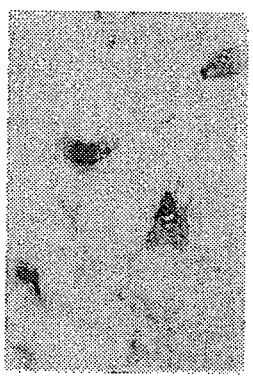
Figure 32Q:
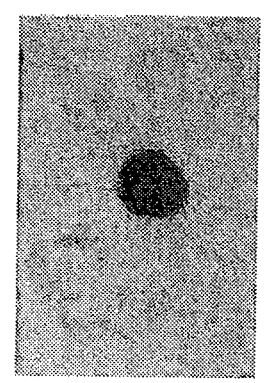
Figure 32R:
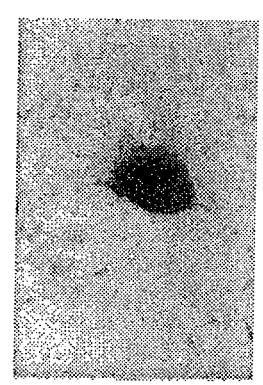
Figure 32S:
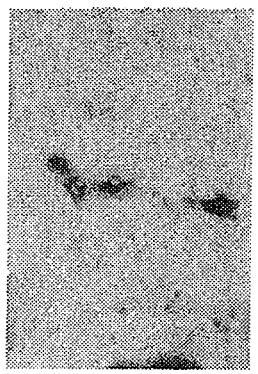
Figure 32T:
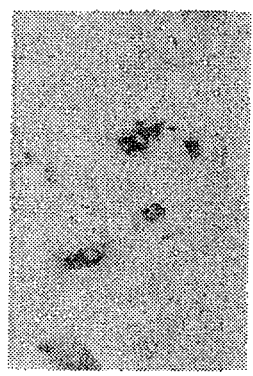
Figure 32U:
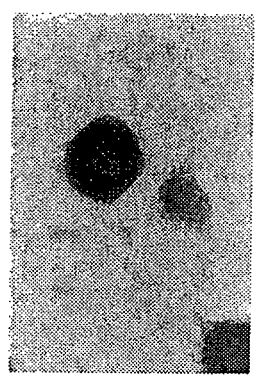
Figure 32V:
Figure 32W:
Figure 32X:
Figure 32Y:
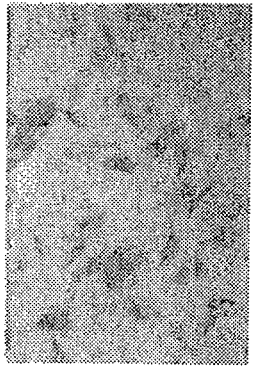

Culture conditions that exhibited multinucleated linear and branched structures that spontaneously contracted were evaluated from day of plating through expression of phenotypes using an enzyme-linked immuno-culture assay (ELICA) to verify the presence of myogenic phenotypic markers within putative skeletal muscle cells, i.e., sarcomeric myosin (MF-20) (FIG. 32D), anti-skeletal muscle fast myosin (MY-32) (FIG. 32E, 32F), myosin heavy chain (Young, et al., 1992a,b; Young, 1999). Cultures that exhibited binucleated and mononucleated polygonal-shaped cells with intracellular fibers were further evaluated by staining with smooth muscle alpha-actin (IA4). Alpha-actin staining of binucleate polygonal-shaped cells (FIG. 32K) is suggestive of a cardiogenic phenotype (Eisenberg and Markwald, 1997), whereas alpha-actin staining of mononucleated polygonal-shaped cells (FIG. 32L) is indicative of smooth muscle cells (Young et al., 1992b). Cultures that exhibited multiple refractile vesicles were further evaluated using Sudan Black-B (FIG. 32M) and Oil Red-O staining to verify the presence of saturated neutral lipids within putative adipocytes (Humanson, 1972; Young et al., 1993, 1995; Young, 1999). Cultures that displayed aggregates of rounded cells containing pericellular matrix halos were further evaluated using both immunochemical and histochemical stains. Putative chondrogenic lineage-committed cells were confirmed using antibodies to type-IX collagen (D19) (FIG. 32P), type-II collagen (HCII) (FIG. 32O), and histochemical stains for chondroitin sulfate and keratan sulfate proteoglycans, i.e., Alcian Blue, pH 1.0 (FIG. 32Q) and Safranin-O, pH 1.0. Alcian Blue, pH 1.0 and Safranin-O, pH 1.0 were further coupled with degradative enzymes specific for chondroitin sulfate proteoglycans (chondroitinase-AC, ICN Biomedicals, Cleveland, Ohio) and keratan sulfate proteoglycans (keratanase, ICN) to verify the existence of these particular proteoglycans within the extracellular matrix surrounding the putative chondrocytic nodules (Young et al., 1989a, 1992b, 1993, 1995; Young, 1999). Cells that exhibited cells embedded within and/or overlain with a three-dimensional matrix were further evaluated using both immunochemical and histochemical procedures. Putative osteogenic lineage-committed cells were probed with antibodies to bone sialoprotein (WV1D1) (FIG. 32S) and osteopontine (MP111) (FIG. 32T), as well as stained using the von Kossa procedure (Silber Protein, Chroma-Gesellschaft) (FIG. 32U) coupled with EGTA (Ethyleneglycol-bis-[beta-Aminoethyl ether] N, N, N',N'-tetraacetic acid, Sigma) pretreatment to verify the presence of calcium phosphate within putative mineralized bone spicules (Young et al., 1989a, 1992b, 1993, 1995).

Figure 33A:
FIG. 33A-R Human cell line incubated with insulin and/or dexamethasone for 0 to six weeks. Morphologies as noted. A, CF-NHDF2 treated for two weeks with 1% or 5% HS+$10^{-6}$ M dexamethasone+2 ug/ml insulin and then stained with antibody to selectin-E (P2H3), note mononuclear-stellate cells with intracellular cytoplasmic staining, selectin-E staining of a mononuclear-stellate is indicative of an endothelial (mesodermal) phenotype, brightfield, 100×; B, CF-NHDF2 treated for two weeks with 1% or 5% HS+$10^{-6}$ M dexamethasone+2 ug/ml insulin and then stained with antibody to CD34 sialomucin (CD34), note mononuclear-stellate cells with intracellular cytoplasmic staining, CD34 sialomucin-staining of a mononuclear-stellate is suggestive of either an endothelial or hematopoietic (mesodermal) lineage, brightfield, 100×; C, CF-NHDF2 treated for four weeks with 1% HS+$10^{-6}$ M dexamethasone+2 ug/ml insulin and then stained with antibody to neural precursor cells (FORSE-1), note mononuclear-stellate cells with intracellular cytoplasmic staining, FORSE-1 intracellular staining of mononuclear-stellate cells is indicative of commitment to the neuronal (ectodermal) lineage, brightfield, 100×; D, CF-NHDF2 treated for four weeks with 1% HS+$10^{-6}$ M dexamethasone+2 ug/ml insulin and then stained with antibody to neurofilaments (RT-97), note mononuclear-stellate cells with intracellular cytoplasmic staining, neurofilament intracellular staining of mononuclear-stellate cells is indicative of commitment to the neuronal (ectodermal) lineage, brightfield, 100×; E, CF-NHDF2 treated for four weeks with 1% HS+$10^{-6}$ M dexamethasone+2 ug/ml insulin and then stained with antibody to neurons (8A2), note mononuclear-stellate cells with intracellular cytoplasmic staining, neuronal intracellular staining of mononuclear-stellate cells is indicative of commitment to the neuronal (ectodermal) lineage, brightfield, 100×; F, CF-NHDF2 treated for four weeks with 1% HS+$10^{-6}$ M dexamethasone+2 ug/ml insulin and then stained with antibody to neuroglia (CNPase), note mononuclear-stellate cells with intracellular cytoplasmic staining, neuroglial staining of mononuclear-stellate cells is indicative of commitment to the neuronal (ectodermal) lineage, brightfield, 100×; G, CF-NHDF2 treated for four weeks with 1% HS+$10^{-6}$ M dexamethasone+2 ug/ml insulin and then stained with antibody to neurons (S-100), note mononuclear-stellate cells with intracellular cytoplasmic staining, neuronal staining of mononuclear-stellate cells is indicative of commitment to the neuronal (ectodermal) lineage, brightfield, 100×; H, CF-NHDF2 treated for four weeks with 1% HS+$10^{-6}$ M dexamethasone+2 ug/ml insulin and then stained with antibody to neuronal filament-200 (N-200), note mononuclear-stellate cells with intracellular neurofilament staining, neurofilament staining of mononuclear-stellate cells is indicative of commitment to the neuronal (ectodermal) lineage, brightfield, 100×; I, CF-NHDF2 treated for four weeks with 1% HS+$10^{-6}$ M dexamethasone+2 ug/ml insulin and then stained with antibody to human-specific nestin, a neural precursor cell marker (HNES), note mononuclear-stellate cells with intracellular cytoplasmic staining, nestin intracellular staining of mononuclear-stellate cells is indicative of commitment to the neuronal (ectodermal) lineage, phase contrast, 100×; J, CF-NHDF2 treated for four weeks with 1% HS+$10^{-6}$ M dexamethasone+2 ug/ml insulin and then stained with antibody to nestin, a neuronal precursor cell marker (MAB-353), note mononuclear-stellate cells with intracellular cytoplasmic staining, nestin intracellular staining of mononuclear-stellate cells is indicative of commitment to the neuronal (ectodermal) lineage, phase contrast, 100×; K, CF-NHDF2 treated for two weeks with 1% or 5% HS+$10^{-6}$ M dexamethasone+2 ug/ml insulin and then stained with antibody to keratinocytes (VM-1), note mononuclear-stellate cells with intracellular cytoplasmic staining, keratinocyte-staining of a mononuclear-stellate is indicative of an epidermal (ectodermal) phenotype, brightfield, 40×; L, CF-NHDF2 treated for two weeks with 1% or 5% HS+$10^{-6}$ M dexamethasone+2 ug/ml insulin and then stained with antibody to human-specific alpha-fetoprotein (HAFP), note mononuclear-stellate cells with intracellular cytoplasmic vesicular staining, alpha-fetoprotein intracellular vesicular staining of mononuclear-stellate cells is indicative of commitment to the hepatic (endodermal) lineage, brightfield, 100×; M, CF-NHDF2 treated for four weeks with 1% or 5% HS+$10^{-6}$ M dexamethasone+2 ug/ml insulin and then stained with antibody to human-specific alpha-fetoprotein (HAFP), note binuclear cell with intracellular cytoplasmic vesicular staining, alpha-fetoprotein intracellular vesicular staining of binuclear cell is indicative of commitment to the hepatic (endodermal) lineage, brightfield, 100×; N, CF-NHDF2 treated for two weeks with 1% or 5% HS+$10^{-6}$ M dexamethasone+2 ug/ml insulin and then stained with antibody to human-specific epithelial-specific antigen (HESA), note mononuclear-stellate cells with intracellular cytoplasmic vesicular staining, epithelial-specific intracellular vesicular staining of mononuclear-stellate cells is indicative of commitment to the epithelial (endodermal) lineage, brightfield, 100×; O, CF-NHDF2 treated with control media for one week and then stained with antibody to stage-specific embryonic antigen 1, SSEA-1 (MC-480), note mononuclear-stellate cells with intracellular cytoplasmic vesicular staining, SSEA-1 staining of mononuclear stellate cells is indicative of embryonic stem cells, brightfield, 100×; P, CF-NHDF2 treated with control media for two weeks and then stained with antibody to stage-specific embryonic antigen-3, SSEA-3 (MC-631), note mononuclear-stellate cells with intracellular cytoplasmic vesicular staining, SSEA-3 staining of mononuclear stellate cells is indicative of embryonic stem cells, brightfield, 100×; Q, CF-NHDF2 treated with control media for four weeks and then stained with antibody to stage-specific embryonic antigen-4, SSEA-4 (MC-813-70), note mononuclear-stellate cells with intracellular cytoplasmic vesicular staining, SSEA-4 staining of mononuclear stellate cells is indicative of embryonic stem cells, brightfield, 100×; and R, CF-NHDF2 treated with control media for six weeks and then stained with antibody to human carcinoembryonic antigen (HCEA), note mononuclear-stellate cells with intracellular cytoplasmic vesicular staining, human carcinoembryonic antigen staining of mononuclear stellate cells is indicative of embryonic stem cells, brightfield, 100×.
Figure 33B:
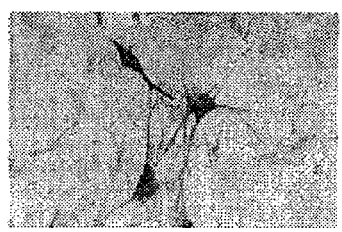
Figure 33C:
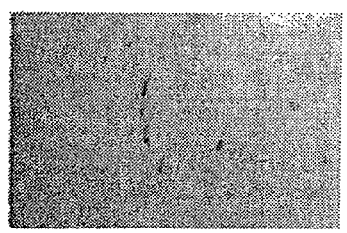
Figure 33D:
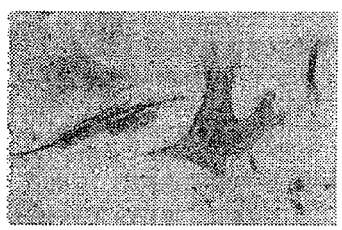
Figure 33E:
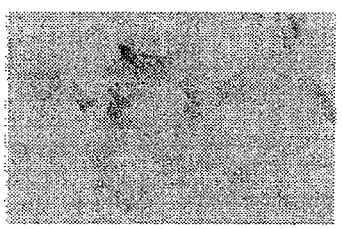
Figure 33F:
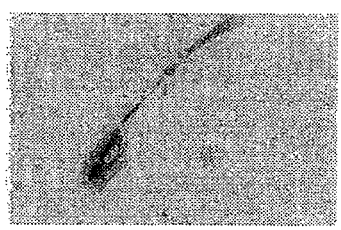
Figure 33G:
Figure 33H:
Figure 33I:
Figure 33J:
Figure 33K:
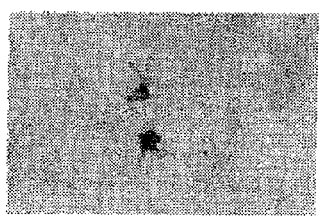
Figure 33L:
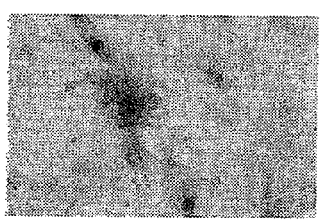
Figure 33M:
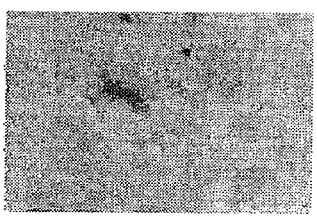
Figure 33N:
Figure 33O:
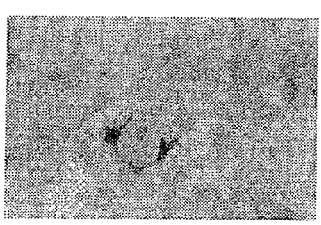
Figure 33P:
Figure 33Q:
Figure 33R:

Culture conditions that engendered round cell bodies with spidery cell processes were further evaluated using antibodies for neuronal phenotypes, i.e., neural precursor cells (FORSE-1) (FIG. 33C), the neural precursor stem cell marker nestin (MAB353) (FIG. 33J), neurofilaments (RT-97) (FIG. 33D), and neurons (8A2) (FIG. 33E). These antibody staining results demonstrated that the human stem cells could form cells of (neuro)ectodermal origin. Mononuclear and binuclear cells with intracellular non-refractile cytoplasmic vesicles, suggestive of commitment to the hepatic (endodermal) lineage were further evaluated using a human-specific antibody for alpha-fetoprotein (HAFP) (FIGS. 33L, 33M). Positive staining was observed, indicating that the pluripotent human stem cells had the potential to also form cells of endodermal origin.

Based on its demonstrated properties, i.e., a high nuclear to cytoplasmic ratio, alkaline phosphatase-positive staining, extended capabilities for self-renewal, high levels of telomerase activity, and induced differentiated cell types showing phenotypic expression markers for skeletal muscle, smooth muscle, cardiac muscle, fat cells, cartilage, bone, endothelial cells, neuronal stem cells, neurons, and endoderm, these cells meet the criteria for pluripotent stem cells and furthermore, closely resemble the attributes of embryonic stem cells derived from mice, primates and humans. These findings demonstrate the retention of pluripotent embryonic-like stem cells within postnatal animals, including humans.

Additional immunochemical and histochemical studies were performed with a series of human cell lines. Human cells CF-NHDF2 (derived from 36 year old female dermis) were propogated to various doubling numbers (cell doublings of between 12 and 47), and examined, as above, for multiple induced mesodermal, ectodermal, endodermal and embryonic lineages. Human cells CM-SkM2 and CF-SkM2, were similarly examined, after propogation to 12 cell doublings. The results are tabulated in TABLES 6-10. TABLE 6 provides a list of the immunocytochemistry and immunohistochemistry markers examined. TABLES 7-9 provides the results of examination of the human cells CF-NHDF2 at progressive cell doublings, under different growth conditions. TABLE 10 provides the results of examination of the human cells CM-SkM2, and CF-SkM2 at progressive cell doublings, under different growth conditions.

A summary of the presence of the endodermal, ectodermal and mesodermal lineage markers in the human cells is provided in TABLE 11.

The above results demonstrate the presence and isolation of pluripotent embryonic-like stem cells, capable of differentiation to cells of endodermal, ectodermal and mesodermal lineages from postnatal animal sources (i.e. not from embryonic tissue), particularly for humans.

TABLE 6

HUMAN CELL MARKERS

| NAME | RECOGNITION | GERM LAYER ORIGIN |
|---|---|---|
| *Immunocytochemistry:* | | |
| 1A4 | smooth muscle alpha actin | mesoderm |
| MF-20 | sarcomeric myosin (skel musc) | mesoderm |
| MY32 | fast skeletal muscle | mesoderm |
| F5D | myogenin (skel musc) | mesoderm |
| WV1D1(9C5) | bone sialoprotein II (bone) | mesoderm |
| MP111 B10(1) | osteopontine (bone) | mesoderm |
| C11C1 | collagen pro type-II (conn tiss) | mesoderm |
| D1-9 | collagen type IX (cart) | mesoderm |
| FORSE-1 | neural precursor cells | ectoderm |
| RT97 | neurofilaments (neural) | ectoderm |
| 8A2 | neurons in all species (neural) | ectoderm |
| MC-480 | SSEA-1 (embryonic antigen) | (emb. cells) |
| MC-631 | SSEA-3 (embryonic antigen) | (emb. cells) |
| MC-813-70 | SSEA-4 (embryonic antigen) | (emb. cells) |
| H-AFP | alpha-fetoprotein | endoderm |
| H-CD34 | CD34 sialomucin | mesoderm |
| H-CD66 | carcinoembryonic antigen | (emb. cells) |
| HCEA | carcinoembryonic antigen | (emb. cells) |
| HESA | epithelial specific antigen | endoderm |
| HFSP | fibroblast specific protein | mesoderm |
| HC-II | collagen type-II | mesoderm |
| H-Endo | endothelial cell surface mark | mesoderm |
| MAB353 | nestin (neural precursor cell) | ectoderm |
| CNPase | neuroglia (oligos/astros) | ectoderm |
| S-100 | neuronal | ectoderm |
| N-200 | neurofilament-200 | ectoderm |
| HNES | nestin (neural marker) | ectoderm |
| P2B1 | PECAM (endothelial) | mesoderm |
| P2H3 | selectin-E | mesoderm |
| P8B1 | VCAM (vascular) | mesoderm |
| VM-1 | keratinocyte | ectoderm |
| ALD-58 | myosin heavy chain | mesoderm |
| A4.74 | myosin fast chain | mesoderm |
| *Histochemistry:* | | |
| Alk-Phos | Alkaline phosphatase | (emb. cells) |
| AB 1.0 | sulfated proteoglycans (cart.) | mesoderm |
| SO 1.0 | sulfated proteglycans (cart.) | mesoderm |
| ORO | saturated neutral lipid (fat) | mesoderm |
| SBB | saturated neural lipid (fat) | mesoderm |
| vK | calcium phosphate (bone) | mesoderm |

TABLE 7

HUMAN CELL RESULTS
CF-NHDF2

| | 13 Doublings (2C-2P-13D) | | 31 Doublings (2C-6P-31D) | |
|---|---|---|---|---|
| Antibody | 1% + I + D | 10% + I + D | 1% + I + D | 10 + I + D |
| 1A4 | + | + | + | + |
| MF-20 | + | + | + | |
| MY-32 | + | + | + | |
| F5D | + | | + | |
| WV1V1(9C5) | | | | + |
| MP111 B10(1) | | | | + |
| C11C1 | | | + | + |
| D1-9 | | | | + |
| FORSE-1 | | + | | |
| RT97 | | | | |
| 8A2 | | | | |
| MC-480 | | | | |
| MC-631 | | | | |
| MC-813-70 | | | + | + |
| H-AFP | + | + | + | + |
| H-CD34 | + | + | + | + |
| H-CD66 | + | + | + | + |
| HCEA | | | | |
| HESA | + | | | + |
| HFSP | + | | | + |
| HC-II | | | | |
| H-Endo | | | | |
| MAB353 | | | | |
| CNPase | + | | | |
| S-100 | + | + | | |
| N-200 | | | | |
| HNES | | | | |
| Alk-Phos | + | + | + | + |
| Alcian Blue | | | | |
| Sudan Black-B | | | | |
| Oil Red-O | | | | |
| von Kossa | | | | |

+: indicates positively stained cells.
+/−: indicates staining slightly above background
0: indicates staining equivalent to background (replaced primary antibody with purified mouse IgG to determine background staining)
A blank space indicates that cells were not tested

TABLE 8

HUMAN CELL RESULTS
CF-NHDF2

| | 37 Doublings (2C-8P-37D) | | 40 Doublings (2C-10-40D) | |
|---|---|---|---|---|
| Antibody | 1% + I + D | 10% + I + D | 1% + I + D | 10 + I + D |
| 1A4 | + | + | + | + |
| MF-20 | + | 0 | + | + |
| MY-32 | + | + | | + |
| F5D | + | | + | |
| WV1V1(9C5) | + | + | + | + |
| MP111B10(1) | + | + | + | + |
| C11C1 | | | | |
| D1-9 | | + | | + |
| FORSE-1 | + | | + | |
| RT97 | | | | |
| 8A2 | | | | |
| MC-480 | | | | |
| MC-631 | | | | |
| MC-813-70 | | | + | |
| H-AFP | + | | + | 0 |
| H-CD34 | + | | + | 0 |
| H-CD66 | + | | + | |
| HCEA | | | + | |
| HESA | + | | + | 0 |
| HFSP | + | + | + | + |
| HC-II | | | | |
| H-Endo | | | | |
| MAB353 | | | | |
| CNPase | + | + | + | + |
| S-100 | + | | | + |
| N-200 | | | | |
| HNES | | | | |
| Alk-Phos | | | + | |
| Alcian Blue | | | | |
| AB 1.0 | | | | |
| SO 1.0 | | | | + |
| Sudan Black-B | | | | |
| Oil Red-O | | | | |
| von Kossa | | | | |

+: indicates positively stained cells.
+/−: indicates staining slightly above background
0: indicates staining equivalent to background (replaced primary antibody with purified mouse IgG to determine background staining)
A blank space indicates that cells were not tested

TABLE 9

HUMAN CELL RESULTS
CF-NHDF2

| Antibody | 45 Doublings (2C-12P-45D) | | 47 Doublings (2C-14P-47D) | |
|---|---|---|---|---|
| | 1% + I + D | 10% + I + D | 1% + I + D | 10% + I + D |
| 1A4 | + | + | + | + |
| MF-20 | + | +/− | + | + |
| MY-32 | + | + | + | + |
| F5D | | + | | + |
| WV1V1(9C5) | + | + | + | + |
| MP111B10(1) | + | + | + | + |
| C11C1 | + | + | + | + |
| D1-9 | + | + | + | + |
| FORSE-1 | + | + | + | + |
| RT97 | + | + | + | + |
| 8A2 | 0 | + | + | + |
| R401 | 0 | + | + | + |
| MC-480 | 0 | + | + | + |
| MC-631 | + | + | 0 | + |
| MC-813-70 | + | + | + | + |
| H-AFP | + | + | + | + |
| H-CD34 | + | + | + | + |
| H-CD66 | + | + | 0 | 0 |
| HCEA | + | + | + | + |
| HESA | + | + | + | + |
| HFSP | + | + | + | + |
| HC-II | 0 | + | 0 | + |
| H-EndoMAB353 | + | + | + | |
| CNPase | + | + | + | + |
| S-100 | + | + | + | + |
| N-200 | + | + | + | + |
| HNES | + | + | + | + |
| Alk-Phos | | | | |
| Alcian Blue | | | | |
| AB 1.0 | | | | |
| SO 1.0 | | | | |
| Sudan Black-B | | | | |
| Oil Red-O | | | | + |
| von Kossa | | | | |

+: indicates positively stained cells.
+/−: indicates staining slightly above background
0: indicates staining equivalent to background (replaced primary antibody with purified mouse IgG to determine background staining)
A blank space indicates that cells were not tested

TABLE 10

HUMAN CELL RESULTS

| Antibody | CM-SKM2 22 Week Old Male (2C-2P-12D) | | CF-SKM2 19 year old Female (2C-2P-12D) | |
|---|---|---|---|---|
| | 1% + I + D | 10% + I + D | 1% + I + D | 10% + I + D |
| 1A4 | + | + | + | + |
| MF-20 | + | 0 | + | + |
| MY-32 | + | + | + | + |
| F5D | + | | + | |
| WV1V1(9C5) | | + | | + |
| MP111 B10(1) | + | + | + | |
| C11C1 | | | | |
| D1-9 | | + | | + |
| FORSE-1 | + | | + | |
| RT97 | | | | |
| 8A2 | | | | |
| MC-480 | | | | |
| MC-631 | | | | |
| MC-813-70 | | | | |
| H-AFP | + | | + | |
| H-CD34 | + | | + | |
| H-CD66 | + | | + | |
| HCEA | | | | |
| HESA | + | | + | |
| HFSP | + | 0 | + | + |
| HC-II | | | | |
| H-Endo | | | | |
| MAB353 | | | | |
| CNPase | + | + | + | + |
| S-100 | | | | + |
| N-200 | | | | |
| HNES | | | | |
| Alk-Phos | | | | |
| Alcian Blue | | | | |
| AB 1.0 | | | | |
| SO 1.0 | | + | | + |
| Sudan Black-B | | | | |
| Oil Red-O | | + | | |
| von Kossa | | | | |

+: indicates positively stained cells.
+/−: indicates staining slightly above background
0: indicates staining equivalent to background (replaced primary antibody with purified mouse IgG to determine background staining)
A blank space indicates that cells were not tested

TABLE 11

Overall Results

| Antibody | Specificity | CF-NHDF2 | CM-SkM | CF-SkM |
|---|---|---|---|---|
| GAL-13 | N/A | na | na | na |
| 1A4 | rat & human | + | + | + |
| MF-20 | rat & human | + | + | |
| MY-32 | rat & human | + | + | + |
| F5D | rat & human | + | + | + |
| ALD-58 | rat & human | | | |
| A4.74 | rat & human | | | |
| WV1V1(9C5) | rat & human | + | + | + |
| MP111 B10(1) | rat & human | + | + | + |
| C11C1 | rat & human | + | | |
| D1-9 | rat & human | + | + | + |
| RAT-401 | rat & human | + | | |
| FORSE-1 | rat & human | + | + | + |
| RT97 | rat & human | + | | |
| 8A2 | rat & human | + | | |
| P2B1 | human only | + | | |
| P8B1 | human only | + | | |
| P2H3 | human only | + | | |
| VM1 | human only | + | | |
| MC-480 | human only | + | | |
| MC-631 | human only | + | | |
| MC-813-70 | human only | + | + | |
| H-AFP | human only | + | + | + |
| H-CD34 | human only | + | + | + |
| H-CD66 | human only | + | + | |
| HCEA | human only | + | | |
| HESA | human only | + | + | + |
| HFSP | human only | + | + | + |
| CNPase | human only | + | + | + |
| S-100 | human only | + | + | + |
| N-200 | human only | + | | |
| RMHC-1 | rat only | na | na | na |
| R-AFP | rat only | na | na | na |
| HC-II | human only | + | | |
| H-Endo | human only | + | | |
| MAB353 | human only | + | | |
| HNES | human only | + | | |
| ALK-PHOS | rat & human | + | | |
| Alcian Blue | rat & human | | | |
| Sudan Black-B | rat & human | | | |
| Oil Red-O | rat & human | + | + | |
| von Kossa | rat & human | + | | |

TABLE 11-continued

| Antibody | Specificity | CF-NHDF2 | CM-SkM | CF-SkM |
|---|---|---|---|---|
| Perf-AB | rat & human | | | |
| S01.0 | rat & human | + | + | + |

+: indicates positively stained cells.
+/−: indicates staining slightly above background
0: indicates staining equivalent to background (replaced primary antibody with purified mouse IgG to determine background staining)
A blank space indicates that cells were not tested Materials and Methods Isolation and Expansion.

Geriatric male cells, designated PAL3, were isolated from a skeletal muscle specimen obtained from a 67-year-old human patient following standard protocols for the isolation and propagation of mesenchymal stem cells.16,18

Adult female cells were purchased as a mixed subconfluent culture of 36-year-old human dermal fibroblasts (NHDF2, catalog #CC-0252, lot #16280, Clonetics. San Diego, Calif.). Upon arrival the cells were transferred to control medium (CM) containing 10% HS9 (horse serum, lot #90H-0701, Sigma) and 2 U/ml ADF (anti-differentiation factor, MorphoGen Pharmaceuticals, Inc., New York, N.Y.). CM consisted of 89% (v/v) Opti-MEM (GIBCO-BRL), 0.01 mM beta-mercapto-ethanol (Sigma, St. Louis, Mo.), 1% (v/v) antibiotic-antimycotic solution (10,000 units/ml penicillin, 10,000 mg/ml streptomycin, and 25 mg/ml amphotericin B as Fungizone, GIBCO-BRL), pH 7.4. Cells were grown in a 95% air/5% $CO_2$ humidified environment, released with trypsin 16, sieved through 90 mm and 20 mm Nitex filters 19, and cryopreserved in medium containing 7.5% (v/v) dimethyl sulfoxide (DMSO, Morton Thiokol, Danvers, Mass.).20 Both populations were expanded further following standard protocols for mesenchymal stem cells.16,18

Phenotypic Analysis.

The cryopreserved cells were thawed and seeded at 1×103 cells per well of 1% gelatinized 96-well plates (Corning, Corning, N.Y.).15,16 The cell lines were incubated with CM only (non-induced) or CM+insulin and/or dexamethasone in a comparison/contrast analysis system to ascertain induced phenotypic expression.7,15 In this assay, insulin accelerates phenotypic expression of lineage-committed progenitor cells but has no effect on the induction of lineage-commitment and subsequent phenotypic expression in pluripotent cells. By contrast, dexamethasone induces lineage-commitment and phenotypic expression in pluripotent cells, but does not alter phenotypic expression in progenitor stem cells.

Cells were cultured for 30-56 days in CM, CM+2 mg/ml insulin, or CM+10-6M Dexamethasone+/−insulin+1%, 5%, or 10% horse serum. Media changes occurred three times per week. Cultures were visually assayed twice weekly for changes in phenotypic expression. These changes were verified using immunological and histochemical analyses.

Immunochemical Analysis.

Cultures were processed per manufacturer's directions or as described.21 Cultures were stained with primary antibodies specific for 1) embryonic cells: stage-specific embryonic antigen-1 [MC-480, Developmental Studies Hybridoma Bank, Iowa City, Iowa, DSHB], stage-specific embryonic antigen-3 [MC-631, DSHB], stage-specific embryonic antigen-4 [MC-813-70, DSHB], human carcinoembryonic antigen [HCEA, Sigma], and carcinoembryonic antigen [CD66, Vector Laboratories, Inc., Burlingame, Calif.]; 2) ectodermal markers for nervous tissue: neural precursor cells [FORSE-1, DSHB], nestin-1 [HNES, Chemicon, Temecula, Calif.], nestin-2 [Rat-401, DSHB], nestin-3 [MAB353, Chemicon], neurons [8A2, DSHB], neuronal marker [S-100, Sigma], neuroglia [CNPase, Sigma], neurofilaments [RT97, DSHB], neurofilament-200 [N-200, Sigma], and skin: keratinocytes [VM-1, DSHB]; 3) mesodermal markers for muscle: myogenin [F5D, DSHB], sarcomeric myosin [MF-20, DSHB], fast-skeletal muscle myosin [MY-32, Sigma], myosin heavy chain [ALD58, DSHB], myosin fast chain [A4.74, DSHB], smooth muscle alpha-actin [1A4, Sigma], cartilage: collagen type-II [CIIC1, DSHB], collagen type-II [II-4CII, ICN Biomedicals Inc., Aurora, Ohio], collagen type-IX [D1-9, DSHB], bone: bone sialoprotein-II [WV1D1, DSHB], osteopontine [MP111, DSHB], fibroblasts: human fibroblast-specific protein [1B10, Sigma], and endothelial cells: human-specific endothelial cell surface marker [P1H12, Accurate, Westbury, N.Y.], PECAM [P2B1, DSHB], VCAM [P8B1, DSHB], E-selectin [P2H3, DSHB], human-specific CD34 sialomucin [HCD34]; and 3) endodermal markers: human-specific alpha-fetoprotein [HAFP, Vector] and human-specific gastrointestinal epithelial-specific antigen [HESA, Sigma]. Secondary antibodies consisted of biotinylated anti-sheep IgG [Vector], biotinylated anti-mouse IgG [Vector], or contained within the Vecstatin ABC Kit [Vector]. The tertiary probe consisted of avidin-HRP contained within the Vecstatin ABC Kit [Vector]. The insoluble HRP substrates VIP Substrate Kit for Peroxidase [blue, Vector], DAB Substrate for Peroxidase [black, Vector], and AEC Staining Kit [red, Sigma] were used to visualize antibody binding. Different colored substrates were utilized to allow for multiple sequential staining of the same culture wells.

Histochemical Analysis.

Cultures were processed as described.15,22 Chondroitin sulfate and keratan sulfate proteoglycans, characteristic of the cartilage were identified by Alcian Blue at pH 1.0 staining.6,16,23 Saturated neutral lipids, characteristic of adipocytes (fat cells), were identified by Sudan Black-B and Oil Red-O staining.6,16,22,23 Calcium phosphate, characteristic of bone, was identified by the von Kossa procedure.6,16,23

Capability for Extended Self-Renewal.

Cells underwent progressive propagation16,20 through 17 passages (NHDF2) and 39 passages (PAL3), respectively. Doubling time averaged 12-24 hr with approximately 4-6 doublings per passage for more than 70 cell doublings (NHDF2) and 200 cell doublings (PAL3). Cells were examined, as above. Results were equivalent as previously shown. This suggested that the cell lines did not lose either their embryonic-like identity or inductive capabilities after propagation past Hayflick's number.

The following antibodies: MC-480 developed by D. Solter, MC-631 developed by D. Solter, MC-813-70 developed by D. Solter, FORSE-1 developed by P. Patterson, RAT-401 developed by S. Hockfield, 8A2 developed by V. Lemmon, RT97 developed by J. Wood, VM-1 developed by V. B. Morhenn, F5D developed by W. E. Wright, MF-20 developed by D. A. Fischman, ALD58 developed by D. A. Fischman, A4.74 developed by H. Blau, CIIC1 developed by R. Holmdahl and K. Rubin, D1-9 developed by X.-J. Ye and K. Terato, WV1D1 developed by M. Solursh and A. Frazen, MP111 developed by M. Solursh and A. Frazen, P2B1 developed by E. A. Wayner and G. Vercellotti, P8B1 developed by E. A. Wayner and T. LeBien, and P2H3 developed by E. A. Wayner and G. Vercellotti were obtained from the Developmental Studies Hybridoma Bank developed under the auspices of the NICHD and maintained by The University of Iowa, Department of Biological Sciences, Iowa City, Iowa 52242.

Cell Harvest and Culture.

Adult female dermal cells were purchased as a subconfluent culture of 36-year-old human dermal fibroblasts (CF-NHDF2, catalog # CC-2511, lot #16280, Clonetics, San Diego, Calif.). Upon arrival the cells were transferred to plating medium-C (PM-C). PM-C consisted of 89% (v/v) Opti-MEM based medium (catalog #22600-050, GIBCO) containing 0.01 mM beta-mercaptoethanol (Sigma), 10% (v/v) horse serum (HS9, lot number 90H-0701, Sigma), 1% antibiotic-antimycotic solution (GIBCO), and 2 U/ml ADF (anti-differentiation factor, MorphoGen Pharmaceuticals, Inc., New York, N.Y.), pH 7.4. Cells were placed into a 95% air/5% $CO_2$ humidified chamber at 37° C., grown to confluence, with media changed three times weekly. Cells were released with trypsin and processed for cryopreservation following our standard protocols. Frozen cells were reconstituted, plated in PM-C medium, grown to confluence, trypsin-released, replated, and grown to confluence. Cells were harvested at designated passage numbers for insulin-dexamethasone analysis and flow cytometry.

Morphological Analysis.

The cultures were screened for the following morphologies throughout the assay: small stellate cells with high nuclear to cytoplasmic ratios (potential stem cells), bipolar cells (potential myoblasts), spindle cells (potential fibroblasts), multinucleated linear and branched cells (potential skeletal myotubes), mononucleate polygonal-shaped cells with intracellular filaments (potential smooth muscle cells), binucleate polygonal-shaped cells with intracellular filaments (potential cardiac myocytes), mononucleate cells with refractile intracellular vesicles (potential fat cells), mononucleate cells without intracellular vesicles (potential endoderm cells), sheets of mononucleated cells in a "cobblestone-like" appearance (potential endothelial cells), rounded cells with pericellular matric halos (potential chondrocytes), aggregates of rounded cells containing pericellular matrix halos (potential cartilage nodules), aggregates of rounded cells overlain with three-dimensional matrices (potential bone nodules), and mononucleate cells with multiple fine "spidery" cell processes (potential neuronal cells).

Histochemical Analysis.

Cultures were processed per manufacturer's directions or as described (Young et al., 1998b). Cultures were stained for an embryonic marker (alkaline phosphatase); for cartilage (chondroitin sulfate and keratan sulfate proteoglycans) using Alcian Blue (Alcian Blau 8GS, Chroma-Gesellschaft, Roboz Surgical Co.) or Safarin-O (Chroma-Gesellschaft) at pH 1.0 coupled with chondroitinase-AC (ICN Biomedicals, Cleveland, Ohio)/keratanase (ICN Biomedicals) digestions to verify the presence of chondroitin sulfate/keratan sulfate glycosaminoglycans located in the pericellular and/or extracellular matrix; for fat cells (saturated neutral lipids) using using Sudan black-B (Roboz Surgical Co., Washington, D.C.) and Oil Red-O (Sigma), and for bone (calcium phosphate) using von Kossa (Silber Protein, Chroma-Gesellschaft) staining coupled with EGTA (Ethyleneglycol-bis-[β-Aminoethyl ether] N, N, N',N'-tetraacetic acid, Sigma) pretreatment to verify the presence of calcium phosphate within putative mineralized bone spicules. Perf-AB was purchased from Fisher-Aldrich. AB1.0, S01.0, SBB and vK were purchased from Chroma-Gesellschaft (Roboz).

Immunochemical Analysis.

Cultures were processed as described (Young et al., 1992b) or per manufacturer's directions. Cultures were stained with antibodies specific for mesodermal markers indicative of muscle (myogenin [F5D, Developmental Studies Hybridoma Bank, DSHB], sarcomeric myosin [MF-20, DSHB], fast-skeletal muscle myosin [MY-32, Sigma], myosin heavy chain [ALD-58, DSHB], myosin fast chain [A4.74, DSHB], smooth muscle (smooth muscle alpha-actin [1A4, Sigma]), cartilage (collagens type-II [CIIC1, DSHB] and -IX [D1-9, DSHB]), bone (bone sialoprotein [WV1D1, DSHB], osteopontine [MP111, DSHB]), endothelial cells (endothelial cell surface marker [H-Endo, Accurate]); ectodermal markers: (epidermal cell [151-Ig, DSHB], neural precursor cells [FORSE-1, DSHB], nestin [RAT-401, DSHB], neurofilaments [RT97, DSHB], neurons [8A2, DSHB]); and endodermal markers (alpha-fetoprotein [HAFP, Chemicon], epithelial cell [HA4c19, DSHB]).

Antibodies

Antibodies GAL-13, 1A4, MY32, DE-U-10, HCEA, HESA, HFSP, CNPase, S-100, N-200 and ORO were purchased from Sigma. H-Endo was purchased from Accurate Scientific. HNES and MAB353 were purchased from Chemicon. HC-II was purchased from ICN. H-AFP, H-CD34, H-CD66 and ALK-PHOS were purchased from Vector Laboratories. MF-20 developed by D. A. Fischman, F5D developed by W. E. Wright, WV1D1 developed by M. Solursh and A. Frazen, MP111 developed by M. Solursh and A. Frazen, CIIC1 developed by R. Holmdahl and K. Rubin, D1-9 developed by X.-J. Ye and K. Terato, FORSE-1 developed by P. Patterson, RT97 developed by J. Wood, 8A2 developed by V. Lemmon, and RAT-401 developed by S. Hockfield were all obtained from the Developmental Studies Hybridoma Bank developed under the auspices of the NICHD and maintained by The University of Iowa, Department of Biological Sciences, Iowa City, Iowa 52242. MC-480, MC-631 and MC-813-70, all recognizing embryonic antigens were also obtained from the Developmental Studies Hybridoma Bank. ALD-58, A4.74, P2B1, P8B1, P2H3 and VM-1 were also obtained from the Developmental Studies Hybridoma Bank.

Example 10

Stimulation of Pluripotent Cells with Differentiation—Specific Factors, Assays and Analysis Pluripotent stem cells, capable of extended self-renewal and multi-lineage differentiation, are a unique and useful source of cells for studies of cell differentiation, cell response to proliferation and differentiation, or lineage-commitment factors, and in assay systems or methods of identifying and characterizing factors, agents or compounds and in identifying genes encoding any such factors, agents compounds, etc., or genes involved in cell proliferation, differentiation and lineage-commitment.

Effects of Bioactive Factors.

Having access to mixed populations of progenitor stem cells, progenitor stem cell clones, and pluripotent stem cell clones permits one to address the influence of various bioactive factors (e.g. recombinant growth factors, purified compounds, and novel inductive factors) on the growth characteristics and phenotypic expression of these stem cells. In initial studies, we have tested fourteen bioactive factors with these cells, both singly and in combination (TABLE 12). Three general categories of activities have been shown (proliferation, lineage-commitment, and lineage-progression). The bioactive factors could produce either stimulatory or inhibitory effects. The effects could be either general across all the lineages or limited to one or more specific tissue lineages.

Endothelial cell growth factor showed no measurable effect on either progenitor or pluripotent stem cells under the assay conditions used. Platelet-derived growth factor-AA (PDGF-AA) and platelet-derived growth factor-BB (PDGF-BB) stimulated proliferation in pluripotent cells and in all lineages of progenitor cells. Platelet-derived endothelial cell growth factor (PDECGF) showed no measurable effect on either progenitor or pluripotent stem cells under the assay conditions used. Basic-fibroblast growth factor (b-FGF) and transforming growth factor-β_(TGF-β) stimulated lineage-progression in fibrogenic progenitor cells, inhibited lineage-progression in all other progenitor cells, and had no effect on pluripotent cells. Dexamethasone (Dex) depressed proliferation in pluripotent stem cells, stimulated general lineage-commitment in pluripotent cells, and acted as a weak stimulator of lineage-progression in all progenitor cells. Muscle morphogenetic protein (MMP) acted as a specific myogenic lineage-commitment agent in pluripotent cells, a weak stimulator of lineage-progression in myogenic progenitor cells, and had no effect on progenitor cells committed to other lineages. Bone morphogenetic protein-2 (BMP-2) acted as a specific chondrogenic lineage-commitment agent in pluripotent cells, a weak stimulator of lineage-progression in chondrogenic progenitor cells, and had no effect on progenitor cells committed to other lineages. Fibroblast morphogenetic protein (FMP) (present and identified by us in fetal calf serum (FCS) (Atlantic Biologicals, lot 3000L)) acted as a specific fibrogenic lineage-commitment agent in pluripotent cells, a stimulator of lineage-progression in fibrogenic progenitor cells, and had no effect on progenitor cells committed to other lineages. Scar inhibitory factor (SIF) acted as a specific inhibitor of the lineage-commitment activity of FMP on pluripotent cells, a specific inhibitor of the lineage-progression activity of FMP on progression in fibrogenic progenitor cells, and had no effect on lineage-induction or lineage-progression for other tissue lineages. Anti-differentiation factor (ADF) acted as a general inhibitor of lineage-commitment activity on pluripotent cells and a general inhibitor of lineage-progression activity on progenitor cells. Insulin, insulin-like growth factor-I (IGF-I), and insulin-like growth factor-II (IGF-II) stimulated lineage-progression in all progenitor cells, but had no measurable effect on pluripotent cells. Transforming growth factor-β and basic-fibroblast growth factor stimulate lineage-progression in fibrogenic progenitor cells, inhibit lineage-progression in all other progenitor cells, and have no effect on pluripotent cells.

Northern Analysis of Expressed mRNAs.

We have used Northern blot analysis to examine the induction of myogenesis by MMP in a mouse pluripotent stem cell clone. We have also used this technique to examine CD marker transcription in human mesenchymal stem cells. MMP induced the transcription of mRNAs for myogenin and MyoD1 gene expression in Swiss-XYP-7, a prenatal mouse pluripotent stem cell clone (Rogers et al 1995; Young et al 1998a). Northern blot analysis also showed that the genes for aminopeptidase (CD13), neural cell adhesion molecule (CD56), and Thy-1 (CD90) were actively being transcribed at time of cell harvest in both prenatal and postnatal human mesenchymal stem cells (see prior Examples)

Similar such studies can be utilized to examine expression of know or unknown genes (through MRNA, etc.), or to generate cDNA libraries or differential display of genes expressed in the pluripotent stem cells, cells derived therefrom, or in any such cells after exposure to known or unknown bioactive factors.

Cell or Lineage Characterization

A combination of histological, functional, immunological, and expression (e.g. mRNA expression, etc.) analyses can be utilized in characterizing and identifying particular cell types. For instance, in characterizing a known or unknown bioactive factor as to particular proliferative, lineage-commitment or lineage-progression capacity, these analyses can be utilized, similar- to the characterizations shown in earlier Examples in characterizing the inherent capacity of the pluripotent embryomic-like stem cells. TABLE 13 provides a tabulation of histological, functional, immunological and cDNA probe markers which might be utilized in characterizing cell types.

Materials and Methods (Material and Methods are as previously described, except as noted below).

Stem Cell Isolation, Cloning, and Expression

To isolate progenitor and pluripotent stem cells, a sample containing connective tissue is harvested aseptically and transported in MSC-1, containing an additional 2× antibiotic-antimycotic solution, to a sterile hood (Lucas et al 1995). MSC-1 culture medium consists of 89% (v/v) medium [either Eagle's Minimal Essential Medium with Earle's salts, EMEM, (GIBCO, Grand Island, N.Y.) (Young et al 1991) or Opti-MEM (GIBCO) containing 0.01 mM β-mercaptoethanol (Sigma Chemical Co., St. Louis, Mo.) (Young et al 1998c,e)], supplemented with 10% serum [either pre-selected horse serum, such as HS7 (lot #17F-0218, Sigma), HS4 (lot #49F-0082, Sigma), HS3 (lot #3M0338, Bio-Whittaker, Walkersville, Md.) (Young et al 1998e) or any non-selected serum containing 2 U/ml anti-differentiation factor (ADF, Morphogen Pharmaceuticals, Inc., New York, N.Y.) (Young et al 1998c,e)], 1% antibiotic-antimycotic solution [10,000 units/ml penicillin, 10,000 μg/ml streptomycin, and 25 μg/ml amphotericin B as Fungizone, GIBCO] (Lucas et al 1995), pH 7.4. Tissue samples are placed in 10 ml of MSC-1 and carefully minced. After mincing, the tissue suspension is centrifuged at 50×g for 20 min. The supernatant is discarded and an estimate made of the volume of the cell pellet. The cell pellet is resuspended in 7 pellet volumes of EMEM (or Opti-MEM+0.01 mM β-mercaptoethanol), pH 7.4, and 2 pellet volumes of collagenase/dispase solution to release the cells by enzymatic action (Lucas et al 1995). The collagenase/dispase solution consists of 37,500 units of collagenase (CLS-I, Worthington Biochemical Corp., Freehold, N.J.) in 50 ml of EMEM (or Opti-MEM+0.01 mM β-mercaptoethanol) added to 100 ml dispase solution (Collaborative Research, Bedford, Mass.). The final concentrations are 250 units/ml collagenase and 33.3 units/ml dispase (Young et al 1992a). The resulting suspension is stirred at 37° C. for 1 hr to disperse the cells and centrifuged at 300×g for 20 min. The supernatant is discarded, and the tissue pellet resuspended in 20 ml of MSC-1 (Lucas et al 1995). The cells are sieved through 90 μm and 20 μm Nitex to obtain a single cell suspension (Young et al 1991). The cell suspension is centrifuged at 150×g for 10 min., the supernatant discarded, and the cell pellet resuspended in 10 ml of MSC-1 (Lucas et al 1995). Cell viability is determined by Trypan blue exclusion assay (Young et al 1991). Cells are seeded at $10^5$ cells per 1% gelatinized (EM Sciences, Gibbstown, N.J.) 100 mm culture dish (Falcon, Becton-Dickinson Labware, Franklin Lakes, N.J.) or T-75 culture flask (Falcon). Cell cultures are propagated to confluence at 37° C. in a 95% air/5% $CO_2$ humidified environment. At confluence the cells are released with trypsin and cryopreserved. Cells are slow frozen (temperature drop of 1 degree per minute) in MSC-1 containing 7.5% (v/v) dimethyl sulfoxide (DMSO, Morton Thiokol, Danvers, Mass.) until a final temperature of −70° to −80° C. is reached (Young et al 1991).

Insulin-Dexamethasone Analysis for Phenotypic Expression.

Cryopreserved cells are thawed and plated in MSC-1 at 5, 10, or 20×10³ cells per well of gelatinized 24-well plates following the standard protocol. Twenty-four hours after initial plating the medium is changed to testing medium (TM) 1 to 6 (TM-1, TM-2, TM-3, TM-4, TM-5, or TM-6). TM-1 to TM-4 consist of Ultraculture (cat. no. 12-725B, lot. nos. OMO455 [TM-1], 1M1724 [TM-2], 2M0420 [TM-3], or 2M0274 [TM-4], Bio-Whittaker, Walkersville, Md.), medium (EMEM or Opti-MEM+0.01 mM β-mercaptoethanol), and 1% (v/v) antibiotic-antimycotic, pH 7.4. TM-5 consists of 98% (v/v) medium, 1% (v/v) HS, and 1% (v/v) antibiotic-antimycotic, pH 7.4. TM-6 consists of 98.5% (v/v) medium, 0.5% (v/v) HS, and 1% (v/v) antibiotic-antimycotic, pH 7.4. Testing medium containing ratios of Ultraculture: medium (EMEM or Opti-MEM+0.01 mM β-mercaptoethanol): antibiotics (+antimycotics) maintained both progenitor and pluripotent cells in "steady-state" conditions for a minimum of 30 days in culture, and as long as 120 days in culture. Four testing media (TM#'s 1-4), each containing various concentrations of Ultraculture, were used as. The ratios of Ultraculture to medium to antibiotics present in each testing medium was determined empirically for each lot of Ultraculture, based on its ability to maintain steady-state culture conditions in both populations of avian progenitor and pluripotent cells. The four Ultraculture-based testing media were: TM-1=15% (v/v) Ultraculture (Lot no. OMO455): 84% (v/v) medium: 1% (v/v) antibiotics; TM-2=15% (v/v) Ultraculture (Lot no. 1M1724): 84% (v/v) medium: 1% (v/v) antibiotics; TM-3=50% (v/v) Ultraculture (Lot no. 2M0420): 49% (v/v) medium: 1% (v/v) antibiotics; and TM-4=75% (v/v) Ultraculture (Lot no. 2M0274): 24% (v/v) medium: 1% (v/v) antibiotics. Pre-incubation for 24 hr in testing medium alone is used to wash out any potential synergistic components in the MSC-1 medium. Twenty-four hours later the testing medium is changed to one of the following. For controls, TM-1 to TM-6 alone is used. To identify clones of progenitor cells, the medium is replaced with TM-1 to TM-6 containing 2 µg/ml insulin (Sigma), an agent that accelerates the appearance of phenotypic expression markers in progenitor cells (TABLE 12). To identify clones of pluripotent cells, the medium is replaced with TM-1 to TM-6 containing $10^{-10}$ to $10^{-6}$ M dexamethasone (Sigma), a general non-specific lineage-inductive agent (TABLE 13). Control and treated cultures are propagated for an additional 30-45 days with medium changes every other day. Four culture wells are used per concentration per experiment. During the 0-45 day time period the cultures are examined subjectively for changes in morphological characteristics on a daily basis. Alterations in phenotypic expression are correlated with the days of treatment and associated insulin or dexamethasone concentrations. The experiment is then repeated utilizing these parameters to confirm objectively the phenotypic expression markers using established histological, functional/histochemical, ELICA/flow cytometry, and molecular assays (TABLE 13).

TABLE 12

Proliferation and Phenotypic Responses of Pluripotent and Progenitor Cells Induced by Various Bioactive Factors

| | Proliferation | | Phenotypic Expression | |
|---|---|---|---|---|
| Agent | Pluripotent | Progenitor | Pluripotent | Progenitor |
| Control | 1 | 1 | 0[a] | All+ |
| PDGF-AA | 16[b] | 16 | 0 | All+ |
| PDGF-BB | 19 | 19 | 0 | All+ |
| PDECGF | 1 | 1 | 0 | All+ |
| b-FGF | 1 | 1 | 0 | F++ |
| TGF-β | −[c] | − | 0 | F++ |
| b-FGF + TGF-β | − | − | 0 | F++ |
| Dex | − | − | All++ | All++ |
| MMP | 2 | 2 | M++++ | M+++/All+ |
| MMP fb[d] Dex | 2 | 2 | M+++++ | M+++/All++ |
| BMP-2 | 2 | 2 | C++++ | C+++/All+ |
| BMP-2 fb Dex | 2 | 2 | C+++++ | C+++/All++ |
| MMP fb BMP-2 | 2 | 2 | M++++ | M+++/C++/All+ |
| BMP-2 fb MMP | 2 | 2 | C++++ | M++/C+++/All+ |
| FMP | 10 | 10 | F+++++ | F++++/All+ |
| SIF | 1 | 1 | 0 | All+ (F−) |
| FMP + SIF | 10 | 10 | 0 | All+ (F−) |
| MMP + SIF | 2 | 2 | M+++++ | M+++/All+(F−) |
| FMP + MMP | 10 | 10 | F+++++ | F++++/All+ |
| FMP + SIF + MMP | 10 | 10 | M+++++ | M+++/All+(F−) |
| ADF | 1 | 1 | 0 | 0 |
| ADF + Dex | − | − | 0 | 0 |
| ADF + MMP | 2 | 2 | 0 | 0 |
| ADF + BMP-2 | 2 | 2 | 0 | 0 |
| ADF + FMP | 10 | 10 | 0 | 0 |
| Insulin | 1 | 2 | 0 | All+++ |
| IGF-I | 1 | 1 | 0 | All+++ |
| IGF-II | 1 | 1 | 0 | All+++ |
| Insulin + IGF-I | 1 | 1 | 0 | All++ |
| Insulin + IGF-II | 1 | 1 | 0 | All++ |
| IGF-I + IGF-II | 1 | 1 | 0 | All++ |
| Ins + IGF-I + IGF-II | − | − | 0 | All++ |
| Dex + Insulin | − | 1 | All+++ | All+++ |
| MMP + Insulin | 2 | 2 | M+++++ | M++++/All+ |
| BMP-2 + Insulin | 2 | 2 | C+++++ | C++++/All+ |

[a]Presence and approximate distribution of differentiated phenotypes within the culture wells. Each individual "+" represents a value of up to 20% of the maximal expression for each phenotype examined: + = 0-20%, ++ = 21-40%, +++ = 41-60%, ++++ = 61-80%, and +++++ = 61-100%. 0, stellate only (no additional differentiated phenotypes noted); M, myogenic; F, fibrogenic; C, chondrogenic; All, all phenotypes (i.e., myogenic, adipogenic, fibrogenic, chondrogenic, osteogenic) expressed.
[b]16, number of times the agent increased the DNA content per well versus its respective control.
[c]−, statistically significant decrease in DNA content per well versus its respective control.
[d]fb, followed by.

TABLE 13

Histological, Functional/Histochemical, ELICA/Flow, and Northern Analyses

| Cell Type | Histological | Functional(Fx)/ Histochemical[a] | ELICA(E)/ Flow Cytometry(F) Antibodies[b] | Northern cDNA Probes |
|---|---|---|---|---|
| Skeletal Muscle | Multinucleated linear and branched structures | Fx: Spontaneous contractility | E: F5D, MF-20, 12/101, 31-2, MF-5, C3/1 M3F7, ALD-58, CH1, 5C6, 2E8, | MyoD1, myogenin, emb. myosin heavy chain, myosin light chain-3, MYD, |

TABLE 13-continued

Histological, Functional/Histochemical, ELICA/Flow, and Northern Analyses

| Cell Type | Histological | Functional(Fx)/Histochemical[a] | ELICA(E)/Flow Cytometry(F) Antibodies[b] | Northern cDNA Probes |
|---|---|---|---|---|
| | | | MF-30, MY-32, ALD-58, A4.74, | MYF5, MYF6, MYH2, MYL1, MYF3, MYF4[c] |
| Smooth Muscle | Polygonal mononucleated cells with stress fibers | | E: IA4 | smooth muscle α-actin |
| Cardiac Muscle | Polygonal binucleate cells | Fx: Contraction rate altered with propanolol and isoproteranol | E: D76, D3, anti-desmin, double staining for MF-20 & IA4 | β-myosin heavy chain, ATP2A2 |
| White fat | Perinucleated cells with multiple refractile vesicles of different sizes | H: Sudan black-B, Oil Red O | | Lipoprotein lipase adipophilin |
| Brown fat | Central nucleated cells with multiple refractile vesicles of similar size | H: Sudan black-B, Oil Red O | | Lipoprotein lipase adipophilin |
| Connective Tissue | spindle-shape cells with fibrillar matrix | H: AB 1.0+, SO 2.5+, CH'ase-AC, CH'ase-ABC, MH-collagen type-I, SO 1.0, Perf-AB | E: M-38, SP1.D8, B3/D6, HFSP | CS-PG core prot.[d], type-I collagen, prepro-α 1(I) collag., collag. type-1 α-2, MMP-1A, MMP-1B |
| Scar Tissue | Spindle-shaped cells with granular matrix | H: AB 1.0+, SO 2.5+, CH'ase-AC, CH'ase-ABC, MH-collagen Type-I, SO 1.0, AB 2.5 | E: M-38, SP1.D8 B3/D6, HFSP | CS-PG core prot.[d], type-I collagen, prepro-α 1(I) collag., collag. type-1 α-2, MMP-1A, MMP-1B |
| Hyaline Cartilage | Aggregates of rounded cells with pericellular matrix halos, surrounded by fibrous tissue | H: SO 1.0+, SO 2.5+, CH'ase-AC & keratanase sensitive AB 1.0, MH-collagen type-II, AB 2.5, Perf-AB | E: 5-D-4, anti-type II collagen, D19 CIIC1, HC-II | KS-PG core prot., CS-PG core prot., CS/KS-PG core prot., type-II collagen |
| Elastic Cartilage | Aggregates of rounded cells with pericellular matrix halos with thin interwoven fibers, with adjacent fibrous tiss. | H: SO 1.0+, AB 2.5 SO 2.5+, Perf-AB, CH'ase-AC & keratanase sens AB 1.0, MH-collagen type-II, Orcein-Fuchsin stain | E: 5-D-4, anti-type II, anti-type-II collagen, anti-elastin, D19, CIIC1, HC-II | KS-PG core prot., CS-PG core prot., CS/KS-PG core prot., type-II collagen, elastin |
| Fibro-cartilage | Sheets of rounded cells with pericellular matrix halos intermingled with thick fibers & surrounded by fibrous tissue | H: SO 1.0+, AB 2.5 SO 2.5+, Perf-AB CH'ase-AC & CH'ase-ABC sens AB 1.0 MH-collagen type-I | E: B3/D6, M-38, SP1.D8, HFSP | CS-PG core prot., type-I collagen, prepro-a 1(I) collag., collagen type-I α-2, MMP-1A, MMP-1B |
| Articular Cartilage | Sheets of rounded cells with pericellular matrix halos | H: SO 1.0+, AB 2.5, SO 2.5+ CH'ase-AC & keratanase sens AB1.0, MH-collagen type-II, Perf-AB | E: 5-D-4, anti type-II, D19, CIIC1, HC-II. | KS-PG core prot., CS-PG core prot., CS/KS-PG core prot., type-II collagen |
| Growth Plate Cartilage | Aggregates of rounded cells with pericellular matrix halos overlain with 3-D matrix | H: SO 1.0+, AB 2.5, SO 2.5+, CH'ase-AC & keratanase sens AB1.0, MH-collagen types-I & -II, von Kossa, Perf-AB | E: 5-D-4, anti-type-II collag, D19, CIIC1, HC-II, B3/D6, M-38, SP1.D8, HFSP, WV1D1, MP111 | KS-PG core prot., CS-PG core prot. CS/KS-PG core prot., type-II collagen, type-I collagen, prepro-1(I) collag., collag. type-I alpha-2, MMP-1A, MMP-1B osteocalcin, osteopontin, osteonectin |

TABLE 13-continued

Histological, Functional/Histochemical, ELICA/Flow, and Northern Analyses

| Cell Type | Histological | Functional(Fx)/ Histochemical[a] | ELICA(E)/Flow Cytometry(F) Antibodies[b] | Northern cDNA Probes |
|---|---|---|---|---|
| Endo chondral Bone | Aggregates of rounded cells with pericellular matrix halos overlain with 3-D matrix | H: SO 1.0+, AB2.5 SO 2.5+, Perf-AB CH'ase-AC & keratanase sens AB1.0, MH-collagen types-I & -II, von Kossa+ | E: 5-D-4, anti-type-II collag, D19 CII-C1, HC-II, B3/D6, M-38, SP1.D8, HFSP, WV1D1, MP111 | KS-PG core prot., CS-PG core prot., CS/KS-PG core prot., type-II collagen, type-I collagen, prepro-α 1(I) collag., collag. type-I α-2, MMP-1A, osteocalcin, osteonectin osteopontine, MMP-1B |
| Intra-Membranous bone | Aggregations of stellate cells overlain with 3-D matrix | H: von Kossa+ | E: M-38, WV1D1 MP111 | type-I collagen prepro-α-1(I)-collag., collag. type-I α-1 & α-2, osteocalcin, osteonectin, osteopontine |
| Tendon/ Ligament | Spindle-shaped cells intermingled with thick fibers | H: ECM: AB 2.5 SO1.0+, SO 2.5+, CH'ase-AC sens AB1.0, Perf-AB, MH-type-I | E: M-38, SP1.D8, B3/D6, HFSP | type-I collagen, prepro-α-1(I)-collag., collag. type-I α-1 & α-2, CS-PG core prot, MMP-1A, collag. MMP-1B |
| Perichondrium | fibrous tissue surrounding cell aggregates with pericellular matrix halos | H: SO 1.0+, AB2.5 SO 2.5+, keratanase, CH'ase-AC sens AB1.0 MH-collagen type-II+ at interface with cell aggregates, collagen type-I at interface with stellate cells, Perf-AB | E: 5-D-4, anti-type-II, CII-C1, HC-II, D19, HFSP SP1.D8, M-38, B3/D6 | KS-PG core CS-PG core prot., KS/CS-PG core prot., collagen types-I & -II, prepro-α-1(I)-collag., collag. type-I α-2, MMP-1A, MM P-1B |
| Periosteum | Fibrous tissue surrounding aggregations of stellate cells overlain with 3-D matrix | H: SO 1.0+, AB2.5 SO 2.5+, CH'ase-ABC sens AB1.0, Perf-AB MH-collagen type-I | E: M-38, anti-osteocalcin, SP1.D8, B3/D6 WV1D1, MP111 | collagen type-I, prepro-α-1(I)-collag., collag. type-I α-2 MMP-1A, MMP-1B, osteocalcin, osteonectin, osteopontine, CS-PG core prot |
| Endothelial cells | Sheets of cobblestone-shaped cells | F: low density lipoprotein uptake | E: Factor-8, P2B1 H-endo, P8B1 P2H3 | endothelial cell surface protein, endothelin-1, endothelin-3, LDL-receptor |
| Hemato-Poietic Cells | Floating & attached refractile cells with differing nuclear shapes | H: Wright's stain | F: CD3, CD4, CD5, CD7, CD8, CD10, CD11b, CD11c, CD13, CD14, CD15, CD16, CD19, CD25, CD33, CD34, CD36, CD38, CD 45 CD56, CD65, CD90, CD117, Glycophorin-A, MHC-I, HLA-II (DR) E: HCD34 | EPO-R, M-CSF-R, G-CSF-R, GM-CSF-R, NCAM isoform 140 kDa, transferrin-R, neutral endopeptidase, aminopeptidase, Thy-1, HSC-GF-R, erythrocyte membrane protein band-3, spectrin α-erythrocytic-1 |

ECTODERMAL LINEAGE

| Cell Type | Histological | Functional(Fx)/ Histochemical[a] | ELICA(E)/Flow Cytometry(F) Antibodies[b] | Northern cDNA Probes |
|---|---|---|---|---|
| Neuronal Cells | Cells with a round central area and spidery cell processes or long polygonal cells with intracellular fibers | | E: FORSE-1, RT97 8A2, CNPase, S-100, N-200, HNES, Rat-401 MAB353 | |
| Epidermal Cell | Polygonal cell | | E: VM-1 | |

ENDODERMAL LINEAGE

| Cell Type | Histological | Functional(Fx)/ Histochemical[a] | ELICA(E)/Flow Cytometry(F) Antibodies[b] | Northern cDNA Probes |
|---|---|---|---|---|
| Liver Cell | Small rounded multi-nucleate or binucleate cell with central | | E: HAFP, HESA, RAFP | |

TABLE 13-continued

Histological, Functional/Histochemical, ELICA/Flow, and Northern Analyses

| Cell Type | Histological | Functional(Fx)/ Histochemical[a] | ELICA(E)/Flow Cytometry(F) Antibodies[b] | Northern cDNA Probes |
|---|---|---|---|---|
| | nucleus and peri-nuclear vescicles | | | |

[a]Histochemistry. Sudan Black-B and Oil Red-O stain saturated neutral lipids indicative of fat cells (adipocytes). CH'ase-AC (Chondroitinase-AC) selectively degrades the chondroitin sulfate glycosaminoglycan chains on chondroitin sulfate proteoglycans. CH'ase-ABC (Chondroitinase-ABC) selectively degrades the chondroitin sulfate glycosaminoglycan chains on chondroitin sulfate proteoglycans and the dermatan sulfate glycosaminoglycan chains on dermatan sulfate proteoglycans. AB 1.0 (Alcian Blue pH 1.0), SO 1.0 (Safranin-O pH 1.0), and Perf-AB (Perfix/Alcec Blue) stains sulfated moieties on the sulfated glycosaminoglycan chains of chondroitin sulfate, dermatan sulfate, keratan sulfate, and heparan sulfate proteoglycans. AB 2.5 (Alcian Blue pH 2.5) and SO 2.5 (Safranin-O pH 2.5) stains carboxylated moieties on the sulfated glycosaminoglycan chains of chondroitin sulfate, dermatan sulfate, keratan sulfate, and heparan sulfate proteoglycans, non-sulfated chondroitin proteoglycans, under-sulfated chondroitin sulfate proteoglycans, and hyaluronic acid. MH (Mallory Heidenhain One-Step) will selectively differentiate between type-I and type-II collagens based on aniline blue complexed with phosphotunsic acid binding affinities. Orcein-Fuchsin will selectively stain elastin fibers. Von Kossa will stain divalent cations, i.e., Ca + 2, Mg + 2, Zn + 2, etc. verification of the presence of calcium phosphate in mineralized tissues such as bone necessitates the use of the specific calcium chelator, EGTA, in a pre-incubation step prior to staining. Use of EDTA is not recommended as a specific test for calcium since EDTA will chelate all divalent cations. Wright's stain identifies individual types of hematopoietic cells based on differential binding capacities of its dyes (Appendix I, Young, 1983, Young et al., 1989a-c, 1993, 1995; Humason, 1972).
[b]Antibodies. F5D, myogenin; MF-20, sarcomeric myosin; MY-32, anti-skeletal muscle fast myosin; ALD-58, myosin heavy chain; A4.74, myosin fast chain; 12/101, skeletal muscle; 31-2, laminin; MF-5, myosin light chain-2 of fast muscle; C3/1, glycoprotein of myoblast plasma membrane; M3F7, type IV collagen; 5C6, type IV collagen; MF-30, neonatal and adult myosin; CHI, myosin tropomyosin; 2E8, laminin; IA4, smooth muscle alpha-actin; D76, desmin; D3, desmin; anti-desmin, desmin; M-38, type-I procollagen; SP1.D8, procollagen type-III; B3/D6, fibronectin; HFSP, human fibroblast surface protein; 5-D-4, keratan sulfate proteoglycan; anti-type-II collagen, type-II collagen; D19, type-IX collagen; CIIC1, collagen pro type-II; HC-II, collagen type-II; anti-elastin, elastin; WV1D1, bone sialoprotein-II; MP111, osteopontine; anti-osteocalcin, osteocalcin; Factor-8, factor-8; P2B1, peripheral endothelial cell adhesion molecule (PECAM); H-Endo, human endothelial cell surface marker; P8B1, vascular (endothelial) cell adhesion molecule (VCAM); P2H3, selectin-E; HCD34, sialomucin; CD3, T-cells, CD4, Class II-MHC restricted T-cells; CD5, T-cells, B-cell subset; CD7, subset of T-cells, CD8, Class I-MHC restricted T-cells; CD10, immature and some mature B-cells; lymphoid progenitors, granulocytes, thymocytes, neutral endopeptidase; CD11b, granulocytes, monocytes, NK cells; CD11c, granulocytes, monocytes/macrophages, NK cells; CD13, monocytes, granulocytes, aminopeptidase; CD14, monocytes; CD15, granulocytes, neutrophils, eosinophils, monocytes; CD16, NK cells, granulocyte, macrophages; CD19, most B-cells; CD25, activated T- and B-cells, activated macrophages; CD33, monocytes, myeloid progenitor cells; CD34, precursors of hematopoietic cells & endothelial cells; CD36, monocytes/macrophages, platelets, some endothelial cells; CD38, plasma cells, thymocytes, activated T-cells; CD45, all hematopoietic cells except erythrocytes; CD56, NK cells; CD65, granulocytes, myeloid; CD90, thymocytes, neurons; CD117, hematopoietic stem cells; Gly-A (Glycophorin-A), erythrocyte membrane; MHC-I, MHC Class-I; DR-II (HLA-DR-II), MHC Class II; FORSE-1, neural precursor cells; RT97, neurofilaments; 8A2, neurons in all species; CNPase, neuroglia (oligodendrocytes, astrocytes); S-100, neuronal cells; N-200, neurofilament-200; HNES, human nestin; Rat-401, nestin; MAB353, nestin; VM-1, keratinocyte; H-AFP, human alpha fetoprotein; RAFP, rat alpha fetoprotein; HESA, human spithelial surface antigen; MC-480, stage specific embryonic antigen-1 (SSEA-1); MC-631, stage specific embryonic antigen-3 (SSEA-3); MC-813, stage specific embryonic antigen-4 (SSEA-4); HCD66, human carcinoembryonic antigen; HCEA, human carcinoembryonic antigen; and RMHC-I, rat major histocompatability antigen Class-I. In addition, purified mouse IgG in place of antibodies was used to determine non-specific background staining.
[c]Each phenotype is probed with cDNA for PDGF-α receptor, PDGF-β receptor, β-actin (as internal control).
[d]CS-PG core prot., chondroitin sulfate proteoglycan core protein; MMP-1A, matrix metalloproteinase-1A; MMP-1B, matrix metalloproteinase-1B; KS-PG core prot., keratan sulfate proteoglycan core protein; CS/KS-PG core prot., chondroitin sulfate/keratan sulfate proteoglycan core protein; LDL-R, low density lipoprotein receptor; EPO-R, erythropoietin receptor; M-CSF-R, macrophage colony stimulating factor receptor; G-CSF-R, granulocyte colony stimulating factor receptor; GM-CSF-R, granulocyte/macrophage colony stimulating factor receptor; NCAM, neural cell adhesion molecule; NK cells; natural killer cells; transferrin-R, transferrin receptor; HSC-GF-R, hematopoietic stem cell growth factor receptor.

The following is an alphabetical list of the references referred to in the above Examples 1-10. The disclosures of the listed references as well as the other publications, Patent disclosures or documents recited herein, are all incorporated herein by reference in their entireties.

REFERENCES

Abbas A K, Lichtman A H, Pober J S. In: Cellular and Molecular Immunology, Third Edition. Philadelphia: W.B. Saunders Company, 1997.

Acheson A, Sunshine J L, Rutishauser U. NCAM polysialic acid can regulate both cell-cell and cell-substrate interactions. J Cell Biol 114:143-153, 1991.

Adkison, L. R., Andrews, R. H., and Koontz, W. L. (1994) Improved detection of fetal cells from maternal blood with polymerase chain reaction. J Obstet. Gyn. 170.

Adolph V R, DiSanto S K, Bleacher J C, Dillon P W, Krummel T M. The potential role of the lymphocyte in fetal wound healing. J Ped Surg. 1993; 28: 1316-20.

Aherns, M., Akenbauer, T, Schroder, D, Hollnagel, A., Mayer, H., and Gross, G. (1993) Expression of Human Bone Morphogenetic Proteins-2 or 4 in Murine Mesenchymal Progenitor C3H10T½ Cells induces differentiation into distinct Mesenchymal cell lineages. DNA and Cell Biology 12:10 871-880.

Ailhaud, G., Grimaldi, P., Negrel, R. Cellular and molecular aspects of adipose tissue development. Annu Rev Nutr 12:207-34, 1992.

Akeson R A, Wujek J R, Roe S, Warren S L, Small S J. Smooth muscle cells transiently express NCAM. Brain Res 464:107-120, 1988.

Andersson A M, Olsen M, Zhernosekov D, Gaardsvoll H, Krog L, Linnemann D, Bock E. Age-related changes in expression of the neural cell adhesion molecule in skeletal muscle: a comparative study of newborn, adult and aged rats. Biochem J 290:641-648, 1993.

Ashton B A, Eaglesom C C, Bab I, Owen M E. Distribution of fibroblastic colony-forming cells in rabbit bone marrow and assay of their osteogenic potential by an in vivo diffusion chamber method. Calcif Tissue Int 1984; 36:83-6.

Bab I, Ashton B A, Syftestad G T, Owen M E. Assessment of an in vivo diffusion chamber method as a quantitative assay for osteogenesis. Calcif Tissue Int 1984; 36:77-82.

Bab I, Howlett C R, Ashton B A, Owen M E. Ultrastructure of bone and cartilage formed in vivo in diffusion chambers. Clin Orthop Rel Res 1984; 187:243-54.

Bab I, Passi-Even L, Gazit D, Sekeles E, Ashton B A, Peylan-Ramu N, Ziv I, Ulmansky M. Osteogenesis in in vivo diffusion chamber cultures of human marrow cells. Bone and Mineral 1988; 4:373-86.

Bader, D., Masaki, T., and Fischman, D. A. (1982) Immunochemical analysis of myosin heavy chain during avian myogenesis in vivo and in vitro. J. Cell Biol. 95:763-770.

Ball E H, Sanwal B D. A synergistic effect of glucocorticoids and insulin on the differentiation of myoblasts. J Cell Physiol 1980; 102:27-36.

Battey, J. F., Way, J. M., Corjay, M. H., Shapira, H., Kusano, K., Harkins, R., Wu, J. M., Slattery, T., Mann, E., and Feldman, R. I. (1991) Molecular cloning of the bombesin/gastrin-releasing peptide receptor from Swiss 3T3 cells. Proc. Natl. Acad. Sci. USA 88: 395-399.

Bellows C G, Heersche J N M, Aubin J E. Determination of the capacity for proliferation and differentiation of osteoprogenitor cells in the presence and absence of dexamethasone. Dev Biol. 1990; 140:132-138.

Benjamini E, Sunshine G, Leskowitz S. In Immunology, A Short Course, 3rd edition. New York: Wiley-Liss, pp. 180-194 and 377-393, 1996.

Bennett N T. Growth factors and wound healing: Part II. Role in normal and chronic wound healing. Am J of Surg. 1993; 166:74-81.

Bennett N T, Schultz G S. Growth factors and wound healing: biochemical properties of growth factors and their receptors. Am J of Surg. 1993; 165:728-37.

Bentley G, Greer G B. 1971. Homotransplantation of isolated epiphyseal and articular chondrocytes into joint surfaces. Nature 230:385-388.

Beresford J N, Joyner C J, Devlin C, Triffitt J T. The effects of dexamethasone and 1,25-dihydroxyvitamin $D_3$ on osteogenic differentiation of human marrow stromal cells in vitro. Archs oral Biol 1994; 39:941-7.

Beresford, J. N. Osteogenic stem cells and the stromal system of bone and marrow. Clin Orthop Rel Res 240: 270-280, 1989.

Bernier S M, Goltzman D. Regulation of the expression of the chondrocyte phenotype in a skeletal cell line. J. Bone Miner Res 1993; 8:475-484.

Bjornson, C. R., Rietze, R. L., Reynolds, B. A., Magli, M. C., & Vescovi, A. L. Turning brain into blood: a hematopoietic fate adopted by adult neural stem cells in vivo. Science 283, 534-537 (1999).

Bleiberg I. Colony forming cell-fibroblast development in extracellular matrix-induced bone and bone marrow formation in rat. Connective Tissue Research 1985; 14:121-7.

Bloom M, Fawcett D W. A Bloom and Fawcett Textbook of Histology, 12th ed. Chapman & Hall, 1994:182-184, 205-205.

Bowerman, S. G., Taylor, S. S., Putnam, L., Young, H. E., Lucas, P. A.: Transforming growth factor-b (TGF-b) stimulates chondrogenesis in cultured embryonic mesenchymal cells. Surgical Forum XLII: 535-536, 1991.

Braun M P, Martin P J, Ledbetter J A, Hansen J A. Granulocytes and cultured human fibroblasts express common acute lymphoblastic leukemia-associated antigens. Blood 61:718-725, 1983.

Breinan H A, Minas T, Hsu H-P, Nehrer S, Sledge C B, Spector M. 1997. Effect of cultured autologous chondrocytes on repair of chondral defects in a canine model. J Bone Joint Surg Am 79:1439-1451.

Brittberg M, Lindahl A, Nilsson A, Ohlsson C, Isaksson O, Peterson L. 1994. Treatment of deep cartilage defects in the knee with autologous chondrocyte implantation. N Eng J Med 331(4):889-895.

Brittberg M, Nilsson A, Lindahl A, Ohlsson C, Peterson L. 1996. Rabbit articular cartilage defects treated with autologous cultured chondrocytes. Clin Orthop Rel Res 326:270-283.

Brown D G, Willington M A, Findlay I, Muggleton-Harris A L. 1992. Criteria that optimize the potential of murine embryonic stem cells for in vitro and in vivo developmental studies. In Vitro Cell Dev Biol 28A(11-12): 773-778.

Burwell R G. The function of bone marrow in the incorporation of a bone graft. Clin Orthop Rel Res 1985; 200: 125-41.

Byeon M K, Sugi Y, Markwald R R, Hoffman S. NCAM polypeptides in heart development: association with Z discs of forms that contain the muscle-specific domain. J Cell Biol 128:209-221, 1995.

Calcutt, A. F., Ossi, P., Young, H. E., Southerland, S. S., and Lucas, P. A. (1993) Mesenchymal stem cells from wound tissue. Clin. Res. 41:336A.

Calcutt, A. F., Southerland, S. S., Ossi, P., Young, H. E., Lucas, P. A.: Granulation tissue contains a population of cells capable of differentiating into several mesenchymal phenotypes. Wound Repair and Regeneration (in press), 1998.

Campbell, G. C., Christian, L. J., and Carter-Su, C. (1993) Evidence for the involvement of the growth hormone receptor-associated tyrosine kinase in actions of growth hormone. J. Biol. Chem. 268: 7427-7434.

Campion, D. R. The muscle satellite cell: a review. Int Rev Cytol 87:225-251, 1984.

Caplan A I, Elyaderani M, Mochizuki Y, Wakitani S, Goldberg V Principles of cartilage repair and regeneration. Clin. Orthop. Rel. Res. 342:254-269, 1997.

Casale L, Cardozo C, Kalb T, Lesser M. Quantitation of endopeptidase 24.11 and endopeptidase 24.15 in human blood leukocytes. Enzyme Protein 48:143-148, 1994.

Chang, S. C., Hoang B., Thomas, J. T., et. al. (1994) Cartilage derived morphogenic proteins. New members of the transforming growth factor-beta superfamily redominantly expressed in long bones during human embryonic development. J Biol Chem 269(45):28227-28234.

Chesterman P J, Smith A U. 1968. Homotransplantation of articular cartilage and isolated chondrocytes. J Bone Joint Surg Br 50:184-197.

Clark R A F. Regulation of fibroplasia in cutaneous wound repair. Am J Med Sci. 1993; 306:42-8.

Connolly D T, Stoddard B L, Harakas N K, Feder J. Human fibroblast-derived growth factor is a mitogen and chemoattractant for endothelial cells. Biochem Biophys Res Comm. 1987; 144:705-12.

Corps, A. N. and Brown, K. D. (1991) Mitogens regulate the production of insulin-like growth factor-binding protein by Swiss 3T3 cells. Endocrinology 128:1057-1064.

Couffinhal, T., Kearney, M., Sullivan, A., Silver, M., Tsurumi, Y., Isner, J. M.: Histochemical staining following LacZ gene transfer underestimates transfection efficiency. Human Gene Therapy, 8:929-934, 1997.

Craig W, Kay R, Cutler R L., Lansdorp P M. Expression of Thy-1 on human hematopoietic progenitor cells. J Exp Med 177:1331-1342, 1993.

Cruess, R. L. In: The Musculoskeletal System Embryology, Biochemistry, and Physiology. New York: Churchill Livingston, pp. 1-33, 109-169, 255-87, 1982.

Davila, D. G., Minoo, P., Estervig, D. N., Kasperbauer, J. L., Tzen, C. Scott, R. E. Linkages in control and differentiation and proliferation in murine mesenchymal stem cells and human keratinocyte progenitor cells: The effects of carcinogenesis. Volume I, Chapter I.

Davis K H, Reeves M L, Southerland S S, Farmer L, Kang M, Estes T, Warejcka D, Lucas P A, Black A C Jr, Young H E Isolation and cloning of rat pluripotent mesenchymal stem cells. FASEB J. 1995; 9:A552.

Davis, E., Williams, J. T., IV, Souza, J., Southerland, S. S., Warejka, D., Young, H. E., Lucas, P. A. Cells isolated from adult rat marrow are capable of differentiating into several mesenchymal phenotypes in culture. FASEB J. 9:A590, 1995.

Denhardt, D. T., Edwards, D. R., Mcleod, M., Norton, G., Parfett, C. L., and Zimmer, M. (1991) Spontaneous immortalization of mouse embryo cells: strain differences and changes in gene expression with particular reference to retroviral gag-pol genes. Exp. Cell Res. 192:128-136.

Deuel T F, Senior R M, Huang J S, Griffin G L. Chemotaxis of monocytes and neutrophils to platelet-derived growth factor. J Clin Invest 1982; 69:1046-9.

Dixon, K., Murphy, R. W., Southerland, S. S., Young, H. E., Dalton, M. L., Lucas, P. A. (1996) Recombinant human bone morphogenetic proteins-2 and 4 (rhBMP-2 and rhBMP-4) induce several mesenchymal phenotypes in culture. Wound Rep. Reg. 4:374-380.

Domin, J., and Rozengurt, E. (1993) Platelet-derived growth factor stimulates a biphasic mobilization of arachidonic acid in Swiss 3T3 cells. J. Biol. Chem. 268:8927-8934.

Eldar, H., Zizman, Y., Ulrich, A., and Livneh, E. (1990) Overexpression of protein kinase C alpha-subtype in Swiss/3T3 fibroblasts causes loss of both high and low affinity receptor numbers for epidermal growth factor. J. Biol. 265:13290-13296.

Evans, M. J. & Kaufman, M. H. Establishment in culture of pluripotential cell from mouse embryos. Nature 292, 154-156, (1981).

Eisenberg, C. A. & Markwald, R. R. Mixed cultures of avian blastoderm cells and the quail mesoderm cell line QCE-6 provide evidence for the pluripotentiality of early mesoderm. Dev. Biol. 191, 167-181, (1997).

Evans, S. C., Lopez, L. C., and Schur, B. D. (1993) Dominant negative mutation in cell surface $\beta$1,4-galactosyl transferase inhibits cell-cell and cell-matrix interactions. J. Cell Biol. 120:1045-1057.

Falanga V. Special issue on wound wound healing: An overview. J Dermatol Surg Oncol. 1993; 19:689-90.

Ferguson M W J. Skin wound healing: Transforming growth factor $\beta$ antagonists decrease scarring and improve quality. J Interferon Res. 1994; 14:303-4.

Figarella-Branger D, Pellissier J F, Bianco N, Pons F, Leger J J, Rougon G. Expression of various NCAM isoforms in human embryonic muscles: correlation with myosin heavy chain phenotypes. J Neuropathol Exp Neurol 51:12-23, 1992.

Folkman J, Klagsbrun M. Angiogenic factors. Science. 1987; 235:442-7.

Frenkel S R, Toolan B, Menche D, Pitman M I, Pachence J M. 1997. Chondrocyte transplantation using collagen bilayer matrix for cartilage repair. J Bone Joint Surg Br 79:831-836.

Friedenstein, A J, Int. Rev. Cyt. 47: 327-359, 1976.

Friedenstein A J. Marrow stromal fibroblasts. Calcif Tissue Int 1995; 56 Suppl 1:S17:S17

Friedman, B., Fujiki. H., and Rosner, M. R. (1990) regulation of the epidermal growth factor receptor by growth modulating agents: effects of staurosporine, a protein kinase inhibitor. Cancer Res. 50:533-538.

Gaardsvoll H, Krog L, Zhernosekov D, Andersson A M, Edvardsen K, Olsen N I, Bock E, Linnemann D. Age-related changes in expression of neural cell adhesion molecule (NCAM) in heart: a comparative study of newborn, adult and aged rats. Eur J Cell Biol 61:100-107, 1993.

Garret J C. 1986. Treatment of osteochondral defects of the distal femur with fresh osteochondral allografts: A preliminary report. Arthroscopy 2:222-226.

Gatti R. Ataxia-telangiectasia (group A): localization of ATA gene to chromosome 11q22-23 and pathogenetic implications. Allergol Immunopathol (Madr) 19:42-46, 1991.

Gilbert, S F, *Developmental Biology, Fifth Edition*. Sinauer Associates, Inc. Sunderland, Mass., 1997.

Goodman and Gilman (1996) Pharmacological Basis of Medical Practice, McGraw-Hill, New York.

Goodson, W, Hohn, D, Hunt, T K, Leung, D Y K. Augmentation of some aspects of wound healing by a skin respiratory factor. J Surg Res. 1976; 21: 125-129.

Grande D A, Pitman M I, Peterson L, Menche D, Klein M. 1989. The repair of experimentally produced defects in rabbit articular cartilage by autologous chondrocyte implantation. J Orthop Res 7:208-218.

Grande, D. A., Southerland, S. S., Manji, R., Pate, D. W., Schwartz, R. E., Lucas, P. A. (1995) Repair of articular cartilage defect using mesenchymal stem cells. Tiss. Eng. 1:345-353.

Graves K H, Moreadith R W. 1993. Derivation and characterization of putative pluripotential embryonic stem cells from preimplantation rabbit embryos. Mol Reprod Dev 36(4):424-433.

Green E, Hinton C, Triffitt J T. The effect of decalcified bone matrix on the osteogenic potential of bone marrow. Clin Orthop Rel Res 1986; 205:292-8.

Green, H. and Olaniyi, K. (1974) Sublines of mouse 3T3 cells that accumulate lipid. Cell 1:113-116

Green H, Meuth M. An established pre-adipose cell line and its differentitation in culture. Cell 1974; 3:127-33.

Green W T. 1977. Articular cartilage repair: Behavior of rabbit chondrocytes during tissue culture and subsequent allografting. Clin Orthop 124:237-250.

Greenberger J S. Corticosteroid-dependent differentiation of human marrow preadipocytes in vitro. In Vitro 1979; 15:823-828.

Grigoriadis, A E, Heersche, J N M, and Aubin, J E. (1988) Differentiation of muscle, fat, cartilage, and bone from progenitor cells present in a bone-derived clonal cell population: effect of dexamethasone. J. Cell Biol. 106: 2139-2151.

Grigoriadis A E, Aubin J E, Heersche J N M. Effects of dexamethasone and vitamin $D_3$ on cartilage differentiation in a clonal chondrogenic cell population. Endocrinology 1989; 125:2103-2110.

Gronthos S, Graves S E, Ohta S, Simmons P J. The STRO-1+ fraction of adult human bone marrow contains the osteogenic precursors. Blood 1994; 84(12):4164-73.

Grotendorst G R, Chang T, Seppa H E J, Kleinman H K, Martin G R. Platelet-derived growth factor is a chemoattractant for vascular smooth muscle cells. J of Cellular Physiology 1982; 113:261-6.

Grounds M D. Factors controlling skeletal muscle regeneration in vivo. In: Kakulas B A, Mastaglia F L eds. Pathogenesis and Therapy of Duchenne and Becker Muscular Dystrophy. Raven Press, 1990:175-185.

Grounds M D. Towards understanding skeletal muscle regeneration. Pathol Res Prac. 1991:118:1-22.

Grounds, M. D., Garrett, K. L., Lai, M. C., Wright, W. E., Beilharz, M. W. Identification of muscle precursor cells in vivo by use of MyoD1 and myogenin probes. Cell Tiss Res 267:99-104, 1992.

Grundel R E, Chapman M W, Yee T, Moore D C. Autogeneic bone marrow and porous biphasic calcium phosphate ceramic for segmental bone defects in the canine ulna. Clin Orthop Rel Res 1991; 266:244-58.

Guerriero V Jr, Florini J R. Dexamethasone effects on myoblast proliferation and differentiation. Endocrinology 1980; 106:1198-1204.

Hayflick L. Human diploid cell strains as hosts for viruses. Perspect Virol 3(13):213-237, 1963.

Hayflick, L. The limited in vitro lifetime of human diploid cell strains. Exper Cell Res 37:614-636, 1965.

Holt, S. E., Wright, W. E., & Shay, J. W. Multiple pathways for the regulation of telomerase activity. Eur. J. Cancer 33, 761-766 (1997).

Homminga G N, Bulstra S K, Bouwmeester P S M, Van Der Linden, A J. 1990. Perichondrial grafting for cartilage lesions of the knee. J Bone Joint Surg Br 72:1003-1007.

Houner H, Schmid P, Pfeiffer E F. Glucocorticoids and insulin promote the differentiation of human adipocyte precursor cells into fat cells. J Clin Endocrin Metab. 1987; 64:832-835.

Humason G. Animal tissue techniques, 3rd ed. San Francisco: WH Freeman and Co, 1972.

Hunt, T K, Ledington, J, Hutchinson, J G P. Effect of hyperbaric oxygen on experimental infections in rabbits. Presented at the Third International Conference on Hyperbaric Medicine, Washington, D.C., 1966.

Hunt T K, LaVan F. Enhancement of wound healing by growth factors. New Eng J. Med. 1989; 321:111-2.

Iannaccone P M, Taborn G U, Garton R L, Caplice M D, Brenin D R. 1994. Pluripotent embryonic stem cells from the rat are capable of producing chimeras. Dev Biol 163(1):288-292.

Iwanmoto I, Kimura A, Ochiai K, Tomioka H, Yoshida S. Distribution of neutral endopeptidase activity in human blood leukocytes. J Leukoc Biol 49:116-125, 1991.

Johnson K A, Howlett C R, Bellenger C R, Armati-Gulson P. Osteogenesis by canine and rabbit bone marrow in diffusion chambers. Calcif Tissue Int 1988; 42:113-8.

Johnson-Wint B, Hollis S. A rapid in situ deoxyribonucleic acid assay to determine cell number in culture and tissue. Anal Biochem 1982; 122:338-344.

Kadiyala S, Young R G., Thiede M A, Bruder S. Culture expanded canine mesenchymal stem cells possess osteochondrogenic potential in vivo and in vitro. Cell Transplanta 6:125-134, 1997.

Kataoka H, Urist M R. Transplant of bone marrow and muscle-derived connective tissue cultures in diffusion chambers for bioassay of bone morphogenetic protein. Clin Orthop Rel Res 1993; 286:262-70.

Kawabe N, Yoshinato M. 1991. The repair of full thickness articular cartilage defects. Immune responses to reparative tissue formed by allogeneic growth plate chondrocytes. Clin Orthop 268:279-293.

Kawamoto S J D, Le A, McClure D, Sato G Development of a serum-free medium for growth of NS-I mouse myeloma cells and its application to the isolation of NS-I hybridomas. Analyt. Biochem. 130:445-453, 1983.

Kishimoto, T., Kikutani, H., Borne, A. E. G. K. r.v.d., Goyert, S. M., Mason, D., Miyasaka, M., Moretta, L., Okumura, K., Shaw, S., Springer, T., Sugamura, K., Zola, H. In: Leucocyte Typing VI, White Cell Differentiation Antigens. Garland Publishing, Hamden, C T, 1997.

Klausmeyer, C. M., Pederson, S. L., Rogers, J. J., Young, H. E.: Bone morphogenetic protein induces chondrogenesis in mouse mesenchymal stem cells. J Cell Biochem 18B: 182, 1994.

Klein B Y, Gal I, Segal D. Marrrow stromal cell commitment to mineralization under the effect of a prolyl Hydroxylase inhibitor. J of Cellular Biochemistry 1994; 54:354-64.

Kolettas E, Buluwela L, Bayliss M, Muir H. 1995. Expression of cartilage-specific molecules is retained on long-term culture of human articular chondrocytes. J Cell Sci 108:1991-1999.

Knudsen K A, McElwee S A, Myers L. A role for neural cell adhesion molecule, NCAM, in myoblast interaction during myogenesis. Dev Biol 138:159-168, 1990.

Kuri-Harcuch W, Green H. Adipose conversion of 3T3 cells depends on a serum factor. Proc Natl Acad Sci USA 1978; 75:6107-9.

Lancki D W, Qian D, Fields P, Gajewski T, Fitch F W. Differential requirement for protein tyrosine kinase Fyn in the functional activation of antigen-specific T lymphocyte clones through the TCR or Thy-1. J Immunol 154:4363-4370, 1995.

Langer, R., and Vacanti, J. P. (1993) Tissue engineering. Science 260:920-926.

Lanier L L. Testi R. Bindi J Phillips J H. Identity of Leu-19 (CD56) leukocyte differentiation antigen and neural cell adhesion molecule. J Exp Med 169:2233-2238, 1989.

Lanier L L, Chang C. Azuma M, Ruitenberg J J, Hemperly J J, Phillips J H. Molecular and functional analysis of human natural killer cell-associated neural cell adhesion molecule (NCSM/CD56). J Immunol 146:4421-4426, 1991.

Larsen S L, Pedersen L O, Buus S, Stryhn A T cell responses affected by aminopeptidase N (CD13)-mediated trimming of major histocompatibility complex class II-bound peptides. J Exp Med 184:183-189, 1996.

Lee Y S, Chuong C M. Adhesion molecules in skeletogenesis: I. Transient expression of neural cell adhesion molecules (NCAM) in osteoblasts during endochondral intramembranous ossification. J Bone Miner Res 7:1435-1446, 1992.

Lennon G, Auffray C, Polymeropoulos M, Soares M B. The I.M.A.G.E. Consortium: An Integrated Molecular Analysis of Genomes and Their Expression. Genomics 33:151-152, 1996.

Letarte M, Vera S, Tran R, Addis J B, Onizuka R J, Quackenbush E J, Jongeneel C V, McInnes R R. Common acute lymphocytic leukemia antigen is identical to neutral endopeptidase. J Exp Med 168:1247-1253, 1988.

Li M, Pevny L, Locell-Badge R, Smith A. 1998. Generation of purified neural precursors from embryonic stem cells by lineage selection. Curr Biol 8:971-974.

Lin G, Finger E, Gutierrez-Ramos J C. Expression of CD34 in endothelial cells, hematopoietic progenitors and nervous cells in fetal and adult mouse tissues. Eur J Immunol 25:1508-1516, 1995.

Linder, D., Gschwendt, M., and Marks, F. (1991) Down-regulation of protein kinase C in Swiss 3T3 fibroblasts is independent of its phosphorylating activity. Biochem. Biophys. Res. Commun. 176:1227-1231.

Lindhold T S, Nilsson O S, Lindholm T C. Extraskeletal and intraskeletal new bone formation induced by demineralized bone matrix combined with bone marrow cells. Clin Orthop Rel Res 1982; 171:251-5.

Lindholm T S, Urist M R. A quantitative analysis of new bone formation by induction in compositive grafts of bone marrow and bone matrix. Clin Orthop Rel Res 1980; 150:288-300.

Llorens-Cortes C, Huang H, Vicart P, Gasc J M, Paulin D, Corvol P. Identification and characterization of neutral endopeptidase in endothelial cells from venous and arterial origins. J Biol Chem 267:14012-14018, 1992.

Locklin R M, Williamson M C, Beresford J N, Triffitt J T, Owen M E. In vitro effects of growth factors and dexamethasone on rat marrow stromal cells. Clin Orthop Rel Res 1995; 313:27-35.

Look A T, Ashmun R A, Shapiro L H, Peiper S C. Human myeloid plasma membrane glycoprotein CD13 (gp150) is identical to aminopeptidase N. J Clin Invest 83:1299-1307, 1989.

Lucas P A, Laurencin C, Syftestad G T, Domb A, Goldberg V M, Caplan A I, Langer, R. Ectopic induction of cartilage and bone by water-soluble proteins from bovine bone using a polyanhydride delivery vehicle. J Biomed Mat Res. 1990; 24:901-11.

Lucas P A, Syftestad G T, Caplan A I. A water-soluble fraction from adult bone stimulates the differentiation of cartilage in explants of embryonic muscle. Differentiation 1988; 37:47-52.

Lucas P A, Young H E, Putnam L S. 1991. Quantitation of chondrogenesis in culturlue staining. FASEB J. 5(4).

Lucas P A, Calcutt A F, Ossi P, Young H E, Southerland S S. 1993. Mesenchymal stem cells from granulation tissue. J Cell Biochem 17E:122.

Lucas, P. A., Calcutt, A. F., Ossi, P., Young, H. E., Southerland, S. S.: Granulation tissue contains cells capable of differentiating into multiple mesenchymal phenotypes. J Cell Biochem, 18C:276, 1994.

Lucas, P. A., Calcutt, A. F., Southerland, S. S., Warejcka, D., Young, H. E. (1995) A population of cells resident within embryonic and newborn rat skeletal muscle is capable of differentiating into multiple mesodermal phenotypes. Wound Rep. Reg. 3:457-468.

Lucas P A, Young H E, Laurencin C T. Skeletal muscle induction and regeneration in vivo. J Surg Res., in press, 1996.

Lucas, P. A., Warejcka, D. J., Zhang, L.-M., Newman, W. H., Young, H. E. (1996) Effect of rat mesenchymal stem cells on the development of abdominal adhesions after surgery. J. Surg. Res. 62:229-232.

Lucas P A, Grande D A, Young H E. 1996a. Use of pluripotent mesenchymal stem cells for tissue repair. Program of the Keystone Symposia on Tissue Engineering and Wound Repair in Context. 1996 (1):15.

Lyons G E, Moore R, Yahara O, Buckingham M E, Walsh F S. Expression of NCAM isoforms during skeletal muscle myogenesis in the mouse embryo. Dev Dynam 194:94-104, 1992.

Maher, P. A. (1993) Modulation of epidermal growth factor receptor by basic fibroblast growth factor. J. Cell. Physiol. 154:350-358.

Mankin H J. 1982. The response of articular cartilage to mechanical injury. J Bone Joint Surg Am 64:460-466.

Martin, G. R. Isolation of a pluripotent cell line from early mouse embryos cultured in medium conditioned by teratocarcinoma stem cells. Proc. Natl. Acad. Sci. USA 78, 7634-7638 (1981).

Matsusue Y, Yamamuro T, Hama H. 1993. Arthroscopic multiple osteochondral transplantation to the chondral defect in the knee associated with anterior cruciate ligament disruption. Arthroscopy 9:318-321.

Mauro, A. (1961) Satellite cell of skeletal muscle fibers. J. Biophys. Biochem. Cytol. 9:493-498.

McDermott A G P, Langer F, Pritzker K P H, Gross A E. 1985. Fresh small-fragment osteochondral allografts. Long-term follow-up study on first 100 cases. Clin Orthop 197:96-102.

McGuire W P. (1998) High-dose chemotherapy and autologous bone marrow or stem cell reconstitution for solid tumors. Curr Probl Cancer 22:135-137.

Meyer M B, Bastholm L, Nielsen M H, Elling F, Rygaard J, Chen W, Obrink B, Bock E, Edvardsen K. Localization of NCAM on NCAM-B-expressing cells with inhibited migration in collagen. APMIS 103:197-208, 1995.

Minas T, Nehrer S. 1997. Current concepts in the treatment of articular cartilage defects. Orthopedics 20(6):525-538.

Miyazawa, H., Izumi, M., Tada, S., Takada, R., Masutani, M., Ui, M., and Hanaoka, F. (1993) Molecular cloning of the cDNAs for the four subunits of mouse DNA polymerase α-primase complex and their gene expression during cell proliferation and the cell cycles. J. Biol. Chem. 268:8111-8122.

Mizuguchi M, Otsuka N, Sato M, Ishii Y, Kon S, Yamada M, Nishina H, Katada T, Ikeda K. Neuronal localization of CD38 antigen in the human brain. Brain Res 697:235-240, 1995.

Morikawa M, Nixon T, Green H. Growth hormone and the adipose conversion of 3T3 cells. Cell 1982; 29:783-9.

Morris R J, Beech J N. Differential expression of Thy-1 on the various components of connective tissue of rat nerve during postnatal development. Dev Biol March 102:32-42, 1984.

Morris R. Thy-1 in developing nervous tissue. Dev Neurosci 7:133-160, 1985.

Moskalewski S. 1991. Transplantation of isolated chondrocytes. Clin Orthop 272:16-20.

Notarianni E, GalliC, Laurie S, Moor R M, Evans M J. 1991. Derivation of pluripotent, embryonic cell lines from the pig and sheep. J Reprod Fertil Suppl 43:255-260.

Nixon T, Green H. Contribution of growth hormone to the adipogenic activity of serum. Endocrinology 1984; 114: 527-32.

O'Driscoll S W, Keeley F W, Salter R B. 1988. Durability of regenerated articular cartilage produced by free autologous periosteal grafts in major full-thickness defects in joint surfaces under the influence of continuous passive motion. J Bone Joint Surg Am 70:595-606.

Ohgushi H, Goldberg V M, Caplan A I. Repair of bone defects with marrow cells and porous ceramic: Experiments in rats. Acta Orthop Scand 1989; 60:334-9

Orgill D, Demling R H. Current concepts and approaches to wound healing. Crit Care Med. 1988; 16:899-908.

Owen M E, Friedenstein A J. Stromal stem cells: marrow-derived osteogenic precursors. Ciba Foundation Symposium 1988; 136:42-60.

Owen M E, Joyner C J. Clonal analysis in vitro of osteogenic differentiation of marrow CFU-F. J Cell Sci. 1987; 87:731-738.

Owen, M. (1988) Marrow stromal cells. J. Cell Sci. Suppl 10:63-76.

Paley D, Young M C, Wiley A M. Fornashier V L, Jackson W J. Percutaneous bone marrow grafting of fractures and bony defects: An experimental study in rabbits. Clin Orthop Rel Res 1986; 208:300-12.

Palis J and Segel G B. (1998) Developmental biology of erythropoiesis. Blood Rev 12:1061-1064.

Pang, L., Decker, S. J., and Saltiel, A. R. (1993) Bombesin And epidermal growth factor stimulate the mitogen-activated protein kinase through different pathways in Swiss 3T3 cells. Biochem. J. 289:283-287.

Pate D W, Southerland S S, Grande D A, Young H E, Lucas P A. Isolation and differentiation of mesenchymal stem cells from rabbit muscle. Surgical Forum 1993; XLIV: 586-9.

Pate, D. W., S. S. Southerland, D. A. Grande, H. E. Young, and P. A. Lucas (1993) Isolation and differentiation of mesenchymal stem cells from rabbit muscle. Surgical Forum XLIV:587-589.

Peck D, Walsh F S. Differential effects of over-expressed neural cell adhesion molecule isoforms on myoblast fusion. J Cell Biol 123:1587-1595, 1993.

Pittenger, M. F. et al. Multilineage potential of adult human mesenchymal stem cells. Science 148, 143-147 (1999).

Postlethwaite A E, Snyderman R, Kang A H. The chemotactic attraction of human fibroblasts to a lymphocyte-derived factor. The J of Experimental Medicine 1976; 144:1188-203.

Postlethwaite A E, Seyer J M, Kang A H. Chemotactic attraction of human fibroblasts to type I, II, and III collagens and collagen-derived peptides. Proc Natl Acad Sci USA 1978; 75:871-5.

Postlethwaite A E, Keski-oka J, Balian G, Kang A H. Induction of fibroblast chemotaxis by fibronectin: Localization of the chemotactic region to a 140,000-molecular weight non-gelatin-binding fragment. J Exp Med 1981; 153:494-9.

Powis, G., Seewald, M. J., Sehgal, I., Iaizzo, P. A., and Olsen, R. A. (1990) Platelet-derived growth factor stimulates non-mitochondrial Ca2+ uptake and inhibits mitogen-induced Ca2+ signalling in Swiss 3T3 fibroblasts. J. Biol. Chem. 265:10266-10273.

Prockop, D. J. (1997) Marrow stromal cells for non-hematopoietic tissues. Science 276:71-74.

Ratajczak M Z, Pletcher C H, Marlicz W, Machlinski B, Moore J, Wasik M, Ratajczak J, and Gewirtz A M. (1998) CD34+, kit+, rhodamine 123 (low) phenotype identifies a marrow cell population highly enriched for human hematopoietic stem cells. Leukemia 12:942-950.

Ratajczak, M. Z. et al. CD34+, kit+, rhodamine 123 (low) phenotype identifies a marrow cell population highly enriched for human hematopoietic stem cells. Leukemia 12, 942-950 (1998).

Reddi A H, Huggins C. Biochemical sequences in the transformation of normal fibroblasts in adolescent rats. Proc Nat Acad. Sci. 1972; 69:1601-5.

Reddi A H, Anderson W A. Collagenous bone matrix-induced endochondral ossification and hemopoiesis. J. Cell Biol. 1976; 69:557-72.

Reddi A H. Cell biology and biochemistry of endochondral bone development. Coll Res. 1981; 1:209-26.

Rickard, D. J., Sullivan, T. A., Shenker, B. J., Leboy, P. S., and Kazhdan, I. (1994) Induction of rapid osteoblast differentiation in rat bone marrow stromal cell cultures by dexamethasone and BMP-2. Dev. Biol. 161:218-228.

Ringold G M, Chapman A B, Knight D M, Torti F M. Hormonal control of adipogenesis. Ann NY Acad Sci 1991; 109-19.

Ritsila V A, Santavira S, Alhopuro S, Poussa M, Jaroma H, Rubak J M, Eskola A, Hoikka V, Snellman O, Osterman K. 1994. Periosteal and perichondrial grafting in reconstructive surgery. Clin. Orthop. 302:259-265.

Rogers, J. J., Adkison, L. R., Black, A. C., Jr., Lucas, P. A., Young, H. E. (1995) Differentiation factors induce expression of muscle, fat, cartilage, and bone in a clone of mouse pluripotent mesenchymal stem cells. The American Surgeon 61(3): 1-6.

Rohn W M, Lee Y J, Benveniste E N. Regulation of class II MHC expression. Crit Rev Immunol 16:311-330, 1996.

Romanska H M, Bishop A E, Moscoso G, Walsh F S, Spitz L, Brereton R J, Polak J M. Neural cell adhesion molecule (NCAM) expression in nerves and muscle of developing human large bowel. J Pediatr Gastroenterol Nutr 22:351-358, 1996.

Rutishauser U, Goridis C. NCAM: the molecule and its genetics. Trends Genet 2:72-76, 1986.

Rutishauser U, Acheson A, Hall A K, Mann D M, Sunshine J. The neural cell adhesion molecule (NCAM) as a regulator of cell-cell interactions. Science 240:53-57, 1988.

Rutishauser U. NCAM and its polysialic acid moiety: a mechanism for pull/push regulation of cell interactions during development? Dev Suppl 99-104, 1992.

Rubak J M. 1982. Reconstruction of articular cartilage defects with free periosteal grafts. Acta Orthop Scand 53:175-179.

Saito, T., Dennis, J. E., Lennon, D. P., Young, R. G., Caplan, A. I. (1995) Myogenic expression of mesenchymal stem cells within myotubes of mdx mice in vitro and in vivo. Tiss. Eng. 1:327-343.

Sambrook J., Fritch E F, Maniatis T. In: Molecular Cloning, A Laboratory Manual. Cold Spring, N.Y.: Cold Springs Harbor Laboratory Press, pp. 7.3-7.84, 1989.

Satoh, T., Endo, M., Nakafuku, M., Nakamara, S., and Kaziro, Y. (1990) Platelet-derived growth factor stimulates formation of active p21ras. GTP complex in Swiss mouse 3T3 cells. Proc. Natl. Acad. Sci. USA 87:5993-5997.

Schilling, J A, Joel, W, Shurley, H M. Wound healing: A comparative study of the histochemical changes in granulation tissue contained in stainless steel wire mesh and polyvinyl sponge cylinders. Surgery 1959; 46:702-710.

Schilling, J A, White, B N, Lockhart, M S, Shurley, H M. Wound healing in the dog: Radioisotope studies of developing connective tissue in the fluid of an artificial deadspace. Am J. Surg. 1969; 117:330-337.

Schiwek O R, Loffler G. Glucocorticoid hormones contribute to the adipocyte activity of human serum. Endocrinology 1987; 120:469-474.

Scott, R. E., and Maercklein, P. B. (1984) An initiator of carcinogenesis selectively and stably inhibits stem cell differentiation: A concept that initiation of carcinogenesis involves multiple phases. Proc Natl Acad Sci USA 82:2995-2999.

Seppa H, Grotendorst G, Seppa S, Schiffmann E, Martin G R. Platelet-derived growth factor is chemotactic for fibroblasts. The J of Cell Biology 1982; 92:584-8.

Shah M, Foreman D M, Ferguson M W J. Control of scarring in adult wounds by neutralising antibody to transforming growth factor β. Lancet. 1992; 339:213-4.

Shah M, Foreman D M, Ferguson M W J. Neutralising antibody to TGF-$β_{1,2}$ reduces cutaneous scarring in adult rodents. J Cell Sci. 1994; 107:1137-57.

Shah M, Foreman D M, Ferguson M W J. Neutralisation of TGF-β1 and TGF-β2 or exogenous addition of TGF-β3 to cutaneous rat wounds reduces scarring. J Cell Sci. 1995; 108:985-1002.

Shamblott, M. J. et al. Derivation of pluripotent stem cells from cultured human primordial germ cells. Proc. Natl. Acad. Sci. USA 95, 13726-13731 (1998).

Shipp M A, Vijayaraghavan J, Schmidt E V, Masteller E L, D'Adamio L, Hersh L B, Reinherz E L. Common acute leukemia antigen (CALLA) is active neutral endopeptidase 24.11 ("enkephalinase"): direct evidence by cDNA transfection analysis. Proc Natl Acad Sci USA 86:297-301, 1989.

Shipp M A, Stefano G B, Switzer S N, Griffin J D, Reinherz E L. CD10 (CALLA)/neutral endopeptidase 24.11 modulates inflammatory peptide-induced changes in neutrophil morphology, migration, and adhesion proteins and is itself regulated by neutrophil activation. Blood 78:1834-1841, 1991.

Simmons D L, Satterthwaite A B, Tenen D G, Seed B. Molecular cloning of a cDNA encoding CD34, a sialomucin of human hematopoietic stem cells. J Immun 148:267-271, 1992.

Sinnet-Smith, J., Lehmann, W., and Rozengurt, E. (1990) Bombesin receptor in membranes from Swiss 3T3 cells. Binding characteristics, affinity labelling and modulation by guanine nucleotides. Biochem. J. 265:485-493.

Skoog T, Johansson S H. 1976. The formation of articular catilage from free perichondrial grafts. Plast Reconstr Surg 57:1-6.

Snow M H. An autoradiographic study of satellite cell differentiation into regnerating myotubes following transplantation of muscle in young rats. Cell Tiss Res. 1978; 186:535-540.

Sparks, R. L, Strauss, E. E., Zygmunt, A. I., and Phelan, T. E. (1991) Antidiabetic AD4743 enhances adipocyte differentiation of 3T3 T Mesemchymal stem cells. Journal of Cellular Physiology 146:101-109.

Sparks, R. L., Allen, B. J., Zygmunt, A. I., and Strauss, E. E. (1993) Loss of differentiation control in transformed 3T3 T proadipocytes. Cancer Res. 53:1770-1776.

Springfield D. Surgical wound healing. In: Verweij J, Pinedo H M, Suit H D, eds. Multidisciplinary Treatment of Soft Tissue Sarcoma. Kluwer Academic Publishers, 1993:81-98.

Strates B S, Connolly J F. Osteogenesis in cranial defects and diffusion chambers: Comparison in rabbits of bone matrix, marrow, and collagen implants. Acta Orthop Scand 1989; 60:200-3.

Sutherland D R, Stewart A K, Keating A. CD34 antigen: molecular features and potential clinical applications. Stem Cells 11:50-57, 1993.

Taylor, S. M. and Jones, P. A. (1979) Multiple new phenotypes induced in 10T½ and 3T3 cells treated with 5-azacytidine. Cell 17:771-779.

Taylor, S. M. and Jones, P. A. (1982) Changes in phenotypic expression in embryonic and adult cells treated with 5-Azacytidine. Journal of Cellular Physiology 111: 187-194.

Teplitz R L. Ataxia telangiectasia. Arch Neurol 35:553-554, 1978.

Theis R S, Bauduy M, Ashton B A, Kurtzberg L, Wozney J M, Rosen V. Recombinant human bone morphogenetic protein-2 induces osteoblastic differentiation in W-20-17 stromal cells. Endocrinology 1992; 130(3): 1318-23.

Thomas, J. T., Kilpatrick, M. W., Lin, K., Erlacher, L., Lembessis, P., Costa, T., et. al. (1997) Disruption of human limb morphogenesis by a dominant negative mutation in CDMP1. Nat Genet 17(1):58-64.

Thomson, J. A. et al., Isolation of a primate embryonic stem cell line. Proc. Natl. Acad. Sci. USA 92, 7844-7848 (1995).

Thomson, J. A., et al. Embryonic stem cells derived from human blastocysts. Science 282, 1145-1147 (1998).

Tiveron M C, Barboni E, Pliego Rivero F B, Gormley A M, Seeley P J, Grosveld F, Morris R. Selective inhibition of neurite outgrowth on mature astrocytes by Thy-1 glycoprotein. Nature 355:745-748, 1992.

Todaro, G. and Green, H. (1963) Quantitative studies of the growth of mouse embryo cells in culture and their development into established cell lines. J. Cell Biol. 17:299-313.

Todaro G., Green, H., and Goldberg, B. D. (1964) Transformation properties of an established cell line by SV40 and polyoma virus. Proc. Natl. Acad. Sci. USA 51:66-73.

Troum, S., Estes, R., Rogers, J. J., Young, H. E., Lucas, P. A.: Swiss-3T3 cells exhibit multiple phenotypes with dexamethasone treatment. Clinical Research 41:350A, 1993.

Tsukamoto A S, Reading C, Carella A, Frassoni F, Gorin C, LaPorte J, Negrin R, Blume K, Cunningham I, Deisseroth A. Biological characterization of stem cell present in mobilized peripheral blood of CML patients. Bone Marrow Transplant 14 Suppl. 3:S25-S32, 1994.

Urist M R. Bone: formation by autoinduction. Science 1965; 150:893-899.

Urist M R, Terashima Y, Nakagawa M, Stamos, C. Cartilage tissue differentiation from mesenchymal cells derived from mature muscle in tissue culture. In Vitro 1978; 14:697-706.

Urist M R. Bone morphogenetic protein, bone regeneration, heterotopic ossification and the bone-bone marrow consortium. Bone Min Res. 1989; 6:57-112.

Vierck, J. L., McNamara, J. P., Dodson, M. V. Proliferation and differentiation of progeny of ovine unilocular fat cells (adipofibroblasts). In Vitro Cell Dev Biol-Animal 32:564-572, 1966.

Vilamitjana-Amedee J. Bareille R, Rouais F, Caplan A I, Harmand M F. Human bone marrow stromal cells express an osteoblastic phenotype in culture. In Vitro Cell Dev Biol Anim 1993; 29A(9):699-707.

Voyta J C, Via D P, Butterfield E, Zetter B R. Identification and isolation of endothelial cells based on their increased uptake of acetylated-low density lipoprotein. J Cell Biol 1984; 99:2034-2040.

Wakitani S, Kimura T, Hirooka A, Ochi T, Yoneda M, Yasui N, Owaki H, Ono K. 1989. Repair of rabbit articular surfaces with allograft chondrocytes embedded in collagen gel. J Bone Joint Surg Br 71:74-80.

Wakitani, S., Goto, T., Pineda, S. J., Young, R. G., Mansour, J. M., Caplan, A. I., Goldberg, V. M. (1994) Mesenchymal cell-based repair of large, full-thickness defects of articular cartilage. J. Bone Joint Surg. Am. 76:579-592.

Warejcka, D. J., Harvey, R., Taylor, B. J., Young, H. E., Lucas, P. A. (1996) A population of cells isolated from rat heart capable of differentiating into several mesodermal phenotypes. J. Surg. Res. 62:233-242.

Wang E A, Rosen V, D'Alessandro J S, Bauduy M, Cordes P, Harada T, Israel D I, Hewick R M, Kerns D M, LaPan P, Luxenberg D P, McQuaid D, Moutsatsos I K, Nove J, Wozney J M. Recombinant human bone morphogenetic protein induces bone formation. Proc Natl Acad Sci USA 1990; 87:2220-2224.

Weber M, Uguccioni M, Baggiolini M, Clark-Lewis I, Dahinden C A. Deletion of the NH2-terminal residue converts monocyte chemotactic protein 1 from an activator of basophil mediator release to an eosinophil chemoattractant. J Exp Med 183:681-685, 1996.

Weintroub S, Weiss J F, Catravas G N, Reddi A H. Influence of whole body irradiation and local shielding on matrix-induced endochondral bone differentiation. Calcif Tissue Int. 1990; 46:38-45.

Weiss R E. Reddi A H. Synthesis and localization of fibronectin during collagenous matrix-mesenchymal cell interaction and differentiation of cartilage and bone in vivo. Proc Natl Acad. Sci. 1980; 77:2074-8.

Weiss R E, Reddi A H. Role of fibronectin in collagenous matrix-induced mesenchymal cell Res. 1981; 133:247-54.

Wier M L, Scott R E. Regulation of the Terminal Event in Cellular Differentiation: biological mechanisms of the loss of proliferative potential. J of Cell Biology 1986; 102: 1955-64.

Yan, D. H. and Hung, M. C. (1993) Differential activity of the RVF enhancer element in the decreased expression of the neu oncogene in NR-6 cells versus parental Swiss Webster 3T3 cells. Mol. Carcinog. 7:44-49.

Yang, B. S., Gilbert, J. D., and Freytag, S. O. (1993) Overexpression of Myc suppresses CCAAT transcription factor/nuclear factor 1-dependent promoters in vivo. Mol. Cell. Biol. 13:3093-3102.

Yates, A. J., VanBrocklyn, J., Saqr, H. E., Guan, Z., Stokes, B. T., And O'Dorisio, M. S. (1993) Mechanisms through which gangliosides inhibit PGDF-stimulated mitogenesis in intact Swiss 3T3 cells: receptor tyrosine phosphorylation, intracellular calcium, and receptor binding. Exp. Cell Res. 204:38-45.

Young H E. 1983. A Temporal Examination of Glycoconjugates During the Initiation Phase of Limb Regeneration in Adult Ambystoma. Lubbock: Tex. Tech University Library Press, Lubbock, Tex.

Young, H. E., Dailey, B. K., Markwald, R. R.: Glycoconjugates in normal wound tissue matrices during the initiation phase of limb regeneration in adult Ambystoma. Anatomical Record, 223:223-230, 1989a.

Young H E, Dailey B K, Markwald R R. 1989b. Effect of selected denervations on glycoconjugate composition and tissue morphology during the initiation phase of limb regeneration in adult Ambystoma. Anat Rec 223:231-241.

Young H E, Young V E, Caplan A I. 1989c. Comparison of fixatives for maximal retention of radiolabeled glycoconjugates for autoradiography, including use of sodium sulfate to release unincorporated [$^{35}$S]sulfate. J Histochem Cytochem 37:223-228.

Young H E, Carrino D A, Caplan A I. 1989d. Histochemical analysis of newly synthesized and resident sulfated glycosaminoglycans during musculogenesis in the embryonic chick leg. J Morph 201:85-103.

Young, H. E., Morrison, D. C., Martin, J. D., and Lucas, P. A.: Cryopreservation of embryonic chick myogenic lineage-committed stem cells. Journal of Tissue Culture Methods, 13:275-284, 1991.

Young, H. E., Ceballos, E. M., Smith, J. C., Lucas, P. A., Morrison, D. C.: Isolation of embryonic chick myosatellite and pluripotent stem cells. Journal of Tissue Culture Methods, 14:85-92, 1992a.

Young, H. E., Sippel, J., Putnam, L. S., Lucas, P. A., Morrison, D. C.: Enzyme-linked immuno-culture assay. Journal of Tissue Culture Methods, 14:31-36, 1992b.

Young, H. E., Ceballos, E. M., Smith, J. C., Mancini, M. L., Wright, R. P., Ragan, B. L., Bushell, I., Lucas, P. A. Pluripotent mesenchymal stem cells reside within avian connective tissue matrices. In Vitro Cellular & Developmental Biology, 29A:723-736, 1993.

Young, H. E., Mancini, M. L., Wright, R. P., Smith, J. C., Black, A. C., Jr., Reagan, C. R., Lucas, P. A. Mesenchymal stem cells reside within the connective tissues of many organs. Developmental Dynamics 202:137-144, 1995.

Young, R. G., Butler, D. L., Weber, W., Caplan, A. I., Gordon, S. L., Fink, D. J. (1998) Use of mesenchymal stem cells in a collagen matrix for Achilles tendon repair. J. Orthop. Res. 16(4):406-413.

Young, H. E., Wright, R. P., Mancini, M. L., Lucas, P. A., Reagan, C. R., Black, A. C., Jr.: Bioactive factors affect proliferation and phenotypic expression in pluripotent and progenitor mesenchymal stem cells. Wound Rep Reg 6(1):65-75, 1998a.

Young, H. E., Rogers, J. J., Adkison, L. R., Lucas, P. A., Black, A. C., Jr. (1998b) Muscle morphognetic protein induces myogenic gene expression in Swiss-3T3 cells. Wound Rep Reg 6(5): 543-554.

Young, H. E., Steele, T., Bray, R. A., Detmer, K., Blake, L. W., Lucas, P. A., Black, A. C., Jr. Human progenitor and pluripotent cells display cell surface cluster differentiation markers CD10, CD13, CD56, and MHC Class-I. Proc. Soc. Exp. Biol. Med. 221: 63-71, 1999.

Zachary, I., Gil, J., Lehmann, W, m Sinnett-Smith, J., and Rozengurt, E. (1991) Bombesin, vasopressin, and endothelin rapidly stimulate tyrosine phosphorylation in intact Swiss 3T3 cells. Proc. Natl. Acad. Sci. USA 88:4577-4581.

Zimmerman B, Cristea R. Dexamethasone induces chondrogenesis in organoid culture of cell mixtures from mouse embryos. Anat Embryol. 1993; 187:67-73.

Zipori D. Stromal cells from the bone marrow: evidence for a restrictive role in regulation of hemopoiesis. Eur J Haematol 1989; 42:225-32.

Example 11

Clonogenic Analysis Reveals Reserve Pluripotent Epiblastic-Like Stem Cells in Postanal Animals Abstract A previous study using serial dilution clonogenic analysis reported the existence of a clonal population of reserve pluripotent mesenchymal stem cells (PPMSC) isolated from connective tissues associated with postnatal rat skeletal muscle. The current study, also using serial dilution clonogenic analysis, reports the existence of another clonal population of pluripotent stem cells. Comparison analysis between these two clonal cell lines demonstrates similarities and differences. Both clonal cell lines are lineage-uncommitted, as determined by an insulin/dexamethasone bioassay. Both clonal cell lines remain quiescent in serum-free media unless activated by exogenous agents. And both clonal cell lines are capable of extended self-renewal, past Hayflick's limit. The PPMSC clone is contact inhibited at confluence. In contrast, the clone reported herein is not contact inhibited and will continue proliferating past confluence. While both clonal cell lines will form cells of mesodermal origin (i.e., skeletal muscle, smooth muscle, fat, cartilage, bone), the clone reported herein will also form cells of ectodermal (i.e., neuronal stem cells, neurons), and endodermal (i.e., liver hepatocyte) origin. Because of its potential to form cells from all three primary germ layers, we have designated this postnatal rat clone as a pluripotent epiblastic-like stem cell. This study suggests the retention of embryonic-like reserve stem cells within postnatal mammals and their potential involvement in the normal maintenance, repair and regeneration of body tissues.

Introduction

Embryonic stem cells have been identified in the blastocyst, inner cell mass and gonadal ridges of rodents and primates, including humans (Evans et al., 1981; Martin, 1981; Thomson et al., 1995, 1998; Shamblott et al., 1998; Gearhart et al, 1999). After isolation these undifferentiated cells express immunological markers for embryonic stem cell antigens, positive alkaline phosphatase staining, capabilities for extended self-renewal, and telomerase activity. When allowed to differentiate in vitro these cells express immunological markers for tissues of ectodermal, mesodermal, and endodermal origin (Thomson et al., 1995, 1998; Shamblott et al., 1998; Gearhart et al, 1999). However, when implanted in vivo the embryonic stem cells form spontaneous teratomas (Thomson et al., 1998; Gearhart et al., 1999). Because of these unique qualities embryonic stem cells have been proposed as a source of donor cells for tissue transplantations (Thomson et al., 1995, 1998; Shamblott et al., 1998; Gearhart et al, 1999).

The current clonogenic study was undertaken to determine whether clonal populations of pluripotent stem cells were present in the connective tissues of postnatal mammals and to examine their functional capabilities. We previously reported (Young et al., 2000a) the existence of a pluripotent mesenchymal stem cell (PPMSC) clonal population, i.e., Clone-A2A2, isolated from connective tissues associated with postnatal rat skeletal muscle. The PPMSC clonal line was lineage-uncommitted, remained quiescent in serum-free media unless activated by exogenous agents, had extended capabilities for self-renewal, was contact inhibited at confluence, and only formed tissues from the mesodermal lineage, i.e., muscle, fat, cartilage, and bone. The current study reports the existence of a second clonal population of pluripotent stem cells derived from postnatal rat connective tissues. This clonal cell line is also lineage uncommitted, will remain quiescent in serum-free media, expresses both alkaline phosphatase and telomerase activity, has extended capabilities for self-renewal, and has its own unique differentiative capabilities.

Materials and Methods

Postnatal Rat Connective Tissue-Derived Stem Cells

The skeletal muscle from postnatal Sprague-Dawley rats was processed for the isolation of mononucleated cells, plating, propagation to confluence, trypsin release, and cryopreservation (Young et al., 2000a). Cells were repeatedly thawed and expanded until 50 cell doublings had been reached (Young et al., 1991, 1993, 1998b; Young, 2000). Individual clones were generated by serial dilution clonogenic analysis (Young et al., 2000a). Each round of cloning resulted in approximately 20 cell doublings. Thus, four clonings resulted in approximately 80 cell doublings in the resultant clones. The resultant clones were propagated, released with trypsin, aliquoted, and cryopreserved (Young et al., 1993, 1998a, 2000a; Rogers et al., 1995). The clone reported herein was designated as Rat-A2B2 and was extensively examined for pluripotency after 130 cell doublings.

Insulin-Dexamethasone Analysis for Differentiative Capabilities

Rat-A2B2 was examined using serum-free medium and serum-free medium containing insulin and dexamethasone to determine its identity as either a lineage-committed progenitor stem cell or a lineage-uncommitted pluripotent stem cell. Progression factors, such as insulin, insulin-like growth factor-I, and insulin-like growth factor-II, accelerate phenotypic expression in progenitor cells but have no effect on the induction of phenotypic expression in pluripotent stem cells (Young et al., 1993, 1998b; Young, 2000). By contrast, lineage-induction agents, such as dexamethasone, bone morphogenetic protein-2, and muscle morphogenetic protein, induce lineage-commitment and expression in pluripotent cells, but do not alter phenotypic expression in progenitor cells (Young et al., 1993, 1998a,b, 1999, 2000a; Young, 2000). Therefore, if progenitor cells alone are present in the culture there will be no difference in the expressed phenotypes for cultures incubated in insulin compared with those incubated with dexamethasone. If the culture is mixed, containing both progenitor and pluripotent cells, then there will be a greater variation in the phenotypes expressed in cultures treated with dexamethasone compared with those treated with insulin. If the culture contains pluripotent cells alone, there will be no expressed phenotypes in cultures treated with insulin. Similar cultures treated with dexamethasone will exhibit the expression of multiple phenotypes. Thus, by comparing the effects of treatment with dexamethasone and insulin, one can identify specific types of progenitor and pluripotent cells within an unknown population of cells (Young et al., 1992, 1995; Lucas et al., 1993, 1995; Pate et al., 1993; Rogers et al., 1995; Warejcka et al., 1996).

The Rat-A2B2 clonal cell line was plated in complete medium (Young et al., 2000a), allowed 24 hr to attach, transferred to serum-free testing medium for 24 hr to wash out any potential synergistic components in the complete medium, and then the testing medium was changed to one of the following. For controls, the serum-free testing medium alone was used. To identify progenitor stem cells, 2 mg/ml insulin (Sigma, St. Louis, Mo.) was added to the testing medium. To identify pluripotent stem cells, $10^{-10}$ to $10^{-6}$ M dexamethasone (Sigma) was added to the testing medium. To further identify pluripotent stem cells, selected sera known to contain multiple inductive agents (Young et al., 1998a,b) were added to testing medium containing 2 mg/ml insulin and $10^{-6}$ M dexamethasone. The selected sera used were HS9 (90H-0701, Sigma) and HS10 (MorphoGen Pharmaceuticals, Inc., San Diego, Calif.). Control and treated cultures were propagated for an additional 30-45 days with medium changes every other day. Three to six culture wells were used per concentration per experiment. During the 30-45 day time period the cultures were examined daily, using subjective analysis of the morphology of the cells. The changes in morphology noted in this study were based on extensive examination from previous studies (Young et al., 1991, 1992a,b, 1993, 1995, 1998a,b, 1999, 2000a,b; Young, 2000). Alterations in phenotypic expression (see below) were correlated with the days of treatment, and concentrations of exogenous agents utilized.

The experiments were then repeated utilizing these parameters to confirm objectively the presence of various established markers for phenotypic expression using previously established histochemical and immunochemical procedures (review, Young et al., 1992b, 1998a,b, 1999, 2000a; Young, 2000). Cultures were processed per manufacturer's directions or as described (Young et al., 1992b, 2000a). The cells were photographed using a Nikon TMS inverted phase contrast/brightfield microscope.

Morphological, Histochemical, and Immunocytochemical Analyses

Our standard morphological bioassay (Young et al., 1998a,b, 1999, 2000a; Young, 2000) for mesodermal phenotypes was increased to include potential differentiated cell types belonging to ectodermal and endodermal lineages. The cultures were screened for the following morphologies throughout the assay.

Putative embryonic-like stem cells were tentatively identified by their relative small size and their large nuclear to cytoplasmic ratio. Verification was accomplished utilizing alkaline phosphatase (Vector Laboratory) histochemistry.

Putative neurons were tentatively identified as mononucleate cells with multiple fine "spidery" cell processes. Neuronal associated cell types were verified by immunochemical staining using antibodies specific for phenotypic markers of the neuroectodermal lineage. These antibodies stained epitopes characteristic for neural precursor cells [FORSE-1, DSHB (Tole et al., 1995a,b)], nestin [RAT-401, DSHB (Hockfield and McKay, 1985)], neurofilaments [RT97, DSHB (Wood and Anderton, 1981)], neurons [8A2, DSHB (Drazba et al., 1991)], and oligodendrocytes [Rip, DSHB( )]. Epithelial associated cell types were verified by immunochemical staining for epithelial growth factor receptor [151-Ig, DSHB].

Putative myoblasts were tentatively identified as mononucleated bipolar-shaped cells. The myoblast phenotype was confirmed using an antibody for myogenin [F5D, DSHB (Wright et al., 1991)].

Putative skeletal myotubes were tentatively identified as multinucleated linear and branched cells. The skeletal muscle phenotype was verified by antibody staining for sarcomeric myosin [MF-20, DSHB (Bader et al., 1982)], fast-skeletal muscle myosin [MY-32, Sigma (Naumann and Pette, 1994)], myosin heavy chain [ALD-58, DSHB (Shafiq et al., 1984)], and myosin fast chain [A4.74, DSHB (Webster et al., 1988)].

Putative smooth muscle cells were tentatively identified as mononucleated polygonal-shaped cells with intracellular filaments. The smooth muscle phenotype was confirmed by antibody staining for smooth muscle alpha-actin [1A4, Sigma (Skalli et al., 1986)].

Putative fat cells were tentatively identified as mononucleated cells with intracellular refractile vesicles. Adipocytes were verified by the presence of saturated neutral lipid-containing intracellular vesicles via histochemical staining with Sudan Black-B (Chroma-Gesellschaft, Roboz Surgical Co, Washington, D.C.) and Oil Red-O (Sigma) (Young et al., 1998a,b, 1999, 2000a; Young, 2000).

Putative cartilage nodules were tentatively identified as aggregates of rounded cells containing pericellular matrix halos. Cartilage nodules were confirmed by both histochemical and immunochemical staining. Histochemically, cartilage nodules were visualized by staining proteoglycans containing glycosaminoglycan side chains with chondroitin sulfate and keratan sulfate in the pericellular and/or extracellular matrix. This was accomplished using Alcian Blue (Alcian Blau 8GS, Chroma-Gesellschaft, Roboz Surgical Co.) or Safranin-O (Chroma-Gesellschaft) at pH 1.0. Verification of glycosaminoglycans specific for cartilage located in the extracellular matrix was confirmed by the loss of staining following digestion of the material with chondroitinase-AC (ICN Biomedicals, Cleveland, Ohio) and keratanase (ICN Biomedicals) (Young et al., 1989a,b, 1993, 1998a,b, 1999, 2000a; Young, 2000). Immunochemically, the chondrogenic phenotype was confirmed by first intracellular followed by extracellular staining for antibodies to type-II collagen [CIIC1, DSHB (Holmdahl et al., 1986)] and type-IX collagen [D1-9, DSHB (Ye et al., 1991)].

Putative bone nodules were tentatively identified as aggregates of rounded cells overlain with dense three-dimensional matrices. Bone nodules were confirmed by both histochemical and immunochemical staining. Histochemically, osteogenic phenotypes were verified by positive staining of the extracellular matrix for calcium phosphate using the von Kossa (Silber Protein, Chroma-Gesellschaft) procedure. Verification of the presence of calcium phosphate in the extracellular matrix was confirmed by the disappearance of positive staining by the von Kossa procedure following pre-treatment with EGTA (Ethyleneglycol-bis-[b-Aminoethyl ether] N, N, N',N'-tetraacetic acid, Sigma), a specific calcium chelator (Young et al., 1998a,b, 1999, 2000a; Young, 2000). Immunocytochemically, the osteogenic phenotype was confirmed by first intracellular followed by extracellular staining for antibodies to bone sialoprotein [WV1D1, DSHB (Kasugai et al., 1992)] and osteopontine [MP111, DSHB (Gorski et al., 1990)].

Putative liver hepatocytes were tentatively identified as mononucleated cells with intracellular vesicles containing non-refractile material. The hepatocytic phenotype was verified by antibody staining for alpha-fetoprotein [RAFP, Chemicon (Mujoo et al., 1983)].

Lastly, the cultures were also stained for rat-specific major histocompatibility complex-I [RMHC-I, Chemicon (Rubin et al., 1984; Prabhala and Wira, 1995)] which is characteristic of differentiated rat cells.

Secondary antibodies consisted of biotinylated anti-sheep IgG (Vector), biotinylated anti-mouse IgG (Vector Laboratory, City, State), or contained within the Vecstatin ABC Kit (Vector). The tertiary probe consisted of avidin-HRP contained within the Vecstatin ABC Kit (Vector). The insoluble HRP substrates VIP Substrate Kit for Peroxidase (blue, Vector), DAB Substrate for Peroxidase (black, Vector), and AEC Staining Kit (red, Sigma) were used to visualize antibody binding. Different colored substrates were utilized to allow for multiple sequential staining of the same culture wells.

Antibodies

The following antibodies: FORSE-1 developed by P. Patterson, RAT-401 developed by S. Hockfield, RT-97 developed by J. Wood, 8A2 developed by V. Lemmon, Rip was developed by S. Hockfield, 151-Ig was developed by A. Hubbard, F5D developed by W. E. Wright, MF-20 developed by D. A. Fischman, ALD-58 was developed by D. A. Fischman, A4.74 was developed by H. M. Blau, CIIC1 developed by R. Holmdahl and K. Rubin, D1-9 developed by X.-J. Ye and K. Terato, WV1D1 developed by M. Solursh and A. Frazen, and MP111 developed by M. Solursh and A. Frazen were obtained from the Developmental Studies Hybridoma Bank developed under the auspices of the NICHD and maintained by The University of Iowa, Department of Biological Sciences, Iowa City, Iowa 52242.

Capability for Extended Self-Renewal.

Starting at 130 cell doublings, the Rat-A2B2 clone was thawed and plated at 100×103 cells per gelatinized T-25 flask. Cells were propagated to post confluence (7-8 days) and released with trypsin (Young et al., 1999, 2000a). Cell numbers ranged from 5 to 6.5×106 cells per flask, or 5-6 cell doublings per passage. Doubling time averaged 18-24 hr. Cells were aliquoted at approximately 1-11×106 cells/ml and cryopreserved. The procedure of propagation past confluence, release with trypsin, and cryopreservation was repeated through 12 additional passages, or 68 cell doublings after cloning. This coupled with the 130 cell doubling starting number resulted in a clone of cells having undergone 198 cell doublings. At each passage interval from 130 to 198 cell doublings, cell aliquots were incubated with insulin and dexamethasone for 30-45 days and examined morphologically, histochemically, and immunochemically.

Telomerase Assay.

Rat-A2B2 at 198 cell doublings was assayed for telomerase activity. Cells were thawed, plated at 100×103 cells per gelatinized T-75 flask, and grown past confluence. Cells were harvested by trypsin release (Young et al., 1999) and the cells processed for telomerase activity as described by manufacturer in Telomerase detection kit (Qiagen kit).

Results

Differentiation Capabilities

Rat-A2B2 clonal cell line was analyzed before and after incubation with insulin, dexamethasone, and/or selected sera in both the original (130 cell doublings) and expanded (130 to 198 cell doubling) comparison/contrast analysis systems. Observation of cultures 24 hr after plating revealed very small cells, about ¼ to ½ the cell size of the clone-A2A2 (PPMSC) cell line. These smaller cells displayed large ratios of nucleus to cytoplasm. Incubation of the Rat-A2B2 clone in serum-free testing medium for six weeks resulted in no appreciable increase in cell numbers and an equivalent morphology to cells viewed 24 hr after plating. Incubation of the Rat-A2B2 clone in testing medium with insulin for 6 weeks resulted in multiple layers of nondescript cells demonstrating loss of contact inhibition. The multiple cell layers demonstrated positive staining for alkaline phosphatase activity (TABLE 14). In contrast, incubation of Rat-A2B2 in testing medium with dexamethasone, testing medium with dexamethasone+insulin, or testing medium with dexamethasone+insulin+selected sera resulted in loss of alkaline phosphatase staining, but expression of differentiated phenotypes. Cells exhibiting markers for ectodermal, mesodermal, and endodermal lineages were observed. For example, cells displaying ectodermal lineage markers were identified using antibodies for neural precursor cells, nestin, neurofilaments, neurons, oligodendrocytes, and epithelial growth factor receptor. Cells displaying mesodermal lineage markers were identified using antibodies or histochemical stains for myogenin, sarcomeric myosin, fast skeletal muscle myosin, myosin heavy chain, myosin fast chain, and smooth muscle actin for the myogenic lineages; saturated neutral lipids for adipocytes; type-II collagen, type-IX collagen, and cartilage nodules containing sulfated proteoglycans for the chondrogenic lineage; and bone sialoprotein, osteopontine, and bone nodules containing calcium phosphate for the osteogenic lineage. Cells displaying an endodermal lineage marker were identified using antibodies for liver hepatocytes. All treatments eliciting ectodermal, mesodermal, and endodermal lineage cell types induced the rat-specific major histocompatibility complex-I (RMHC-1) epitope identifying them as differentiated cells (TABLE 1).

Extended Self-Renewal

Rat-A2B2 was assayed at each of 12 passages post 130 cell doublings to determine capability for extended self-renewal while maintaining their pluripotent state. After each passage the Rat-A2B2 clone was processed as above in the insulin/dexamethasone bioassay. Results were equivalent and indistinguishable at all passage levels assayed.

Telomerase Activity

Rat-A2B2 was assayed at 198 cell doublings for the presence or absence of telomerase activity. As shown in FIG. 2, telomerase activity was present at relatively high levels in the stem cells at this 198 cell doubling number.

Discussion

Postnatal Pluripotent Stem Cell

Serial dilution clonogenic analysis of cells isolated from the connective tissues associated with skeletal muscle of postnatal rats generated multiple clones. One of the clones, designated Rat-A2B2, was examined in this study. Rat-A2B2 did not exhibit alteration of its stellate morphology following long-term incubation with or without insulin (TABLE 14). The lack of response to either serum-free medium or insulin suggested that the clone was not a lineage-committed progenitor stem cell (Young et al., 1998a, b, 1999, 2000a; Young, 2000). In contrast, expression by these cells of alkaline phosphatase activity suggested that these cells share some attributes with embryonic stem cells (Thomas et al., 1998; Gearhart et al., 1999). Indeed, incubation with dexamethasone with or without insulin and selected sera elicited alterations in phenotypic expression (TABLE 14). These results suggested that the clone was some form of lineage-uncommitted pluripotent stem cell. In contrast to the PPMSC clone-A2A2 (Young et al., 2000a) which demonstrated only mesodermal differentiated cell types, the phenotypic alterations noted with Rat-A2B2 were shown for all three primary germ layers, i.e., ectoderm, mesoderm, and endoderm (TABLE 14). Phenotypic alterations noted included the appearance of neural precursor cells, nestin, neurofilaments, neurons, oligodendrocytes, epithelial growth factor receptor, myoblasts, skeletal muscle, smooth muscle, fat cells, cartilage, bone, and liver hepatocytes. All treatments eliciting ectodermal, mesodermal, and endodermal lineage cell types also induced the rat-specific major histocompatibility complex-I (RMHC-1) epitope identifying differentiated cells (TABLE 14). When the clone was tested for extended self-renewal we noted no deviation in its differentiation potential. Lastly, at 198 cell doublings Rat-A2B2 demonstrated telomerase activity.

Because of its expression of alkaline phosphatase activity, potential for extended self-renewal, expression of telomerase activity, and potential to form differentiated cells from all three primary germ layers, we have designated this postnatal rat clone, Rat-A2B2, as a pluripotent epiblastic-like stem cell (PPELSC).

As discussed previously, embryonic stem cells demonstrate alkaline phosphatase activity, the capacity for extended self-renewal, telomerase activity, spontaneous differentiation, and the ability to differentiate into cells of ectodermal, mesodermal, and endodermal origin (Thomson et al., 1995, 1998; Gearhart et al., 1999). Other aspects of embryonic stem cells were not directly addressed in this study. These aspects included immunological markers for embryonic stem cell antigens or formation of spontaneous teratomas when implanted in vivo (Thomas et al., 1995, 1998; Gearhart et al., 1999). However, data from this study (alkaline phosphatase activity, extended capabilities for self-renewal, telomerase activity, and ability to form cells from all three primary germ layers) suggests the possibility that "embryonic"-like reserve stem cells, i.e., pluripotent epiblastic-like stem cells, are retained within the connective tissue compartments of postnatal mammals.

Reserve Stem Cells within Postnatal Species

Previous clonogenic analyses (Young et al., 1993, 1998a, 2000a) coupled with this study suggest at least two general categories of reserve stem cells, lineage-committed progenitor cells and lineage-uncommitted pluripotent cells. Within each general category of reserve stem cell there also appear to be subcategories of stem cells. We and others have noted the presence of multiple types of lineage-committed progenitor stem cells, i.e., unipotent stem cells (Young et al., 1993; Grounds, 1999; Yotsuyanagi et al., 1999; Gordon et al., 2000), bipotent stem cells (Young et al., 1993; Bonner-Wier et al., 2000; Ramiya et al., 2000), tripotent stem cells (Prokop, 1997; Yoo et al., 1998; Pittenger et al., 1999), and multipotent stem cells (Palis and Segel, 1998; McGuire, 1998; Ratajczak et al., 1998). In these instances the progenitor stem cells form specific lineage-directed cell types and conform to Hayflick's limit (Hayflick, 1965), after which they undergo programmed cell senescence and death. We have also isolated and cloned lineage-uncommitted pluripotent mesenchymal stem cells (Young et al., 1993, 1998a, 2000a; Young, 2000; Rogers et al., 1995) and lineage-uncommitted pluripotent epiblastic-like stem cells (this study). These pluripotent stem cells are lineage uncommitted. These cells have extended capabilities for self-renewal as long as they remain lineage-uncommitted. The pluripotent stem cells remain quiescent unless acted upon by exogenous agents. These stem cells require inductive agents to commit them to any particular tissue lineage. The pluripotent stem cells will form anything downstream along their developmental pathway. Once pluripotent stem cells commit to a particular tissue lineage they will assume all the characteristics of lineage-committed progenitor stem cells, i.e., form lineage-restricted phenotypes and conform to Halfback's limit. Thus, this study suggests the retention of an embryonic-like reserve stem cell within postnatal mammals and their potential involvement in the normal maintenance, repair and regeneration of body tissues.

Based on the current and previous studies (Young et al., 1991, 1992a,b, 1993, 1995, 1998a,b, 1999, 2000a,b; Young, 2000; Grigoriadis et al., 1988; Caplan et al., 1993; Pate et al., 1993; Lucas et al., 1995, 1996; Rogers et al., 1995; Saito et al, 1995; Dixon et al., 1996; Warejcka et al., 1996; Clark et al., 2000), we would propose that there are at least ten categories of reserve stem cells present within postnatal animals, including humans. The proposed categories are pluripotent epiblastic-like stem cells, pluripotent ectodermal stem cells, pluripotent mesenchymal (mesodermal) stem cells, pluripotent endodermal stem cells, pluripotent neuronal stem cells, pluripotent epidermal stem cells, multipotent progenitor stem cells, tripotent progenitor stem cells, bipotent progenitor stem cells, and unipotent progenitor stem cells. We would also propose that one or more of these categories of reserve stem cells could and should be used for transplantation therapies. Indeed, there have been numerous reports concerning the use of reserve postnatal stem cells for transplantation therapies. For example, Grande et al. (1995) reported the implantation of adult pluripotent mesenchymal stem cells for the repair of cartilage and bone in a full thickness articular cartilage defect model. Eglitis and Mezey reported that hematopoietic cells differentiate into neuronal supportive cells in the brains of adult mice. Caplan et al. (1997; Wakitani et al., 1994) reported use of bone marrow stromal-derived mesenchymal stem cells for cartilage regeneration. Young et al. (R G Young et al., 1998) reported the use of bone marrow stromal-derived postnatal mesenchymal stem cells embedded in a collagen matrix for Achilles tendon repair. Asahara et al. (1999; Kalka et al., 2000) reported the use of endothelial progenitor cells for neovascularization. Bjornson et al. (1999) reported using adult neural stem cells to form blood cells. Bonner-Weir et al. (2000) and Ramiya et al. (2000) reported using preductal stem cells to form pancreatic insulin-secreting beta cells. Grounds (1999) reviewed the use of stem cells for muscle repair. Gussoni et al. (1999) reported the restoration of dystrophin expression in mdx mice by stem cell transplantation. Jackson and Goodell (1999) reported the hematopoietic potential of stem cells isolated from skeletal muscle. Niklason (1999; et al., 1999) reported the generation of blood vessels ex vivo using progenitor stem cells. Petersen et al. (1999) reported using bone marrow stem cells as a source for hepatic oval cells. Yotsuyanagi et al. (1999) reported the reconstruction of cartilage using stem cells from the perichondrium. Gordon et al. (2000) reported liver regeneration utilizing native resident stem cells.

TABLE 14

Phenotypic Analysis of Rat-A2B2 Clone Incubated in the Presence of Lineage-Inductive Agents

| Antibody | TM* | TM + Ins** | TM + Inductive Agents*** |
|---|---|---|---|
| No Primary | 0 | 0 | 0 |
| No Secondary | 0 | 0 | 0 |
| Tertiary | 0 | 0 | 0 |
| F5D | 0 | 0 | + |
| MF-20 | 0 | 0 | + |
| MY-32 | 0 | 0 | + |
| ALD-58 | 0 | 0 | + |
| A4.74 | 0 | 0 | + |
| IA4 | 0 | 0 | + |
| WV1D1 | 0 | 0 | + |
| MP111 | 0 | 0 | + |
| C11C1 | 0 | 0 | + |

TABLE 14-continued

Phenotypic Analysis of Rat-A2B2 Clone Incubated in the Presence of Lineage-Inductive Agents

| Antibody | TM* | TM + Ins** | TM + Inductive Agents*** |
|---|---|---|---|
| D19 | 0 | 0 | + |
| Forse-1 | 0 | 0 | + |
| RT-97 | 0 | 0 | + |
| 8A2 | 0 | 0 | + |
| Rat-401 | 0 | 0 | + |
| Rip | 0 | 0 | + |
| 151-Ig | 0 | 0 | + |
| R-AFP | 0 | 0 | + |
| R-MHC-1 | 0 | 0 | + |
| ORO | 0 | 0 | + |

*TM, testing medium, consisted of Opti-MEM + betamercaptoethanol + antibiotic/antimycotic, pH 7.4.
**TM + Ins, testing medium + insulin, consisted of testing medium containing 2 mg/ml insulin.
***TM + Inductive Agents, testing medium + inductive agents, consisted of testing medium containing one of the following combinations: 2 mg/ml insulin + 10-6M dexamethasone + 0.5% HS9; 2 mg/ml insulin + 10-6M dexamethasone + 1% HS9; 2 mg/ml insulin + 10-6M dexamethasone + 5% HS9; 2 mg/ml insulin + 10-6M dexamethasone + 10% HS9; 2 mg/ml insulin + 10-6M dexamethasone + 1% HS10; 2 mg/ml insulin + 10-6M dexamethasone + 5% HS10; 2 mg/ml insulin + 10-6M dexamethasone + 10% HS10; 2 mg/ml insulin + 10-6M dexamethasone + 1% MFCS1; 2 mg/ml insulin + 10-6M dexamethasone + 5% MFCS1; 2 mg/ml insulin + 10-6M dexamethasone + 10% MFCS1; 2 mg/ml insulin + 10-6M dexamethasone + 15% MFCS1; 2 mg/ml insulin + 10-6M dexamethasone + 1% HS9 + 3% HS7; 2 mg/ml insulin + 10-6M dexamethasone + 5% HS9 + 3% HS7; 2 mg/ml insulin + 10-6M dexamethasone + 10% HS9 + 3% HS7; 1% HS7, 3% HS7, and 3% HS7.

REFERENCES

Clarke D L, Johansson C B, Wilbertz J, Veress B, Nilsson E, Karlstrom H, Lendahl U, Frisen J. 2000. Generalized potential of adult neural stem cells. Science. 288:1660-1663.

Niklason L E 1999 Techview: medical technology. Replacement arteries made to order. Science 286(5444):1493-4.

Niklason L E, Gao J, Abbott W M, Hirschi K K, Houser S, Marini R, Langer R. 1999 Functional arteries grown in vitro. Science 284:489-93.

Young, H. E., Dailey, B. K., Markwald, R. R.: Glycoconjugates in normal wound tissue matrices during the initiation phase of limb regeneration in adult Ambystoma. Anatomical Record, 223:223-230, 1989a.

Young, H. E., Carrino, D. A., Caplan, A. I.: Histochemical analysis of newly synthesized and resident sulfated glycosaminoglycans during musculogenesis in the embryonic chick leg. Journal of Morphology, 201:85-103, 1989b.

Young H E, Morrison D C, Martin J D, Lucas P A. 1991. Cryopreservation of embryonic chick myogenic lineage-committed stem cells. J Tiss Cult Meth 13:275-284.

Young H E, Ceballos E M, Smith J C, Lucas P A, Morrison D C. 1992a. Isolation of embryonic chick myosatellite and pluripotent mesenchymal stem cells. J Tiss Cult Meth 14:85-92.

Young H E, Sippel J, Putnam L S, Lucas P A, Morrison D C. 1992b. Enzyme-linked immuno-culture assay. J Tiss Cult Meth 14:31-36.

Young H E, Ceballos E M, Smith J C, Mancini M L, Wright R P, Ragan B L, Bushell I, Lucas P A. 1993. Pluripotent mesenchymal stem cells reside within avian connective tissue matrices. In Vitro Cell Dev Biol Anim 29A:723-36.

Young H E, Mancini M L, Wright R P, Smith J C, Black A C Jr, Reagan C R, Lucas P A. 1995. Mesenchymal stem cells reside within the connective tissues of many organs. Dev Dynam 202: 137-144.

Young H E. Rogers J J, Adkison L R. Lucas P A, Black A C Jr. 1998a. Muscle morphogenetic protein induces myogenic gene expression in Swiss-3T3 cells. Wound Rep Reg 6(5):530-541.

Young H E, Wright R P, Mancini M L, Lucas P A, Reagan C R, Black A C Jr. 1998b. Bioactive factors affect proliferation and phenotypic expression in pluripotent and progenitor mesenchymal stem cells. Wound Rep Reg 6:65-75.

Young H E, Steele T A, Bray R A, Detmer K, Blake L W, Lucas P A, Black A C Jr. 1999. Human pluripotent and progenitor cells display cell surface cluster differentiation markers CD10, CD13, CD56, and MHC Class-I. Proc. Soc. Exp. Biol. Med. 221:63-71.

Young, H. E., Duplaa, C., Young, T. M., Floyd, J. A., Reeves, M. L., Davis, K. H., Mancini, G. J., Eaton, M. E., Hill, J. D., Thomas, K., Austin, T., Edwards, C., Cuzzourt, J., Parikh, A., Warren, J., Hudson, J., Black, A. C., Jr. 2000. Clonogenic analysis reveals reserve stem cells in postnatal mammals. I. Pluripotent mesenchymal stem cells. Anat. Rec. (accepted)

Young, H. E. Stem cells and tissue engineering. In: Gene Therapy in Orthopaedic and Sports Medicine, J. Huard and F. H. Fu, eds., Springer-Verlag New York, Inc., Chap. 9, pg. 143-173, 2000.

Young R G, Butler D L, Weber W, Caplan A I, Gordon S L, Fink D J. 1998. Use of mesenchymal stem cells in a collagen matrix for Achilles tendon repair. J Orthop Res 16:406-413.

Example 12

Implantation of Rat Pluripotent Epiblastic-Like Stem Cell Clone A2B2-scl-40 into Outbred Sprague-Dawley Rats does not Induce Graft Versus Host Disease Previous implantation studies using allogeneic donors demonstrate the induction of an inflammatory response within the host tissues. This response, designated graft-versus-host disease, occurs due to an HLA mismatch between donor and host tissues. The objective of this study was to determine if a rat pluripotent epiblastic-like stem cell clone, derived from postnatal out-bred Sprague-Dawley rats, would induce a graft-versus-host response in adult out-bred Sprague-Dawley rats.

The postnatal pluripotent epiblastic-like stem cell clone, designated A2B2-scl-40, was previously transfected with a stable genomic marker, the Lac-Z gene for beta-galactosidase expression, to track the stem cells both in vivo and in co-culture experiments in vitro. The A2B2-scl-40 stem cells were grown to confluence, harvested and processed for implantation. The stem cells were washed extensively with Dulbecco's phosphate buffered saline and 100 ml of buffer containing 1×106 stem cells (experimentals) or 100 ml buffer only (controls) were incubated with 5-mm3 pieces of sterile gel-foam for 24 hrs at 37° C. in a 95% air/5% CO2 humidified environment.

Experimental gel-foam (containing genomically-labeled stem cells) and control gel-foam (buffer only) were then randomly implanted into the right and left regions of the neck (between parotid gland and sternocleidomastoid muscle) of adult male out-bred Sprague-Dawley rats. Rats were then harvested 24 hrs after initial implantation and then at weekly intervals for five weeks thereafter. The animals were necropsied to ascertain for gross inflammatory response and the gel-foam implants removed with adherent tissues, cut into thirds and processed for histology (2 thirds) and cell culture (1 third). Necropsy results noted no gross inflammatory response in any animal examined. Histology results noted no large infiltration of inflammatory cells into either control or experimental gel-foam pieces. Tissue culture results noted ingrowth of pluripotent stem cells into the control gel-foam and retention of pluripotency by implanted Lac-Z-labeled stem cells in the experimental gel-foam throughout the entire length of the study.

Example 13

Isolation of Rat Pluripotent Stem Cells and Culture Expression of Neural Markers PPSCs were isolated from ROSA26 LacZ labeled mice (denoted ROSA26 PPSCs) and from rat skeletal muscle (denoted RmSC-1) according to the same protocol used for the isolation of PPMSCs and cultured in the same media used for PPMSCs, including the same selected horse serum (Lucas et al Wound Rep. Reg. 3:457-468). ROSA26 mice are transgenic mice expressing B-galactosidase and were obtained from Jackson Laboratories. RmSC-1 cells were isolated from skeletal muscle of male and female newborn rat pups as described in Lucas et al (Lucas et al Wound Rep. Reg. 3:457-468). In cultures of ROSA26 PPSCs and RmSC-1 PPSCs treated with dexamethasone, mesodermal phenotypes differentiated in the cultures alongside the neuronal cells—adipocytes, skeletal myotubes, chondrocytes, osteoblasts, etc. The isolation procedure used for PPMSCs is also capable of isolating cells capable of differentiating into nerves as well as mesodermal phenotypes.

The ROSA26 PPSCs and RmSC-1 PPSCs were cultured in induction dexamethasone conditions, were co-cultured with astrocytes, and were cultured with conditioned medium from astrocytes and the resultant cells evaluated for neuronal phenotypes by antibody staining. Cells were plated in 24 well culture dishes and evaluated by antibody staining using methods and materials described above. X-gal was utilized to stain ROSA B-galactosidase expressing cells. Neuronal antibody markers were GFAP (astrocyte), CNPase (neuronal marker for nerve), IA4, and RT-97 (neural filament), obtained from DHSB and further characterized in the above Examples (Example 9 and 10). The neuronal antibodies were used as primary antibodies, goat ant-mouse labeled with HRP was used as secondary antibody. The color reagent for the immunostaining was TrueBlue (KPL, Inc.) which is a chromagen for HRP.

ROSA26 PPSCs were co-cultured with rat astrocytes for 21 days and stained with antibodies against X-gal (which recognizes the product of the LacZ gene and therefore recognizes ROSA cells) and neuronal marker GFAP. FIG. 35 shows the co-culture of ROSA26 PPSCs and rat astrocytes for 21 days stained with X-gal and GFAP. Cells were found that stained only with X-gal and that double stained for both the Xgal and GFAP. Black arrows point to double-stained cells and white arrows to ROSA PPSCs not stained for GFAP. FIG. 36 shows the co-culture of ROSA26 PPSCs and rat astrocytes for 21 days stained with X-gal and GFAP. Astrocytes stained stained only with GFAP are noted (white arrows) and also ROSA-derived cells double-stained for X-gal and GFAP (black arrows). Co-culture of ROSA26 PPSCs and rat astrocytes for 21 days stained with X-gal and GFAP is also shown in FIG. 37. White arrows point to ROSA26 PPSCs single stained for X-gal (undifferentiated) while black arrows point to ROSA cells double stained for X-gal and GFAP (differentiated).

PPSCs isolated from rat skeletal muscle (RmSC-1) were treated with 10-7 M dexamethasone for 21 days to induce differentiation and then stained with various neuronal-specific antibodies. FIG. 38 depicts PPSCs isolated from rat skeletal muscle (RmSC-1) treated with 10-7 M dexamethasone for 21 days and then stained with anti-CNPase, with cells positive for CNPase. anti-CNPase shown by black arrows. Dexamethasone treated RmSC-1 cells stained with antibody to IA4 are shown in FIG. 39.

FIG. 40 shows RmSC-1 cells treated with conditioned medium from rat astrocytes for 21 days and stained with antibody RT-97. A positive staining cell is noted by an arrow. Cells positive for CNPase and GFAP were also observed on staining after growth of RmSC-1 cells in conditioned medium from rat astrocytes for 21 days.

Example 14

Multiple Stem Cell Populations Isolated from Adult Human

Stem cells were isolated from the dermis of a 17-year old female, designated CT3F cells, using the protocol described above and provided by Young et al (Young, H. E. et al (1991) Journal of Tissue Culture Methods 13:275-284; Young, H. E. et al (1992a) Journal of Tissue Culture Methods 14:85-92). The CT3F cells have been karyotyped and proved to be a 46, XX normal female (FIG. 41). This karyotype was performed when the CT3F cells were at 37 cell doublings. After 37 cell doublings, the CT3F cells were divided in half and placed in two different culture conditions—one in the presence of 10% selected serum HS10, the second in the presence of 15% selected serum MFCS1. Two populations of stem cells, pluripotent mesenchymal stem cells and pluripotent embryonic-like stem cells, designated PPMSCs and PPELSCs respectively, were isolated in these serum conditions. The PPMSC cells have the capacity to form any and all mesenchymal cell types. The PPELSC cells have the capacity to form cell types in the mesodermal, ectodermal and endodermal lineage. CD marker flow analysis was performed on those two populations of cells. The population, designated PPMSCs, was at 72 cell doublings, while the population, designated PPELSC, was at 70 cell doublings when the CD marker analysis was performed. In the analysis, 58 CD markers were utilized.

The PPELSCs were positive for CD10 and CD66e and were negative for 56 additional CD marker antibodies tested, specifically: CD1a, CD2, CD3, CD4, CD5, CD7, CD8, CD9, CD11b, CD11c, CD13, CD14, CD15, CD16, CD18, CD19, CD20, CD22, CD23, CD24, CD25, CD31, CD33, CD34, CD36, CD38, CD41, CD42b, CD44, CD45, CD49d, CD55, CD56, CD57, CD59, CD61, CD62E, CD65, CD68, CD69, CD71, CD79, CD83, CD90, CD95, CD105, CD117, CD123, CD166, Glycophorin-A, DRII, Class-I, FLT3, FMC-7, Annexin, and LIN. The PPELSCs showed no positive staining for any CD marker tested.

The PPMSCs demonstrated positive staining for CD markers CD10, CD13, CD34, CD56, CD90 and MHC Class-I. This result correlates with the CD marker studies presented on PPMSCs above in Examples 7 and 8. The PPMSCs were negative for 52 antibodies: CD1a, CD2, CD3, CD4, CD5, CD7, CD8, CD9, CD11b, CD11c, CD14, CD15, CD16, CD18, CD19, CD20, CD22, CD23, CD24, CD25, CD31, CD33, CD36, CD38, CD41, CD42b, CD44, CD45, CD49d, CD55, CD57, CD59, CD61, CD62E, CD65, CD66e, CD68, CD69, CD71, CD79, CD83, CD95, CD105, CD117, CD123, CD166, Glycophorin-A, DRII, FLT3, FMC-7, Annexin, and LIN.

Additional populations of adult reserve stem cells, based on unique CD marker profiles, were isolated from the CT3F cells. These populations were tested for the same 58 CD markers noted above. The first population is positive for CD1a, CD10, CD41, CD66e and Annexin, and negative for all other markers. CD66e is an embryonic antigen marker. The second population is positive for CD1a, CD10, CD22 and Annexin and negative for all others. The third population is positive for CD10 and CD22 and negative for all other markers. These results indicate the presence of additional stem cell populations with possibly distinct proliferative and differentiative capacities.

Example 15

Hematopoietic Reconstitution by Human Pluripotent Stem Cells In Vivo in NOD/SCID Mice Summary of Protocol The purpose of this study is to determine the feasibility of using naïve postnatal pluripotent stem cells or postnatal pluripotent stem cell-induced hematopoietic stem cells for human stem cell therapy. Postnatal human pluripotent stem cells, derived from a 67 year old male and a 17 year old female, are co-transplanted individually as naïve and hematopoietic-induced stem cells, with murine hematopoietic stem cells into sublethally irradiated immune-deficient NOD/SCID. Human specific CD45 antigen expression on cells in mouse blood and bone marrow will be used to identify incorporation of the human cells into the mice. CD-marker profiles for B-cells, granulocytes, megakaryocytes, and erythrocytes are used to identify hematopoietic repopulating activity of the human stem cells. Identification of human cells expressing human specific CD45 antigen mixed with mouse cells serves as a positive endpoint and indicates that the human stem cells have incorporated into the mice. Identification of human cells expressing human hematopoietic CD markers of both myeloid and lymphoid lineages serves as a positive endpoint and indicates that the human stem cells are regenerating the hematopoietic system.

Detailed Protocol

All animals used are immune-deficient NOD/SCID pretested for evidence of T cell leakiness. (n=6 for each group) The animals are grouped and treated as indicated below in TABLE 15.

TABLE 15

| Grp# | Treatment | Assay |
|---|---|---|
| 1 | Sublethally irradiated mice, infused with naïve 67-yo PPSCs | 1, 2a, 2b, 2c |
| 2 | Sublethally irradiated mice, infused with naïve 17-yo PPSCs | 1, 2a, 2b, 2c |
| 3 | Sublethally irradiated mice, infused with hemato-67-yo PPSCs | 1, 2a, 2b, 2c |
| 4 | Sublethally irradiated mice, infused with hemato-17-yo PPSCs | 1, 2a, 2b, 2c |
| 5 | Sublethally irradiated mice, non-treated = controls | 1, 2a, 2b |
| 6 | Non-irradiated, non-treated = controls | 1, 2a, 2b |

Assay Parameters for human cell engraftment:

blood (1) and bone marrow (2a,b,c) from transplanted and control mice are analyzed at 8 (3 mice) and 12 weeks (3 mice) post-infusion. Cells (1,2a) are stained for the human hematopoietic CD markers with multiparameter flow cytometric analysis using the FACScan. The CD-marker profiles for B-cells, granulocytes, and erythrocytes will be used to identify incorporation of the human cells in mouse tissue. In each experiment, cells from non-transplanted mice are stained with the same antibodies as a negative control.

Identification of human cells expressing hematopoietic markers mixed with mouse cells serves as a positive endpoint and indicates that the human stem cells are regenerating the hematopoietic system in both myeloid and lymphoid compartments.

Bone marrow (2b) from all mice is stained for human specific MHC-I and HLA-DR-II antigens by immunocytochemistry. Identification of human cells mixed with mouse cells serves as a positive endpoint and indicates that the human stem cells have incorporated into the mice and are regenerating the hematopoietic system.

Further analysis of incorporation of human cells into mouse bone marrow involves stimulating isolated bone marrow cells with human growth factors known to stimulate colony formation of human hematopoietic cells. Thus, bone marrow cells from transplanted mice (2c) are plated in methylcellulose cultures and the cultures stimulated with human plasma and hu-IL-3 (10 U/ml), hu-GM-CSF (1 U/ml), hu-SCF (50 ng/ml), and hu-EPO (2 U/ml). Morphological criteria and histological staining are used to identify human colonies derived from colony-forming unit-granulocyte-macrophage (CFU-GM), burst-forming unit erythroid (BFU-E), and colony-forming unit granulocyte-erythroid-megakaryocyte-macrophage (CFU-GEMM) progenitors. The specificity of the assay is confirmed by using PCR to amplify human dystrophin RNA in individual colonies.

Results

NOD/SCID mice were sublethally irradiated (300 cGy) and injected via tail vein with CT3F PPELSC cells at $4.8 \times 10^6$ (Mo #1-3) or $1.2 \times 10^6$ (Mo #4-6) per mouse. At higher cells concentrations, mice did not survive. On a recent experiment, we included 20 U/ml heparin in the injection solution (IMDM with 0.2% BSA, and 20 U/ml heparin) and were able to inject $3 \times 10^6$ per mouse (n=1).

At 8 weeks post-transplant, six mice were sacrificed, and bone marrow, spleen, and peripheral blood analyzed for human cells with the following markers: Class I, CD45, CD34, CD38, CD19, CD3, CD117. All markers were negative except for Class I in the bone marrow. Approximately 0.5% of the bone marrow contained human Class I positive cells. In the spleen and peripheral blood, no human cells were detected using the markers listed above.

Example 16

Rat Stem Cells Retain Pluripotency after Genomic Labeling and Retroviral Gene Transfer Abstract Post-natal rat skeletal muscle was harvested and mesenchymal stem cells isolated. Clonogenic analysis revealed that pluripotent stem cells do indeed exist in post-natal mammals and that they retain their ability to form at least four mesodermal lineage tissues (e.g., skeletal muscle, fat, cartilage, and bone) after cloning. Clones were then examined for retention of pluripotency after genomic labeling and extended self-renewal. This ability was retained after genomic labeling with β-galactosidase and after extended self-renewal, i.e., 200+ cell doublings post-cloning. The existence of pluripotent stem cells within connective tissue matrices and their retention of pluripotency after cloning, gene transfection, and extended self-renewal suggest that these stem cells may be important contributors to gene therapy and/or the repair and regeneration of tissues in post-natal animals.

Materials and Methods

Genomic Labeling

Clone (Rat-A2B2) (described above in Example 11) was grown in Modified Eagle's media (MEM) (GIBCO-BRL, Life Technologies, Cergy Pontoise, France), with 10% horse serum (GIBCO-BRL), 5 mM Hepes (GIBCO-BRL), 50 U/ml penicillin –50 mg/ml streptomycin (GIBCO-BRL) and 50 U/ml recombinant human anti-differentiation factor factor (ADF, Morphogen Pharmaceuticals, Inc., NY). A stable Rat-A2B2 cell line expressing nuclear targeted LacZ gene (nls-LacZ) was constructed using the plasmid pUT651 (selectable reported gene Sh ble::lacZ). Cells were plated at $5 \times 10^3$ cells/cm2 on six-well plastic dishes (Falcon) (Becton Dickinson, Le pont-de claix, France) in serum-containing medium and allowed to attach overnight. The cells were then incubated overnight with 2 mg of pUT651 using lipofectin reagent (Gibco-BRL) during 16 hr in serum free medium (Opti-mem, GIBCO-BRL). Transfected cells were split 1:10 into the selection medium supplemented with 250 mg zeocin (Invitrogen, Netherlands). One clone among twelve resistant clones expressing the highest level of β-Gal was subcloned and used. β-Gal expression was evaluated by histochemical and immunochemical techniques. After fixation in 0.2% paraformaldehyde for 10 min at room temperature or fixation in ice cold methanol for 5 min, rinsed in PBS, LacZ expression was evaluated in the cells by histochemical staining with the chromogenic substrate X-Gal and by immunostaining with the polyclonal (Chemicon, Temecula, Calif.) anti-β-Gal antibody (Couffinhal et al., 1997). Antibody binding was visualized using the Vector-HRP-DAB expression system (Vector Labs) with biotintylated anti-mouse IgG preadsorbed to rat immunoglobulins (Vector).

Insulin—Dexamethasone Analysis for Phenotypic Expression

Cryopreserved clones were thawed and plated in MSC-1 medium at 5, 10, or $20 \times 10^3$ cells per well of gelatinized 24-well plates following standard protocol. Twenty-four hours after initial plating the medium was changed to testing medium (TM) 1 to 4 (TM-1, TM-2, TM-3, TM-4) or 5 (TM-5). Testing medium (TM) contained ratios of Ultraculture: EMEM: antibiotics which maintained both avian progenitor and pluripotent cells in "steady-state" conditions for a minimum of 30 days in culture, and as long as 120 days in culture. Four testing media (TM#'s 1-4), each containing various concentrations of Ultraculture, were used. The ratios of Ultraculture to EMEM to antibiotics present in each testing medium was determined empirically for each lot of Ultraculture, based on its ability to maintain steady-state culture conditions in both populations of avian progenitor and pluripotent cells. The four Ultraculture-based testing media were: TM#1=15% (v/v) Ultraculture (Lot no. OMO455): 84% (v/v) EMEM: 1% (v/v) antibiotics; TM#2=15% (v/v) Ultraculture (Lot no. 1M1724): 84% (v/v) EMEM: 1% (v/v) antibiotics; TM#3=50% (v/v) Ultraculture (Lot no. 2M0420): 49% (v/v) EMEM: 1% (v/v) antibiotics; and TM#4=75% (v/v) Ultraculture (Lot no. 2M0274): 24% (v/v) EMEM: 1% (v/v) antibiotics. TM-1 to TM-4 consisted of Ultraculture (cat. no. 12-725B, lot. nos. OMO455 [TM-1], 1M1724 [TM-2], 2M0420 [TM-3], or 2M0274 [TM-4], Bio-Whittaker, Walkersville, Md.), EMEM[1], and 1% (v/v) Pen/Strep, pH 7.4. TM-5 consisted of 98% (v/v) EMEM, 1% (v/v) HS, and 1% (v/v) Pen/Strep, pH 7.4.

Pre-incubation for 24 hr in testing medium only was used to wash out any potential synergistic components in the MSC-1 medium. Twenty-four hours later the testing medium was changed to testing medium only (Controls) or testing medium (TM-1 to TM-5) containing either 2 μg/ml insulin (Sigma), an agent that accelerates the appearance of phenotypic expression markers in progenitor cells (Young et al., 1998a), to identify clones of progenitor cells, or $10^{-10}$ to $10^{-6}$ M dexamethasone (Sigma), a general non-specific lineage-inductive agent (Grigoriadis et al., 1988; Young et al., 1993, 1998a) to identify clones of pluripotent cells. Control and treated cultures were propagated for an additional 30-45 days with medium changes every other day. Four culture wells were used per concentration per experiment. During the 30-45 day time period the cultures were examined (subjectively) on a daily basis for alterations in phenotypic expression (see below), days of treatment, and associated insulin or dexamethasone concentrations. The experiment was then repeated utilizing these parameters to (objectively) confirm the phenotypic expression markers using established immunochemical and histochemical procedures (Young et al., 1992b, 1993, 1995, 1998a,b; Rogers et al., 1995) and the results photographed using a Nikon TMS inverted phase contrast/brightfield microscope.

Cultures that displayed multinucleated linear and branched structures that spontaneously contracted were further evaluated using a myosin-enzyme linked immunoculture assay (myosin-ELICA) to verify the presence of sarcomeric myosin within putative skeletal muscle cells (Bader et al., 1982; Young et al., 1992a,b, 1993, 1995). Cultures that exhibited multiple refractile vesicles were further evaluated using Sudan black-B (Roboz Surgical Co., Washington, D.C.) staining to verify the presence of saturated neutral lipids within putative adipocytes (Young et al., 1992a, 1993, 1995). Cultures that displayed aggregates of rounded cells containing pericellular matrix halos were further evaluated using Alcian Blue (Alcian Blau 8GS, Chroma-Gesellschaft, Roboz Surgical Co.) at pH 1.0 coupled with chondroitinase-AC (ICN Biomedicals, Cleveland, Ohio)/keratanase (ICN Biomedicals) digestions to verify the presence of pericellular- and/or extracellular matrix-located chondroitin sulfate/keratan sulfate glycosaminoglycans surrounding putative chondrocytes (Young et al., 1989, 1992a, 1993, 1995). Cultures that exhibited cells embedded within and/or overlain with a three-dimensional matrix were further evaluated using von Kossa (Silber Protein, Chroma-Gesellschaft) staining coupled with EGTA (Ethyleneglycol-bis-[β-Aminoethyl ether] N, N, N',N'-tetraacetic acid, Sigma) pre-treatment to verify the presence of calcium phosphate within the putative mineralized bone spicule (Young et al., 1992a, 1993, 1995). Cultures displaying confluent layer(s) of cells embedded within either a granular or fibrillar extracellular matrix were further evaluated using Alcian Blue pH 1.0 staining coupled with chondroitinase-ABC (ICN Biomedicals) digestion to verify the presence of extracellular chondroitin sulfate/dermatan sulfate glycosaminoglycans surrounding putative fibroblasts (Young et al., 1989, 1992a, 1993, 1995).

Results

The clone designated "RAT-A2B2" (described in Example 11) was evaluated after genomic labeling by β-galactosidase retroviral transfection. Throughout all evaluations the A2B2 cells demonstrated no change in phenotypic expression during incubation with insulin. However, A2B2 cells exhibited multiple morphologies when incubated with a concentration range of dexamethasone after genomic labeling. The changes in phenotypic expression noted were those of myogenic, adipogenic, chondrogenic, and osteogenic morphologies. The A2B2 cells were specifically selected during clonogenic analysis for retention of stellate morphology and loss of contact inhibition. RAT-A2B2 has lost contact inhibition at confluence. But, once induced to commit to a particular lineage, i.e., to become lineage-specific progenitor cells, RAT-A2B2 assume contact inhibition at confluence.

Discussion

Every year millions of Americans suffer tissue loss or end-stage organ failure. The total national health care costs for these patients exceed 400 billion dollars per year. Currently over 8 million surgical procedures are performed annually in the United States to treat these disorders and 40 to 90 million hospital days are required. Although allogeneic therapies have saved and improved countless lives, they remain imperfect solutions. Allogeneic tissue transplantation and surgical intervention are severely limited by critical donor shortages, long term morbidity and mortality (Langer and Vacanti, 1993). The long term objectives of this research are to determine the utility of autologous pluripotent stem cells for use as HLA-matched donor tissue for regeneration and repair and as potential delivery vehicles for gene therapies. For pluripotent stem cells to be utilized as autologous donor tissue necessitates their existence within the organism, ease of isolation, ability to manipulate their phenotypic expression, adaptability, incorporation into existing tissue, survivability, and functionality.

Studies in this report have shown that pluripotent stem cells, particularly Rat A2B2 (described in more detail in Example 11 above) can be retrovirally transfected without loss of pluripotency while retaining the activity of the transfected gene. From these studies we would propose the following hypothesis, that autologous pluripotent stem cells could be used as HLA-matched donor tissue for tissue transplantation, regeneration, and gene therapies, especially in instances where large numbers of cells are needed and transplant tissues are in short supply.

Example 17

Retroviral Mediated Gene Transfer to Pluripotent Stem Cells

Purpose of Study

1) To use retroviral vectors to deliver genes to PPSC and test the ability of infected PPSC to maintain their pluripotency. 2) To compare the ability of control and myoD expressing PPSC to disperse upon transplantation into atrophied muscle and fuse with myofibers Summary of Study One long term goal is to use cellular and/or pharmacologic methods to enhance the growth of postnatal skeletal muscle. PPSC represent one potential strategy for the treatment of atrophied skeletal muscle that occurs in neuromuscular disease, disuse, spaceflight, prolonged bed rest and aging. In an effort to achieve the goal of growth of postnatal skeletal muscle, retroviruses have been utilized to deliver genes to cells in four different ways: 1) to deliver markers such as b-galactosidase to track myogenic cells after transplantation; 2) to deliver reporter constructs to study the involvement of specific signaling pathways in cell physiology; 3) to overexpress transcription factors; 4) to deliver genetic inhibitors of specific signaling pathways. In order eventually to use PPSC as cellular therapy for muscle wasting, it is necessary to first stably introduce marker genes into the PPSC and determine that the pluripotency of the cells is maintained. In addition, it is necessary to determine the behavior of transplanted PPSC within normal and atrophied skeletal muscles. MyoD is a muscle-specific transcription factor that can induce non-muscle cells to become myogenic as well as induce myogenesis in stem cells. We will test the ability of forced expression of myoD to increase the efficiency of PPSC recruitment and incorporation into atrophied myofibers.

Animals

Immunodeficient scid/bg mice will be used as recipients for PPSC transplantation. Scid/bg mice lack functional T and B cells and have low natural killer activity. The scid/bg mice show a more stable SCID phenotype and are, in general, better recipients for allograft transplantation.

Detailed Protocol

I. Determine the efficiency of retroviral mediated gene transfer of the lac Z gene to PPMSC (pluripotent mesenchymal stem cells) and PPELSC (pluripotent embryonic-like stem cells).
a) Retrovirally infect the two kinds of stem cells using established techniques.
b) 48 hrs after infection, perform enzymatic assay for b-galactosidase expression in single cells. Infected cells will be blue.
c) Score % of blue cells.
d) If percentage of blue cells is low, repeat retroviral infection protocol but use 2 rounds of infection 6-8 hrs apart.
e) Repeat b-c.
f) Repeat experiment two times using the protocol that gives the highest percentage of blue cells to determine reproducibility of the method.

II. Test ability of the two kinds of retrovirally infected SC to maintain pluripotency after infection
a) Infect cells with the protocol that gives the highest percentage of blue cells.
b) 24 hrs after infection, trypsinize cells and plate cells in 96 well plates for use in ELICA assays. Uninfected cells are also set up in 96 well plates as controls. Also set up cells in 12 well plates to observe morphology of cells.
c) 48 hrs after infection, change media to inductive media.
d) 2-6 weeks after infection, test induction of specific cellular phenotypes (+retroviral infection) in 96 well plates using dexamethasone methods earlier described.
e) Perform b-galactosidase enzymatic assay on 12 well plates and observe whether morphologic signs of phenotype induction occur in blue cells.
f) Compare induction of specific phenotypes in control vs. retrovirally infected cells.

III. Compare behavior of control and myoD expressing PPMSC and PPELSC transplanted into control and atrophied skeletal muscles.
a) Two weeks prior to transplantation perform unilateral transection of the sciatic nerve in scid/bg mice in order to induce denervation atrophy of the tibialis anterior muscle.
b) Infect PPSC with either control or myoD expressing retroviruses. 48 hrs after infection test for myoD expression using immunohistochemistry in parallel plates.
c) Transplant cells into each tibialis anterior as follows in TABLE 16:

TABLE 16

| Group # | Treatment (Left leg) | Treatment (Right leg) | Cell Type |
|---|---|---|---|
| 1 (n = 8) | Control | Denervation atrophy | Control PPMSC |
| 2 (n = 8) | Control | Denervation atrophy | MyoD PPMSC |
| 3 (n = 8) | Control | Denervation atrophy | Control PPELSC |
| 4 (n = 8) | Control | Denervation atrophy | MyoD PPELSC | d) Six weeks after transplantation collected transplanted muscles, serially section and perform enzymatic assay for b-galactosidase on muscle sections.

1) Score number of blue nuclei inside of myofibers. These represent PPSC that have converted to the myogenic lineage and have fused with endogenous myofibers of the host.
2) Compare distribution of blue nuclei relative to the injection site.
3) Compare the ability of control and myoD expressing PPMSC vs. control and myoD expressing PPELSC to convert to the myogenic lineage and fuse with myofibers.
4) Analyze the data obtained in 3) above as a function of atrophied vs. normal muscle.

Defined Endpoints:

The endpoint is the ability of pluripotent stem cells retrovirally infected with a marker gene to maintain their pluripotency and upon transplantation disperse over a broad area of the muscle and fuse with high efficiency with endogenous myofibers of the host. Success will be determined by the ability to infect PPMSC and PPELSC to high efficiency with the lacZ gene and have them maintain their pluripotency. The transplantation experiments are deemed successful if the implanted cells disperse throughout the width and length of the muscle and fuse with high efficiency to atrophied myofibers.

Example 18

Signal Processes Involved in Endothelial Cell Differentiation

ROSA26 PPSC cells and rat A2B2 cells tranfected with B-gal (described above in Example 16) were utilized to assess their hematopoietic-endothelial cell capacity and the signal processes involved with endothelial cell differentiation from a common hematopoietic-endothelial precursor cell.

A2B2 B-gal PPSCs were grown in 1% selected HS10 serum in the presence of various growth factors and their in vitro commitment induction to endothelial cell lineage assessed. The cells were grown in 1% HS10 alone, 1% HS10 plus a cocktail of growth factors VEGF, bFGF, EGF and IGF-1; 1% HS10 plus bFGF (50 ng/ml), 1% HS10 plus VEGF (50 ng/ml), 1% HS10 plus T-cell stimulating conditioned medium, and 1% HS10 plus bFGF for two days after which VEGF was added. The culture dishes were coated with either gelatin, collagen type IV, rat vitronectin and gelatin combined with rat vitronectin. The most differentiation was observed on rat virtonectin coated dishes. The thus grown cells were evaluated by: morphological assessment; bioactivity in an MTS assay; Matrigel assay which detects tube formation (capillary formation) after reseeding cells on Matrigel, (Matrigel, available from R&D Systems, is a basement membrane product for coating culture/growth dishes containing basement membrane components Type IV collagen, laminin, entactin, nidogen and heparin sulfate proteoglycan); and immunostaining with various endothelial cell antigen markers (CD31 (pecam), BS-B (BS-B4 isoform lectin stain), SM a-actin (smooth muscle pericyte marker).

PPSCs showed enhanced staining for endothelial cell markers CD31, BS-B abd SM actin in the presence of the combined growth factors VEGF, bFGF, EGF and IGF-1, and in the presence of bFGF or VEGF.

In the Matrigel assay, PPSCs seeded on Matrigel developed tube formation and capillary like structures (FIG. 42), particularly in the presence of growth factors (FIG. 43).

A2B2 B-gal PPSCs were administered and tested in vivo in an hindlimb ischemic model in rat SCID animals. The femoral artery was tied off to generate the ischemia model.

PPSC cells were administered by intravenous (IV) in the rat tail vein or intramuscular (IM) locally to hindlimb prior to or after the hindlimb ischemia was generated. Histology was performed 1 week post injection of PPSCs to assess the presence and nature of B-gal labeled cells. PPSCs (B-gal positive cells) were incorporated into the hindlimb at the ischemic site when administered IM or IV. On gross anatomy review these cells appeared to track to the vasculature in the hindlimb, showing a parrallel line pattern of B-gal expression. In addition, on IV injection into an ischemic animal, significant incorporation of B-gal positive cells was observed in the bone marrow (FIG. 44).

Example 19

Pluripotent Stem Cell Responses to Growth Factors and Assessment in a Hindlimb Ischemia Model Human ELSCs (CT3F) and rat ELSCs were cultured on gelatin coated plates in media containing 1% HS10 serum or 5% FBS [MFCS-1], supplemented with the following:
1 no supplement
2 conditioned media of T-lymphocyte stimulated by PHA.
3 VEGF (10 ng/ml)
4 VEGF (10 ng/ml)+bFGF (5 ng/ml) [basic Fibroblast Growth Factor]
5 VEGF (10 ng/ml)+SCF (10 ng/ml) [Stem Cell Factor]
6 VEGF (10 ng/ml)+bFGF (5 ng/ml)+SCF (10 ng/ml)
7 BMP-4 (10 ng/ml)
8 BMP-4 (10 ng/ml)+VEGF (10 ng/ml)
9 BMP-4 (10 ng/ml)+VEGF (10 ng/ml)+bFGF (5 ng/ml)+SCF (10 ng/ml)

After 1 week in the above conditions, cells were suspended and reseeded onto Matrigel and morphological cell changes were observed.

The structural morphologies of cells under each condition 12 hours after reseeding to Matrigel are shown in FIG. 45. The first panel, labeled HUVECs, shows the positive control of HUVEC cells (Human Umbilical Vein Endothelial Cells) as a totally differentiated endothelial cell in Matrigel. HUVEC forms crossing cord-like structures. Several conditions, particularly VEGF treatment and BMP-4+VEGF+bFGF+SCF treatment in 5% FBS, resulted in similar cord-like structures.

FIG. 46 presents follow-up pictures of human ELSC conditioned cells in Matrigel. Upper left-most picture demonstrates crossing cord-like structure by cells cultured in 1% HS10 for 1 wk at 24 hours after reseeding to Matrigel. The upper central picture shows sprouts from a colony of cells treated in T cell stimulated conditioned media for 1 wk at 1 wk after Matrigel culture. The lower left picture illustrates magnified sprout forms. It is believed that certain hematopoietic stem cells will cause sprouting of endothelial cells. There were small glomerular-like clusters seen in Matrigel culture of cells conditioned by VEGF+bFGF for 1 wk (upper right). BMP-4+VEGF+bFGF+SCF conditioned cells present thicker sprouts from colonies (lower right).

In FIG. 47, several colonies are demonstrated in Matrigel culture of human cells conditioned with BMP-4 (10 ng/ml) for 1 wk. At 3 days in Matrigel culture, sprouting colonies are observed (lower left). These colonies develop several colonies that stain brown (upper left and lower right), similar to a erythroblastic colony, and other colonies look similar to a hematopoietic monocyte colony (lower right).

Rat ELSCs (A2B2scl) were delivered into hindlimb ischemia models. Nude (immunodeficient) rats suffered from hindlimb ischemia by ligation of femoral artery. Rat ELSCs (A2B2 scl) were injected intramuscularly [1.0 to $5.0 \times 10^5$ cells (in 100 microliters)] immediately after surgery. At 2 wks after transplantation, rats were sacrificed and transplanted muscles were harvested for X-gal staining.

FIG. 48 and FIG. 49 macroscopically demonstrate muscle bundle-like organs generated from ELSC-derived cells in the hindlimb ischemia model. They locate to the severe ischemic area and form longitudinal organs along with survived recipient muscles. FIG. 49 (upper right photo) demonstrates a thin muscle-like structure staining positive which is independently generated. FIG. 49 (lower photo) demonstrates localization of ELSC-derived cells on the surface of what appears to be connective tissue.

Histological samples shown in FIGS. 50, 51 and 52 present newly forming ELSC-derived (blue) muscle bundle-like organs accompanied with neovascularization stained brown with endothelial specific isolectin B4. The ELSC-derived cells locate among pre-existing nude rat recipient muscles. Vasculatures involved in newly forming organs are composed of ELSC-derived endothelial and periendothelial cells. In FIG. 52 the oval-like structures in the left panel with the eccentric blue nucleus are the new stem cell derived muscle.

Example 20

RNA Expression of ELSCs

Differential RNA expression was evaluated on human ELSCs (CT3Fs) or its derivatives by RT-PCR. Human CT3F cells were assayed by RT-PCR with various primers after culture in HS10 serum or MFCS1 serum. RT-PCR was performed with primers for each of the following RNAs:

| | |
|---|---|
| VE-Cadherin: | Vascular Endothelial Adhesion Molecule |
| KDR: | VEG-F receptor |
| Nestin: | Nerve and Endothelial marker |
| Oct4: | Immature stem cell marker |
| HNF1b: | Liver and digestive tissue marker |
| AFP: | Liver |
| GATA2: | Hematopoietic stem cells |
| Sm22a: | Smooth muscle lineage |
| CD45: | Hematopoietic stem cells |
| GATA1: | Early hematopoietic stem cells |
| Myogenin: | Skeletal muscle |
| GATA4: | Cardial myouyte |
| CVFA1: | Osteoblast/Chondroblast |

FIG. 53 depicts results of differential RNA expression evaluation of human CT3F cells after adhesion culture in 1% HS10 following 4-day suspension culture. The CT3F cells demonstrated GATA-1 (hematopoietic), GATA-2 (hematopietic, endothelial) and CVFA-1 (chondroblast or osteoblast) expression. Although similarly analyzed HUVEC cells demonstrated VE-Cadherin, KDR and Nestin expression by RT-PCR, an RT-PCR product was not observed in CT3F cells with these primers.

CT3F cells were grown in HS10 Serum (denoted M) or MFCS1 Serum (denoted E) and assayed for expression of various RNAs by RT-PCR as shown in FIG. 54. Cells of embryoid body (EB)-like clusters (cell suspension culture for 1 day or 4 days) were also assessed. FIG. 54 demonstrates that CT3F cells expressed Musashi (neuronal), Sm22a (smooth muscle) and CVFA-1 (chondroblast or osteoblast) RNA, but not the endothelial specific marker (KDR) in this experiment. The results with the nestin primer are inconclusive because the control (brain) sample did not express nestin on RT-PCR control analysis. EB-like clusters expressed KDR (endothelial), Musashi and Sm22 at day 1, but only KDR at day 4.

FIG. 55 depicts additional RT-PCR analysis, including control assays. CT3F cells (E1 and E2 grown in MFCS1 serum, and M grown in HS10 serum) appear to express Oct4 MRNA.

Example 21

Assessment of Pluripotent Stem Cells in Cardiac Repair In Vivo

Summary

The purpose of this study is to evaluate induction of cardiac myocyte differentiation in beta-galactosidase-labeled rat postnatal pluripotent stem cell clones (PPSC) (A2B2-scl-40). Beta-galactosidase-labeled rat postnatal pluripotent stem cell clones will be processed for microinjection seeding into healthy rat hearts and myocardial infarcted rat hearts. The hypothesis is that the in vivo microenvironment of the heart will induce the stems cells to attach and differentiate into cardiac myocytes and possibly fibroblasts, resulting in exogenously created myocardium.

Rats are an excellent species to study heart development and tissue engineering of artificial myocardium since the myocardial structure is similar to that of the human, especially at the level of the myocyte-ECM microenvironment. During a myocardial infarction (heart attack) the muscular tissue in the affected area dies and is replaced by scar tissue. Overall functionality of the heart is reduced because this scar tissue does not participate in contraction and expulsion of blood from the organ. Indeed, the scar contributes to the overall stiffness of the heart and impedes proper functionality. There currently is no mechanism or procedure to replace or repair the effected area. Pluripotential stem cells could provide a means to repair the affected area by replacement of muscle tissue. These primitive cells are adult derived and have been demonstrated to differentiate into cardiac myocytes in vitro. These experiments will allow us to test the hypothesis that the in vivo microenvironment of the heart will induce the stems cells to attach and differentiate into cardiac myocytes and possibly fibroblasts, resulting in exogenously created myocardium.

A myocardial infarction is created by ligation of the left anterior descending artery. Alternatively, cryo-freezing of the heart muscle may be performed to generate an infarct. Animals will be anestized and prepped for surgery. A Left thoracotomy will be performed. The heart will be exposed and the LADA will be ligated. Animals will then be allowed to recover as described in the surgical procedure. After a recover period as described in TABLE 18, animals will be anestized and prepped for surgery. A subxiphoid window will be created, the heart exposed and stem cells injected. Animals will be allowed to recover as described in the surgical procedure. A series of experiments will determine if the PPSCs will differentiate in a diseased heart and the effect of timing of the microinjections on differentiation and eventual phenotype.

Detailed Protocol

1. Propagate Beta-Galactosidase-Labeled Rat Postnatal Pluripotent Stem Cell Clones.

The ELSC stem cells are grown to multi-layered confluence, harvested by trypsin release, and the cell suspension is added to horse serum and medium per the standard protocol, the cells are then pelleted, and reconstituted (with several washings) in DPBS without calcium. Using DPBS without calcium has two reasons: 1) to get rid of any serum proteins that might cause cells to clump during injection, and 2) to remove calcium as a co-factor for cell attachment (clumping). No clumping of the cells was observed at time of injection. The cells are diluted to 1-2 million cells per ml of DPBS-without calcium and injected in volumes of 100 to 500 microliters (ml) [100,000 to 500,000 cells per rat] using a 1.5 inch 25 gauge needle.

2. Determine Minimum Needle Size to Allow Cell Passage without Excess Shear:

a) Seed cells in T-25 flasks using 18, 20, 22, 24, and 26 gauge needles.
b) Culture for 24 hrs and examine cultures for ratio of live to dead cells.
c) Document results.

3. Examine In Vivo Induction of PPSCs into Cardiac Muscle Cells.

Group I: Implantation of Stem Cells into Normal Rat Left Ventricle Using a Subxiphoid Window.

After induction of anesthesia, the abdomen will be shaved. The area will be prepped with betadine and sterile drapes placed. The subxiphoid area will be infused with 1% lidocaine. A skin incision will be made in the midline. The subxiphoid area will be dissected at the midline until the pericardium is opened. Once opened, alliquots of stem cells will be injected into the left ventricle at 10 different sites using a 26 gauge micro syringe needle. Micro inject healthy rat heart in several locations with up to 20 µl of PPCSs in DPBS without divalent cations or similar carrier vehicle. The midline will be closed with 2.0 vicryl suture and the skin closed with 4.0 vicryl suture. All instruments will be sterilized be the most appropriate method and the procedure completed in a surgical suite reserved for small animal procedures. The animals will be allowed to recover in a warmed environment.

Group 2: Implantation of Stem Cells into Myocardial Infarction Rat

Step 1: Creation of Myocardial Infarction by the Jones, et al Model

After induction of anesthesia, the rat's left chest will be shaved, prepped with betadine, and sterile drapes applied. 1% lidocaine will be infused into the soft tissue of the left chest. A left thoracotomy is performed. The chest will be entered at the level of the fourth intercostal space. The apex of the heart will be stabilized with gentle traction between the thumb and forefinger. A 6.0 silk suture will be passed around the left descending coronary artery in a figure of 8 stitch. The apex will be released and the suture tied. Positive pressure will be given while closing the chest. The chest is closed with 2.0 vicryl suture. This will be done in an oxygen rich environment so that any remaining pneumothorax will resorb faster. Muscle and skin closure will be obtained with 3.0 and 4.0 vicryl suture. Any residual pneumothorax will be aspirated with a #22 Jelco.

Step 2: Implantation of the Stem Cells, ICM.

Once adequate time has passed since the myocardial infarction, as prescribed in the experimental outline in TABLE 18, stem cells will be placed in the infarcted left ventricle using the subxiphoid window approach as in group 1. After induction of anesthesia, the abdomen will be shaved. The area will be prepped with betadine and sterile drapes placed. The subxiphoid area will be infused with 1% lidocaine. A skin incision will be made in the midline. The subxiphoid area will be dissected at the midline until the pericardium is opened. Once opened, aliquots of stem cells will be injected into the left ventricle at 10 different sites.

Micro inject healthy rat heart in several locations with up to 20 μl of PPCSs in DPBS without divalent cations or similar carrier vehicle. The midline will be closed with 2.0 vicryl suture and the skin closed with 4.0 vicryl suture.

Step 2: Implantation of Stem Cells, Tail Vein Injection.

Once adequate time has passed since the myocardial infarction, as prescribed in the experimental outline in TABLE 18, stem cells will be placed in the tail vein of the rat using a 25-gauge needle on a microinjection syringe.

Assay for Cardiac Muscle-Specific Phenotypic Expression Markers

Confocal microscopy of Rhodamin Phalloidin stained myofibril organization.

Confocal microscopy of TNi using troponin C antibody specific to cardiac tissue.

Confocal microscopy to test for myoD using antibody specific to myoD skeletal muscle tissue.

Confocal microscopy to identify Beta-galactosidase using antibody specific to Beta-galactosidase.

If differentiation has taken place, the muscle will be further characterized histologically and physiologically.

Defined Endpoints

The endpoints we are looking for are the co-localization of beta-galactosidase label with phenotypic expression markers for cardiac muscle in postnatal pluripotent stem cells. Animals will be euthanized at specific time points as outlined in TABLES 17 and 18. Animals will be monitored post op. Success will be realized if beta-galactosidase co-labels with phenotypic expression markers for cardiac muscle.

TABLE 17

Differentiation of Pluripotential cells in the myocardial in vivo environment
Group I Healthy Animals

| Sub group number | Procedure | Number of animals |
|---|---|---|
| 1 | Sham | 3 |
| 2 | vehicle only | 3 |
| 3 | control | 3 |
| | 10 micro-liters × 10 locations | |
| 4 | 1 day | 5 |
| 5 | 3 days | 5 |
| 6 | 5 days | 5 |
| 7 | 10 days | 5 |
| 8 | 21 days | 5 |
| | 20 micro-liters × 10 locations | |
| 9 | time point 1 | 5 |
| 10 | time point 2 | 5 |
| 11 | time point 3 | 5 |
| Sub total Goup I | | 49 |
| Contingency @ 10% | | 5 |
| Total Group I | | 54 |

TABLE 18

Differentiation of Pluripotential cells in the myocardial in vivo environment
Group II Myocardial Infarct

| Sub group number | Procedure | Number of animals |
|---|---|---|
| 1 | Sham | 3 |
| 2 | MI only | 3 |
| 3 | MI and Vehicle only | 3 |
| 4 | control | 3 |
| | ICM injection injection 1 day after MI | |
| 5 | time point 1 | 5 |
| 6 | time point 2 | 5 |
| | injection 3 days after MI | |
| 7 | time point 1 | 5 |
| 8 | time point 2 | 5 |
| | injection 5 days after MI | |
| 9 | time point 1 | 5 |
| 10 | time point 2 | 5 |
| | injection 10 days after MI | |
| 11 | time point 1 | 5 |
| 12 | time point 2 | 5 |
| | injection 21 days after MI | |
| 13 | time point 1 | 5 |
| 14 | time point 2 | 5 |
| | Circulatory system injection time point 1 after MI | |
| 15 | time point 1 | 5 |
| 16 | time point 2 | 5 |
| | time point 2 after MI | |
| 17 | time point 1 | 5 |
| 18 | time point 2 | 5 |
| Sub Total Group II | | 82 |
| Loss after MI @ 25% | | 21 |
| Failure to induce MI @ 20% | | 21 |
| Contingency @ 10% | | 13 |
| Grand Total Group II | | 137 |

Results

Normal and infected rats were examined by cenforal microscopy to assess the incorporation and differentiation of the ELSC stem cells. Exemplary microscopy results are shown in FIGS. 56 through 64. Rhodamine phalloidin was utilized to stain f-actin, thereby visualizing myofibrils as red in all images. The striations on the red fibers are clear indications of cardiac muscle fibers. TOPRO3, a DNA intercalating dye was used to stain nuclei blue. FITC-labeled B-galactosidase stain the stem cells green. Differentiation of the ELSC stem cell is indicated by co-labeling of green and blue nucleus with red striated fibers in close proximity.

FIGS. 56-59 are images of Rat 14. Rat 14 received a cryogenic MI, and was injected with 200 UL stem cells at 2.0×10 6 cells per ml eight (8) days later. Its heart was harvested eleven (11) days after infusion of stem cells and analyzed. B-galactosidase positive stem cells are clearly seen (green nuclei). FIGS. 58 and 59 show B-gal labeled cells and small myofibrils inside the infected area. Yellow color is from simultaneous collection of all three channels.

FIGS. 60 and 61 are images of Rat 36, which received a stem cell injection from a sub xiphoid window and whose heart was harvested one (1) day later. The images from Rat 36 show the green labeled B-gal positive stem cells as a group. The stem cells have not yet dispersed throughout the myocardium.

FIGS. 62 and 63 are again Rat 14, showing integrated stem cells; the stem cells are incorporated into the damaged myocardium. FIG. 64 is an image from Rat 47, which received DPBS only as a control. There is little FITC staining and no co-labeling of the nucleus.

Example 22

Neuronal Potential of Adult Rat Muscle-Derived Pluripotent Stem Cells

Abstract

Stem cells were isolated from adult rat muscle and exposed to growth factors and defined differentiating conditions for 5 and 24 hours. Cells were examined with immunocytochemistry and fluorescence assisted cell sorting. At 5 hours, more than 90% of the cells co-expressed phenotypic markers of mature neurons and glial cells. This pattern of co-expression has been previously shown in neuro-glial progenitors, suggesting that stem cells from adult muscle can differentiate along a neuroectodermal lineage. At 24 hours, most cells still expressed neuronal markers whereas only a subset co-expressed glial markers. Our study confirms the presence of multipotent stem cells in adult muscle and shows that these cells are able to overcome germ lineage restriction and express the characteristics of neural stem cells. Therefore, stem cells isolated from adult rat muscle could provide a novel source for autologous cell replacement in neurodegenerative diseases.

Introduction

Stem cells were thought to be life-time-committed to specific lineages depending on their germ layer (Faust and Magnuson, 1993). Recent studies, however, have demonstrated lineage interconversion within the same or even different germ layers (Jackson et al., 1999; Kopen et al., 1999; Mezey et al. 2000; Tsai and McKay, 2000). Thus stem cells derived form adult tissues may retain plasticity in their commitment, and their differentiation may be influenced by environment rather than by lineage.

Stem cells have been identified within the connective tissues of skeletal muscle (Pate et al., 1993; Young et al., 1999; Jackson et al. 1999). These cells can differentiate into multiple phenotypes of the mesenchymal and other lineages (Jackson et al. 1999; Young, unpublished observations), suggesting that they are multipotent stem cells. It is unclear, however, whether these cells can be induced to primarily express a neural phenotype.

If stem cells isolated from adult muscle could differentiate into neurons and glia, they could provide a unique source of cells for neural repair. Indeed, clinical evidence indicates that transplantation of fetal brain tissue is a viable therapy for some neurodegenerative diseases (Bjorklund and Lindvall, 2000). However, restricted availability of fetal human tissue, ethical hurdles and the need for toxic immunosupressant drugs, have seriously limited this therapeutic approach.

Autologous transplantation avoids the use of immunosuppressants and the risk of infection from the graft. Recent studies have shown that exogenous bone marrow stem cells can differentiate into neurons in vitro (Woodbury et al. 2000) and when transplanted into brain (Kopen et al., 1999; Mezey et al., 2000; Brazelton et al., 2000). The use of bone marrow cells, however, has its own limitations and an alternate source of stem cells that could be easily and safely harvested from the patient him/herself would be highly desirable. The goal of the present study was to determine whether multipotent stem cells isolated from adult muscle could be directed to express a neural phenotype in vitro.

Material and Methods

Cell Isolation:

Rat pluripotent stem cells (PPSCs) were isolated from the gactrocnemius and flexor digitorum of 6 months-old Sprague Dawley rats (Charles River Laboratories, Los Angeles, Calif.) as described previously (Lucas et al., 1995; Young et al., 1999). In accordance with the guidelines of the UCLA Office for Protection of Research Subjects. RMSCs originally cultured in E-MEM (GIBCO BRL, Grand Island, N.Y.) were released with Trypsin-EDTA buffer, and then plated in gelatin coated flasks with a Basic Medium consisting of OPTIMem (GIBCO), 0.01 mM β-mercaptoethanol (Sigma, St Louis, Mo.), 0.028 M sodium bicarbonate (Sigma), 100 U penicillin G, 100 U streptomycin and 250 ng amphotericin B (GIBCO), supplemented with 10% horse serum (HS) (BioWhittaker, Walkersville, Md.) (Basic Medium/HS) or with fetal bovine serum (FBS) 15% (Omega Scientific, Tarzana, Calif.) (Basic Medium/FBS). The cells were passaged and cryopreserved after each passage in one of these two media at least 3 times.

Neuroectodermal Differentiation:

Cyropreserved cells were thawed and plated on 1% gelatin-coated plastic dishes or poly-ornithine/laminin (PO/L) coated coverslips and maintained in Basic Medium/HS or Basic Medium/FBS for at least two days. When cells reached 70% confluency they were transferred to a Basic Medium/HS or Basic Medium/FBS containing basic fibroblast growth factor (bFGF) 10 mg/ml (GIBCO) for 24 hours. After this preincubation the cells were washed with Dubelcco's phosphate buffered saline (GIBCO) and transferred to a differentiation medium modified from that used by Woodbury et al., (2000). This medium consisted of the Basic Medium without serum, containing 2% dimethylsulfoxide, 200 Fm butylated hydroxyanisole, 25 mM KCl, 2 mM Valproic acid, 10 FM forskolin, 1 FM hydrocortisone, and 5 Fg/ml of insulin (all from Sigma). The cells were maintained in this Differentiation Medium for either 5 or 24 hours. They were then washed with 0.1 M phosphate buffered saline (PBS) and processed for immunocytochemistry or flow cytometry as described below.

Immunocytochemistry:

The cells were plated in gelatin-coated-24 wells plates (5 hours treatment) or on PO/L-coated-coverslips (24 hours treatment, to improve adhesion of differentiated cells) at a density of 2-3,000 cells per well and treated as described above. Each marker was examined in at least three independent experiments. After each treatment the cells were fixed 20 min in cold para-formaldehyde (PFA) 4% in 0.1 M phosphate buffer. The cells were washed with Phosphate buffered saline (PBS) and treated with a quenching solution: 3.6 mg/ml Glucose, 0.13 mg/ml sodium azide and 0.1 mg/ml glucose oxidase (all from Sigma) in PBS for 1 hour at 37?C to decrease internal peroxidase activity. Cells were washed and incubated 2 hours at room temperature (RT) in a blocking solution (BSA 1%, 0.25 Triton, and 5% of normal serum). The cells were then covered with a solution containing Triton-X (0.25%) (except for neuron specific enolase antibody) and 2.5% of the appropriate serum and the primary antibody, and incubated at RT overnight. The cells were washed in PBS and incubated 1 hour at RT with the secondary antibodies: goat anti-mouse IgM 1:200 (Vector, Burlingame, Calif.) or an IgG antibody supplied in the Vector ABC Elite kit, 1:200 in 0.25% triton-X (except for NSE) and 1% serum. The cells were washed in PBS and then incubated for 45 minutes in the AB solution of the ABC Elite kit (Vector). After washes, the antigen/antibody complexes were visualized with 0.33 mg/ml diaminobenzidine (DAB) as chromagen and 0.06% $H_2O_2$.

Primary antibody used and source: mouse anti-Nestin, monoclonal 1:1000 (Hybridoma Bank. Iowa). Rabbit anti-glial fibrillaric acidic protein, polyclonal (GFAP) 1:250 (Zymed, S. Francisco, Calif.). Mouse anti-beta-tubuline III, monoclonal 1:400 and mouse anti-smooth muscle actin, monoclonal 1:300 (Sigma). Mouse anti-GFAP, monoclonal 1:200, mouse anti-tau protein, monoclonal 1:250, mouse anti-NeuN, monoclonal 1:200, rabbit anti-Neurofilament 145 kD, polyclonal 1:400, mouse anti-Neurofilament 200 kDa, monoclonal, rabbit anti-NG2, polyclonal 1:400, rabbit anti-neuron specific enolase, polyclonal (NSE) 1:250, mouse anti-A2B5, monoclonal 1:200, mouse anti-myelin oligoderldrocytes specific protein, monoclonal 1:600 and mouse anti-galactocerebroside, monoclonal (GAL) 1:200 (Chemicon, Temecula, Calif.).

Each experiment included wells without primary or secondary antibody as controls. Only experiments where no staining was observed in the control wells were further analyzed. Cells in coverslips were dehydrated, de-fatted in xylene, and mounted with Eukit (Calibrated Instruments, Hawthorne, N.Y.); and visualized with a Axioscope Zeiss microscope (Germany) and photographed with a Spot camera (Diagnostic Instruments inc., USA). The cells in wells were visualized with an inverted microscope (Leica DMIL) under 20× and 40× lens, and photographed with a Kodak Digital Still Camera DKC-CM30. For quantification, 6 non-overlapping fields of each well were viewed with a 20× objective and captured. Positive and total cells were counted in each field, the numbers added for each well, and the percentage of positive cells calculated. Means and standard deviations were calculated from three separated experiments.

Flow Cytometry:

After incubation in the differentiation medium, cells were released with Trypsin/EDTA and stained with 0.2% trypan blue (Sigma) before being counted with an hemocytometer to confirm that cell viability was greater than 90%. The cell suspension was centrifuged and washed with PBS, and this process was repeated twice. The cells were fixed in PFA at 4° C. for 20 minutes, centrifuged and washed with PBS twice. The blocking step and incubation with the primary antibodies were as described for immunocytochemistry. The primary antibodies used were: NSE, NF145, GFAP polyclonal and NG2. The secondary antibodies were a phycoerythrin-coupled anti-rabbit or a FITC-coupled anti-rabbit (Jackson ImmunoResearch, West Grove, Pa.). The cells were incubated in the secondary antibodies for 1 hour at room temperature in 0.25% triton and 1% normal goat serum. They were washed 5 minutes with PBS and centrifuged twice. The cells were resuspended in PBS with 1% PFA, and then processed for fluorescence assisted cell sorting (FACScan, Becton Dickinson). An isotype control was included in each experiment to identify background fluorescence, which included the cells incubated with the secondary antibody in the absence of primary antibody.

Results

Rapid Morphological Changes of PPSCs after Exposure to the Differentiation Medium.

When grown in the Basic Medium with serum, undifferentiated RMSCs had a flat, polygonal morphology (FIG. 65A). After 30 minutes in the differentiation medium, 90-98% of the RMSCs showed a contraction of the cell body and the emergence of processes. The processes continued to develop, with the appearance of growth-cone-like tips and filopodial-like extensions. A relatively complex network of processes was observed in the wells after 5 hours (FIG. 65B). At this time, four populations of cells with round cell bodies were observed: numerous small cells with one to three main processes (FIG. 65B) and large cells with a multipolar dendritic trees, that were usually isolated (10-20% of morphologically differentiated cells, FIG. 1C). Rarely large bipolar cells making contacts with their neighbors (FIG. 65D) and small cells with triangular cell body were observed (FIG. 66B).

After 24 hours in the differentiation medium, the cells could be divided in two different populations according to the presence or absence of processes. The cells with processes showed diverse morphologies: 20% cells had small round cell bodies and usually two, or more rarely three, processes similar to the ones observed after 5 hours; 25% of the cells were small, with triangular and polygonal cell bodies with long processes; 10% of the cells had multipolar processes. At this time, as many as 45% of the cells were large, polygonal, with a large nucleus and no processes.

Non-Treated PPSCs are Negative for Neuronal and Glial Markers.

PPSCs were immunostained prior to incubation in the differentiation medium. A few PPSCs showed a weak staining for NG2, an oligodendrocytic marker. Sporadically, when expanded in FBS, round cells with processes were observed and these were weakly stained for the neuronal markers NF 145 and tau. PPSCs were negative for the other neuronal or glial markers. A few cells with the typical morphology of myocytes were stained with a muscle-specific actin antibody, suggesting that a few cells (less than a 4%) are continuously differentiating in the basic medium with serum.

PPSCs were Positive for Neuronal and Glial Markers after 5 and 24 Hours in the Differentiation Medium.

Results are summarized in TABLE 19. Nestin is an early marker for brain cells that is present in neural progenitors (Lendahl et al., 1990) and in muscle precursors cells (Zimmerman et al., 1994). When RMSCs were expanded in HS and differentiated for 5 or 24 hours, 60% of cells with round cell bodies and processes showed a high level of immunostaining for nestin in the cytoplasm and processes (FIG. 66A). Some of the triangular and polygonal cells with processes showed a weak, diffuse staining but flat cells were always negative. Less reliable immunostaining for nestin was observed when cells were expanded in FBS.

TABLE 19

Antigenic Properties of RMSCs Pre and Post-Differentiation for 5 and 24 Hours.

| Antigen | Control | | 5 hr. diff. | | 24 hr. diff. | |
|---|---|---|---|---|---|---|
| | HS | FBS | HS | FBS | HS | FBS |
| Nestin | — | — | +++/− | +/− | ++/+/− | — |
| NF145 | — | −/+* | +++/− | +++/− | +++/+/− | +++/+/− |
| NF200 | — | — | ++/− | ++/− | ++/+/− | ++/+/− |
| Tou | — | −/+* | +++/− | +++/− | ++/+/− | +++/+/− |
| NSE | — | — | +/− | ++/+/− | ++/− | ++/− |
| A2B5 | — | — | — | — | — | — |
| GFAPm | — | — | +/− | +/− | +/− | +/− |
| GFAPp | — | — | ++/− | +++/− | ++/− | ++/− |
| NG2 | −/+* | −/+ | +++/++/− | +++/++/− | 0 | ++/+/− |
| GalC | — | — | — | — | — | — |
| MOS | — | — | — | — | — | — |

TABLE 19-continued

Antigenic Properties of RMSCs Pre and Post-Differentiation for 5 and 24 Hours.

|  | Control | | 5 hr. diff. | | 24 hr. diff. | |
| --- | --- | --- | --- | --- | --- | --- |
| Antigen | HS | FBS | HS | FBS | HS | FBS |
| NeuN | — | — | — | — | −/+* | −/+* |
| BTubIII | — | — | — | — | — | −/+* |

Control were non-treated RMSCs.
+++ strong labeling;
++ moderate labeled;
+ weak labeling;
− not labeled,
−/+* only very few (<5%) rounder cell with processes show weak staining;
GFAPm: Glial fibrillary acidic protein monoclonal;
GFAPp: Glial fibrillary acidic protein polyclonal;
β-Tub III: β-tubuline III;
NeuN: neuronal nuclei;
NF145: Neurofilament MW 145 KD;
NF200: Neurofilament MW 200 kDa;
NG2: NG2 chondroitin sulfate proteoglycan;
MOS: myelin oligodendrocytes specific protein;
GalC: galactocerebroside.

Neurofilaments are heteropolymeric, neuron-specific filaments required for proper radial growth, neurite formation and maintenance (Lee and Cleveland, 1996). Antibodies that recognize neurofilaments of medium molecular weight (MW 145 kDa: NF145), and of higher molecular weight, usually found in mature neurons (MW 200 kDa: NF200), were used. Both antibodies showed a similar pattern of immunostaining in the cells bodies, and some cells exhibited intensely stained processes after 5 hours of differentiation (FIG. 66B, C). Flat cells were not-stained. At 24 hours, the majority of cells with processes was strongly (for NF145) or moderate (for NF200) immunostained, whereas polygonal cells showed weak, diffuse staining or no staining (FIG. 67A, B). A similar pattern was observed with another neuronal marker, tau, a microtubule associated protein expressed by differentiating neurons (Kosik, 1993; FIG. 66E, 67C).

We also tested an antibody against neuron specific enolase (NSE), a brain specific isozyme of the glycolytic enzyme enolase that is present in the cytoplasm of mature neurons (Iwanaga et al., 1989). Cultures were positive for NSE after 5 hours (FIG. 66D) and the staining intensity increased in a subset of the cells exhibiting round or triangular morphology with processes at 24 hours. Flat polygonal cells were negative.

PPSCs were negative for A2B5, a ganglioside marker of glial progenitors (data not shown). In contrast, at 5 hours PPSCs showed staining with the two antibodies against GFAP, a marker of mature astrocytes and Schwann cells (FIG. 66G). Flat cells did not stain with either antibody. At 24 hours the staining decreased in most of the cells, however a subset of round and multipolar cells with processes showed intense labeling (FIG. 67D).

NG2 is a proteoglycan present in the membranes of progenitors as well as differentiated oligodendrocytes (Dawson et al., 2000). At 5 hours approximately 60% of the cells expanded in FBS, and more of the cells expanded in HS, showed immunostaining of strong or medium intensity (FIG. 66F). The remainder of the cells was devoid of staining. Intense labeling was found in cells of all morphological types and the morphology of immunopositive and immunonegative cells was similar. At 5 hours a fraction of the remaining flat cells (5-10% of the total) showed weak membrane staining for NG2. At 24 hours, all the cells expanded in HS showed moderate staining for NG2 (FIG. 67E). However, the cells expanded in FBS showed variable levels of staining from none to moderate. No staining was observed for myelin oligodendrocyte specific protein and galactocerebroside, two molecules associated with mature oligodendrocytes.

NeuN, a nuclear protein related to the initiation of terminal differentiation of neurons and a marker for post-mitotic cells, was also examined (Sarnat et al., 1998). At 5 and 24 hours, very few differentiated cells were positively stained. No staining was observed with the antibody for beta-Tubuline type III at 5 hours in cells expanded in HS or FBS. A few of the cells expanded in FBS but none of the cells expanded in HS, were positive at 24 hours The Majority of PPSCs Co-Express Glial and Neuronal Markers after Differentiation.

At 5 hours, the percentage of cells expanded in HS and in FBS that stained for NF145 was 71.2±3.8 and 97.0±1.4, respectively. For NSE the percentage were 74.3±9.1 and 87.2±6.6 for cells expanded in HS and FBS, respectively. For GFAP, 68.4±11.1% cells were positive when expanded in HS and 92.8±1.3% in FBS. The percentage of cells positive for the NG2 chondroitin sulfate was 51.8±7.5 in HS and 63.1±16.5 in FBS. (The results are the average of 3 experiments±standard deviation).

To further measure of the relative number of cells expressing either neuronal or glial phenotypic markers, fluorescence assisted cell sorting (FACS) was performed on cells immunostained with the following antibodies: NF145 or NSE as neuronal markers, GFAP as a astroglial marker, and NG2 as a oligodendroglial marker (FIG. 67G). Only PPSCs expanded in FBS and differentiated for 24 hours were examined by FACS. 61.9±23.3% of the cells were positive for NG2, 52.6±16.9% were positive for GFAP, while 90.7±5.0% were positive for NF145 and 50.3±22.6% for NSE (result are the average of three experiments±standard deviation). So, although the vast majority of cells reproducibly expressed the neuronal marker NF145, expression of the other markers was more variable form one experiment to the other.

Discussion

We show that muscles of adult rats contain pluripotent stem cells that can be directed towards the neuroectodermal lineage in vitro. Indeed, a well controlled treatment directed more than 80% of these cells to co-express phenotypic markers of mature neurons and glial cells. Interestingly, roughly similar conditions can induce the differentiation of bone marrow cells into cells expressing neuronal markers, although the co-existence of glial markers in these cells has not been fully characterized (Woodbury et al., 2000). Therefore, similar environmental cues can lead stem cells of different origin (bone marrow or muscle) towards a neuronal fate. To our knowledge, this is the first report of differentiation of muscle stem cells into neural progenitors. We suggest that these cells represent a novel source for neuroglial replacement in vivo.

In our study, PPSCs were directed to a non-mesenchymal lineage, as shown by the expression of proteins located almost exclusively in neurons and glia. After 5 hours of differentiation, the PPSCs co-expressed nestin, an intermediate filament used as a marker for neural progenitors in the mammalian CNS, as well as neuronal and glial markers such as neurofilaments and GFAP, respectively. A similar stage of co-expression of nestin and neuronal or glial markers has been observed in cultures of human fetal brain cells and can represent a transition period towards either glial or neuronal fates (Messam et al., 2000). This is supported by the decreased immunostaining for nestin at 24 hours, while neuronal markers remained strongly expressed.

After 5 and 24 hours, a variable proportion of cells expressed the NG2 protein, a marker of oligodendrocytes progenitors (Dawson et al., 2000), while also expressing neuronal markers. Rat progenitor oligodendrocytes can give rise to astroglia, neurons and oligodendrocytes, depending of the culture conditions, indicating that oligodendrocyte precursors cells are not irreversibly committed towards the glial fate (Kondo and Raff, 2000). Thus NG2/neurofilament positive cells derived from adult RMSCs could represent a population of multipotent neural cells.

Co-localization of glial and neuronal marker has been previously observed in hippocampal stem cells in vitro after treatment with bFGF in a serum free medium (Gage et al., 1995), in rat embryonic cells from striatum at early stages of differentiation (Rosser et al., 1997), in fetal human brain cells in culture (Piper et al. 2000), and in immortalized embryonic mesencephalic mouse cells in culture (Colucci-D'Amato et al., 1999). Similarly, postnatal forebrain neural progenitors can display mixed glial and neuronal properties in vitro, while expressing NSE, NF and GFAP (Feldman et al., 1996). Therefore, co-expression of glial and neuronal markers is a common pattern that reflects multipotentiality at early stages of differentiation. Co-expression of glial and neuronal markers in PPSCs at 5 hours indicate that they are at an early stage in the neuroectodermal lineage and have not yet been committed to a specific fate. This coexpression was not always present when PPSCs were differentiated for 24 hours, as GFAP staining was present only in a subset of cells. In contrast, some of the neuronal markers, specifically tau and neurofilaments, were strongly expressed in most cells at 24 hours, suggesting that more early progenitors present at 5 hour are committed towards the neuronal than the glial phenotype in our conditions.

In conclusion, our study confirms the presence of pluripotent stem cells in adult muscle and shows that these cells are able to overcome germ lineage restrictions and express the characteristics of neural stem cells. Therefore, stem cells isolated from adult rat muscle could provide a novel source for autologous cell replacement in neurodegenerative diseases. A distinct advantage of these stem cells is that they can be safely and easily harvested, even from senior individuals, can be expanded in vitro, and cryopreserved without losing their multipotentiality. Preliminary data from our laboratory shows that these cells can survive long periods (2 months) after transplantation into the CNS, do not migrate away from the injection area and do not form tumors (see Example 23 below).

REFERENCES

Bjorklund A, Lindvall O (2000) Cell replacement therapies for central nervous system disorders. Nat Neurosci 3: 537-544.

Brazelton T R, Rossi F M, Keshet G I, Blau H M (2000) From marrow to brain: expression of neuronal phenotypes in adult mice. Science 290: 1775-1779.

Colucci-D'Amato G L, Tino A, Pernas-Alonso R, ffrench-Mullen J M, di Porzio U (1999) Neuronal and glial properties coexist in a novel mouse CNS immortalized cell line. Exp Cell Res 252: 383-391.

Dawson M R, Levine J M, Reynolds R (2000) NG2-expressing cells in the central nervous system: Are they oligodendroglial progenitors? J Neurosci Res 61: 471-479.

Faust C, Magnuson T (1993) Genetic control of gastrulation in the mouse. Curr Opin Genet Dev 3: 491-498.

Feldman D H, Thinschimidt J S, Peel A L, Papke R L, Reier P J (1996) Differentiation of ionic currents in CNS progenitor cells: dependence upon substrate attachment and epidermal growth factor. Exp Neurol 140: 206-217.

Gage F H, Coates P W, Palmer T D, Kuhn H G. Fisher L J, Suhonen J O, Peterson D A, Suhr S T, Ray J (1995) Survival and differentiation of adult neuronal progenitor cells transplanted to the adult brain. Proc Natl Acad Sci USA 92: 11879-11883.

Iwanaga T, Takahashi Y, Fujita T (1989) Immunohistochemistry of neuron-specific and glia-specific proteins. Arch Histol Cytol 52 Suppl: 13-24.

Jackson K A, Mi T, Goodell M A (1999) Hematopoietic potential of stem cells isolated from murine skeletal muscle. Proc Natl Acad Sci USA 96: 14482-14486.

Kondo T, Raff M (2000) Oligodendrocyte precursor cells reprogrammed to become multipotential CNS stem cells. Science 289: 1754-1757.

Kopen G C, Prockop D J, Phinney D G (1999) Marrow stromal cells migrate throughout forebrain and cerebellum, and they differentiate into astrocytes after injection into neonatal mouse brains. Proc Natl Acad Sci USA 96: 10711-10716.

Kosik K S (1993) The molecular and cellular biology of tau. Brain Pathol 3: 39-43.

Lee M K, Cleveland D W (1996) Neuronal intermediate filaments. Annu Rev Neurosci 19: 187-217.

Lendahl U, Zimmerman L B, McKay R D (1990) CNS stem cells express a new class of intermediate filament protein. Cell 60: 585-595.

Lucas P A, Calcutt A F, Southerland S S, Warejcka D, Young H E (1995) A population of cells resident within embryonic and newborn rat skeletal muscle is capable of differentiating onto multiple mesodermal phenotypes. Wound Repair and Regeneration 3: 457-468.

Messam C A, Hou J, Major E O (2000) Coexpression of nestin in neural and glial cells in the developing human CNS defined by a human-specific anti-nestin antibody. Exp Neurol 161: 585-596.

Mezey E, Chandross K J, Harta G, Maki R A, McKercher S R (2000) Turning blood into brain: cells bearing neuronal antigens generated in vivo from bone marrow. Science 290: 1779-1782.

Pate, D. W., Southerland, S. S., Grande, D. A., Young, H. E., and Lucas, P. A. Isolation and differentiation of mesenchymal stem cell from rabbit muscle. Surgical Forum XLIV, 587-589.1993.

Piper D R, Mujtaba T, Rao M S, Lucero M T (2000) Immunocytochemical and physiological characterization of a population of cultured human neural precursors. J Neurophysiol 84: 534-548.

Rosser A E, Tyers P, ter Borg M, Dunnett S B, Svendsen C N (1997) Co-expression of MAP-2 and GFAP in cells developing from rat EGF responsive precursor cells. Brain Res Dev Brain Res 98: 291-295.

Sarnat H B, Nochlin D, Born D E (1998) Neuronal nuclear antigen (NeuN): a marker of neuronal maturation in early human fetal nervous system. Brain Dev 20: 88-94.

Tsai R Y, McKay R D (2000) Cell contact regulates fate choice by cortical stem cells. J Neurosci 20: 3725-3735.

Woodbury D, Schwarz E J, Prockop D J, Black I B (2000) Adult rat and human bone marrow stromal cells differentiate into neurons. J Neurosci Res 61: 364-370.

Young H E, Steele T A, Bray R A, Detmer K, Blake L W, Lucas P W, Black A C (1999) Human pluripotent and progenitor cells display cell surface cluster differentiation markers CD10, CD13, CD56, and MHC class-I. Proc Soc Exp Biol Med 221: 63-71.

Zimmerman L, Parr B, Lendahl U, Cunningham M, McKay R, Gavin B, Mann J, Vassileva G. McMahon A (1994) Independent regulatory elements in the nestin gene direct transgene expression to neural stem cells or muscle precursors. Neuron 12: 11-24.

Example 23

In Vivo Assessment of Neural Phenotypes

Transplants of PPSCs into the striatum of adult rats were performed. PPSC were isolated form muscles from a newborn rat and grown in horse or fetal bovine serum and injected into the striatum of adult rats. Briefly, PPSC were released with 0.025% trypsin-EDTA. The trypsin was neutralized with horse serum and the suspension centrifuged at 150×g for 20 minutes. The supernatant was discarded and the cell pellet resuspended in Opti-MEM+10% horse serum or 15% fetal bovine serum and PPSCs were counted on a hemocytometer. For injection into Sprague Dawley rats (250-300 g), PPSCs were centrifuged again at 150×g for 20 minutes. The supernatant was discarded and the cell pellet resuspended in phosphate buffered saline (pH 7.4) and the concentration adjusted to 250,000 cells/μl. 125,000 cells were implanted stereotaxically into the striatum (in 0.5 μl saline) slowly with a rate of 0.1 μl/min. The rats were sacrificed one or two months after transplantation. Animals were perfused through the heart with fixative under deep anesthesia, the brain removed, and tissue sections of the striatum were processed as described below.

FIG. 68 shows photomicrographs from rats that were sacrificed one month (A, C, D and E) or two months (B) after transplantation. A and B: PPSCs incubated with bromodeoxyuridine (BrDU) prior to transplantation and detected in tissue sections with an antibody against BrDU. Positively labeled cells were confined to the area of the injection (open arrows), and few cells have moved in the vicinity of the needle track (filled arrows). No labeled cells were found far from the needle track or in other brain regions. C and D: PPSC transfected with a vector expressing Green Fluorescence Protein (GFP). C: Low magnification photomicrograph showing the transplant with numerous fluorescent cells. Some cells with processes expressing GFP were observed at high magnification (D: arrows). E: PPSCs transfected with beta-galactosidase (β-Gal): the cells were visualized one month post-transplantation with histochemistry. The cells did not migrate from the injection area, but were localized in the needle track (open arrow) or its vicinity (filled arrow). It should be noted that photomicrographs shown in A, B and E were taken at a distance from the center of the transplant. Therefore the area of labeled cells does not represent the maximal extent of the transplant. Scale bars: 20 μm. F: Schematic diagram of a frontal section of rat brain at the level of the striatum, showing the area of injection photographed in A, B, C, D and E.

Example 24

Induced Pancreatic Islet Formation in Rodent Pluripotent Epiblastic-Like Stem Cells Rat-A2B2-scl-40 (rat pluripotent epiblastic-like stem cells isolated and cloned from the skeletal muscle connective tissue of postnatal rats) and ROSA (mouse pluripotent epiblastic-like stem cells isolated from the skeletal muscle of adult ROSA mice) were used for the experiment. The cells were plated at 1000 cells per well in 1% gelatin-coated 96-well tissue culture plates in complete medium (Opti-MEM+B-mercaptoethanol+penicillin/streptomycin/fungizone+15% MFCS1, pH 7.4) and maintained in a 37° C. humidified tissue culture incubator. The cells were allowed to attach for 24 hr and then washed repeatedly with buffer (Dulbecco's Phosphate buffered saline at pH 7.4) to remove plating medium and any dead cells and debris from the plating procedure. The cells were then fed induction medium every other day for 7 days. Induction medium was composed of (Opti-MEM+B-mercaptoethanol+penicillin/streptomycin/fungizone+2 mg/ml insulin+10–6 M dexamethasone+ 10% HS10, pH 7.4)

At termination of experiment the cells were washed with buffer, fixed with glutaraldehyde/formaldehyde, and stained with antibodies to endodermal germ layer lineage cells, endodermal progenitor cells, liver, pancreas, and pancreatic islet cells. Antibodies utilized were directed against one or more of the following epitopes: RAFP (rat alpha-fetoprotein, an endodermal germ layer lineage marker), OC2 (endodermal progenitor cell marker), OV6 (endodermal progenitor cell marker), DESMO (endodermal epithelial marker), H1 (endodermal cell surface marker), H4 (liver cytoplasmic marker), cytokeratin-19 (pancreas marker), insulin (insulin secreting cell in pancreatic islet), and glucagon (glucagon secreting cell in pancreatic islet).

The results of the antibody studies are presented in TABLE 20.

TABLE 20

| Antibodies | A2B2-scl-40 | ROSA |
| --- | --- | --- |
| a-RAFP | + | + |
| a-OC2 | + | n/d |
| a-OV6 | + | n/d |
| a-DESMO | + | n/d |
| a-H1 | + | + |
| a-H4 | − | − |
| a-Cytokeratin-19 | + | + |
| a-Insulin | + | + |
| a-Glucagon | + | + |

+ indicates staining observed.
− indicate no staining observed.
n/d not done.

FIGS. 69 through 72 depict the results with species (A2B2-scl-40 or ROSA) and antibodies utilized (see above). Data demonstrates induction of functional endodermal lineage pancreatic islet cells in postnatal pluripotent epiblastic-like stem cells from two different rodent species, rat and mouse.

Quantitative ELICA

Three wells per serum concentration were examined in quantitative ELICA for insulin secretion. In the ELICA procedure, after unbound tertiary probe (avidin-HRP) is removed from the system the wells are incubated with the soluble HRP substrate ABTS for 30 min in the dark. In the presence of bound peroxidase enzyme the normally clear substrate turns green in color and can be measured at 405 nm. Negative control is unreacted substrate. Positive control is the ABTS substrate reacted with 5 ml of avidin-HRP. Mean values for the range of HS10 serum are as noted below in TABLE 21.

TABLE 21

| Conc. HS10 | Mean Value (n = 3) |
|---|---|
| Opti Only | 1.101 |
| 1% | 1.071 |
| 2.5% | 1.199 |
| 5% | 0.865 |
| 7.5% | 0.963 |
| 10% | 1.099 |
| 12.5% | 1.214 |
| 15% | 0.781 |
| 17.5% | 1.088 |
| +control | 1.336 |
| −control | 0.024 |

As shown, there is really no difference with respect to presence or absence of HS10 serum in the medium and the presence of insulin-secreting islets in the wells.

Example 25

PDX1 Gene Expression by ELSCS Cultured to Express Pancreatic Phenotypes

ELSCs (CT3F) cells were cultured in accordance with published protocols of Bonner-Weir et al for induction of islet cell phenotypes (Bonner-Weir et al (2000) PNAS 97:7999-8004; Ron et al (1993) JBC 268:2984-2988). Total RNA was isolated and subjected to RT PCR using the Qiagen Rneast kit. The PCR reaction was conducted with primers designed specifically for the human pdx1 gene. An RT-PCR product of the expected approximately 300 base pair size was detected in the cultured CT3F cells.

Example 26

Evaluation of PPSCs in an Osteochondral Defect In Vivo

Background

Previous studies had indicated that implanting PPSCs in a polyglycolic acid (PGA) felt into full-thickness critical sized defects in adult rabbits resulted in histological regeneration of both the cartilage and bone. This regeneration could be detected initially at 12 weeks and was complete at 18 weeks. However, numbers were relatively few and there was question about the mechanical strength of the regenerated tissue and whether it would persist with time. Therefore, we sought to determine if the application of allogenic MSCs to an osteochondral defect will result in cartilage and bone that is morphologically and mechanically identical to the original. Specifically, this was be done at 26 weeks postimplantation to determine the long term viability of the regenerated tissue.

Materials and Methods
Isolation of PPSCs:

PPSCs were isolated as above described from skeletal muscle of adult male rabbits. The rabbit was euthanized, then portions of the gluteus maximus, gluteus minimus, and quadratus muscle were dissected. Great care was taken to avoid major blood vessels, tendons, or nerves. The muscle was transferred to a 100 mm plastic culture dish in a tissue culture hood in 10 ml of Eagle's Minimal Essential Media with Earle's salts (EMEM) (GIBCO, Grand Island. N.Y.) supplemented with 10% pre-selected horse serum. The muscle tissue was then carefully minced using sterile curved scissors. The solution was transferred to a sterile 50 ml conical centrifuge tube and centrifuged at 50×g for 20 minutes The supernatant was discarded and an estimate made of the pellet volume.

The cell pellet was resuspended in 7 volumes of EMEM and 2 volumes collagenase/dispase solution to enzymatically release the cells. The collagenase solution consisted of 37,500 units of collagenase (CLS-1 Worthington Biochemicals. Freehold, N.J.) in 50 ml EMEM added to 100 ml dispase solution (Collaborative Research. Bedford. Mass.). The final concentrations were 250 units/ml collagenase and 333 units/ml dispase. The tissue suspension was transferred to a sterile 100 ml media bottle containing a magnetic stir bar stirred at 37° C. for 1 hour until the tissue was digested. The suspension was transferred to centrifuge tubes and centrifuged at 300×g for 20 minutes. The supernatant was discarded and the cells resuspended in 20 ml of EMEM with 10% horse serum. The cells were filtered through a 20 μm Nitex filter to obtain a single cell suspension, centrifuged at 150×g for 10 minutes. The supernatant discarded, and the pellet resuspended in 10 ml of EMEM+10% horse serum. The cells were counted on a hemocytometer and plated at 100,000 cells per 100 mm culture dish. The dishes were precoated with 1% bovine gelatin (EM Sciences. Cherry Hills N.J.).

After the cells grew to confluence (approximately 8 days in culture), they consisted of multinucleated myotubes and a large population of mononucleated cells. The cultures were released from the dish with 0.025% trypsin in Dulbecco's Phosphate Buffered Saline (DPBS) with 0.01% ethylenediaminetetraacetic acid (EDTA) and filtered through a 20 μm filter. This filtration removes the myotubes leaving only the population of mononucleated cells. These cells were then frozen in aliquots of 1 ml containing $10^6$ cells in EMEM+ 10% horse serum and 7.5% DMSO (Sigma). Cryopreservation was performed in freezing chambers (Fisher Scientific. Norcross, Ga.) to slow freeze the cells to −80° C. [12]. After being frozen for at least 24 hours, aliquots of the frozen cells were thawed and plated at a density of 100,000 cells 100 mm culture dish for expansion prior to seeding in PGA felt or plated at 20,000 cells per 16 mm well in 24-well gelatin-coated culture plates (Corning Glass Works, Corning, N.Y.) in EMEM+10% horse serum for dexamethasone testing. In either case, these cells are designated as secondary cultures.

Testing with dexamethasone confirmed the differentiation of chondrocytes, osteoblasts, skeletal myotubes, smooth muscle cells, and endothelial cells, from the PPSCs in vitro.
Seeding PPSCs into PGA Felt:

PPSCs were seeded into PGA felt as described in the Phase I grant. PGA felt (obtained in a 30×60 cm sheet) was cut into circles 10 mm in diameter and sterilized with ethylene oxide. Secondary cultures in 100 mm dishes as described above were grown to confluence. At this point there were from 2-4 million cells per dish. The cells were detached from the dish with 0.025% trypsin in a solution of 3:1 Dulbecco's phosphate-buffered saline (DPBS) without $Ca^{2+}$, $Mg^{2+}$, and DPBS-EDTA. The trypsin was neutralized with horse serum and the suspension was centrifuged at 150×g for 20 minutes. The supernatant was discarded and the cell pellet resuspended in EMEM+10% horse serum. The cells were counted on a hemocytometer and the concentration adjusted to $20×10^6$ cells/ml. The cell suspension (200 μl) was placed on the PGA felt disc and the disc squeezed with a forceps. This allowed the felt to absorb the cell suspension as a sponge absorbs water. The PGA felt discs with cells were then incubated at 37° C. in a humidified atmosphere containing 5% $CO_2$ to permit cell adhesion to, and entrapment within, the polymer scaffold. Six hours after the PPSCs were seeded 1.0 ml of culture medium was carefully be added, and 1.0 ml more of medium the next morning. For the PPSCs cultured in vitro for 24 hours group, the PPSCs+PGA felts were washed 2× with sterile PBS the next morning and then implanted into animals as described below. For the PPSCs cultured in vitro for 2 weeks, medium was replaced every 2-3 days for 2 weeks of tissue culture. At this time the PPSCs+PGA felts were washed 2× with 1.0 ml of sterile PBS prior to implantation.

Immediately prior to implantation, a 4 mm trephine was used to remove a 4 mm diameter plug from the PGA felt disc. This plug was press-fit into the defect. Experience has shown that the implant will remain in the defect without further manipulation and this seemed to be confirmed in this study.

Defects and Experimental Groups:

Defects were 3 mm in diameter and were prepared as previously described. Arthrotomies (using sterile operating technique) were performed on adult female rabbits that were at least 8 months old and the femoropatellar groove and medial condyle exposed. The defects were drilled using a hand drill in the center of the femoropatellar groove and in the medial condyle. The defects went through the articular cartilage and the subchondral plate just into the trabecular bone. The drill bit was flat with a small triangular projection and the defects were drilled such that blood was just visible in the central dimple drilled by the projection. Blood did not ooze from the defect. Experimental groups were:

Group 1 Empty defect. The osteochondral defect was created and left empty as a control Group 2 Polymer alone. The osteochondral defect was filled with sterilized polymer cultured in media alone for 2 weeks to serve as a vehicle control.

Group 3. The osteochondral defect received PGA felt cultured with PPSCs for 2 weeks prior to implantation. This group is identical to previous studies [18].

Group 4 The osteochondral defect received PGA felt cultured with PPSCs for 24 hours prior to plating This is also an experimental group, but represented an attempt to determine if the 2 week culture in the PGA felt was necessary.

A total of 30 animals were used. Using both knees, this means 15 femoropatellar defects and 15 medial condyle defects per treatment group. Eight were used for histology and 7 for mechanical testing. All animals were euthanized 26 weeks post-operatively.

Histology:

Animals were euthanized 26 weeks post-op and those tasked for histology had the distal femur removed (containing both defects) and fixed in 10% neutral buffered formalin+10% cetylpyridinium chloride. They were decalcified in Decal I (Fisher Scientific). At this point both the femoropatellar groove and the medial condyle defect was bisected with a razor blade perpendicular to the long axis of the femur. The defects were then processed for paraffin histology with the center of the defect facing the microtome blade. Thus, when sectioning began, the sections were taken through the center of the defect. The remaining halves of the defects are currently stored in 70% ethanol against future need. Seven µm sections were obtained and stained with either Toluidine blue or Mallory-Heidenhain stain.

Mechanical Testing:

Animals were euthanized with most of the femur used (to provide a post for embedment for mechanical testing) and immediately stored at −20° C. until testing. The femurs were thawed immediately prior to mechanical testing with the distal femur covered with a cloth saturated with PBS. The proximal end of the femur was "potted" in polymethyl methacrylate (PMMA). The specimens were covered in damp paper towels after thawing in order to keep them moist and not change any of the biomechanical properties that may occur if they were to dry out. The potted femur was placed in an MTS (Eden Prairie, Minn.) Model 858 Mini-Bionix servohydraulic, bi-axial materials testing apparatus. The specimen was secured to the load cell with a four jawed chuck and a 2-mm flat probe was centered over the defect. The probe was secured to the vertical accuator by a custom designed gripping system, which consisted of two screws and two aluminum plates, where the probe was placed and tightened between the two plates. The vertical accuator advanced the probe 0.001 mm/s and the force was recorded at each increment until a depth of 0.5 mm was reached. Four tests were performed on each specimen. The first was the defect in the patella femoral groove and then its control was tested in the distal patella femoral groove. The next two tests were the defect in the medial femoral condyle and its control on the lateral femoral condyle. This procedure provided an internal control to minimize variation between animals. The data was collected at a rate of 10 Hertz via the Test Star II controller, then to a computer utilizing Test Ware SX software. The data obtained by the Test Star was graphically and statistically analyzed using a Microsoft Excel package. Force vs displacement curves were plotted for each defect and control and the stiffness calculated from the slope over the linear portion of the curve. Results are expressed as percent of the normal cartilage for each defect.

Results

Histology:

Femoropatellar Groove:

Empty defects were filled with either fibrocartilage or connective tissue that was not metachromatic in Toluidine blue, indicating a lack of proteoglycans (FIG. 73A). Some defects had very little healing and the edges where the drill bit removed the original tissue was clearly visible (FIG. 73B).

Defects with polymer alone exhibited fibrocartilage in the defect with good regeneration of subchondral bone. However, most had very distinct edges and poor integration with the host cartilage (FIG. 74)

Defects treated with PPSCs in PGA felt for 24 hours had highly variable histology. Most had histology similar to FIG. 75. There was some cartilage at the edges of the defect but the center of the defect was either connective tissue or fat (FIG. 75). However, some samples showed good fibrocartilage and subchondral bone throughout the defect. In both cases there was excellent integration of the tissue in the defect with the host cartilage. The reason for this variability is not completely clear, but it was noted that the PPSCs did not seem tightly attached to the PGA felt. When the residual material (the polymers were kept in 35 mm culture dishes during the operation and polymer+PBS after the 4 mm discs were cut from the 1 cm disk) was examined it was noted that there were considerable numbers of PPSCs floating in the PBS that were not attached to the polymer. Therefore we speculate that this loose attachment of PPSCs to the felt after 24 hours results in variable numbers of PPSCs being delivered to the defect.

In contrast, PGA felt with PPSCs cultured for 2 weeks in vitro showed consistent regeneration (FIG. 76). There was excellent integration of the tissue in the defect to the host cartilage to the extent that often the edge could not be detected even at high magnification. The cartilage in the defect showed the zonation of mature articular cartilage, including calcified cartilage and a tidemark. There were isogenous nests within the radial zone. There was complete regeneration of the subchondral bone.

Medial Condyle:

The histology of the different treatment groups in the medial condylar defects was very similar to that of the femoropatellar groove. Empty defects had predominantly connective tissue in the defect with some fibrocartilage present (FIG. 77). The surface was irregular with tissue often extending beyond the adjacent cartilage surface into the joint space. There was poor integration of the repair tissue with the adjacent undamaged cartilage.

Defects with PGA felt alone looked very similar to empty defects (FIG. 78). The surface was often irregular and the defect was filled with fibrocartilage. Integration of repair tissue with adjacent cartilage was very poor.

Defects with PGA felt+PPSCs cultured for 24 hrs in vitro showed the same type of variability observed in the femoropatellar groove. Some defects showed only fibrocartilage and connective tissue (FIG. 79A) but others had very good regeneration (FIG. 79B). It was noted that the animals that had poor regeneration in the femoropatellar groove also had poor regeneration in the condyle and those with regeneration in the femoropatellar groove also had regeneration in the medial condylar defect. For instance, FIG. 75A and FIG. 79A are from the same animal while FIG. 75B and FIG. 79B are from the same animal. This reinforces our hypothesis that seeding at 24 hours is variable.

Defects treated with PGA felt+PPSCs cultured in vitro for 2 weeks showed consistent regeneration histologically (FIG. 80). There was good integration with adjacent cartilage, regeneration of subchondral bone, articular cartilage in zones, and isogenous nests.

The mechanical properties reflected the histological observations. The data for the femoropatellar groove is shown in TABLE 22.

TABLE 22

Mechanical Data For Femoropatellar Groove

|  | Empty | Polymer Alone | PPSCs cultured in Polymer 24 hrs. | PPSCs cultured in Polymer 2 wks. |
| --- | --- | --- | --- | --- |
| Mean | 24.73 | 40.07 | 64.67* | 87.07*† |
| Standard Deviation | 21.36 | 28.17 | 20.78 | 14.57 |
| Standard Error of the mean | 11.15 | 9.76 | 7.85 | 7.29 |

Groups with * are significantly different from empty defects rat p < 0.05.
Groups with † are significantly different from Polymer above at p < 0.05.

ANOVA analysis indicated that there was significant difference among the four treatments in the femoropatellar groove. Analysis of the means of each group showed that polymer alone was not significantly different from empty defects. However, there were significant differences in the mechanical strength between empty defects and defects that were treated with PPSCs, whether the PPSCs were in the polymer for 24 hours prior to implantation or were cultured for 2 weeks prior to implantation. When polymer alone was compared to PPSC treated, there was no significant difference in mechanical strength compared to PPSCs culture in the polymer for 24 hrs, although the p value was 0.063. There was a significant difference in mechanical strength between polymer alone and PPSCs cultured for 2 weeks in vitro. It appears that there would be a significant difference between the mechanical strength of defects treated with PPSCs culture for 24 hours vs. defects treated with PPSCs cultured for 2 weeks. This is not the case, but the p value was 0.07. The mechanical strength of these defects ranged from a high of 88.17% to a low of 28.41% of adjacent normal cartilage. This wide range reflects what we observed histologically, namely the wide variation of responses in defects treated with PPSCs cultured for 24 hrs.

The data for the mechanical properties of the medial condyle is shown in TABLE 23.

TABLE 23

Mechanical Data For Medial Condyle

|  | Empty | Polymer Alone | PPSCs cultured in Polymer 24 hrs. | PPSCs cultured in Polymer 2 wks. |
| --- | --- | --- | --- | --- |
| Mean | 29.74 | 40.65 | 52.56 | 80.19*†‡ |
| Standard Deviation | 19.27 | 20.85 | 22.23 | 17.25 |
| Standard Error of the mean | 6.42 | 9.32 | 9.08 | 7.71 |

Groups with * are significantly different from empty defects rat p < 0.05.
Groups with † are significantly different from Polymer above at p < 0.05.
Groups with ‡ are significantly different from PPSCs cultured in polymer for 24 hrs at P < 0.05.

ANOVA analysis indicated significant differences between treatments in the mechanical strength in the medial condyle. Analysis of the means of each group showed a very similar pattern observed in the femoropatellar groove. Again defects treated with PPSCs cultured for 2 weeks in vitro had significantly greater mechanical strength than empty defects or defects treated with polymer alone. In the condyle, however, defects treated with PPSCs cultured for 24 hrs were not significantly different from either empty defects or defects treated with polymer alone. Once again the defects treated with PPSCs cultured for 24 hrs showed considerable variability in their mechanical strength, ranging from a low of 23.47% to a high of 82.21% of adjacent cartilage. In this case, the variability was so great that there was no significant difference compared with empty defects although the p value was 0.067. However, in the condyle the difference between PPSCs cultured for 24 hrs was significantly different from PPSCs cultured for 2 wks (p=0.045). Thus, the difference in mechanical strength between defects treated with PPSCs cultured for 24 hrs and those treated with PPSCs cultured for 2 weeks is right at the edge of statistical significance. We believe, based on the data and the observed variability in histology, that there is a biologically important difference between the two treatments.

Conclusions:

The results of this study clearly confirm that implanting PPSCs into full-thickness critical sized defects in adult rabbits resulted in histological regeneration of both the cartilage and bone. PPSCs cultured in PGA felt for 2 weeks resulted in regeneration of articular cartilage in both femoropatellar groove and medial condyle defects. This was observed histologically and confirmed with mechanical strength. We have thus demonstrated regeneration of both histology and mechanical properties of articular cartilage. Additionally, we have demonstrated that the regenerated tissue persists for 26 weeks without subsequent degeneration. This indicates that the regenerated tissue is stable and will resist normal mechanical stresses. It should be emphasized that there was no attempt to manipulate or differentiate the PPSCs ex vivo in this study. The PPSCs responded to endogenous differentiation signals.

Example 27

Use of PPSCS in Neural Regeneration and for Spinal Cord Injury

Experiments were undertaken to demonstrate that PPSCs could restore locomotor function to a spinal cord injured animal.
1. The PPSCs were administered immediately following injury, with a delay of not more than 2 hours.
2. Improvement was observed in locomotor function in the 6 weeks that the post-op evaluation was initially conducted.

To determine whether transplantation of pluripotent stem cells (PPSCs) into the injured spinal cord can enhance locomotor recovery, groups of untreated or PPSC-injected rats were evaluated for locomotor function following spinal cord contusion injury. PPSCs, which can be isolated from most tissues, are capable of differentiating into different cell types including nerve cells in vitro. They have been shown to differentiate in vivo in response to local cues. A model of spinal cord injury was used in which contusion injury is produced in rats with a weight-drop device. A vertical guide in the device allows a 10 g rod with 2.5-mm diameter tip to drop from a preset height (25-mm) unto the exposed dura of the spinal cord at the level of T10. Locomotor function was determined for six weeks following injury with the 21 point Basso, Beattie and Bresnahan (BBB) scale.

PPSCs were previously isolated from the skeletal muscle of a rat and grown in culture for two weeks. Cultured PPSCs were then transplanted into the spinal cord injury site by injection with a 1-ml syringe with a 26-gauge needle. 106 PPSCs were suspended in 25 µl of saline and injected into the center of the spinal cord at the contusion site immediately following injury.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

What is claimed is:

1. A method of providing a host with isolated cells derived from postnatal human tissues, the method comprising administering into the host the isolated cells, wherein the isolated cells express SSEA4, do not express CD34, have a normal karyotype, do not form tumors in the host, are capable of self-renewal, and are capable of differentiation to cells of endodermal, ectodermal and mesodermal lineages, said isolated cells having been produced by expanding, in culture, a cultured cell clone from a postnatal human tissue.

2. The method of claim 1 wherein the isolated cells are administered in combination with one or more proliferation factors or lineage commitment factors.

3. The method of claim 1 wherein the expansion is greater than 50 cell doublings.

4. The method of claim 1 wherein the expansion comprises cell doublings of between 12 and 47.

5. The method of claim 1 wherein the isolated cells have been passaged and cryopreserved after passage prior to introduction to the host.

* * * * *